(12) United States Patent
Greenwood

(10) Patent No.: US 10,565,329 B2
(45) Date of Patent: Feb. 18, 2020

(54) SYSTEM AND METHOD FOR MODELLING SYSTEM BEHAVIOUR

(71) Applicant: Evolving Machine Intelligence Pty Ltd, Milton, Queensland (AU)

(72) Inventor: Nigel John Conrad Greenwood, Brassall (AU)

(73) Assignee: Evolving Machine Intelligence PTY LTD, Milton, Queensland (AU)

( * ) Notice: Subject to any disclaimer, the term of this patent is extended or adjusted under 35 U.S.C. 154(b) by 284 days.

(21) Appl. No.: 15/323,199

(22) PCT Filed: Jun. 29, 2015

(86) PCT No.: PCT/AU2015/050362
§ 371 (c)(1),
(2) Date: Dec. 30, 2016

(87) PCT Pub. No.: WO2016/000035
PCT Pub. Date: Jan. 7, 2016

(65) Prior Publication Data
US 2017/0147722 A1    May 25, 2017

(30) Foreign Application Priority Data
Jun. 30, 2014  (AU) ................. 2014902494

(51) Int. Cl.
G06F 17/50       (2006.01)
G16H 50/50       (2018.01)
G06F 17/13       (2006.01)

(52) U.S. Cl.
CPC .......... *G06F 17/5009* (2013.01); *G06F 17/13* (2013.01); *G16H 50/50* (2018.01)

(58) Field of Classification Search
None
See application file for complete search history.

(56) References Cited

U.S. PATENT DOCUMENTS 5,285,793 A    2/1994   Slovut et al.
5,971,922 A   10/1999   Arita et al.
(Continued)

FOREIGN PATENT DOCUMENTS

GB    2 401 949 A    11/2004
WO    94/06088 A1     3/1994
(Continued)

OTHER PUBLICATIONS

Alpaydin et al. "An Evolutionary Approach to Automatic Synthesis of High-Performance Analog Integrated Circuits", IEEE Transactions on Evolutionary Computation vol. 7, No. 3, Jun. 2003, pp. 240-252. (Year: 2003).*
(Continued)

*Primary Examiner* — Suzanne Lo
(74) *Attorney, Agent, or Firm* — Umberg Zipser LLP

(57) ABSTRACT

A method of modelling system behaviour of a physical system, the method including, in one or more electronic processing devices obtaining quantified system data measured for the physical system, the quantified system data being at least partially indicative of the system behaviour for at least a time period, forming at least one population of model units, each model unit including model parameters and at least part of a model, the model parameters being at least partially based on the quantified system data, each model including one or more mathematical equations for modelling system behaviour, for each model unit calculating at least one solution trajectory for at least part of the at least one time period; determining a fitness value based at least in part on the at least one solution trajectory; and, selecting a combination of model units using the fitness values of each model unit, the combination of model units representing a collective model that models the system behaviour.

19 Claims, 26 Drawing Sheets

(56) References Cited

U.S. PATENT DOCUMENTS

| | | | |
|---|---|---|---|
| 6,063,028 | A | 5/2000 | Luciano |
| 6,381,577 | B1 | 4/2002 | Brown |
| 6,835,175 | B1 | 12/2004 | Porumbescu |
| 8,626,522 | B2 | 1/2014 | Greenwood |
| 2001/0013006 | A1 | 8/2001 | Brown |
| 2002/0095099 | A1 | 7/2002 | Quyen et al. |
| 2002/0095258 | A1 | 7/2002 | Agur et al. |
| 2010/0121618 | A1 | 5/2010 | Greenwood |
| 2013/0304388 | A1 | 11/2013 | Greenwood |

FOREIGN PATENT DOCUMENTS

| | | | |
|---|---|---|---|
| WO | 97/28737 | A1 | 8/1997 |
| WO | 00/05671 | A1 | 2/2000 |
| WO | 02/32458 | A2 | 4/2002 |
| WO | 03/013351 | A1 | 2/2003 |
| WO | 2004/027674 | A1 | 4/2004 |
| WO | 2006/107630 | A1 | 10/2006 |
| WO | 2007/104093 | A1 | 9/2007 |

OTHER PUBLICATIONS

Veluswami et al. "The Application of Neural Networks to EM-Based Simulation and Optimization of Interconnects in High-Speed VLSI Circuits", IEEE Transactions on Microwave Theory and Techniques, vol. 45, No. 5, May 1997, pp. 712-722. (Year: 1997).*

Abraham, Ajith. "Meta-Learning Evolutionary Artificial Neural Networks", 25 pages. (Year: 2004).*

Noriega et al. "A Direct Adaptive Neural-Network Control for Unknown Nonlinear Systems and Its Application", IEEE Transactions on Neural Networks, vol. 9 No. 1, Jan. 1998, pp. 27-34. (Year: 1998).*

Ashlock et al. "Genetic Algorithms for Automated Texture Classification" Proc of SPIE, Oct. 1996, 11 pages. (Year: 1996).*

Kitano, Hiroaki. "Designing Neural Networks Using Genetic Algorithms with Graph Generation System", Complex Systems 4, 1990, pp. 461-476. (Year: 1990).*

Batke et al., "Suicide Inhibition of Monoamine Oxidases A and B by (-)-Deprenyl," Biochemical Pharmacology, 1993; 46(4):597-602.

Bergman et al., "Quantitative estimation of insulin sensitivity," Am. J. Physiol.: Endocrinol, Metab. Gastrointest. Physiol., 1979; 5(6):E667-E677.

Cobelli, et al., "On a simple model of insulin secretion," Med. & Biol. Eng. & Comput., 1980; 18:457-463.

Cobelli et al., "An Integrated Mathematical Model of the Dynamics of Blood Glucose and Its Hormonal Control," Mathematical Biosciences, 1982; 58:27-60.

Corless et al., "Control of uncertain systems with neglected dynamics," Deterministic Control of Uncertain Systems, IEE Publishers; 1987:252-268.

Corless et al., "Adaptive Control for Avoidance or Evasion in an Uncertain Environment," Comput. Math. Applic., 1987; 13(1-3)1-11.

Csete et al., "Reverse Engineering of Biological Complexity," Science, Mar. 2002; 295:1664-1669.

De Gaetano et al., "Mathematical modelling of the intravenous glucose tolerance test," J. Math. Biol., 2000; 40:136-168.

Ditto, William, "Applications of Chaos in Biology and Medicine," AIP Conf. Proceedings, 1996; 376:175-201.

Friedrich et al., "Extracting Model Equations from Experimental Data," Physics Letters A, Jun. 19, 2000; 271:217-222.

Fudenberg et al., "Game Theory," Cambridge:MIT Press, 1995; pp. 336-337.

Gastaldelli et al., "Glucose kinetics in interstitial fluid can be predicted by compartmental modeling," Am. J. Physiol., 1997; 272:E494-505.

Getz et al., "Qualitative Differential Games with Two Targets," Journal of Mathematical Analysis and Applications, 1979; 68:421-430.

Greenwood et al., "A Computational Proof of Concept of a Machine-Intelligent Artificial Pancreas Using Lyapunov Stability and Differential Game Theory," Journal of Diabetes Science and Technology, 2014; 8(4):791-806.

Guevara et al., "Phase Locking, Period-Doubling Bifurcations, and Irregular Dynamics in Periodically Stimulated Cardiac Cells," Science, Dec. 18, 1981; 214:1350-1353.

Huang et al., "Modelling approach for separating blood time-activity curves in positron emission tomographic studies," Phys. Med. Biol., 1991; 36(6):749-761.

Isaacs, R., "Differential Games," New York:John Wiley and Sons, Inc., 1965; pp. 25-41.

Kraegen et al., "Insulin responses to varying profiles of subcutaneous insulin infusion: kinetic modelling studies," Diabetologia, 1984; 26:208-213.

Leitmann et al., "Avoidance Control," Journal of Optimization Theory and Applications, Dec. 1977; 23(4):581-591.

Leitman et al., "The Calculus of Variations and Optimal Control: An Introduction," New York:Plenum, 1981; pp. 88-123.

Leitman et al., "A Note on Avoidance Control," Optimal Control Applications & Methods, 1983; 4:335-342.

Papadimitriou, C., "Games against Nature," Journal of Computer and System Sciences, 1985; 31:288-301.

Porenta et al., "A Mathematical Model of the Dopaminergic Synapse: Stability and Sensitivity Analyses, and Simulation of Parkinson's Disease and Aging Processes," Cybernetics and Systems: An International Journal, 1982; 13:257-274.

Pyatigorskaya et al., "A review of the use of magnetic resonance imaging in Parkinson's disease," 2014, 7(4):206-220.

Regittnig et al., "Plasma and Interstitial Glucose Dymanics After Intravenous Glucose Injection—Evaluation of the Single-Compartment Glucose Distribution Assumption in the Minimal Models," Diabetes, May 1999, 48:1070-1081.

Skowronski, JM, "Winning Controllers for nonlinear Air Combat Game with Reduced Dynamics," Proceedings of the AIAA Guidance, Navigation and Control Conference, Minneapolis, 1988; pp. 866-873.

Skowronski, JM, "Control of Nonlinear Mechanical Systems," New York:Plenum Press, 1991; pp. 67-71, 121, 162-169, 376 & 377.

Skowronski et al., "A Map of a Two Person Qualitative Differential Game," Proceedings of the AIAA Guidance, Navigation and Control Conference, Monterey, California, 1987; 35 pgs.

Skowronski et al., "Two-Person Qualitative Differential Games With Two Objectives," Comput. Math. Applic., 1989; 18(1-3):133-150.

Tolic et al., "Modeling the Insulin-Glucose Feedback System: the Significance of Pulsatile Insulin Secretion," J. theor. Biol., 2000; 207:361-375.

Tuljapurkar et al., "Liapunov Functions: Geometry and Stability," J. Math. Biology, 1979; 8:25-32.

Ujam et al., "Modeling Performance Characteristics of a Turbojet Engine," International Journal of Manufacturing, Material and Mechanical Engineering Research, Sep. 2013; 1(1):1-16.

Veazie, Peter J., "Treatment Strategies for the Management of Chronic Illness: Is Specialization Always Better?" System Dynamics Society, 2001; 21 pgs.

Vincent et al., "Control of a Chaotic System," Dynamics and Control, 1991; 1(1):35-52.

Zare et al., "Simplified Mathematical Model for a Single Spool and No Bypass Jet Engine," Conference of Aeronautical Science, Szolnok, Budapest, Apr. 11, 2013; pp. 39-52.

\* cited by examiner

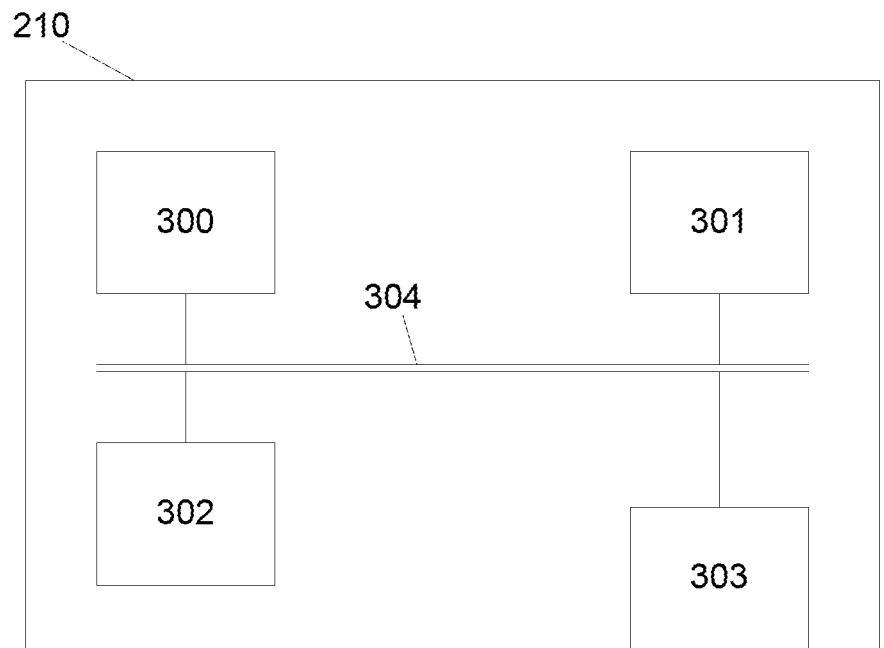
Prior Art
Fig. 3
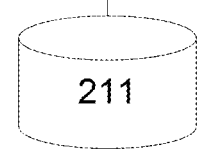
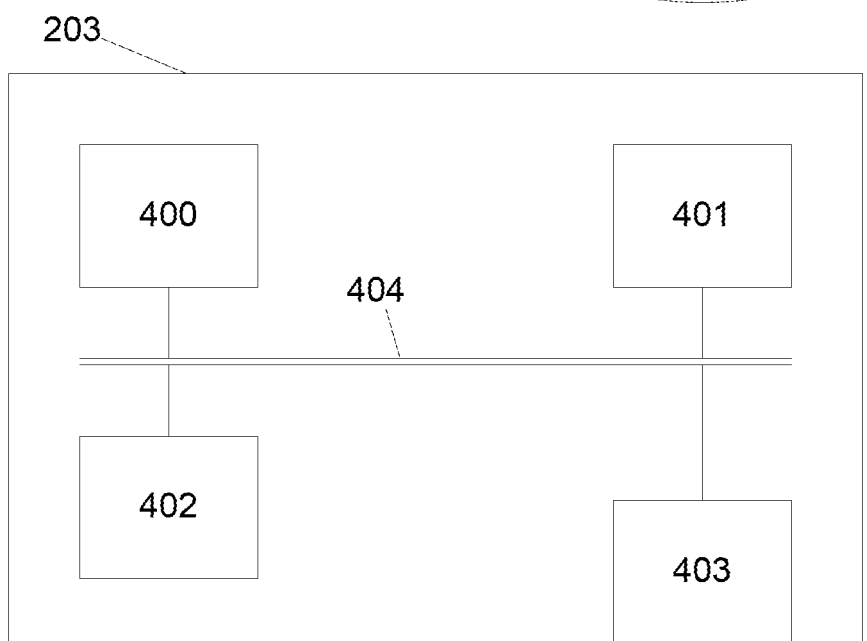
Prior Art
Fig. 4
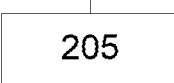

SYSTEM AND METHOD FOR MODELLING SYSTEM BEHAVIOUR

BACKGROUND OF THE INVENTION

This invention relates to a method and apparatus for modelling system behaviour of a physical system and to a method and apparatus for controlling the behaviour of a physical system.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

It is known to model behaviour of systems, such as biological subjects and other complex dynamical systems, for the purpose of analysing conditions, preparing a treatment or control program and implementing that treatment or control program.

WO2007/104093 describes method of modelling the biological response of a biological subject. The method includes, in a processing system: for a model including one or more equations and associated parameters, comparing at least one measured subject attribute and at least one corresponding model value. The model is then modified in accordance with results of the comparison to thereby more effectively model the biological response.

WO2004/027674 describes a method of determining a treatment program for a subject. The method includes obtaining subject data representing the subject's condition. The subject data is used together with a model of the condition, to determine system values representing the condition. These system values are then used to determining one or more trajectories representing the progression of the condition in accordance with the model. From this, it is possible to determine a treatment program in accordance with the determined trajectories.

Calculating solutions that accurately model the behaviour of a subject is computationally expensive and accordingly, improved modelling techniques are desirable. Furthermore, in real-world applications the available information is typically noise-polluted and underdetermines the system to be modelled and controlled, while there may also be exogenous uncertainties affecting ongoing system behaviour, hence a machine implementable technique that enables improved modelling and control of systems under these difficult circumstances is desirable.

SUMMARY OF THE PRESENT INVENTION

In one broad form the present invention seeks to provide a method of modelling system behaviour of a physical system, the method including, in one or more electronic processing devices:
a) obtaining quantified system data measured for the physical system, the quantified system data being at least partially indicative of the system behaviour for at least a time period;
b) forming at least one population of model units, each model unit including model parameters and at least part of a model, the model parameters being at least partially based on the quantified system data, each model including one or more mathematical equations for modelling system behaviour;
c) for each model unit:
   i) calculating at least one solution trajectory for at least part of the at least one time period;
   ii) determining a fitness value based at least in part on the at least one solution trajectory; and,
d) selecting a combination of model units using the fitness values of each model unit, the combination of model units representing a collective model that models the system behaviour.

Typically the method includes:
a) forming a plurality of populations; and,
b) selecting a combination of model units including model units from at least two populations.

Typically the method includes exchanging, between the populations, at least one of:
a) model parameters;
b) at least part of a model; and,
c) model units.

Typically the method includes:
a) selectively isolating a number of model units in an isolated population; and,
b) selectively reintroducing model units from the isolated population.

Typically the method includes, modifying the model units at least one of:
a) iteratively over a number of generations;
b) by at least one of inheritance, mutation, selection, and crossover;
c) in accordance with the fitness value of each model unit; and,
d) in accordance with speciation constraints.

Typically the method includes, modifying at least one of:
a) at least part of the model; and,
b) the model parameters.

Typically each model unit includes:
a) at least part of the model;
b) a chromosome indicative of the model parameters and fitness value; and,
c) details indicative of behaviour of at least some solution trajectories calculated for the model unit.

Typically the method includes, modifying the model units by exchanging or modifying at least part of the chromosome.

Typically the method includes, determining the fitness value at least in part using a behaviour of the at least one solution trajectory.

Typically the method includes, determining the fitness of a model unit by comparing the at least one solution trajectory to quantified system data indicative of system behaviour.

Typically the method includes, determining the fitness value at least in part using a texture set representing a geometrical set in state space.

Typically the method includes, in accordance with the behaviour of at least one solution trajectory, at least one of:
a) introducing the texture set into state space;
b) deleting the texture set from state space;
c) moving the texture set through state space;
d) modifying the texture set by at least one of:
   i) enlarging;
   ii) compressing;
   iii) deforming; and,
   iv) subdividing.

Typically the method includes, determining the fitness value at least in part using fitness criteria based on:

a) qualitative behaviour of solution trajectories in state space;
b) quantitative behaviour of solution trajectories in state space;
c) collision of solution trajectories with sets in state space;
d) capture of solution trajectories by sets in state space;
e) avoidance of sets in state space by solution trajectories;
f) divergence of solution trajectories in state space; and,
g) intersection with a geometrical surface in state space.

Typically the method includes modifying the fitness criteria for successive generations of model units.

Typically the method includes at least one of selectively activating and deactivating fitness criteria for at least one generation of model units.

Typically at least one of:
a) the sets in state space are texture sets; and,
b) the texture sets undergo changes within generations of a population of model units.

Typically the method includes:
a) determining control variable values representing control inputs; and,
b) determining the solution trajectory in accordance with the control variable values.

Typically the method includes:
a) segmenting quantified system data into respective time period segments; and,
b) determining respective model units for each time period segment.

Typically the method includes selecting the combination of model units so as to include model units for each of the time period segments.

Typically the method includes selecting the combination of model units using an optimisation technique.

Typically the method includes:
a) selecting a number of model units in accordance with the fitness values;
b) determining a plurality of candidate combinations of model units;
c) determining a combination fitness value for each candidate combination; and,
d) selecting the combination in accordance with the combination fitness value.

Typically the method includes:
a) defining a plurality of circuits, each circuit including a sequence of Blocks, each Block representing a respective population of model units;
b) transferring at least one of model units and model parameters between the Blocks in accordance with circuit connections; and,
c) using the circuit to select at least one of the combination of model units and model parameters.

Typically the method includes modifying the circuits by modifying model units of the Blocks.

Typically the method includes:
a) generating a network including a number of nodes;
b) associating parts of a model with a node;
c) for each node on a path through the network:
   i) determining at least one model unit using parts of a model associated with the node; and,
   ii) optimising model parameters of the at least one model unit; and,
d) generating a candidate model based on the model units and model parameters.

Typically the method includes optimising the path to determine the combination.

Typically the method includes optimising the path by:
a) traversing at least one path;
b) assessing the resulting candidate combination; and,
c) traversing modified paths based on the assessment of the candidate combination.

Typically the method includes optimising the path using a swarm optimisation technique.

Typically the method includes:
a) defining a plurality of circuits, each circuit including a sequence of Blocks;
b) for each node in the network populating each Block with parts of models associated with the node;
c) transferring at least one of model units and model parameters between the Blocks in accordance with circuit connections to thereby optimise model parameters of the model units.

Typically the method includes:
a) transferring a plurality of circuits along respective paths in the network;
b) at each node, calculating a respective circuit fitness; and,
c) selecting an optimum path using the circuit fitness, the selected path representing the combination.

Typically the method includes using the model to at least one of:
a) develop a control program including one or more control variable values indicative of control inputs to the system to modify system behaviour in a desirable manner;
b) derive system data that cannot be physical measured; and,
c) determine a scenario or likelihood of system behaviour resulting in a failure.

Typically the method includes:
a) comparing at least one of system data and system behaviour to defined limits; and,
b) determining a scenario or likelihood of failure in accordance with results of the comparison.

Typically the method includes:
a) determining a selected model parameter corresponding to system data that cannot be at least one of directly manipulated and directly measured;
b) comparing the selected model parameter to a respective operating range; and
c) in response to the selected model parameter falling outside the respective range, determining a control input either to at least one of:
   i) prevent the selected model parameter falling outside the respective range; and,
   ii) restore the selected model parameter to within the respective range once the excursion has occurred.

Typically the method includes, using a modular system including at least one of:
a) a Model Selector module for selecting the at least part of a model;
b) an Identifier module for identifying the combination of model units; and,
c) a Controller module that uses the combination of model units to determine a control program.

Typically, in use, the Identifier module requests parts of a model from the Model Selector.

Typically the method includes manipulating or altering the behaviour of the physical system at least partially by applying the control program.

Typically the method includes:
a) defining meta-model units representing different combinations of model units; and, b) optimising the meta-model units to determine a combination of model units.

Typically the method includes:
a) defining meta-model units representing different Blocks, each representing a respective population of model units; and,
b) optimising the meta-model units to determine an optimal Block.

In one broad form the present invention seeks to provide a method of modelling system behaviour of a physical system, the method including, in one or more electronic processing devices:
a) generating a network including a number of nodes;
b) associating parts of a model with a node;
c) for each node on a path through the network determining at least one model unit, each model unit including model parameters and at least part of a model, the model parameters being at least partially based on quantified system data, each model including one or more mathematical equations for modelling system behaviour, and the model unit being determined using the parts of the model associated with the node;
d) optimising model parameters of each model unit; and,
e) generating a candidate combination of model units based on the model units and model parameters, the candidate combination of model units representing a candidate collective model that models the system behaviour.

Typically the method includes:
a) generating a candidate model for each of a number of different paths; and,
b) selecting one a combination of model units based on the candidate combinations.

Typically the method includes assessing multiple paths to determine a combination of model units representing a collective model that models the system behaviour.

Typically the method includes optimising the model parameters by:
a) determining a solution trajectory for different sets of model parameters;
b) determining a fitness value for each solution trajectory; and,
c) modifying the model parameters based on the determined fitness values.

In one broad form the present invention seeks to provide a method of determining a control program for controlling the system behaviour of a physical system, the method including, in one or more electronic processing devices:
a) determining a model of the physical system, the model including:
 i) one or more mathematical equations for modelling system behaviour; and,
 ii) model parameters, the model parameters being at least partially based on quantified system data measured for the physical system and including control variables representing controller inputs for controlling the physical system;
b) determining at least one of:
 i) one or more targets representing desired system behaviour; and,
 ii) one or more anti-targets representing undesired system behaviour;
c) determining a plurality of solution trajectories using the model for a number of different control variable values;
d) selecting one or more of the plurality of solution trajectories using at least one of the targets and the anti-targets; and,
e) determining a control program for controlling the behaviour of the physical system at least in part using the control variable values associated with one or more selected solution trajectories.

Typically the method includes:
a) determining one or more anti-targets representing undesirable system behaviour; and,
b) selecting one or more of the plurality of solution trajectories using the targets and anti-targets.

Typically the method includes:
a) determining a plurality of sets of solution trajectories;
b) for each set, determining numbers of solution trajectories that:
 i) move towards targets;
 ii) move towards targets and avoid any anti-targets; and,
 iii) avoid any anti-targets; and,
c) selecting the one or more of the plurality of solution trajectories by selecting at least one set of solution trajectories in accordance with the determined numbers.

Typically the targets represent sets in state space corresponding to a desired physical system outcome.

Typically anti-targets represent sets in state space corresponding to physically lethal, dangerous, unstable or uncontrollable conditions.

Typically the method includes:
a) determining one or more desirable states; and,
b) selecting one or more solution trajectories passing through one more desirable states.

Typically the desirable states represent sets in state space corresponding with physically or technically advantageous conditions.

Typically the method includes determining and manipulating solution trajectories using one or more Lyapunov functions.

Typically the method includes, using gradient descent criteria to impose control on the behaviour of solution trajectories.

Typically the method includes, using gradient descent criteria to determine control variable values leading to solution trajectories that at least one of:
a) move towards targets; and,
b) avoid anti-targets.

Typically the method includes at least one of determining and manipulating solution trajectories using uncertainty variables representing uncertainties including at least one of noise, external perturbations and unknown values for state variables, parameters or dynamical structures.

Typically the method includes:
a) using a game against Nature to determine the effect of different uncertainties; and,
b) selecting the one or more solution trajectories to mitigate the impact of the uncertainties.

Typically the method includes:
a) determining, for a range of uncertainty variable values, if candidate solution trajectories can be made to meet the gradient conditions associated with one or more Lyapunov functions; and,
b) selecting one or more solution trajectories from the candidate solution trajectories at least partially in accordance with the results of the determination.

Typically the method includes determining gradient conditions associated with one or more Lyapunov functions using the targets and any anti-targets.

Typically the method includes:
a) calculating control variable values to steer the solution trajectories towards a desired gradient direction;
b) selecting candidate solution trajectories that meet the gradient conditions.

Typically the method includes:
a) calculating uncertainty variable values to steer the candidate solution trajectories away from the desired gradient direction;
b) determining disrupted candidate trajectory solutions using the uncertainty variable values; and,
c) at least one of:
   i) determining if the disrupted candidate trajectory solutions meet the gradient conditions; and,
   ii) determining if control variable values of the disrupted candidate trajectory solutions can be modified so that the disrupted candidate trajectory solutions to meet the gradient conditions.

Typically the method includes selecting the one or more solution trajectories from any disrupted candidate trajectories that at least one of:
a) move towards targets; and,
b) avoid any anti-targets.

Typically the method includes manipulating or altering the behaviour of the physical system at least partially by applying the control program.

In one broad form the present invention seeks to provide apparatus for modelling system behaviour of a physical system, the apparatus including, one or more electronic processing devices that:
a) obtain quantified system data measured for the physical system, the quantified system data being at least partially indicative of the system behaviour for at least a time period;
b) form at least one population of model units, each model unit including model parameters and at least part of a model, the model parameters being at least partially based on the quantified system data, each model including one or more mathematical equations for modelling system behaviour;
c) for each model unit:
   i) calculate at least one solution trajectory for at least part of the at least one time period;
   ii) determine a fitness value based at least in part on the at least one solution trajectory; and,
d) select a combination of model units using the fitness values of each model unit, the combination of model units representing a collective model that models the system behaviour.

In one broad form the present invention seeks to provide apparatus for modelling system behaviour of a physical system, the apparatus including one or more electronic processing devices that:
a) generate a network including a number of nodes;
b) associate parts of a model with a node;
c) for each node on a path through the network determine at least one model unit, each model unit including model parameters and at least part of a model, the model parameters being at least partially based on quantified system data, each model including one or more mathematical equations for modelling system behaviour, and the model unit being determined using the parts of the model associated with the node;
d) optimise model parameters of each model unit; and,
e) generate a candidate combination of model units based on the model units and model parameters, the candidate combination of model units representing a candidate collective model that models the system behaviour.

In one broad form the present invention seeks to provide apparatus for determining a control program for controlling the system behaviour of a physical system, the apparatus including one or more electronic processing devices that:
a) determine a model of the physical system, the model including:
   i) one or more mathematical equations for modelling system behaviour; and,
   ii) model parameters, the model parameters being at least partially based on quantified system data measured for the physical system and including control variables representing controller inputs for controlling the physical system;
b) determine at least one of:
   i) one or more targets representing desired system behaviour; and,
   ii) one or more anti-targets representing undesired system behaviour;
c) determine a plurality of solution trajectories using the model for a number of different control variable values;
d) select one or more of the plurality of solution trajectories using at least one of the targets and the anti-targets; and,
e) determine a control program for controlling the behaviour of the physical system at least in part using the control variable values associated with one or more selected solution trajectories.

In one broad form the present invention seeks to provide a control method for controlling the system behaviour of a physical system, the method including, in one or more electronic processing devices:
a) determining a model of the physical system, the model including:
   i) one or more mathematical equations for modelling system behaviour; and,
   ii) model parameters, the model parameters being at least partially based on quantified system data measured for the physical system and including control variables representing controller inputs for controlling the physical system;
b) determining at least one of:
   i) one or more targets representing desired system behaviour;
   ii) one or more anti-targets representing undesired system behaviour;
c) determining a plurality of solution trajectories using the model for a number of different control variable values;
d) selecting one or more of the plurality of solution trajectories using the targets and anti-targets;
e) determining a control program for controlling the behaviour of the physical system at least in part using the control variable values associated with one or more selected solution trajectories to thereby modify system behaviour in a desirable manner; and,
f) controlling the physical system using a controller that provides controller inputs to the system in accordance with the control variable values in the control program.

Typically the method includes:
a) comparing at least one of system data and system behaviour to defined limits; and,
b) determining a scenario or likelihood of failure in accordance with results of the comparison.

Typically the method includes:
a) determining a selected model parameter corresponding to system data that cannot be at least one of directly manipulated and directly measured;
b) comparing the selected model parameter to a respective operating range; and
c) in response to the selected model parameter falling outside the respective range, determining a control input either to at least one of:
   i) prevent the selected model parameter falling outside the respective range; and,
   ii) restore the selected model parameter to within the respective range once the excursion has occurred.

In one broad form the present invention seeks to provide a control system for controlling the system behaviour of a physical system, the control system including in one or more electronic processing devices that:
a) determine a model of the physical system, the model including:
   i) one or more mathematical equations for modelling system behaviour; and,
   ii) model parameters, the model parameters being at least partially based on quantified system data measured for the physical system and including control variables representing controller inputs for controlling the physical system;
b) determining at least one of:
   i) one or more targets representing desired system behaviour;
   ii) one or more anti-targets representing undesired system behaviour;
c) determine a plurality of solution trajectories using the model for a number of different control variable values;
d) select one or more of the plurality of solution trajectories using at least one of the targets and the anti-targets;
e) determine a control program for controlling the behaviour of the physical system at least in part using the control variable values associated with one or more selected solution trajectories to thereby modify system behaviour in a desirable manner; and,
f) control the physical system using a controller that provides controller inputs to the system in accordance with the control variable values in the control program.

In one broad form the present invention seeks to provide a method of diagnosing a system condition, the method including, in one or more electronic processing devices:
a) obtaining quantified system data measured for the physical system, the quantified system data being at least partially indicative of the system behaviour for at least a time period;
b) determining a plurality of models of the physical system, each model corresponding to a respective system condition and each model including:
   i) one or more mathematical equations for modelling system behaviour; and,
   ii) model parameters, the model parameters being at least partially based on quantified system data measured for the physical system and including control variables representing controller inputs for controlling the physical system;
c) for each of the plurality of models:
   i) forming at least one population of model units, each model unit including model parameters and at least part of the model;
   ii) for each model unit:
      (1) calculating at least one solution trajectory for at least part of the at least one time period;
      (2) determining a fitness value based at least in part on the at least one solution trajectory; and,
   iii) selecting a combination of model units using the fitness values of each model unit, the combination of model units representing a collective model that models the system behaviour; and,
   iv) determining a model fitness value for the collective model; and,
d) comparing the model fitness values to select one of the plurality of models, the selected model being indicative of the system condition.

In one broad form the present invention seeks to provide a system for diagnosing a system condition, the system including, in one or more electronic processing devices that:
a) obtain quantified system data measured for the physical system, the quantified system data being at least partially indicative of the system behaviour for at least a time period;
b) determine a plurality of models of the physical system, each model corresponding to a respective system condition and each model including:
   i) one or more mathematical equations for modelling system behaviour; and,
   ii) model parameters, the model parameters being at least partially based on quantified system data measured for the physical system and including control variables representing controller inputs for controlling the physical system;
c) for each of the plurality of models:
   i) form at least one population of model units, each model unit including model parameters and at least part of the model;
   ii) for each model unit:
      (1) calculate at least one solution trajectory for at least part of the at least one time period;
      (2) determine a fitness value based at least in part on the at least one solution trajectory; and,
   iii) select a combination of model units using the fitness values of each model unit, the combination of model units representing a collective model that models the system behaviour; and,
   iv) determine a model fitness value for the collective model; and,
d) compare the model fitness values to select one of the plurality of models, the selected model being indicative of the system condition.

It will be appreciated that the broad forms of the invention and their respective features can be used independently, in conjunction or interchangeably, and reference to respective broad forms is not intended to be limiting.

BRIEF DESCRIPTION OF THE DRAWINGS

An example of the present invention will now be described with reference to the accompanying drawings, in which: —

FIG. 3 is a schematic diagram of an example of a processing system of FIG. 2;

FIG. 4 is a schematic diagram of an example of a computer system of FIG. 2;

DETAILED DESCRIPTION OF THE PREFERRED EMBODIMENTS

Examples of methods for modelling system behaviour will now be described with reference to FIGS. 1A and 1B.

In this example, it is assumed that the process is performed at least in part using one or more electronic processing devices forming part of one or more processing systems, which may in turn be connected to one or more other computer systems via a network architecture, as will be described in more detail below.

Figure 1A:
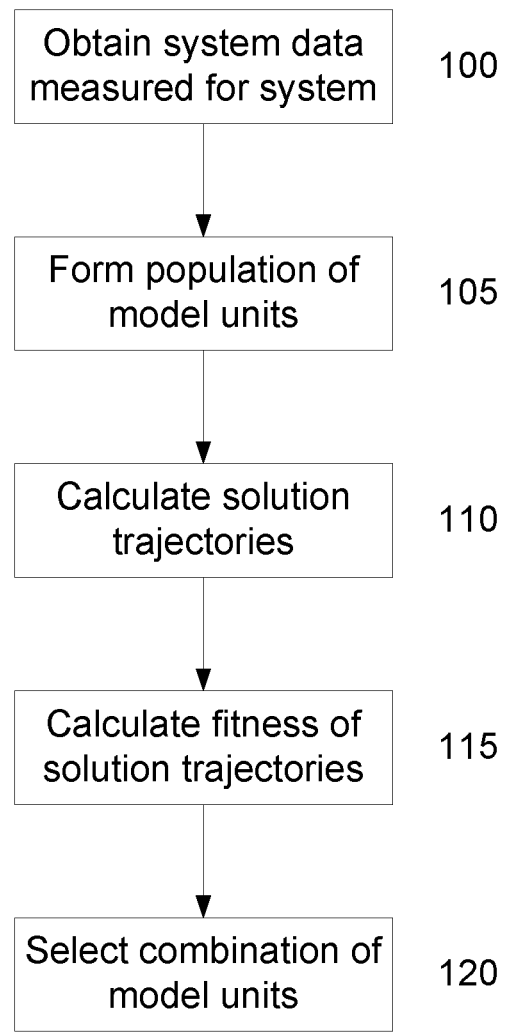
FIG. 1A is a flow chart of a first example of a method for modelling system behaviour of a physical system.
Figure 1B:
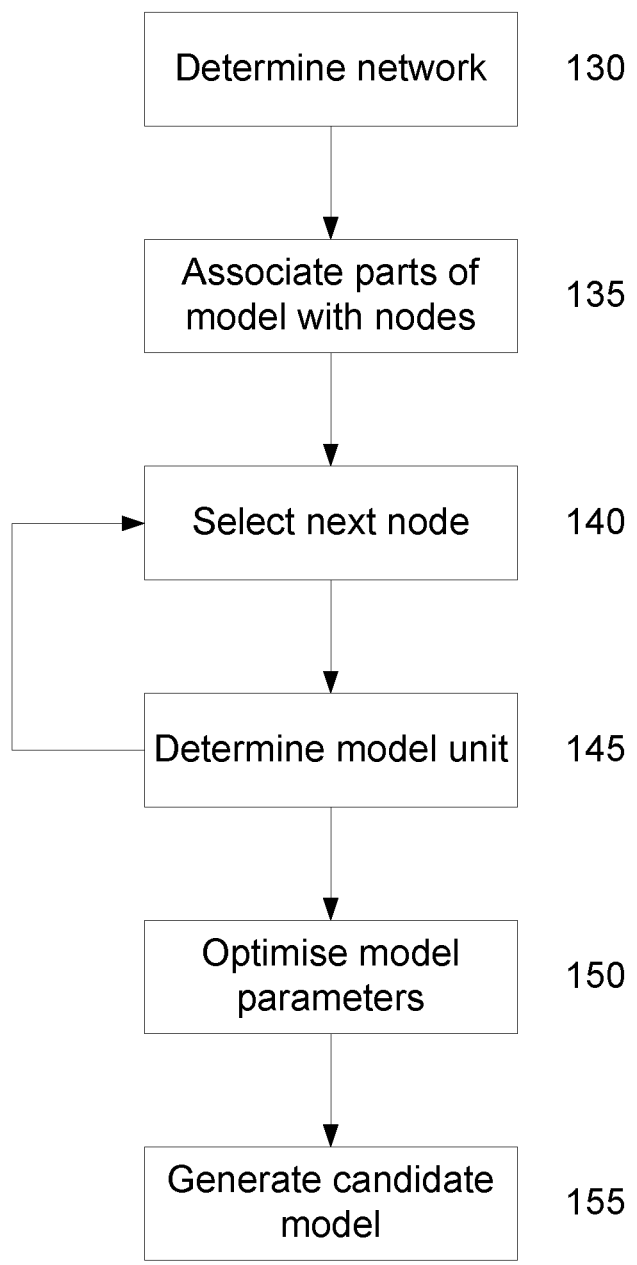
FIG. 1B is a flow chart of a second example of a method for modelling system behaviour of a physical system.

In the first example of FIG. 1A, at step 100 the one or more electronic processing devices obtain quantified system data measured for the physical system, the quantified system data being at least partially indicative of the system behaviour for at least a time period.

The quantified system data can be obtained in any suitable manner and could include measuring attributes of a physical system, receiving sensor data from sensors and optionally deriving the system data therefrom. Alternatively the quantified system data could be determined based on user input commands, retrieved from a database or the like. This will typically depend on the preferred implementation, the manner in which data regarding system behaviour is collected and the nature of the system data.

In general the system data represent not only attributes of the physical system, but also the interaction of the physical system with the environment, including for example any inputs or outputs of the system. This will depend largely on the nature of the physical system, which will vary depending on the preferred implementation.

At step 105, at least one population of model units is formed. In this regard, each model unit includes model parameters and at least part of a model. Model parameters are at least initially partially based on the quantified system data, with each model including one or more mathematical equations for modelling system behaviour. Thus, for example, the particular equations will usually be associated with model parameters in the form of coefficients that will be derived from the quantified system data. It will be appreciated that the model parameters could include state variables representing rapidly changing attributes, control variables representing attributes that can be controlled or parameter values representing slowly changing or constant attributes of the system.

The models can be of any suitable form and could include ordinary differential equations, difference equations, stochastic differential equations, partial differential equations, or fractional-order differential equations. Alternatively it could include mathematical functions of any specified structure such that the function describes solution trajectories to these equations. It will be appreciated that the particular equations and model used will vary depending on the nature of the physical system and based on which model most accurately represents the system behaviour. In one example, a number of different models can be stored for a range of physical systems of interest, with the one or more electronic processing devices operating to access a database of the models and retrieve at least part of a model based on the nature of the physical system.

Different models for modelling the behaviour of different physical systems can be obtained from a range of different sources. For example, the Food and Drug Administration pharmacometrics group, which is involved in disease-drug-trial models research for diseases of public health importance, maintains a library of models including models for Alzheimer's disease, Bipolar disease, Obesity, Parkinson Disease, Non-small cell lung cancer. There are also many published mathematical models relating to complex physical systems, such as jet engines. Examples of these include: "Modeling Performance Characteristics Of A Turbojet Engine" by Ujam, A. J., Ifeacho, F. C, and Anakudo, G published in International Journal of Manufacturing, Material and Mechanical Engineering Research Vol. 1, No. 1, pp. 1-16, September 2013, and "Simplified Mathematical Model For A Single Spool And No Bypass Jet Engine" by Foroozan Zare, Dr. Árpád Veress, Károly Beneda. It will be appreciated that many other such published models are available for a wide range of physical systems and that it will be within the ability of the skilled addressee to locate these within the literature.

For each model unit, at least one solution is calculated at step 110, for at least a segment of the time period. The solution trajectory represents progression of the system behaviour and is typically a solution trajectory in state space as will become apparent from the following description. The solution trajectory is typically calculated based on the model parameters and the model or model part, for example by calculating a solution to the equations of the model using the model parameters.

At step 115 a fitness value is calculated based at least in part on the at least one solution trajectory. The fitness value will typically be determined based on how closely the solution trajectory tracks, follows or converges with the actual system behaviour and could be based on a textured fitness, as will be described in more detail below.

A second, alternative implementation is where the system behaviour is made in part to track, follow or converge with the solution trajectory, and the fitness value is determined based on how closely the system behaviour and solution trajectory mutually converge. A third alternative implementation is the particular instance where there is no system distinct from the model (including applications of software or hardware development, where the system is entirely artificial and isomorphic to the model), where the fitness is determined by how well the solution trajectory complies with some specified performance criteria. Again, these implementations could be based on a textured fitness, as will be described in more detail below.

At step 120 a combination of model units is selected using the fitness values of each model unit, with the combination of the model units representing a collective model of the system behaviour. Thus, the one or more electronic processing devices can examine the different model units, and in particular their model parts and associated model parameters, and select which combination of model units best represents the behaviour of the system.

In this regard, the model units can go through an iterative optimisation process, such as using evolutionary algorithms, in order to optimise the model parameters for the selected model parts. As part of this, a range of different models or parts of models can be used within different model units, so that one or more electronic processing devices can determine not only which models and model parts are more effective for modelling the behaviour of the physical system, but also which model parameters should be used for which model parts.

The above described process can be performed on selected a segment of the time period, allowing different model units to be used as to represent the behaviour of the different time period segments. This in turn allows the combination of models embodied by the different model units to represent the behaviour of the physical system at different time period segments, and hence in different circumstances, to more effectively model the overall behaviour of the system.

By way of example, for a physical system in the form of a patient suffering from diabetes, a number different models may be available for modelling insulin/glucose levels within the patient. For example one model may be used while the person is asleep, a different model can be used during early-morning waking hours, other waking hours and a further model can be used after eating. Accordingly, the above described technique allows a combination of different model units to be combined into a collective model that can more accurately model the system behaviour as a whole.

A second example of a method of modelling the system behaviour of a physical system will now be described with reference to FIG. 1B.

In this example, at step 130 the one or more processing devices determine a network including a number of nodes at step 150. The network can be determined in any suitable manner and could be designed by an operator of the one or more electronic processing devices, or generated automatically based on knowledge of the physical system. A further alternative is for predefined networks to be stored in a database or other repository, with a particular network being selected based on the nature of the physical system.

At step 135 parts of one or more models are associated with each of the different nodes of the network. This may be performed at a single one-off process or alternatively could be performed dynamically allowing different model parts to be associated with different nodes as the following process is performed.

At step 140 a next node on a path through the network is selected, with a model unit, and in one example the structure of a model unit being determined based on the model parts associated with that selected node, at step 145. Thus, as in the previous example, model units typically includes model parameters at least partially based on quantified system data and at least part of the model including one or more mathematical equations for modelling system behaviour. In this instance, the part of the model used in the model unit is the part of the model associated with the respective node, so that as each node in the network is traversed, model units are propagated with different parts of a model. In this regard, at this point, the process may return to step 140 allowing a next node to be determined, with this being repeated until all nodes for a particular path have been traversed.

At step 150 the model parameters of the at least one model unit are optimised, which could be performed using any appropriate technique, such as an iterative evolutionary algorithm or the like, with this being used to determine a candidate model at step 175, based on the model units and associated model parameters.

Thus, in this example, a path through the network, which traverses multiple nodes, represents a particular candidate combination of model units which can model the system behaviour. By traversing multiple paths, this allows different combinations of model units to be derived, in turn allowing an optimum combination to be determined.

In one particular example, the above described techniques can be combined so that the process of FIG. 1A is effectively performed at each node within the network, allowing the one or more processing devices to traverse the network and select optimum combinations of model units, thereby maximising the effectiveness of the resulting collective model.

Figure 1C:
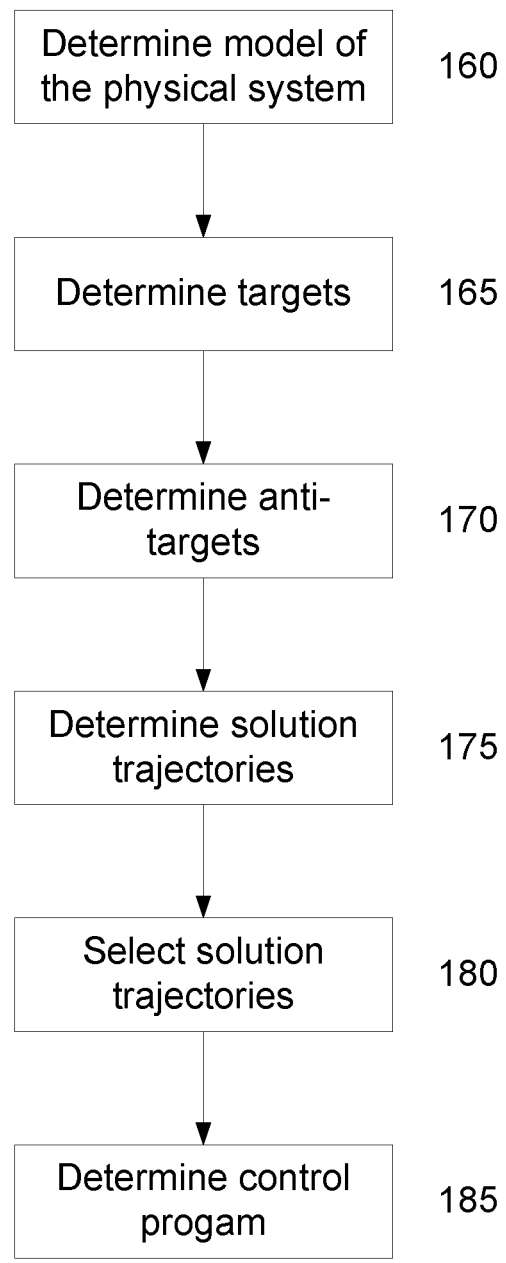
FIG. 1C is a flow chart of an example of a method of determining a control program for controlling the system behaviour of a physical system.

A method of determining a control program for controlling the system behaviour of a physical system will now be described with reference to FIG. 1C.

In this example, at step 160, the method includes, in the one or more electronic processing devices, determining a model of the physical system. The model includes one or more mathematical equations for modelling system behaviour and model parameters at least partially based on quantified system data measured for the physical system and including control variables representing controller inputs for controlling the physical system. Accordingly, it will be appreciated that in one example this can be achieved using the techniques described above with respect to FIGS. 1A and/or 1B.

At step 165, one or more targets representing desired system behaviour are determined, with these typically representing a desired end goal for the system behaviour. This could include for example a desired blood glucose level for a diabetic, or the like. This will typically be determined on a case by case basis, or could be based on predefined target behaviours stored in a database or the like.

At step 170, one or more anti-targets representing undesirable system behaviour are determined, in circumstances where such undesirable behaviour exists. The anti-targets represent conditions that should be avoided, such regions of uncontrollable behaviour, chaotic regions or the like, and this could correspond to adverse medical events, such as hypoglycaemia or hyperglycaemia, or the like. It will also be appreciated that the applications could include non-medical applications, in which case the anti-targets would be of a different form. For example, in the case of missile guidance, this could correspond to flight paths that a missile would not be capable of flying, or else could correspond to flight paths passing through the killing zones of high-lethality countermeasures, e.g. Phalanx. Again these could be defined on a case by case basis, retrieved from a database, computer system memory, or the like.

At step 175, solution trajectories are determined using the model, for example by attempting to solve the model equations based on the model parameters, as will be described in more detail below. The solution trajectories are then reviewed against the targets and anti-targets, allowing solution trajectories to be selected based on the targets and anti-targets. In an ideal situation, this would involve selecting solution trajectories that approach the targets whilst avoiding the anti-targets. However, this is not always possible and accordingly, in some examples sets or groups of solution trajectories are selected for which the majority of solution trajectories avoid the anti-targets and head towards the targets, as will be described in more detail below.

The selected solution trajectories are then used to generate a control program at step 185, particularly by using the control variable values associated with one or more selected solution trajectories.

Accordingly, this allows a control program to be readily developed once the model of system behaviour has been created.

A number of further features will now be described.

In one example, the method includes forming a plurality of populations of model units, and selecting a combination of model units including model units from at least two of the populations. In this example, the different populations can be used to represent different models, different parts of the same or different models, or different model fragments, with each of these being optimised to ensure the model parameters associated with each model unit are the most suitable. The combination of model units can then be selected across the different populations, to thereby allow a more effective model to be determined.

The method typically includes modifying model units iteratively over a number of generations, with this being performed using breeding techniques including one or more of inheritance, mutation, selection and crossover. This process is typically performed in accordance with the fitness value of each model unit and/or speciation constraints, so that the success of any one model unit in modelling the behaviour of the physical system can be used to selectively control modification of the model units. Thus, fitter model units will typically be used in preference to less-fit model units as a basis for any breeding, thereby helping drive an improvement in model parameters and model selection.

In this example, the method can include exchanging model units, model parameters, or parts of a model between the populations. Thus, separate populations of model units can be established with optimisation being performed on each population independently. During this process, model units and/or model parameters are exchanged between the populations, thereby helping avoid a population stagnating or dying out, as can occur in standard evolutionary genetic algorithms. Such cross population breeding can be controlled in a manner that mimics evolutionary breeding situations, and is also typically performed based on each model unit fitness, as will be described in more detail below.

In one particular example, when optimisation is being performed iteratively, the method can also include selectively isolating a number of model units in an isolated population and selectively reintroducing model units from the isolated population, for example periodically, sporadically or based on specified conditions being satisfied. This can also be performed to avoid stagnation or die-out of model units, which occurs when no model units meet minimum fitness levels.

To assist with this process, each model unit is typically encoded as three separate parts (referred to as a "trinity" in the specific examples below), which include at least part of the model, such as the one or more equations that are being selected for this particular model unit; a chromosome indicative of the model parameters and typically a fitness value; and, typically, details indicative of behaviour of at least one solution trajectory calculated for the model unit. This information is typically stored in a database or other computer memory, as model unit data and is updated with each iteration of the optimisation process. Thus, during each iteration of the optimisation process, the chromosome will be updated with new model parameters and a new fitness value determined for the new model parameters, so that the chromosome represents the current model parameters and their fitness, whilst details of solution trajectories and/or their behaviour at each iteration are stored so that progression, such as improvement or worsening of the solutions trajectories, can be tracked.

The model units can be modified by exchanging or modifying at least part of the chromosome. Thus, chromosomes or portions of chromosomes can be interchanged between different modelling units, or mutated, allowing for different combinations of model parameters to be assessed.

As previously mentioned, the fitness value is typically determined at least in part by behaviour of the at least one solution trajectory. In particular, this is typically achieved by comparing the at least one solution trajectory to system behaviour and determining how accurately the trajectory tracks or converges with system behaviour. The fitness value is also typically determined at least in part using a texture set representing a geometrical set in state space, which will be described in more detail below. In one example, the method includes, in accordance with the behaviour of at least one solution trajectory, at least one of: introducing the texture set into state space; deleting the texture set from state space; moving the texture set through state space; modifying the texture set by at least one of: enlarging; compressing; deforming; and, subdividing.

In one example, the method includes, determining the fitness value at least in part using fitness criteria based on qualitative behaviour of solution trajectories in state space; quantitative behaviour of solution trajectories in state space; collision of solution trajectories with sets in state space; capture of solution trajectories by sets in state space; avoidance of sets in state space by solution trajectories; divergence of solution trajectories in state space; and, intersection with a geometrical surface in state space. In this regard, the sets in state space are typically texture sets, which may undergo changes within generations of a population of model units. This can be used to define constraints on the trajectories, for example to exclude, improve or reduce the fitness level of those passing through certain regions of state space, as will be described in more detail below.

In one example, the method includes modifying the fitness criteria for successive generations of model units. This can include selectively activating and/or deactivating fitness criteria for at least one generation of model units in a process referred to as Texture Ratcheting, as will be described in more detail below. This can be used to further enhance the effectiveness of the texturing process.

In one example, the model parameters may be determined based on quantified system data for a first time period, with this then being used to predict system behaviour for a subsequent second time period. The solution trajectory of the model unit can then be compared to quantified system data during the second time period allowing a fitness of the model unit to be ascertained.

The method can also include determining control variables representing controller inputs to the physical system and determining the solution trajectory in accordance with the control variable values. In this regard, the model parameters can be based at part on control variable values so that the calculation of the solution trajectory is automatically performed taking the control variables into account. A range of different control variable values can be tried allowing the process to determine the ability of control inputs to alter system behaviour. This can in turn be used to assess how well control solutions, such as a treatment program for a patient, may function, and allow an optimum control program to be developed.

The process can involve segmenting quantified system data to respective time period segments and determining respective model units for each time period segment. As previously mentioned, this can be used to establish an optimum model for each time period segment with these models being combined into a collective model to more accurately model system behaviour. Alternatively or additionally, the process can involve subdividing quantified system data into smaller subsets of types of quantified system data across the same time period segment, determining respective model units for each subset, establishing an optimal model for each subset, and then combining these models into a collective model to more accurately model system behaviour across this same time period segment. The time period segments can be of fixed intervals, but more typically are of variable length and correspond to certain aspects of system behaviour or external system control inputs. Thus for example, in a diabetic this could correspond to sleeping, early-morning waking or eating. It will therefore be appreciated that the segmentation of the quantified system could be performed solely on the basis of time, but more typically is performed on the basis of events that are relevant to system behaviour, such as changes in external variables, or the like.

The method typically includes selecting the combination of model units utilising an optimisation technique. Thus, a pool of candidate model units is established from model units that have been individually optimised so that they have respective optimised model parameters. Different combinations of model unit can then be selected from the pool and assessed in order to determine an optimum combination. This can be performed in any of a number of ways but this would typically involve selecting model units in accordance with fitness values, determining a combination fitness value for each candidate combination and then selecting the combination in accordance with the combination fitness value. Thus, this would allow the fitness of each of a number of combinations of model units to be ascertained and used to select particular combinations.

In one particular example, a plurality of circuits can be defined with each circuit including a plurality of Blocks. Each Block represents a population of model units typically undergoing some form of optimisation, including an evolutionary algorithm. The circuits are analogous to electrical circuits and include components in the form of Blocks, allowing various combinations of processes to be performed on model parameters or units, which represent signals being transferred between the Blocks, as will be described in more detail below. Thus, model units and/or model parameters can be transferred between the Blocks in accordance with circuit connections, with the circuit being used to select the optimum combination of model parameters and/or model units for the model and model parts embodied therein. Different circuit arrangements can be populated with similar model parts, allowing a range of different approaches to be used to determine optimum model parameters for given model parts.

Additionally, circuits can be populated with different models, allowing different combinations of models and model parts to be considered. Thus, a circuit representing a predefined sequence of Blocks could be replicated, with each of the Blocks then being populated with different model units, or different parts of models, with this being used to select a candidate combination.

In one example, a combination of model units is determined by generating a network including a number of nodes, associating parts of one or more models with the nodes and then for each node on a path through the network, determining at least one model unit using the parts of the model associated with the node and then optimising model parameters of the at least one model unit. A candidate model is then constructed from the model units and model parameters. In this particular case, multiple paths through the network could then be considered, with each path corresponding to a different combination of parts of models and hence a different candidate combination.

In one particular preferred example, a plurality of different circuits are produced each of which includes a particular combination of Blocks. Each of these circuits is then used to traverse the network along a different path, so that each different type of circuit is populated with different parts of models depending on the path taken, and in particular the nodes traversed. Thus, at each node in the network a Block of the circuit is populated with parts of a model associated with the node, with this being repeated at each node until the Blocks of the circuit are completely populated. Following, or during this process, model parameters can be optimised, and a particular combination of model parameters and model parts being established based on the circuit connections. Thus as each of the plurality of circuits is transferred along a respective pathway in the network, it is populated with model parts, allowing a respective fitness to be determined, representing the fitness of the circuit for the given path. An optimum path and circuit combination can then be determined, for example using a technique such as a swarm optimisation technique that is broadly analogous to ant colony optimisation (albeit that the "food reward" is typically not located at a specific node in the network, but is generated across the network through appropriate combinations of paths traversed by the agents ("ants") and the particular circuits carried by those individual agents), or the like, as will be described in more detail below.

This process therefore operates to simultaneously optimise not only the individual model parts used, but also how these are combined in circuits, as well as the optimum model parameters that should be used. This therefore provides for multi-dimensional optimisation allowing for an optimum collective model to be established in a computational less expensive process than can be achieved using traditional techniques.

The above described processes can be used to develop a system specific model which can then be used in developing a control program including one or more control variable values indicative of a control inputs to the system to modify system behaviour in a desirable manner, or alternatively deriving system data that cannot be physical measured. This can in turn be used to determine a scenario or likelihood of system behaviour resulting in a failure. In this regard, the term "failure" will be understood to refer to any situation in which the system is behaving in an undesirable manner, including but not limited to the failure by the system to achieve or maintain a necessary process (e.g. homeostasis); dysfunction; malfunction or severe adverse event.

Determining a failure can involve comparing at least one of system data and system behaviour to defined limits and determining a scenario or likelihood of failure in accordance with results of the comparison. In one particular example, this involves determining a selected model parameter corresponding to system data that cannot be directly measured or directly manipulated, comparing the selected model parameter to a respective operating range and in response to the selected model parameter falling outside the respective range, determining a control input to achieve at least one of preventing the selected model parameter falling outside the respective range or else restoring the model parameter back to within the range. Thus in the event that the solution trajectories predict that model parameters corresponding to aspects of operation of the system or behaviour of the system will fall outside defined ranges, this can be used to predict a system failure or scenario or likelihood of system failure, in turn allowing actions to be taken to mitigate the situation.

In one example this process is performed using a modular system including a Model Selector module for selecting at least part of the model, an Identifier module for identifying the combination of model units and a control module that uses the combination model units to determine the control program. In this above mentioned example, at each node in the network, the Identifier module requests part of a model from the Model Selector.

The method can also include controlling the physical system at least partially in control with the control program, which could be achieved using a variety of different techniques, depending on the nature of the physical system. For example, if the physical system is a patient, this could include administering medication, either in a manual or automated fashion, for example using an automated dosing system. Additionally and/or alternatively, the control program could be in the form of instructions that are presented to the patient, for example instructing them to eat or not eat certain foods, take medication, exercise, or the like. In contrast, in the case of an aircraft or missile, this would typically be in the form of electronic instructions provided to an onboard controller, such as an auto-pilot or the like.

Additionally, the method can include defining meta-model units representing different combinations of model units; and, optimising the meta-model units to determine a combination of model units and this meta-optimisation process will be described in more detail below.

In the control process outlined above, the method typically includes determining a plurality of sets of solution trajectories and then assessing each set by determining numbers of solution trajectories that move towards targets; move towards targets and avoid anti-targets; and avoid anti-targets. Following this, the one or more of the plurality of solution trajectories are selected by selecting at least one set of solution trajectories in accordance with the determined numbers. Thus, this avoids the need for every solution trajectory to move towards targets and avoid anti-targets, but instead allows a set of solution trajectories to be selected, which overall perform better than other sets. Thus, typically a majority of solution trajectories within the set perform acceptably, in which case the controller will attempt to steer the system behaviour towards the more successful solution trajectories within the set. This provides a mechanism for selecting a set of solution trajectories that will be the best solution possible, accepting that in some situations, it will not be possible to obtain an optimal outcome. This helps ensure the control process does not stall simply because a best outcome cannot be obtained.

As previously mentioned, the targets represent sets in state space corresponding to one or more desired physical system outcomes, whilst the anti-targets represent sets in state space corresponding to physically lethal, dangerous, unstable or uncontrollable conditions, as will be described in more detail below.

The method typically includes determining one or more desirable states and then selecting one or more solution trajectories passing through one more desirable states. The desirable states represent sets in state space corresponding with physically or technically advantageous conditions, and can for example correspond to stabilisation of a patient before any attempt is made to treat the patient.

The method typically includes determining and/or manipulating solution trajectories using one or more Lyapunov functions and in one example involves using gradient descent criteria to impose control of solution trajectories. In this example, the gradient descent criteria are used to determine control variable values leading to solution trajectories that move towards targets and/or avoid anti-targets.

The method also typically includes determining and/or manipulating solution trajectories using uncertainty variables representing uncertainties including at least one of noise, external perturbations and unknown values for state variables, parameters or dynamical structures. Thus, this takes into account as yet unknown factors that could adversely impact on the control of system behaviour. By taking this account, this allows solution trajectories to be identified that can most easily accommodate undesired effects. In this example, the method can include using a game against Nature to determine the effect of different uncertainties and selecting the one or more solution trajectories to mitigate the impact of the uncertainties, where "Nature" denotes an intelligent adversary playing against the desired control objectives.

In one example, the game against Nature is implemented by determining, for a range of uncertainty variable values, if candidate solution trajectories can be made to meet the gradient conditions associated with one or more Lyapunov functions and then selecting one or more solution trajectories from the candidate solution trajectories at least partially in accordance with the results of the determination. As part of this process, the gradient conditions associated with one or more Lyapunov functions are determined using the targets and anti-targets.

The method typically includes calculating control variable values to steer the solution trajectories towards a desired gradient direction and selecting candidate solution trajectories that meet the gradient conditions. Following this, uncertainty variable values are calculated that steer the candidate solution trajectories away from the desired gradient direction, with this being used to determine disrupted candidate trajectory solutions using the uncertainty variables. The disrupted candidate trajectory solutions are then reviewed to determining if the disrupted candidate trajectory solutions meet the gradient conditions and, if not, whether control variable values of the disrupted candidate trajectory solutions can be modified so that the disrupted candidate trajectory solutions do meet the gradient conditions. Thus, this assesses whether the solution trajectories can overcome or at least mitigate the effect of uncertainties, with resulting solution trajectories being selected from any disrupted candidate trajectories that still move towards targets and/or avoid anti-targets.

The above described control processes can be used to perform control of systems by determining a control program and then controlling the physical system using a controller that provides controller inputs to the system in accordance with the control variable values in the control program.

The system and method can also be used for diagnosing a system condition. In this instance, after obtaining quantified system data measured for the physical system, a plurality of models of the physical system are determined, each of which corresponds to a respective system condition. Each of these models is then optimised by forming at least one population of model units, calculating at least one solution trajectory, determining a fitness value based on the solution trajectory and selecting a combination of model units using the fitness values of each model unit. Once this has been done a model fitness value is determined for each collective model, with these being compared to select one of the plurality of models, the selected model being indicative of the system condition.

It will be appreciated that in this instance, if a system has an unknown condition, such as if a patient presents with an undiagnosed disease, a range of different models can be evaluated, each of which corresponds to a different condition. In this instance, the ability of the models to fit the behaviour of the system based on the current condition can be used to eliminate models that do not fit, and ultimately select one or mode models that provide a best fit, thereby providing, or assisting in providing a diagnosis.

Figure 2:
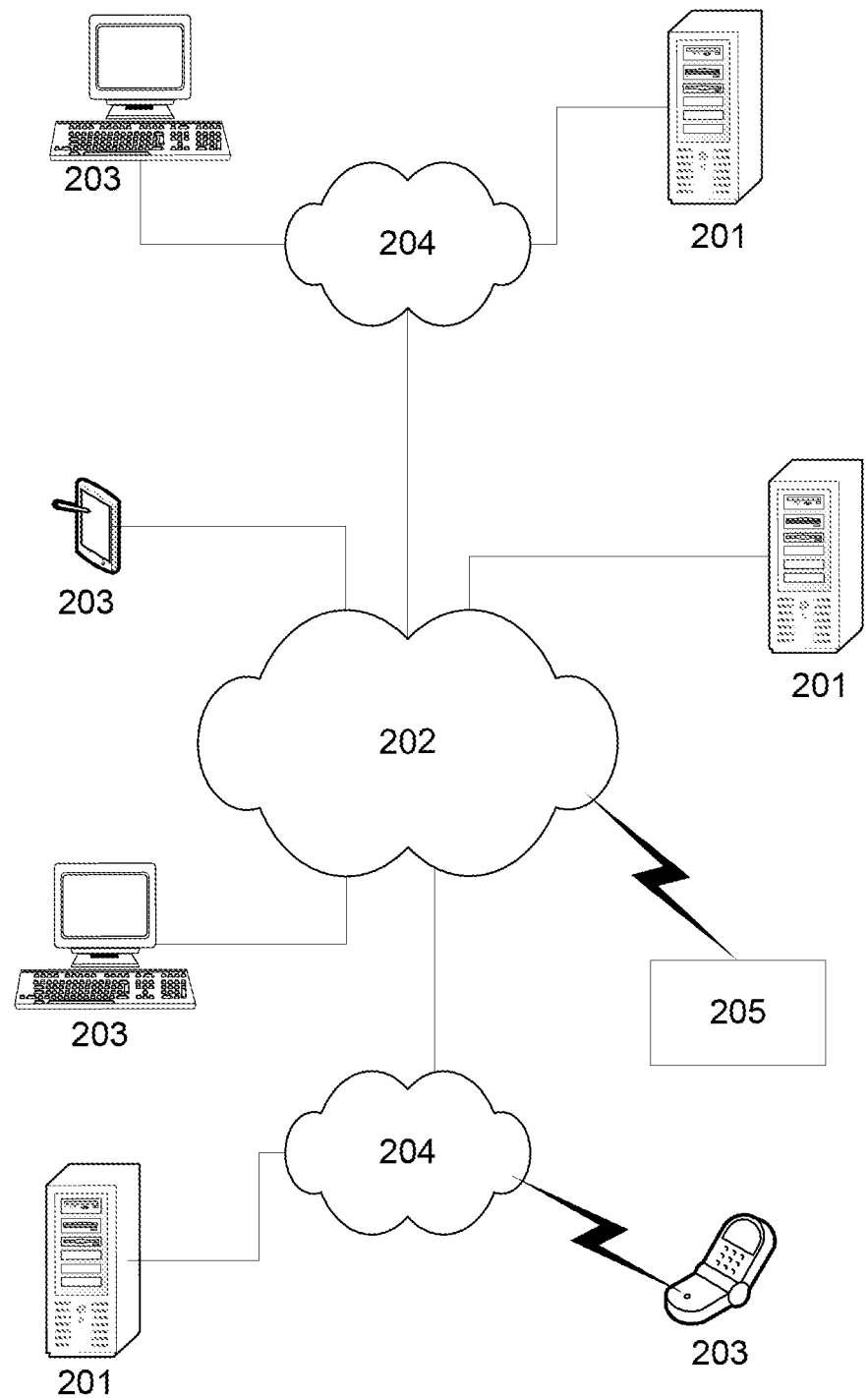
FIG. 2 is a schematic diagram of an example of a distributed computer architecture.

In one example, the process is performed by one or more electronic processing devices operating as part of a distributed architecture, an example of which will now be described with reference to FIG. 2.

In this example, a base station 201 is coupled via a communications network, such as the Internet 202, and/or a number of local area networks (LANs) 204, to a number of computer systems 203. It will be appreciated that the configuration of the networks 202, 204 are for the purpose of example only, and in practice the base station 201 and computer systems 203 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

A number of sensors 205 can also be coupled either directly to the networks 202, 204, the base stations 201 and/or to the computer systems 203, allowing data regarding physical systems to be collected. The sensors can be of any suitable form, and will typically vary depending on the nature of the physical system. For example, the sensors 205 could include medical monitoring systems, MM, X-ray or other similar equipment when the system includes a patient. It will be appreciated however that other sensors could be used for different types of physical system, such as position/motion sensors, temperature/humidity sensors, radar, sonar, or the like.

In one example, the base station 201 includes one or more processing systems 210 coupled to one or more databases 211. The base station 201 is adapted to be used in modelling behaviour of a physical system, with the computer systems 203 being adapted to communicate with the base station 201 to allow the process to be controlled.

Whilst the base station 201 is a shown as a single entity, it will be appreciated that the base station 201 can be distributed over a number of geographically separate locations, for example by using processing systems 210 and/or databases 211 that are provided as part of a cloud based environment. However, the above described arrangement is not essential and other suitable configurations could be used.

An example of a suitable processing system 210 is shown in FIG. 3. In this example, the processing system 210 includes at least one microprocessor 300, a memory 301, an optional input/output device 302, such as a keyboard, sensor and/or display, and an external interface 303, interconnected via a bus 304 as shown. In this example the external interface 303 can be utilised for connecting the processing system 210 to peripheral devices, such as the communications networks 202, 204, databases 211, other storage devices, other sensors, or the like. Although a single external interface 303 is shown, this is for the purpose of example only, and in practice multiple interfaces using various methods (eg. Ethernet, serial, USB, wireless or the like) may be provided.

In use, the microprocessor 300 executes instructions in the form of applications software stored in the memory 301 to allow at least part of the modelling process to be performed, as well as to perform any other required processes, such as communicating with other processing systems 210 or the computer systems 203. The applications software may include one or more software modules, and may be executed in a suitable execution environment, such as an operating system environment, or the like.

Accordingly, it will be appreciated that the processing system 210 may be formed from any suitable processing system, such as a suitably programmed computer system, PC, web server, network server, or the like. In one particular example, the processing system 210 is a server based system which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement.

As shown in FIG. 4, in one example, the computer system 203 includes at least one microprocessor 400, a memory 401, an input/output device 402, such as a keyboard, sensor inputs, display and/or some other human-machine or machine-machine interface, and an external interface 403, interconnected via a bus 404 as shown. In this example the external interface 403 can be utilised for connecting the computer system 203 to peripheral devices, such as the communications networks 202, 204, databases 211, other storage devices, or the like. Although a single external interface 403 is shown, this is for the purpose of example only, and in practice multiple interfaces using various methods (eg. Ethernet, serial, USB, wireless or the like) may be provided.

In use, the microprocessor 400 executes instructions in the form of applications software stored in the memory 401 to allow communication with the base station 201, for example to allow data to be supplied thereto and allowing models or control programs to be received therefrom.

Accordingly, it will be appreciated that the computer systems 203 may be formed from any suitable processing system, such as a suitably programmed PC, Internet terminal, lap-top, hand-held PC, smart phone, PDA, wearable computing platform, medical implant, web server, or the like. Thus, in one example, the processing system 210 is a standard processing system such as a 32-bit or 64-bit Intel Architecture based processing system, which executes software applications stored on volatile or non-volatile (e.g., hard disk) storage, although this is not essential. However, it will also be understood that the computer systems 203 can be any electronic processing device such as a microprocessor, microchip processor, logic gate configuration, firmware optionally associated with implementing logic such as an FPGA (Field Programmable Gate Array), or any other electronic device, system or arrangement.

For example, the computer system 203 could be part of a medical device for monitoring a patient and then providing control variable values, for example to control administration of medication, provide guidance for lifestyle changes, such as diet or exercise, or the like; or a medication control law, administering actual doses of drug to the patient. Alternatively it could be part of an onboard flight-control system in an autonomous or networked Unmanned Aerial Vehicle (UAV), modelling vehicle system dynamics from ongoing sensor data, monitoring changes in parameter values in engine performance and aerodynamics and modifying the flight control law accordingly.

Examples of the modelling process will now be described in further detail. For the purpose of these examples, it is assumed that the process is performed by a plurality of processing systems 210 operating in parallel, for example as part of a massively parallel architecture. The processing systems 210 maintain a database of pre-existing models, and interact with the computer systems 203 allowing quantified system data to be determined and allowing a model to be developed. To achieve this the processing systems 210 typically execute applications software for performing the modelling, including selection of models, determination of model parameters or the like, as well as communicating with the computer system 203 via a communications network, or the like, depending on the particular network infrastructure available.

It will also be assumed that the user interacts with the processing system 210 via a GUI (Graphical User Interface), or the like presented on the computer system 203, with actions performed by the computer system 203 are performed by the processor 401 in accordance with instructions stored as applications software in the memory 402 and/or input commands received from a user via the I/O device 403.

However, it will be appreciated that the above described configuration assumed for the purpose of the following examples is not essential, and numerous other configurations may be used. It will also be appreciated that the partitioning of functionality between the computer systems 203, and the base station 201 may vary, depending on the particular implementation.

Figure 5A:
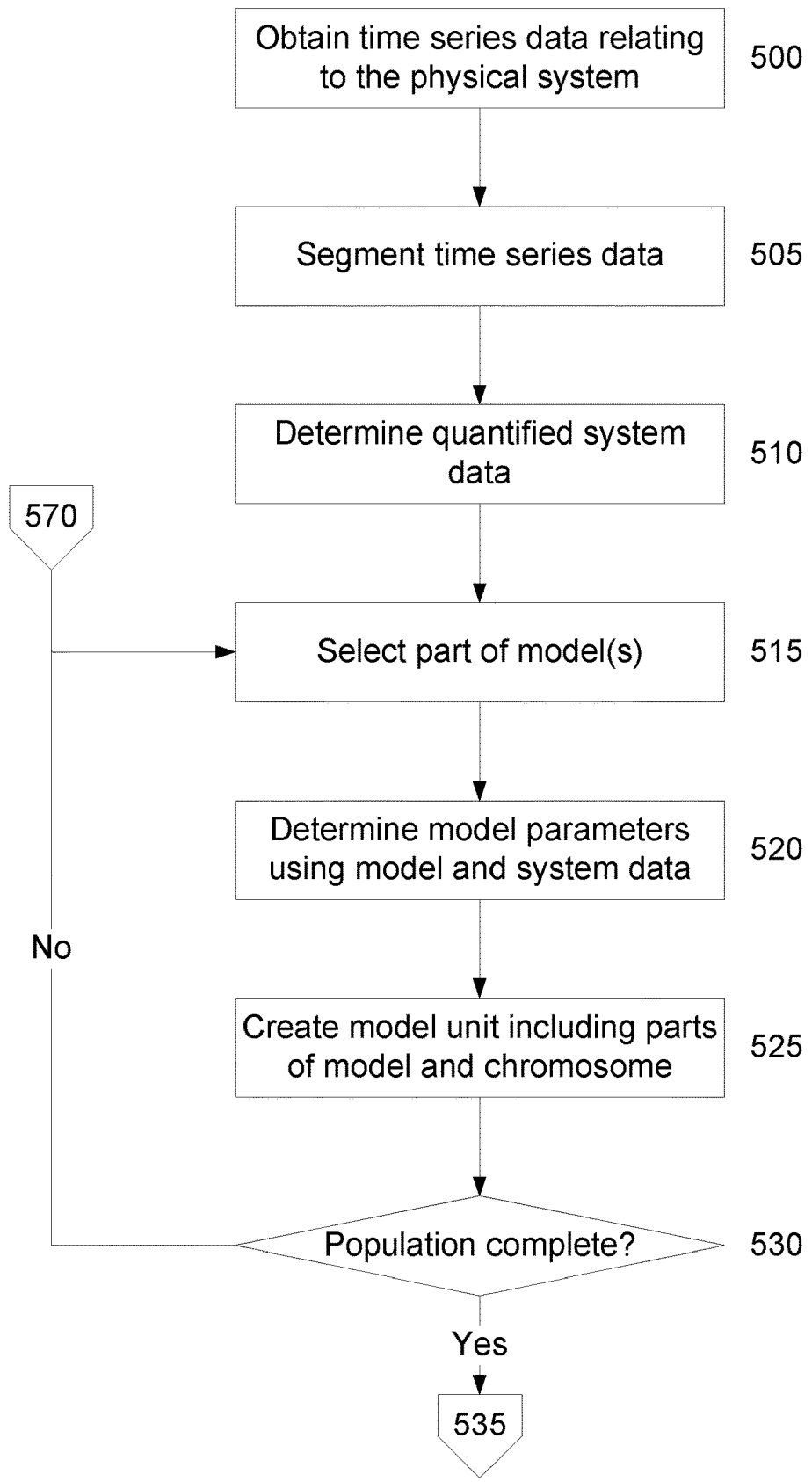
FIGS. 5A and 5B are a flow chart of a first specific example of a method for modelling system behaviour of a physical system.
Figure 5B:
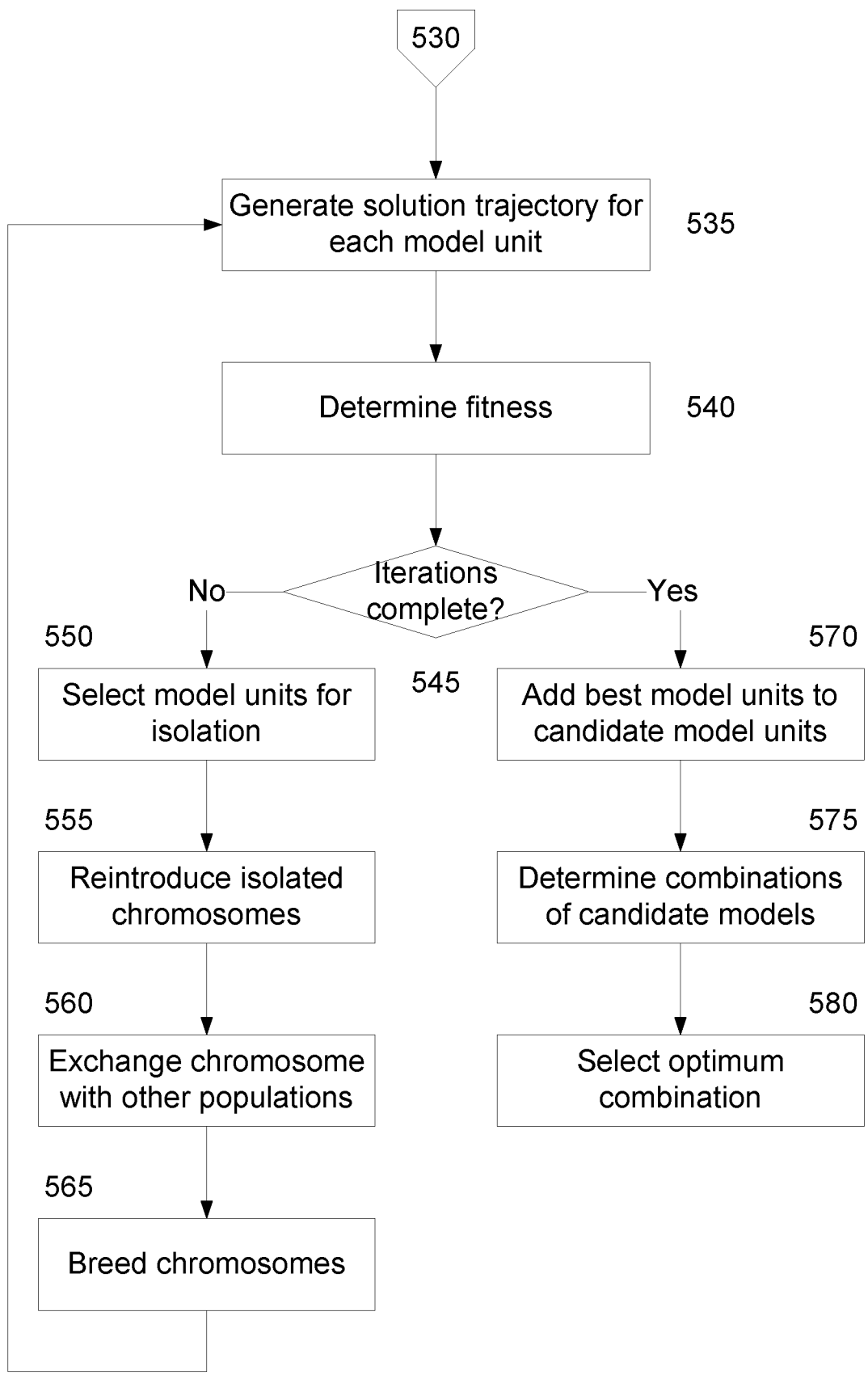

An example process for modelling the physical system will now be described in more detail with reference to FIGS. 5A and 5B.

In this example, at step 500 the processing system 210 obtains time series data relating to the physical system. The time series data will typically include details of measured attributes of the physical system, as well as optional environmental attributes that have an impact on the physical system, such as inputs, outputs, constraints or the like.

At step 505 the processing system 210 operates to segment the time series data into a number of different time period segments and may further subdivide the time series data for a specified time period segment to enable component parts of complex behaviour to be modelled individually. The time period segments can be ascertained in any one of a number of ways but typically this will involve identifying particular events within or associated with the time series data that could lead to different system behaviours. This may include for example identifying step wise changes in attributes and/or environmental inputs and using these as points of segmentation, or else choosing points of segmentation on either side of such changes, to study the consequent changes in system behaviour induced by these events. The purpose of this is to attempt to identify different time period segments where the system behaviour could be operating in accordance with a different regime and therefore may require a different model; or else to identify different time period segments where system is expected to have the same model applicable but with different aspects exhibited; or else to identify different time period segments where the system exhibits sufficiently different behaviour, such that one or more segments are used for modelling and other segments are used for testing the validity of such models.

At step 510, the processing system 210 determines quantified system data from the time series data. In this regard, it will be appreciated that the time series data may include physical values corresponding to readings from sensors or the like, and that these may require interpretation in order to define a meaningful system datum. It will also be appreciated however that this may not be required and will depend largely on the implementation of the invention, the nature of the physical system and any sensors used for collecting data about the system behaviour.

The above described steps can be performed using a single processing system to establish the system data. Following this, multiple processing systems 210 are typically used in parallel to establish and optimise model units. This can include model units within a single population, but more typically includes multiple different populations, with model units in each population being based on at least partially related models, and each processing system processing a respective population.

In this instance, for each model unit a respective processing system 210 selects one or more parts of a model at step 515. This may involve selecting one or more model equations from one or more models stored in a model database. Initial model parameters are then determined for the model equations using the system data at step 520. In this regard, it will be appreciated that the model parameters will typically be coefficients for the model equations that attempt to embody the system behaviour, plus initial conditions for those equations. The model parameters are typically coarsely defined based on the system data, before being refined using the following generational optimisation process. In any event, following determination of the model parameters, the processing systems 210 create a model unit including the parts of the model and a chromosome which embodies the model parameters at step 525.

At step 530 it is determined if sufficient model units have been developed to form a population of model units and if not, the process returns to step 515, allowing further model unit to be created. It will be appreciated that steps 515 to 530 are typically repeated by multiple processing systems 210, each of which establishes a respective population, although this is not essential.

For each population, at step 535 the processing system 210 generates at least one solution trajectory for each model unit and then operates to determine an associated fitness of this solution trajectory at step 540. The fitness can be determined in any one of the number of ways, but typically this process involves utilising a textured fitness algorithm that examines the solution trajectory against one or more geometric sets in state space. The fitness will typically be determined at least partially based on convergence between the solution trajectory and system behaviour, so that a solution trajectory that more accurately models system behaviour will be given a higher fitness. This process will be described in more detail below.

At step 545, it is determined if all iterations are complete. This can be determined based on a variety of considerations, such as the number of iterations performed, the current best and/or worst fitness, the degree of fitness improvement over previous iterations, or the like, as will be appreciated by persons skilled in the art.

If the iterations are not complete, at step 550, a number of model units may be selected for isolation, depending on the preferred implementation. This is typically performed at least partially based on the fitness value. These can be removed from, or copied from the current population and are set aside in a separate population that is not accessed for breeding by the current population. At step 555 previously isolated model units can be reintroduced, based on selection criteria, as will be described in more detail below. At step 560 chromosomes and/or model units can be selectively exchanged with other populations, assuming a suitable degree of compatibility between the models used. These processes are performed to maximise the degree of variability within the population within any one generation, thereby reducing the likelihood of model units stagnating or dying out.

At step 565, the chromosomes of the model units are bred in order to create modified model units, and in particular modified chromosomes containing new combinations of model parameters. This can be achieved through a variety of breeding techniques, including mutation, cross-over or the like. The breeding is typically performed at least in part on the basis of fitness of the model unit solution trajectories, so that for example chromosomes with a low fitness will be overwritten, whilst chromosomes with a higher fitness can preferentially breed, so that aspects of these are more extensively distributed throughout the model units within the population.

Following this, further reiterations are performed with solution trajectories being calculated at step 535 and this process being repeated.

Once all iterations are complete, model units having an acceptable fitness are added to a pool of candidate model units at step 570. Thus, it will be appreciated that the pool of candidates can be established from a number of different populations, and will therefore include model units formed from a number of different model parts, each having associated optimised model parameters.

Combinations of candidate model units can then be determined at step 575, with this being assessed to select the best candidate model unit at step 580. It will be appreciated that selection of a best combination can be performed using a further optimisation technique. This could be achieved using a similar process to that described above, in which different combinations of model units represent meta-model units, which are then optimised in a meta-optimisation process similar to that described above.

Another example for determining a model will now be described with reference to FIG. 6.

In this example, at step 600 the processing system 210 determines a network including a number of nodes. This can be achieved by retrieving the network from a repository of predetermined networks, for example based on the nature of the physical system under consideration, or alternatively generating the network automatically and/or in accordance with user input commands.

At step 605 a circuit including Blocks is constructed by the processing system 210. Examples of these circuits will described in more detail below, but typically, each circuit includes a number of Blocks interconnected in respective sequences, the Blocks representing a population of model units.

At step 610, for a next circuit, the processing system selects a next network node on a path. Each network node has a model part associated with it, so that traversing a node on a path causes that model part to be integrated into the circuit, so each Block within the circuit is populated by at least part of a model. In one example, the model units are constructed utilising techniques similar to those described above with respect to steps 515 to steps 530, for each Block of the circuit, and it will be appreciated as part of this, that steps 500 to 510 would also be performed in order to determine initial model parameters.

At step 625, it is determined if the path is complete, and if not the process returns to step 610 to select a next node in the network. Thus, the circuit traverses the network until each Block has been completed with model units based on model parts from respective nodes.

Once this has been completed, at step 630 the model units are then optimised, for example by performing the steps 530 to 570, until optimised chromosome values are determined. At step 635, an overall fitness for the circuit and path combination can be determined, with this being used to select candidate models. In this regard, it will be appreciated that the results of this process represents a combination of model units, as determined from each of the nodes. This process can therefore be repeated over a number of different paths, to thereby represent different model unit combinations, with this also be repeated for different circuits.

As part of this process the path fitness for the circuit can be stored as part of the node and/or arc (the line joining two nodes in a network, otherwise called an "edge" in the literature). In the event of agent-based methods such as swarm optimisation techniques, ant colony optimisation or the like, being employed, this can be done using a "pheromone trail" or similar, marking the path through the network, the strength of the pheromone signal laid down being proportional to the path fitness for the circuit. Alternatively the path fitness for the circuit can be marked on a map of the network held by the agent carrying the circuit. Using any of the above methods, the path fitness for the circuit can be used to assess which nodes are more effective, which can be used in subsequent iterations when deciding the path through the network that should be traversed. During subsequent iterations, this allows the path traversed to be at least partially based on a path fitness of the nodes for that circuit, so that the path is optimised as more routes are traversed.

Alternatively, the model parameters can be optimised at each node, with this being repeated as the circuit traverses the network. The above two processes represent two different methods of traversing and evaluating paths in the network, namely node-by-node assessment and whole-path assessment. It should be apparent that these processes can be further combined, including performing whole-path assessment first to achieve a heuristic global optimum or near-optimum and then endeavouring to refine this in subsequent iterations using node-by-node assessment.

Thus, it will be appreciated that having a circuit traverse a number of nodes leads to a combination of model parts and associated model parameters, that can be assessed based on the path fitness, for their ability to accurately model the physical system. Having a number of different circuits, allows different model parameter combinations to be developed, with different paths representing different model part combinations. Thus, this allows a variety of combinations and associated model parameters to be assessed.

Additionally, the processing system 210 can use information regarding the fitness of particular path/circuit combinations to attempt to find a fitter path in subsequent iterations. In this regard, the path taken on subsequent iterations is influenced by the current path, for example using ant colony optimisation, or the like thereby allowing improved paths to be progressively developed.

Figure 6:
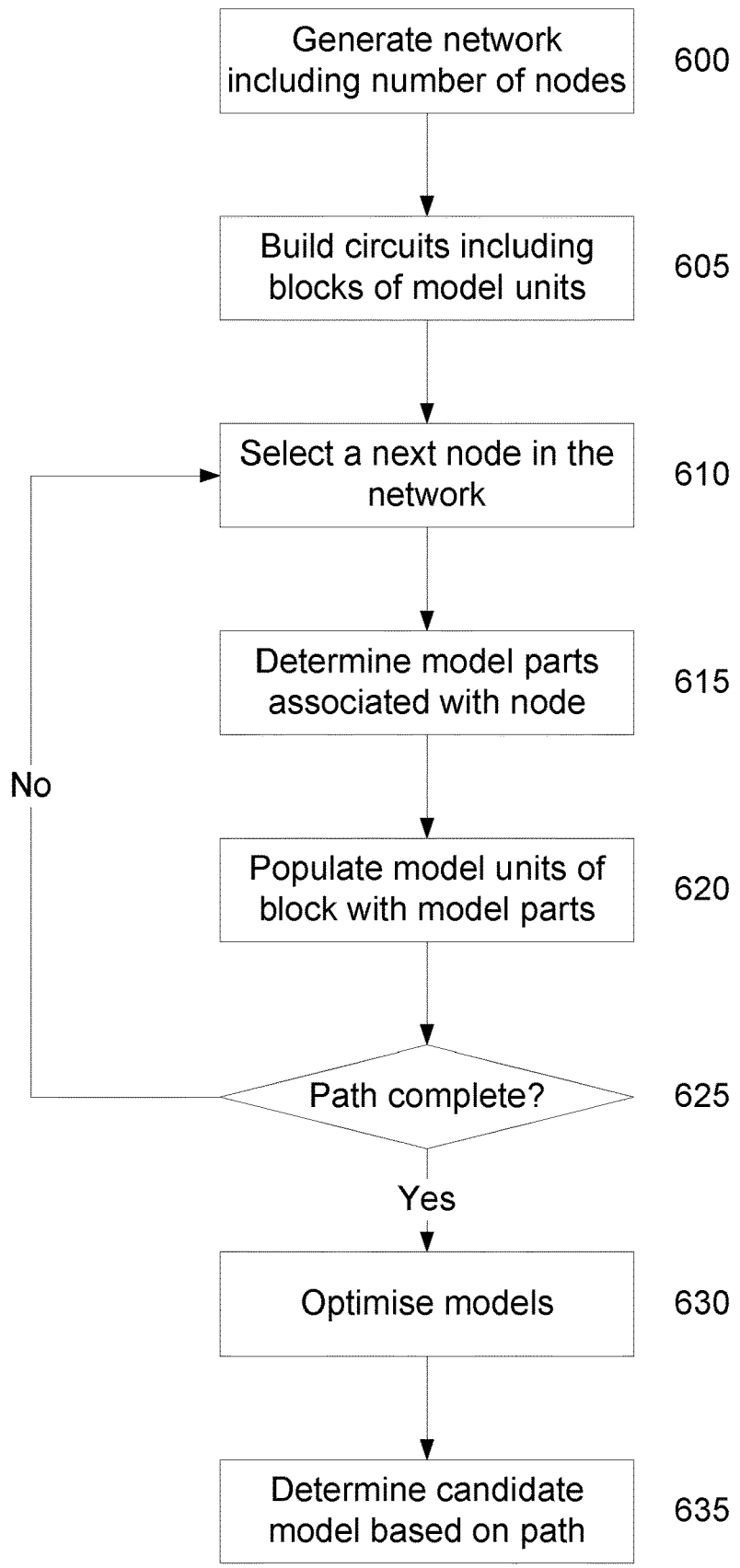
FIG. 6 is a flow chart of a second specific example of a method for modelling system behaviour of a physical system.

Thus, the process of FIG. 6, allows for the determination and optimisation of model combinations, as described for example in steps 575 and 580.

Figure 7A:
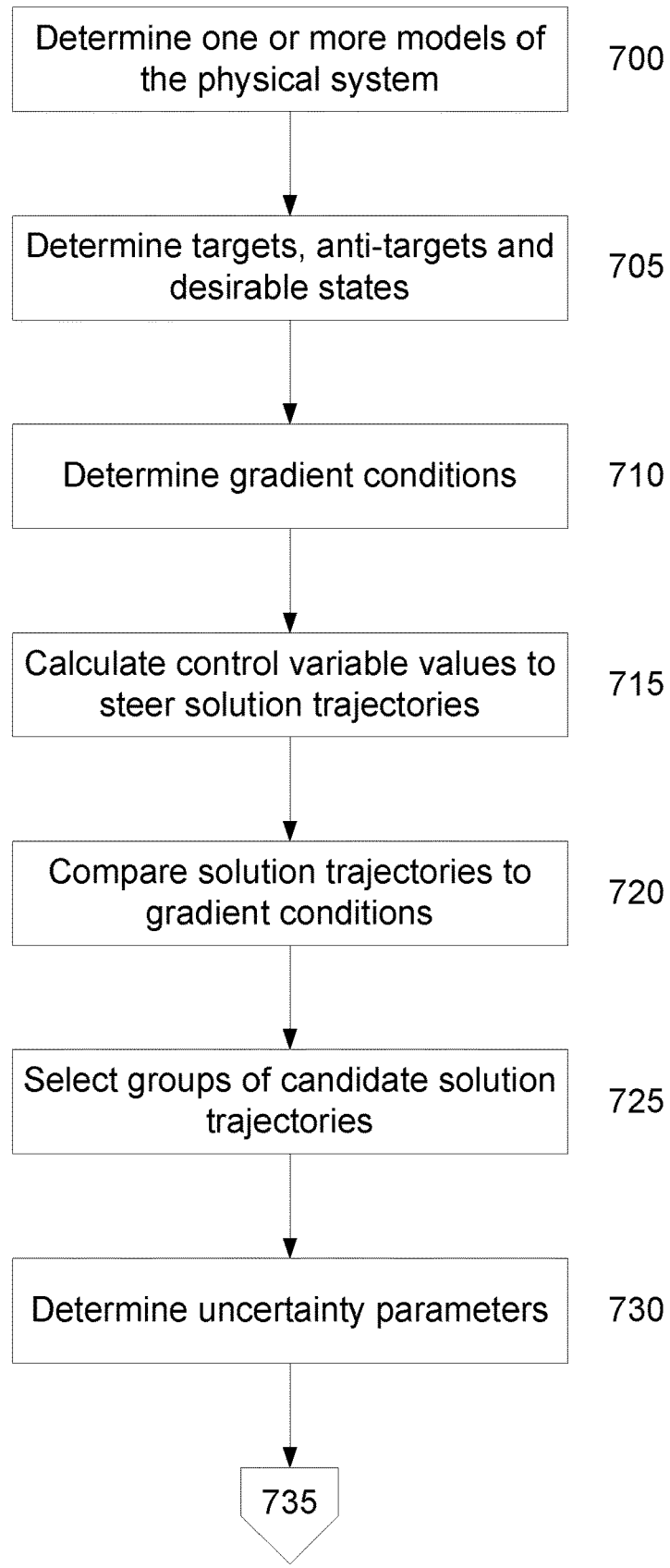
FIGS. 7A and 7B are a flow chart of a specific example of a method of determining a control program for controlling the system behaviour of a physical system.
Figure 7B:
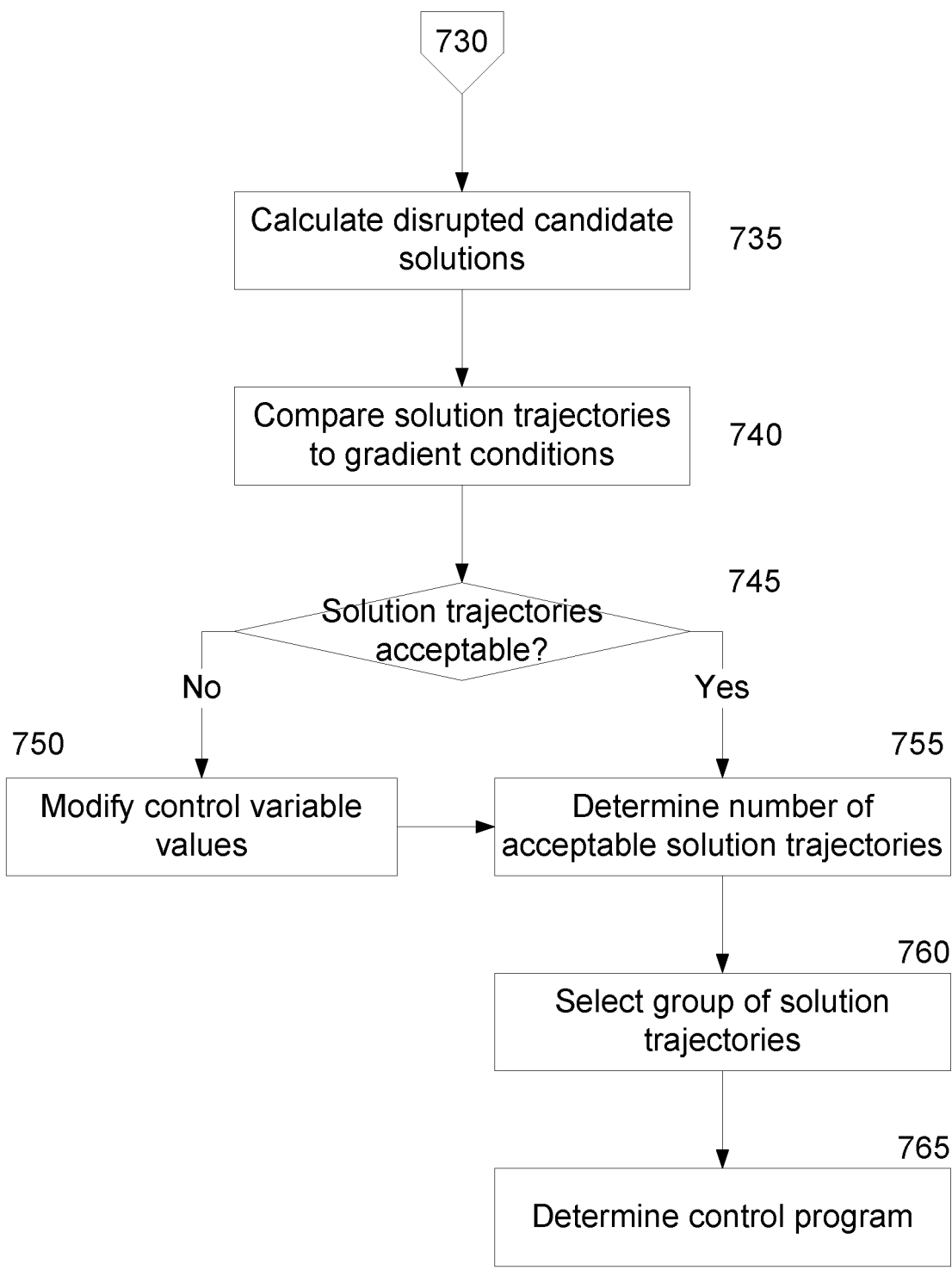

An example of a method for determining a control program for controlling the system behaviour of a physical system will now be described with reference to FIGS. 7A and 7B.

In this example, at step 700 one or more models of the physical system are determined, typically using the techniques outlined above. At step 705 one or more targets, anti-targets and desirable states are determined. These corresponding to regions in state space that represent excellent, adverse or desirable conditions or outcomes for the system behaviour, and would typically be determined by an operator of the system, optionally using defined targets etc. stored in a database or the like.

At step 710, the targets, anti-targets and desirable states are used to determine Lyapunov function gradient conditions, with this being used by the processing system 210 at step 715, to calculate control variable values to steer the solution trajectories in a desired gradient direction. The manner in which this is achieved will be described in more detail below.

At step 720, the solution trajectories are compared to the gradient conditions to select one or more sets of solution trajectories that are acceptable at step 725. This typically involves identifying solution trajectories that move towards targets whilst avoiding anti-targets and preferably passing through desirable states.

At step 730, uncertainty variables are determined, which typically correspond to a range of different conditions that may arise, for example due to noise, system uncertainty or the like. These may be determined in any one of a number of ways, such as based on example values for similar physical systems, based on comparison of models with measured behaviour, or the like. At step 735, the processing system 210 used the uncertainty variables to determine disrupted solution trajectories. This is performed using a game against Nature approach in which the uncertainty variables are used to attempt to steer the solution trajectories against the desired gradient direction of the Lyapunov function.

The disrupted solution trajectories are then compared to the gradient conditions at step 740 to determine if the disrupted candidate solution trajectories remain acceptable at step 745. If not, the process moves on to step 750 to determine if the control variables associated with the disrupted candidate solution trajectory can be altered so as to make the disrupted candidate solution trajectory acceptable. This process is performed to determine whether when the resulting control program is being used, the impact of noise or other adverse events can be accommodated by adjustment of the control variables, or whether the solution trajectory is simply unsuitable for use.

At step 755, the processing system 210 determines a number of acceptable solution trajectories in each of a number of different sets of solution trajectories, using this to select the best set at step 760. Thus, a number of different sets of related solution trajectories, for example those based on common models or model parts, are assessed. The set which contains the most solution trajectories that approach targets, whilst avoiding anti-targets and passing through desirable states, is then typically selected as a basis for the control program at step 765. Thus, this process selects the optimum group of solution trajectories using this as the basis for the control program.

The decision-making process at steps 755 and 760 is typically weighted by the relative undesirability or lethality of the one or more anti-targets or the relative desirability of the one or more targets, creating an ordered list of priorities ("priority list" or "preference ordering") to be achieved. Under circumstances where no such optimal group exists (i.e. a sufficiently-large set of solution trajectories cannot be found that both approaches the targets and avoids the anti-targets) and/or the desirability of the one or more targets, or the undesirability of the one or more anti-targets is of paramount importance, then the decision-making process uses this ordered list of priorities to select a compromise group of solution trajectories and uses this selection as a basis for the control program at step 765.

For instance, if the target corresponds with desirable conditions but the anti-target corresponds with absolute lethality, the processing system will typically select a group containing the most solution trajectories that avoid the anti-target and use this group as a basis for the control program at step 765, despite the fact some of these solution trajectories may then fail to approach the target. Conversely if the anti-target corresponds with adverse but survivable conditions but the target is associated with conditions essential for survival, the processing system will typically select a group containing the most solution trajectories that approach the target and use this group as a basis for the control program at step 765, despite the fact some of these solution trajectories may then also pass through the anti-target.

The above process of weighting targets and anti-targets, to establish a priority list for choosing a group as a basis for the control program at step 765, is similarly also applied to solution trajectories passing through desirable states and less-desirable states in state space, further refining that priority list.

A more in-depth specific example will now be described.

For the purpose of ease of illustration, the modelling and control methods will be referred to collectively as a modelling system, but it will be appreciated that this is not intended to be limiting.

The modelling system provides a mathematical architecture for artificial intelligence (AI) with at least analogous capabilities to neural networks in the hypothesis-forming stage, but with key capability advantages in the machine-intelligent processes of formulating hypotheses and acting upon them. Then in the Control stage this AI provides a robust method for generating nonlinear control laws that have:

A high confidence of being stable under uncertainty, under appropriate conditions;

An ability to map these conditions (regions of controllability/strong controllability) so as to be "aware" of confidence levels, and Machine-implementable methods for generating strategies to improve those control laws, to cope with or mitigate those uncertainties.

The modelling system can provide a number of key advantages over neural networks and examples of these will now be described.

In the formulation of hypotheses, neural networks, being inherently numerical, are notorious for the opacity of their hypothesis formulation process. They may extract patterns from data that are distinct from and irrelevant to the patterns that need to be extracted for the task at hand. This is dangerous for time- and mission-critical applications involving machine intelligence. In contrast, the modelling system's hypothesis formulation process is transparent and rapidly assessable by either a human or machine intelligence, using geometrical and algebraic structures rather than purely numerical processes.

In the assessment of uncertainty or ambiguity, the modelling system asserts that the uncertainty or ambiguity associated with one or more hypotheses can be as important as the hypotheses themselves. Consequently the spread of uncertainty across multiple strong and weak hypotheses is also expressed in a transparent fashion again, in stark contrast to a neural network, enabling interfacing with game-theoretic techniques to handle such uncertainties.

The modelling system allows for evolutionary recursion of structures for adaptive design. In this regard, sometimes algorithms produce the wrong answer because, at a structural level, they were designed to ask the wrong question. The modelling system typically employs multiple, stacked layers of structural information specifying the algorithm. These layers are each capable of independent evolution, so that failures to formulate good hypotheses at one layer can be used as a machine-implementable trigger to re-examine structural assumptions at a higher layer. As a result the modelling system provides for structurally-recursive evolutionary optimisation.

Alternatively, algorithms can provide an answer that is adequate but sub-optimal. Again, these algorithms are designed so that their hypothesis-generating structures can be modified using evolutionary mechanisms, in response to previously-generated hypotheses, to improve the next generation of hypotheses and associated context. By allowing alternative structures to evolve in response to how well they are interpreting and responding to the information being analysed, this ensures that the algorithm is able to re-design itself adaptively to handle the data being analysed.

The modelling system is constructed based on the hypothesis that biological ecosystems represent a unified, efficient computational architecture deployed across multiple scales, from the genetic scale through to multi-herd behaviour, including predator-prey dynamics, intra-species mating behaviour, migration across landscapes and speciation, including also the external, physical constraints imposed by divided landscapes.

This hypothesis goes well beyond the already-common recognition of the biological metaphors used in a Genetic Algorithm (GA), which cherry-picks the evolutionary processes at a chromosomal level, to introduce a broader evolutionary algorithm (EA) paradigm (which includes GA as a specific, limited instance).

Using this hypothesis to design algorithms built on novel EA that import other concepts from different branches of mathematics resulted in various artificial evolutionary optimisation architectures, ultimately resulting in sophisticated, novel forms of analogue cellular automata (an analogue counterpart to digital cellular automata) and multiple layers of structures that are both Turing-complete and evolutionary.

The modelling system demonstrates the construction of various forms of such evolutionary optimisation architectures and then puts these various forms to work, primarily in machine-intelligent algorithms for Identification of complex systems from noise-polluted partial information. (Alternative, non-Identification tasks that they can be used for are subsequently introduced.) These forms are then exploited in a larger machine-intelligent algorithmic architecture for controlling complex systems in the presence of noise-polluted data and significant dynamic uncertainty.

A specific example of the modelling system will now be described with reference to FIG. 8A, which shows a modular implementation. In this regard, the modules include a Model Selector M, a Model Identifier I and a Controller C, having sub-modules implementing respective algorithms, including Game against Nature (GaN) algorithms $C_{GaN}$, Model Reference Adaptive Control (MRAC) algorithms $C_{MRAC}$, single-objective Controller algorithms $C_S$ and Identification-related Controller algorithms $C_I$.

Given the existence of poorly-understood dynamical systems that need to be controlled using partial information, the modelling system consists of a novel evolutionary method of achieving nonlinear Identification, a term denoting computational reconstruction of system dynamics, typically based on noise-polluted partial information in the form of available time-series measurements of some variables) and machine-intelligent Control, a term denoting the use of mathematical algorithms to generate a sequence of modifications of the system, typically by manipulating one or more control variables, that cause the system to exhibit desired behaviour.

The mathematical sequence of modifications of the system, typically generated in response to time-series sensor measurements of ongoing system behaviour, is referred to as the control program, control strategy or control law (these terms are interchangeable); the algorithm that generates it is called the Controller.

Typically in the literature, a dynamical system for which there is only partial information uses an "Observer", i.e. a method of predicting the values of state variables that cannot be directly measured (the internal states of the system). Examples include the Luenberger Observer, the Kalman Filter and the Extended Kalman Filter.

These processes typically involve explicit "Model" selection, for instance choosing a set of ordinary differential equations (ODEs), difference equations (DEs), stochastic differential equations (SDEs), partial differential equations (PDEs) or fractional-order differential modelling to describe the system. (For the purposes of this specification, an ODE format is assumed, as it is the easiest to understand for exposition; extension and conversion to the other forms of dynamical modelling should be apparent to the reader.)

Identification is then performed to construct the Observer. The Observer then informs the choices made by the Controller to decide the control program.

The modelling system enjoys significant capability advantages over status quo technologies, in that it is able to achieve Identification of highly nonlinear, complex dynamical systems that cannot be linearised, including under conditions of significant ongoing dynamic uncertainty. Such dynamic uncertainty typically includes inherent and exogenous uncertainties. Inherent uncertainties typically arise when the system's dynamical structure is known but insufficient information is available to determine the system dynamics uniquely (they are said to be underdetermined); and/or when internal dynamic uncertainties exist that are finite (with known bounds) but of poorly-known or unknown structure, again preventing unique prediction of system dynamics. Exogenous uncertainties typically include uncertainties that are imposed externally on the system dynamics.

Typically Identification involves the complete or partial reconstruction of one or more Models, such that one or more sets of numbers, are generated, such that the Model dynamics incorporating these numbers tracks the observed behaviour of an underlying dynamical system to within a specified error or accuracy. The sets of numbers typically including at least one of: Parameters, Initial conditions of the dynamical system, and/or Constraints on dynamical behaviour, parameter values or available controller variables, Typically Identification in the Invention is performed using an "Evolving Identifier", that uses a "φ-Textured Evolutionary Algorithm" (φ-TEA) and "Circuits" constructed therefrom. The Identifier typically includes at least one population of chromosomes carrying encoded information regarding the Model, to be optimised using evolutionary processes, such that the Model behaviour using this information tracks the observed behaviour of an underlying dynamical system to within a specified error or accuracy, and/or until some other performance criterion is fulfilled.

The evolutionary optimisation of this population of chromosomes is performed using at least one of φ-Textured Evolutionary Algorithm(s) (φ-TEA), that uses trajectory behaviour and specified sets in state space to "texture" evolutionary Fitness, and/or at least one Modified Genetic Algorithm (MGA), defined in more detail below.

Optimisation can also use "circuits", comprised of wires transmitting sets of chromosomes, to and from one or more "Blocks", each Block typically embodying the processing of one or more populations of φ-TEA under specified conditions and/or recursive meta-optimising structures, that optimise the performance of one or more φ-TEA, MGA, Blocks, Circuits and/or other aspects of the Evolving Identifier. In the case of meta-optimising structures, typically this is done by encoding this information into a chromosome format (a "meta-chromosome") and optimising such meta-chromosomes.

Typical criteria for such optimisation include factors such as processing time; computational resources required for processing the Identification; Identification accuracy; or Maximum complexity of the system or model that can be Identified. Typically this optimisation is again done through the use of φ-TEA, MGA, Blocks and Circuits, typically performed in a distinct layer (the Meta-Optimising Layer).

One benefit of the modelling system is that under conditions where a conventional unique Observer does not exist, or else exists but is unreliable or undesirable (e.g. a common Observer, the Extended Kalman Filter, relies on linearisation of a nonlinear system, leading to dubious assumptions when studying a highly-nonlinear system), the modelling system replaces the use of a single Observer with a set of candidate solution trajectories for the system that encloses the poorly-known system dynamics within a bounded envelope, creating a volume in state space. For the purpose of explanation this bounded envelope and its enclosed volume will be referred to as the system's "dynamic envelope". It should be apparent that calculating the dynamic envelope typically includes estimating, using a finite number of trajectories, what differential game theory literature calls the "reachable set" of the dynamical system over time.

This concept of a "set of trajectories enclosing a volume" while passing through state space could be implemented in a number of different ways, such as by using convex hulls, constructing polytopes, or the like. Other analogous geometrical methods in the literature can alternatively be used.

When using convex hulls, the process typically includes, at any moment in time, drawing a convex hull around the positions occupied by trajectories in space and calling this the "enclosed area" at that moment. The enclosed volume is then the union of all such enclosed areas over time. Alternatively, this can involve constructing local neighbourhoods around each trajectory of some specified radius (think of a cylinder enclosing each trajectory) and then constructing a convex hull around the positions in space occupied by these neighbourhoods at any given moment, to form the enclosed area and then the enclosed volume is the union of all such enclosed areas over time.

In the case of constructing polytopes, polytopes are determined whose facets are external to, or on the external sides of, the outermost trajectories at any given moment, such that all the trajectories are enclosed within the polytope. These polytopes are typically constructed using either a linear combination of the linearised models or from the combination of exterior tangent planes derived at each polytopic point. Then the enclosed volume is constructed from the interiors of such polytopes over time. Alternatively, the polytopes can be constructed around local neighbourhoods surrounding each trajectory.

The above techniques can be extended to include the instance where the set of solution trajectories bifurcates into two or more subsets of trajectories flowing through state space, so that the smaller multiple volumes enclosed by these bifurcated subsets are analysed rather than simply a single unwieldy volume. Typically the criterion for deciding whether or not to adopt this further method of analysing volumes of multiple subsets is where solution trajectories flowing through state space congregate into two or more subsets separated by large regions of empty space, suggesting that the dynamic envelope should ignore these empty regions.

When the dynamic envelope is used to predict system behaviour, this is referred to as a "Dynamic Envelope Observer". Typically only a subset of the dynamic envelope is physically plausible, due to real-world constraints imposed upon the system, and/or the requirement for compliance of the Observer with additional data sets, e.g. additional history of the system, not used in the Identification process, with which the Observer must be consistent. Consequently the implausible elements are typically discarded, leaving a "reduced dynamic envelope" as the relevant bounded envelope upon the system dynamics and a "Reduced Dynamic Envelope Observer" as the mechanism that then predicts system behaviour from this envelope. If no such constraints exist, then the reduced dynamic envelope is identical to the dynamical envelope and the Reduced Dynamic Envelope Observer is simply the Dynamic Envelope Observer.

Further analysis can be performed using Lyapunov functions, and/or differential game theory to manipulate this reduced dynamic envelope, with the underlying system dynamics being manipulated despite these uncertainties. Note that this approach is distinct from the usual method of handling persistent uncertainties, namely statistical analysis (e.g. Bayesian analysis, particle filters, stochastic control).

Under conditions where the information set, underlying dynamics and computational resources allow it, statistical methods (including Bayesian analysis and derived techniques, such as particle filters) may be overlaid onto the dynamic envelope to apply probabilistic weights to various candidate trajectories, weighting the manipulation of the reduced dynamic envelope as will be described later with respect to the Game against Nature.

Machine-intelligent adaptive control of such systems can be performed including under conditions of significant ongoing dynamic uncertainty. The machine-intelligent algorithms typically employ methods from differential game theory, including the Game against Nature, where a hypothetical intelligent adversary ('Nature') is postulated. In this regard, game theory typically designs strategies by postulating the existence of one or more 'Players', synonymous with the system being intelligently manipulated in cooperation or conflict. In this specification, where needed the desired Controller will be associated with 'the first Player' or 'Player One', while Nature will be designated 'the second Player' or 'Player Two', with corresponding subscripts.

Ongoing refinement of algorithm components can be performed including of the model(s) selected and used to describe the system dynamics; the algorithms used to perform the analysis of the system dynamics, most obviously for model selection and the system Identification; and the controller algorithm. This can be performed either to optimise the internal performance of the machine, or else to improve the machine's ability to cope with one or more external threat(s) or impediment(s).

Figure 8A:
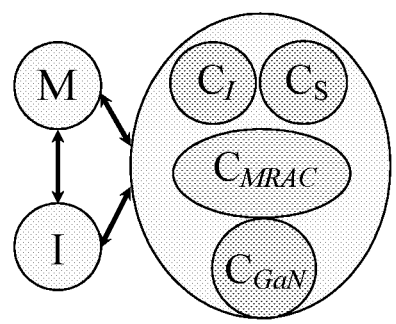
FIG. 8A is a schematic diagram of an example of a modular modelling system.

As previously mentioned, the basic form of the modelling system, shown in FIG. 8A, consists of three algorithm modules including the Model Selector M, the Identifier I, which constructs the Observer, including a Reduced Dynamic Envelope Observer and the Controller C. The Controller typically employs the Observer, including a Reduced Dynamic Envelope Observer, to generate a control program.

The modules of the modelling system can be combined to operate either in parallel (so-called 'dual control'), with the Model Selector and Identifier selecting and refining the model choice and associated Observer simultaneous to the Controller steering the system, or else, sequentially, including with the Controller operating after the other two modules (so a candidate model is chosen and Identified by data-mining historical time-series, generating candidate parameter values, producing an Observer; then the Controller is brought online to steer this system to a desired state, then the cycle repeats, refining the model choice and associated parameter estimates and hence the Observer; then the Controller is reactivated to steer the system to another desired state, . . . etc.); or else one or more of these modules can be used individually as stand-alone devices (for instance, where Identification of a known medical condition is required, enabling diagnosis of the stage of that condition present in a human patient, without requiring the Controller or the Model Selector; or where a complete model of a dynamical system is already known, but requires the Controller to manipulate it).

Typically the Controller module includes the following four types of algorithm, which will now be described in further detail.

The Identification-related Controller algorithms $C_I$, typically perturbs the system being studied to improve the accuracy of the model describing it. This is typically employed under one of the following circumstances:

The system is formally under-determined, i.e. the available measurable data is insufficient to produce a unique (within the constraints of noise) numerical model of the system using Identification methods. In this case the control variable would typically be modified to change the dynamical conditions under which the system was being observed, with a view to generating further information about the system.

The control variable is modified by the Controller to translate the system's initial conditions from place to place within state-space, to search for equilibrium conditions, regions of attraction, unstable regions and/or limit cycles by studying trajectory behaviour in state-space;

The system changes its stability or related behaviour across two or more subsets in state space: for instance, as the system trajectory travels across state-space, period-doubling and mathematical chaos are observed. In this case, the control variable would typically be modified by the Controller to translate the initial conditions of the systems across various locations in state space, to enable mapping of this dynamical behaviour of the system and its associated boundaries, or to move the system to conditions where stable control is more easily achieved.

Identification fails, and a Controller algorithm is triggered to translate the state of the system in state-space to a new state in state-space where Identification may have better results.

A combination of more than one of the above.

The single-objective Controller algorithms G includes conventional control methods such as stochastic control, linear or quasi-linear control methods, methods based on Euler-Lagrange optimal control, Fuzzy Logic controllers, plus control methods using a single Lyapunov function, for instance as outlined in WO2004/027674). It also includes published Controller algorithms for control of chaotic dynamical systems.

Model Reference Adaptive Control algorithms $C_{MRAC}$, modifying the control program manipulating a dynamical system with significant remaining uncertainties, to ensure that system eventually tracks a specified path based on the behaviour of a known model. This is distinct from standard Controllers, in that the parameters being used by the Controller are themselves typically being manipulated in parallel with the Controller.

Game against Nature algorithms $C_{GaN}$ use machine-intelligent gaming of the control program against dynamical uncertainties, including methods involving two or more Lyapunov functions, for instance as outlined in WO2004/027674.

It should be noted that these different forms of Controller are not necessarily mutually exclusive; for instance, the modelling system introduces a combination of Game against Nature and Model Reference Adaptive Control algorithms. Other algorithms are also typically associated with Controller algorithms in the modelling system, including those for estimation of Regions of Controllability and Strong Controllability in state space.

Additionally, the modelling system can include implementations where the "Identifier" task is not tracking-based Identification of a dynamical system but optimisation of some other payoff function, without a separate underlying system, hereinafter referred to as an "Orphan Identifier". A typical application of an Orphan Identifier is for optimising complex artificial systems, the design of which is initially poorly-known and must be evolved, with system construction occurring as a closed-loop process involving the Modular modelling system.

Figure 8B:
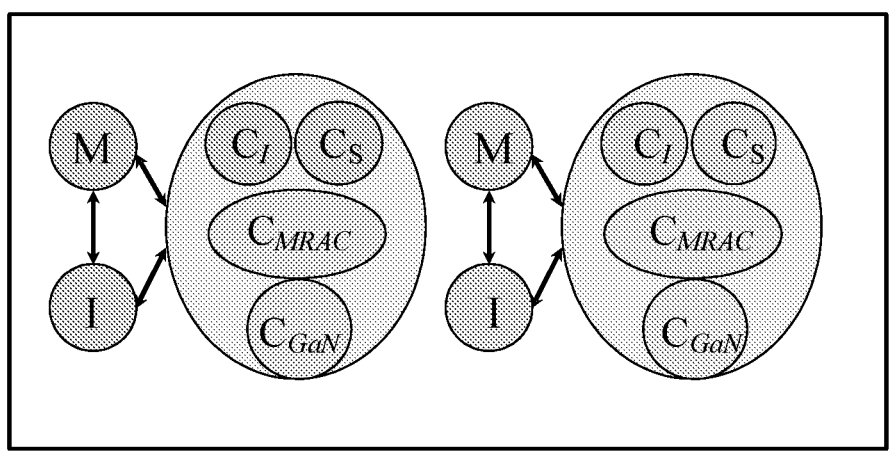
FIG. 8B is a schematic diagram of an example of multiple modular modelling systems.

Multiple modular modelling systems can also be implemented in parallel, as shown in FIG. 8B, with different systems being referred to as red and blue for ease of description.

Parallel deployment can be used in direct zero-sum conflict, which enables differential game theory analysis of intelligent systems in conflict, each using incomplete noise-polluted information to map out enemy strategies and generate counter-strategies. This is typically implemented iteratively: Red generates Blue's strategies and computes counter-strategies and Blue generates Red's strategies and generates counter-strategies. Following this Red independently maps out Blue's likely counter-strategies and computes responses, incorporating these in its strategies; and Blue does the same to Red. The result is a mixture of Game of Kind qualitative strategies and Game of Degree min-max strategies.

Examples uses of such arrangements include:

Anti-shipping missiles endeavouring to penetrate air-defences coordinated by Fire Control Systems on board a high-value asset such as an aircraft carrier. In this context Modular modelling systems could be used under real-time combat conditions, either:
To produce machine-intelligent fire-control and countermeasures deployment to protect the asset under conditions of noise-polluted partial information, or else
In the case of a missile able to have its guidance and control algorithms electronically reprogrammed in real time, to produce a machine-intelligent anti-shipping missile better able to penetrate the defences of a high-value asset, again under conditions of noise-polluted partial information.
A perfect-information simulator of the above is also valuable: an Orphan version of this same configuration used in multiple training and analysis simulations (not combat), either:
To train and inform strategy development and countermeasures deployment for Fire-Control Systems, to increase the probability of defeating missiles with a single-objective guidance law, or
To construct candidate missile guidance laws and underlying parameter sets for deployment (including machine-intelligent deployment), or
Both.
Anti-doping measures being deployed to detect artefacts in blood revealing previous illegal use of performance-enhancing drugs, versus an athlete attempting to conceal such use; and a strategy-simulator exploring these dynamics.

Parallel deployment can be used in non-zero-sum conflict, this enables differential game theory analysis of intelligent systems with at least partial cooperation. Examples uses include:

Foreign exchange traders (human or algorithmic), trying to achieve best-possible competitive trades themselves while cooperatively avoiding market collapse.

Air traffic control systems, where aircraft are inherently cooperative, but uncertainty in available information introduces conflict in the flight coordination task and associated holding pattern.

Additionally, multiple modular modelling systems can be deployed where a Modular modelling system is embedded within another Modular modelling system.

A number of components that can be implemented as part of the system will now be described.

The φ-TEA

A phi-Textured Evolutionary Algorithm (φ-TEA) is an evolutionary algorithm that is analogous to conventional genetic algorithms (GA).

The φ-TEA encodes candidate values of interest as genes on a chromosome. These genes are typically encoded in an analogous fashion to GA chromosomes, namely using an encoding scheme that can include: Gray Code, conventional binary, other bases (e.g. mimicking the 4 symbols G, C, A, T of actual DNA), hexadecimal numbers, real numbers and cycles of other lexicographical symbols in the literature.

There exists at least one population of such chromosomes, such that initially the population typically carries diverse values for each gene. These chromosomes breed across generations, based on how well the gene values along a chromosome satisfy some specified criterion. This is typically assessed using a "Fitness function", the form of which is defined and applied universally across all chromosomes and is typically calculated using the information carried by each individual chromosome, plus information carried by the entire chromosome population, and/or some external criterion or set applied uniformly to all members of the population in a single generation, and uniformly across generations. To achieve this, a Fitness value is bestowed on each chromosome individually, which dictates the likelihood that that chromosome will be chosen for reproduction and have some or all of its genes passed on to the next generation of chromosomes.

Chromosomes are typically modified, via processes of crossover and/or mutation. This constitutes a form of heuristic optimisation, whereby the "best" (or near-best) combinations of gene values to conform with the Fitness function are found over a sufficiently-large number of generations.

Given a model of a dynamical system comprising one or more ODEs, DEs, PDEs, SDEs, fractional-order differential modelling or similar, the φ-TEA typically encodes candidate values for as genes on the chromosome for at least one of the following:

Model parameters, and/or

A partial or complete set of initial conditions for model state variables, and/or Constraints on model dynamics, including boundary conditions on:
  Controller variables
  Controller programs and/or
  Solution trajectories to the model and/or
  Noise or uncertainty.

Unlike conventional genetic algorithms in the literature, such as those described in "Genetic Algorithms in Search, Optimization and Machine Learning" by David E Goldberg, 1st Addison-Wesley Longman Publishing Co., Inc. Boston, Mass., USA ©1989 ISBN:0201157675 or "An Introduction to Genetic Algorithms" by Melanie Mitchell MIT Press Cambridge, Mass., USA ©1998 ISBN:0262631857, each chromosome is used in each generation to generate one or more solution trajectories to the model equations in state space, based on the information carried in its genes. If more than one solution trajectory is generated by a chromosome, this plurality typically arises due to the presence of simulated noise or uncertainty in the model equations and/or its variables, e.g. where a controller variable exists but no controller program (or "control program") has been formulated, uncertainty about the controller program to be employed means a generalised differential equation or its equivalent is constructed from each chromosome, defined across the space of possible controller strategies and generating a plurality of possible solution trajectories for that chromosome.

The one or more solution trajectories are permanently associated with the chromosome as part of a "Trinity" for that chromosome, as will be described in more detail below and are typically assigned additional information not carried by the chromosome, including:

Partial or complete initial conditions for state variables and/or control variables, if not completely specified by the chromosome's genes;

Modifications in trajectory behaviour due to application of a controller program to the model equations;

Additionally, in a φ-TEA, a basic Fitness function is typically computed for each chromosome, analogously to a GA. However this Fitness function is then modified ("textured") using information neither carried by the individual chromosome nor the chromosome population, namely at least one of:

i. The behaviour of one or more trajectories in state space associated with this chromosome, with respect to trajectories of other chromosomes (e.g. convergence or divergence);

ii. Interactions between such trajectories and "texture sets" (being geometrical sets in state space, the properties of which are initially defined independently of the chromosomes), such texture sets typically moving through state space across generations of chromosomes.

A φ-TEA also typically incorporates a memory or history capability, plus logical analysis of events recorded by this capability, whereby the behaviour of one or more trajectories in previous generations with respect to one another and/or with respect to specified texture sets in state space, if it satisfies some specified logical condition, typically modifies the geometrical attributes of these texture sets for future generations of chromosomes. This typically includes a texture set being introduced into state space, moved through state space, enlarged, compressed, deformed, subdivided or deleted from state space, depending on how many trajectories in a previous chromosome generation interacted with it and/or other texture sets and how such trajectories interacted with them (e.g. collided with it/them, captured by it/them, avoided it/them).

Consequently, in stark contrast to a conventional GA where a key feature is uniform application of Fitness across chromosomes and generations, the concept of texture is inherently asymmetrical. For example, the same chromosome may be textured differently, depending on the values of external conditions, not included in its genes, that affect the behaviour of its trajectory. This includes the effects of simulated noise and/or externally-imposed initial conditions. The same chromosome may also be textured differently in different generations, due to the movement or other changes in geometry of the texture sets in state space over generations (hence changing the ways a solution trajectory might interact with the sets), or due to changes in the relative geometry between this solution trajectory and other solution trajectories corresponding with other chromosomes. Hence Textured Fitness is typically applied in a non-uniform way, both on chromosomes within a generation and on chromosomes across generations.

Given that a φ-TEA uses Textured Fitness instead of the usual concept of Fitness, this gives φ-TEA a different structure compared to conventional GAs.

The fundamental building-block of any φ-TEA is called a Trinity, denoted ($\mathfrak{M}$, $\bar{c}$, $\{\mathcal{P}_\mathfrak{M}\}$). It comprises a combination of:

- A model $\mathfrak{M}$ of a dynamical system, comprising one or more ODEs, DEs, PDEs, SDEs or similar (or else comprising one or more candidate functions, expressed algebraically, such that these functions could describe solution trajectories for such a set of ODEs or similar), with its associated numerical parameters, initial conditions and constraints typically all written in algebraic (non-numerical) form;
- A chromosome $\bar{c}$ that specifies some or all of the numerical information required to generate one or more solution trajectories $\mathcal{P}_\mathfrak{M}$ from this model; and
- The set $\{\mathcal{P}_\mathfrak{M}\}$ of one or more solution trajectories $\mathcal{P}_\mathfrak{M}$ generated by the model $\mathfrak{M}$ using:
  - The information specified by $\bar{c}$, plus
  - Any further information required for solution trajectory generation (for instance, some choice of simulated noise vector $\omega(t) \in W$, where w is some compact set of possible noise values, including the noiseless scenario $0 \in W$).

It should be noted that more precisely $\mathfrak{M}$ describes the model structure (ODEs or similar; or one or more functions corresponding with the structure of candidate solutions to such ODEs or similar) with all relevant fixed numerical quantities (parameters etc.) written in algebraic form; $\mathfrak{M}(\lambda)$ (where $\lambda \equiv \bar{c}$ some chromosome $\bar{c}$) denotes the model with all of the numerical information carried by the chromosome inserted in the appropriate places.

Throughout the following specification, whenever a chromosome $\bar{c}$ or its associated solution trajectories are discussed in the context of a φ-TEA, it is assumed that these are part of a Trinity (so the set $\{\bar{c}_j\}_{j=1}^Z$ is more formally written $\{(\mathfrak{M}, \bar{c}_j, \{\mathcal{P}_\mathfrak{M}\}(j))\}_{j=1}^Z$). However, this notation is complicated and of limited utility when explaining the basic operation of a φ-TEA, so its use will be limited to remarking that:

Unless explicitly stated otherwise,
  Typically only Trinities with a common model structure $\mathfrak{M}$ interact; so if the chromosomes $\bar{c}_i$ and $\bar{c}_j$ breed, it implies that their Trinities have the same model structure;
  Hence all members of any given population of chromosomes $\{\bar{c}_j\}_{j=1}^Z$ typically have Trinities with the same model structure $\mathfrak{M}$;
  In the case of the Identifier, typically $\mathfrak{M}$ is already assumed specified and the $\bar{c}$ and $\{\mathcal{P}_\mathfrak{M}\}$ are to be generated consistent with this, whereas
  In the case of the Model Selector, $\mathfrak{M}$ has to be constructed or chosen prior to, or in parallel with, the Identification process.

The φ-TEA also has a number of other features, including:
Population reproductive schemes based on Textured Fitness, including those designated Weak TEA, Stochastic Weak TEA, Strong TEA, Stochastic Strong TEA and/or Stochastic Uniformly-Strong TEA.

"Speciation-based constraints" on heterogeneous breeding (either by imposing constraints on particular genes on each chromosome, or associating values or symbols with each chromosome that constrain heterogeneous breeding), making breeding between "sufficiently-different" chromosomes more difficult or impossible.

"Predators", providing an additional culling mechanism within a population apart from that of reproductive penalties for uncompetitive Fitness;

So-called "ecological spatial networks" of multiple contemporary populations of chromosomes (each population belonging to a φ-TEA, MGA or conventional GA), linked by "transfer protocols", sets of logical rules dictating the (typically intermittent) passage of chromosomes (and/or predators, in some schemes) between populations. The rules governing these transfer protocols are typically based on sets of rules designed to mimic various forms of animal behaviour in actual ecosystems that are typically combined to produce more complex behaviour.

Typically transfer protocols operate, transmitting one or more chromosomes and/or predators in a specified direction, when specific criteria are fulfilled predicated based on Textured Fitness (either relative or absolute, of members of one or both populations); Population size (either relative or absolute, of chromosomes and/or predators in one or both populations); or Probability.
  In the case of chromosomes, these transfer protocols typically include five specified "behavioural archetypes";
  In the case of predators, they typically include the use of: logic tables, at least one of three specified predation schemes ("Implicit", "Dynamic" or "Static"), and a specified transfer protocol geometry (either "Fixed" or "Opportunistic").
  Transfer protocols also typically include additional logical rules to prevent the emergence of limit cycles (whereby the same sets of chromosomes or predators are moved back and forth between two populations without any evolutionary effect on either population).

"Sequential networks" of populations, connected using various topological structures (simple chain, torus etc.), where these networks can represent different kinds of sequential analysis of the system being studied. Sequential transfer is determined either by the elapsing of a specified number of generations, or using more complex switching rules, typically embodied in various Blocks, enabling circuits of φ-TEA populations to be constructed.

Furthermore a φ-TEA typically allows modification of the geometrical and algorithmic structures of these populations, networks and transfer protocols to maximise the efficiency of the evolutionary processes they embody, typically using a "Meta-Optimising Layer" (MOL), a separate layer of evolutionary algorithm manipulating the metadata for these structures and processes, that again has analogous features to these outlined above for the basic (or "Base Layer") φ-TEA, in a recursive design. Typically this metadata is itself expressed in a chromosome format (meta-chromosomes) and the MOL constructs its own versions of φ-TEA or GA to optimise these meta-chromosomes for the Base Layer φ-TEA.

It should also be apparent that a number of features of the φ-TEA can be implemented in ordinary GA in the literature to provide "Modified Genetic Algorithms" (MGA) that are more advanced than standard GAs. Furthermore in the rest of this specification, where reference is made to GA (as distinct from MGA) forming part of this invention, it should be understood that these refer to populations operating under rules analogous to conventional GA, but populations of Trinities rather than conventional chromosomes.

Concepts of Texture Used by the φ-TEA: Sets and Trajectories

As outlined above, in a φ-TEA the Fitness of any chromosome is "textured" based on the behaviour of the one or more trajectories it has generated in state space, with respect to the trajectories associated with other chromosomes and/or interacting with texture sets. The methods for "texturing" Fitness in this way will now be described.

Texturing can be achieved through one or more solution trajectories achieving one or more discretely-distributed qualitative objectives in state space, defined in discrete terms of the trajectories' collision, capture or avoidance with, by, or of one or more specified sets in state space (i.e. given a specified set in state space, if the trajectory collides with it, is captured by it or deliberately avoids it, the Textured Fitness is different in each case from that for a trajectory that fails to do any of these things).

Texturing can be achieved through one or more solution trajectories exhibiting specified behaviour re qualitative objectives in state space described by a continuously-distributed function, by assigning relative measurements to the extent which a trajectory performs this behaviour (for instance, given two trajectories that collide with a specified set and spend different lengths of time within that set, their Textured Fitnesses will differ, influenced by the difference in the time spent within that set).

Texturing can be achieved through one or more solution trajectories exhibiting specified continuously-distributed quantitative behaviour (or at least stepwise continuously-distributed quantitative behaviour). State space and parameter space are permeated by contours associated with one or more Lyapunov functions and/or the derivatives of Lyapunov functions. A descent condition is imposed across these contours; the Fitness of each chromosome is modified ("textured") based on whether the solution trajectory generated by that chromosome obeys or disobeys that descent condition. It will be appreciated that this could be achieved using Lyapunov functions and derivatives in a manner similar to that described in WO2007/104093, albeit with it being used in this context to modify the Fitness of an evolutionary algorithm to encourage the survival and/or breeding of those chromosomes corresponding with models that have solution trajectories that converge to subject behaviour.

Texturing can be achieved through "divergence-based speciation", based on the divergence of solution trajectories across state space. In contrast with the previous three methods, which modify the Real-valued Fitness by mapping it to a Real-valued Textured Fitness, this method represents mapping the Fitness to a more complicated mathematical structure that also captures this geometrical information (typically a vector). This typically uses Complex numbers, given their well-established capacity to describe vector-valued spatial information. Distinct chromosomes corresponding with trajectories that remain geometrically "close" in state space have Textured Fitness vectors that are mutually "close", whereas distinct chromosomes corresponding with trajectories that diverge in state space have Textured Fitness vectors that are mutually "distant". Typically pairs of chromosomes with Textured Fitness vectors that are "close" to each other are able to reproduce easily, whereas pairs of chromosomes with Textured Fitness vectors that are mutually "distant" from each other have reproduction made more unlikely or impossible.

Texturing can be achieved through "surface-based speciation". In this example, a patterning algorithm is used to generate a pattern of values over some geometrical surface (where the term "surface" also includes hypersurfaces). The values associated with the pattern on this surface are then mapped to the Complex plane, with this surface then being mapped to or inserted into the state space, such that trajectories corresponding with chromosomes cross it. Based on the Complex value of the surface pattern at the point where it is crossed by each trajectory, the Fitness of the associated chromosome is then modified ("textured") by this Complex value. Again, typically pairs of chromosomes with Textured Fitness vectors that are "close" to each other are then able to reproduce easily, whereas pairs of chromosomes with Textured Fitness vectors that are mutually "distant" from each other have reproduction made more unlikely or impossible.

In the above description, Fitness is typically calculated based on how well trajectories track or predict observed data, while Texture is based on other additional considerations such as trajectory interaction with Texture Sets. These sets may themselves be built from other mathematical formulations of the interactions between trajectory elements and observed data, or from other considerations. However it should be apparent that this relationship can be "flipped": Fitness being constructed from how well the trajectories interact with the Texture sets and this Fitness being textured based on how well the trajectories track or predict the observed data. This "flipped" format is also encompassed within the techniques described herein.

Blocks and Circuits

As previously mentioned, the modelling system uses circuits comprising one or more φ-TEA, MGA or GA. Such circuits typically comprise one or more "wires" and "Blocks".

Wires are analogous to wires in an electrical circuit. Wires here transmit signals consisting of sets of chromosomes (rather than electrons). In the absence of suitable output from one or more Blocks (below), the default signal carried by a wire is assumed to correspond with the empty set $\emptyset$.

Blocks are units which are connected to wires for their input and output, and operate on the signals (sets of chromosomes) carried by the wires, performing one or more of evolutionary computation of one or more populations of φ-TEA, MGA or GA, including their associated features (such as reproductive schemes based on Textured Fitness; predators; ecological spatial networks etc.), chromosome analysis and/or switching, whereby a chromosome set emitted along a wire is analysed and routed, based on whether it satisfies specified criteria; or some other form of modification of the chromosome set, including "grounding" the set (i.e. deleting it from the circuit), or the like.

In the case of evolutionary computation, the Block typically either takes a set of chromosomes as input from its input wire (or else generates the set, if it's the first Block in the circuit). It uses this chromosome set as the first generation of some specified evolutionary computation (φ-TEA, MGA or GA, as specified); and then performs that evolutionary computation. After a suitable number of generations have elapsed the final generation of chromosomes arising from the computation is emitted as the Block output. This output is then sent along the output wire to the next Block in the circuit.

As evolutionary computation is an heuristic process, it is possible that no suitable chromosome set is emitted after the final generation. Depending on the Block design, it is typically assumed that either the Block re-runs the computation, to seek a suitable result, or else declares a failed computation, for instance by emitting a pre-defined distinctive signal along the wire, such as an interrupted null signal {Ø,Ø}. Depending on the circuit design, this may trigger an earlier Block to repeat its own computations, altering the input to the failed Block; or else it may trigger some other response.

Typically these circuits are again able to be optimised using a Meta-Optimising Layer (MOL), a separate layer of evolutionary algorithm manipulating the metadata for these structures and processes, by expressing this metadata in a chromosome format "meta-chromosome" and recursively using structures, such as circuits of wires and Blocks, to analyse and optimise this metadata.

Machine-Intelligent Employment of "Triage Logic" in Formulating Controller Strategies Typically this method uses either a single Lyapunov function, or multiple Lyapunov functions, to calculate an appropriate Controller strategy or program to impose on a dynamical system.

The process also typically uses sets, specified in state space. In this regard, there is typically a desired target set T in state space $\Delta$, into which the dynamical system is ultimately to be steered by the Controller, possibly via one or more lesser target sets along the way.

There is also typically one or more anti-target sets $T_i^{\blacksquare} \subset \Delta$, i=1, ..., B, corresponding with physically lethal, dangerous, unstable or uncontrollable conditions, which are to be avoided by the dynamical system under the Controller. Examples of these anti-targets typically include, but are not limited to:
  Threats inherent to the dynamical system or model, such as physically lethal or dangerous conditions;
  Threats associated with the stability of the dynamical system or model, such as loss of conditions sufficient or necessary for asymptotic stability or stability, or the onset of conditions associated with chaotic behaviour, period-doubling or other undesirable dynamical behaviour in phase space;
  Threats associated with the controllability of the dynamical system or model, such as loss of conditions sufficient or necessary for strong controllability or controllability.

Typically each anti-target describes a different threat, or different levels of danger associated with a threat.

Similarly, as well as the desired target set T, there are also typically one or more other highly-desirable sets in state space, denoted $T_i^{\square} \subset \Delta$, i=1, ..., b, corresponding with physically or technically advantageous conditions that should be established prior to, or as part of, ultimately steering the trajectory to the target. These sets are described as "lesser targets". Examples include, but are not limited to:
  Physical conditions that are advantageous to establish prior to seeking the desired target. Examples include: in critical-care medicine, ensuring the patient's appropriate vital signs such as blood pressure and oxygen levels are first steered to within desired intervals prior to staging an invasive medical intervention; in aerospace, ensuring a vehicle first has established sufficient specific energy, prior to engaging in high-drag manoeuvres intended ultimately to reach a desired configuration.
  Improvements in stability conditions, such as:
    Reaching regions in state space and/or parameter space that enable stable or asymptotically-stable dynamics (typically from a region of uncertain stability or known instability), or
    Passing from regions in state space and/or parameter space that require significant resource expenditure to make or keep stable/asymptotically stable, to a region that requires less resource expenditure to be made or kept stable/asymptotically stable.
  Improvements in controllability conditions, such as:
    Reaching regions in state space and/or parameter space that enable controllability or strong-controllability of the system or model dynamics (typically from regions corresponding with uncertain controllability, or controllability only under specified conditions, or known non-controllability), or
    Passing from regions in state space and/or parameter space that require significant resource expenditure to make or keep controllable or strongly-controllable, to a region that requires less resource expenditure to be made or kept controllable or strongly-controllable.

Typically this method employs gradient descent criteria on such Lyapunov functions to impose control of solution trajectories describing the dynamics of some model or system, such that these trajectories achieve avoidance of anti-target sets, and collision with or capture of designated target sets in state space.

The term "gradient descent" also encompasses related concepts of stochastic gradient descent, stochastic sub-gradient descent and sub-gradient methods as described in the literature.

These trajectories are typically associated with a set of vectors $\{\lambda_i\}_{i=1}^Z$ under the $\varphi$-TEA formulation ($\varphi$-TEA chromosomes), such that each chromosome $\lambda_i$ represents a distinct set of proposed parameter values and/or initial conditions of state variables of a model of a dynamical system, such that the model dynamics are either completely or partially specified by that chromosome. Consequently each chromosome corresponds with one or more possible solution trajectories describing or predicting the dynamics of the model and/or each chromosome corresponds with a different possible hypothesis regarding a poorly-understood dynamical system.

Where not all trajectories corresponding with elements in $\{\lambda_i\}_{i=1}^Z$ can be steered to the desired target, a form of triage logic (the term adopted from emergency medicine) is applied, whereby the algorithm secures the best (or least-worst) compromise, based on its ability to manipulate membership of a subset $\{\lambda_i\}_{i=1}^Y \subseteq \{\lambda_i\}_{i=1}^Z$.

Typically, the dynamical systems being studied suffer from large-scale uncertainties in their dynamics, including noise, external perturbations or unknown values for state variables, parameters or dynamical structures, that may interfere with Controller objectives or prevent them from being met. Typically, possible values for some of these uncertainties (such as various possible values for important parameters) are described by different members of $\{\lambda_i\}_{i=1}^Z$, while other forms of uncertainty (including noise) are kept external to all chromosomes.

Accordingly, the system can decide a controller strategy to be imposed on the dynamical model (and hence the underlying system) by manipulating membership of $\{\lambda_i\}_{i=1}^Y \subseteq \{\lambda_i\}_{i=1}^Z$, and using the trajectories associated with these chromosomes $\{\lambda_i\}_{i=1}^Y$, obeying (or disobeying) gradient-descent criteria for the one or more Lyapunov functions, and interacting with the specified target and anti-target sets in state space.

Consequently the system typically uses the task of deciding which members of a subset $\{\lambda_i\}_{i=1}^{Y} \subseteq \{\lambda_i\}_{i=1}^{Z}$ reach one or more targets or avoid one or more anti-targets as a machine-implementable way of mitigating risk when controlling a dynamical system under uncertain and dangerous conditions.

The system can also typically employ Game against Nature ('GaN') algorithms, seeking further to compensate for uncertainties by postulating a hostile intelligence ("Nature") that manipulates all such uncertainties to try to prevent Controller objectives from being met. The Controller responds by computing a maximally-robust control strategy that endeavours to overcome Nature's efforts. This is typically done by collecting all uncertainties into a set of possible control values $U_2$ such that Nature chooses a control vector $u_2(t) \in U_2$ for any given moment. The Controller typically endeavours to make the solution trajectories associated with $\{\lambda_i\}_{i=1}^{Y} \subseteq \{\lambda_i\}_{i=1}^{Z}$ obey gradient conditions associated with one or more Lyapunov functions, and thus collide with/capture one or more target sets and avoid anti-target sets. During this process, Nature responds, generating its control strategy to oppose all such endeavours; trying to push trajectories up Lyapunov gradients the Controller is trying to enforce descent down, and/or trying to force trajectories down Lyapunov gradients where the Controller is trying to pull them upwards.

Typically, given some uncertainties are embodied in different members of $\{\lambda_i\}_{i=1}^{Z}$, at any given moment Nature chooses which member(s) of $\{\lambda_i\}_{i=1}^{Z}$ currently represent the "real" underlying system and the Controller must respond by endeavouring to manipulate the trajectories of these chromosomes, to obey Lyapunov gradient criteria, and/or to reach specified target sets and avoid specified anti-targets. Similarly, given that some uncertainties are typically expressed in a finite noise vector w(t) with bounded components, and that this noise vector affects all trajectories, Nature typically manipulates w(t) as part of its control vector $u_2(t) \in U_2$ to hinder the Controller's efforts. As the actual noise vector cannot be reproduced precisely, typically a simulated noise vector $\omega(t)$ is employed by the model and manipulated by Nature. This noise vector typically has finite magnitude, with a frequency spectrum and/or probability distribution specified by the MOL.

Typically by examining which trajectories of which chromosomes can nonetheless have their desired behaviour enforced under the Controller's available resources (the control vector $u_1(t) \in U_1$), and which trajectories fail to be controlled adequately, and the outcomes of that control failure (including trajectories intersecting one or more anti-targets, and/or failing to intersect lesser targets, and the implications of this), the Controller decides which of the chromosomes in $\{\lambda_i\}_{i=1}^{Z}$ should be used as members of the subset $\{\lambda_i\}_{i=1}^{Y} \subseteq \{\lambda_i\}_{i=1}^{Z}$, to formulate the control strategy to be applied to the model and underlying dynamical system.

The system also typically employs nonlinear Model Reference Adaptive Control (MRAC) methods, in particular those methods in the literature that employ Lyapunov functions, to force convergence between dynamical system and model behaviour, by combining such methods with other methods described herein.

Model-Reference Adaptive Control Algorithms, Evolving MRAC and Variants

The Controller typically includes a library of published Model-Reference Adaptive Control (MRAC) algorithms. As well as standard linear and quasi-linear methods, this also includes non-linear MRAC algorithms, such as the Product State Space Technique (PSST) and its components, discussed in the literature, including Leitmann and Skowronski (1977); Corless, Leitmann and Ryan (1984, 1985, 1987); Corless, Leitmann and Skowronski (1987); Skowronski (1990, 1991) and Kang, Horowitz and Leitmann (1998), as well as more recent published work on these methods, e.g. by Dusan Stipanovic and colleagues.

In the PSST, having converted the reference model's fixed parameter vector $\lambda$ into a modifiable vector $\mu(t)$ such that $\mu(t)=\lambda$, and writing the notional error between the system's "true" parameter vector and the model's parameter vector as $\alpha(t)=\beta-\mu(t)$, we must then design an "adaptive law" $f_a$ for the adjustable parts of the model's parameter vector, defined as: $\dot{\mu}(t)=-f_a$, such that the observed system dynamics and the model dynamics converge.

Conventionally this is done in the PSST by at least one of specifying a path for the model dynamics, and/or imposing a control law on both the system and model dynamics, and then using the adaptive law to manipulate values for the vector $\mu(t)\mu(t)$ so that observed system behaviour and expected model behaviour converge. Conventionally in the PSST the adaptive law $f_a$ manipulates values for components of using gradient-descent methods on Lyapunov functions or similar to search for local convergence between observed system behaviour and expected model behaviour.

The current system incorporates the PSST, typically employing at least one of conventional local search algorithms for gradient-descent methods on Lyapunov functions, and/or heuristic global search methods, such methods including the use of at least one of: novel φ-TEA and/or MGA methods; conventional GA; or other known global heuristic search algorithms including simulated annealing.

Where the current system uses Lyapunov functions within φ-TEA for MRAC and/or Identification, it uses the Lyapunov function or its derivative to modify the Fitness of an evolutionary algorithm to encourage the survival and/or breeding of those chromosomes corresponding with models that have solution trajectories that converge to subject behaviour.

The current system also typically incorporates the PSST and other MRAC methods, as partly or completed informed by at least one of: an Evolving Identifier, and/or a reduced dynamic envelope, and/or an Evolving MRAC Engine, where this is defined to be an Evolving Identifier with the direction of convergence reversed.

In the Evolving Identifier, the adaptive law $f_a$ forces the model values to change such that model behaviour converges with observed system behaviour, whereas in the Evolving MRAC Engine, the model parameter values (in terms of being a description of the system dynamics by the Identifier) are fixed; subsequent modifications to the model parameter values (setting $\mu(t)$ such that $\mu(0)=\lambda$ and then modifying $\mu(t)$ using the adaptive law) are done artificially as part of the Controller to force the system behaviour to follow the model behaviour, typically by fixing a stipulated path in state space that both model and system must follow. In this example, the use of φ-TEA transforms nonlinear adaptive MRAC from being a local search to achieve convergence using Lyapunov functions, to being a global search to achieve convergence using evolutionary algorithms textured via Lyapunov functions, texture sets or trajectory divergence.

The system typically employs a combination of Controller algorithms as required. Relevant scenarios requiring such combinations should be apparent to the reader, but in any event can include the following example:

Noise-polluted incomplete data from a dynamical system is analysed using an Evolving Identifier;

Identification is completed, but significant parametric uncertainty (expressed as a set of candidate chromosomes) remains due to the system being underdetermined;

A reduced dynamic envelope is constructed;

The relevant control strategy is generated using a combination of Evolving MRAC (to steer system dynamics to specified acceptable safe behaviour) and machine-intelligent Triage Logic (typically using either a single or multiple Lyapunov function(s), to generate strategies robust against remaining uncertainties using the Game against Nature);

This combination is employed either using:

Intermittent switching between Controller regimes employing sequential Evolving MRAC and Game against Nature/Triage Logic, or else Combination of the mathematical structures of the two regimes (such that the uncertain system dynamics under Nature's control strategy are also forced to converge to model behaviour).

Applications of Modular Modelling Systems and Components Thereof

It will be appreciated that the above described techniques can be used in a wide variety of circumstances and manners, depending on the implementation. The following is a list of applications of Modular modelling systems and/or the components thereof. Each application refers not only to the present system and/or its components as one or more standalone devices, but also to the integration or incorporation of this system, its components and capabilities into other third-party hardware, firmware or software to enhance their capabilities, performance and/or reliability.

In the following list, the terms "dynamics" and "dynamical processes" are used in their sense as a term of art within systems theory in applied mathematics, namely to encompass physical dynamics and kinematics of rigid bodies and particles, dynamics of force fields such as generated by electromagnetic fields, fluid dynamics, thermodynamics, plasma dynamics, the dynamics of chemical reactions and processes, medical pharmacokinetics and pharmacodynamics, logistical processes, trading behaviour in markets and the propagation of signals across networks, as appropriate.

In any event, applications and embodiments of the system include software implementations of all or part of the system, including encoding Blocks as software Objects or similar and electronic implementations of all or part of the system, including using Field Programmable Gate Array and/or Field Programmable Analogue Array computing.

The system allows for computationally-enhanced diagnosis and/or therapies and associated activities for medical, veterinary, pharmaceutical or biotechnology applications, including as applied to humans, animals, tissue samples or microbiological cultures or colonies, in vivo and/or in vitro and/or via simulation in silico. This can include devices for reconstructing in vivo the functional pharmacokinetics (PK) of the host organism's system biology and/or of specific tissue (original or implanted) within the host, from available time-series data, and/or the pharmacodynamics (PD) of associated therapies, with a view to enabling or assisting:

Deciding the presence or absence of a medical condition;

Deciding the success or failure or ongoing viability or performance of a previous medical intervention;

Deciding the appropriate therapy and dose for a medical intervention, and/or alerting the user for other interventions (e.g. the need for a meal in response to low blood glucose levels), with particular emphasis on applications where such interventions must operate within a therapeutic window.

Suggesting to a medical patient or treating clinician one or more sets of appropriate therapies and associated doses, as a decision-support tool.

Administering an appropriate therapy or dose, via automated medication-delivery systems.

The system can be used for computation of improved dosing regimens for therapies, reducing risks associated with doses or other relevant variables exceeding or dropping below therapeutic windows, as well as construction of organ-scale or tissue-scale personalised models and therapies, including the computation of such personalised models and therapies without recourse to genomic techniques or technologies.

The system can be used for analysis, modelling and prediction of the epidemiology of a disease, including estimating the dynamics of its propagation and computing candidate counter-strategies and/or quantitative analysis and optimisation of tissue culture, growth, dynamical behaviour and functional performance, transplantation and post-transplant function, including transplants of mature cells, cultured cells and/or stem-cell transplants, bone-marrow, pancreatic beta-cells and/or liver tissue or including construction and transplantation of wholly artificially-constructed tissues and/or organs. The system can also be used for quantitative analysis of the dynamics of observed cell-death pathways and consequent modification of therapeutic interventions.

Whilst the system can be used for a range of different applications, some specific medical applications include, but are not limited to:

Diabetes, including Type-1 (e.g. Greenwood and Gunton (2014); Dalla Man et al., (2007); Magni et al. (2007)) and Type-2 diabetes and the associated improvement of therapies, including hormone-based therapies, such as applied insulin and glucagon, and/or transplant-based therapies, such as pancreatic beta-cell transplants and/or including "artificial pancreas" software and devices (whether fully-automated or user-in-the-loop) for machine-intelligent dosing of insulin and its analogues to insulin-using diabetics. Examples of this are described in "A Computational Proof of Concept of a Machine-Intelligent Artificial Pancreas Using Lyapunov Stability and Differential Game Theory" by Nigel J. C. Greenwood and Jenny E. Gunton Diabetes Sci Technol 2014 8: 791 DOI: 10.1177/1932296814536271, the contents of which are incorporated herein by reference;

Chronic degenerative diseases and associated therapies, including Parkinson's Disease, Alzheimer's Disease and/or Huntington's Disease;

HIV/AIDS and associated therapies

Cardiac disorders, including reconstruction of cardiac rhythms, function, arrhythmia and/or other cardiac output;

Drug-based control of blood pressure and/or blood clotting;

Demyelinating diseases;

Autoimmune disorders, including Myasthenia gravis, Asthma and/or Rheumatoid arthritis;

Schizophrenia and other disorders involving anti-psychotic therapies;

Neuromuscular disorders, including muscular dystrophies;

Poisoning, including snakebite and treatment of other venom-based disorders;

Clinical trialling of drugs, including analysis and enhancement of efficacy and safety based on time-series data obtained from individual subjects and/or adaptive design of associated drug regimens;

Pathogen diagnosis, analysis and therapeutic treatments, including enhanced treatment of therapy-resistant pathogens, including Identification and control tasks associated with elucidating the mechanisms of pathogen action and the likely pharmacokinetics and pharmacodynamics of candidate therapies, improving the effectiveness of antibiotic and antiviral therapies, including enhanced "cycling" of such therapies;

The enhancement of therapies aimed at augmenting impaired biological function, including the improved quantitative application of agonists, antagonists, hormones and ligand precursors and enzyme inhibitors, including L-dopa and related drugs for Parkinson's Disease; Insulin and insulin analogues for insulin-dependent diabetes; Neurotransmitter modulation, including reuptake inhibitors for depressive and bipolar disorders and Monoamine oxidase inhibition;

The application and use of drugs, the purpose of which is to stabilise the disease-therapy dynamics, including the translation of such dynamics from chaotic, unstable or period-doubling states to a non-chaotic state: including stabilisation of cardiac dynamics and/or stabilisation of Parkinsonian (Parkinson's Disease) dynamics, including under the influence of L-dopa or other dopamine precursor therapies;

Immunotherapy, including enhancing the modulation of immune responses by improving the modelling of immune system dynamics;

Cytotoxic therapies, including chemotherapy and radiotherapy and including their application to tumours, cancers and/or pathogens;

Critical care therapies, including burns therapies;

Athletic conditioning and athletic anti-doping measures for humans and animals, including using time-series of blood tests and residual biomarkers to reconstruct earlier perturbations to metabolism and muscle growth;

Forensic pathology, including using time-series measurements to reconstruct earlier dynamics of chemical, biochemical and biological processes;

Any other instances of medication or application of a drug or therapy to a subject, such that repeated doses are administered over time to maintain levels of a drug, ligand or other biological attribute to within a desired interval of values, in the presence of dissipative processes such as pharmacokinetic processes of uptake or absorption, distribution or transport, metabolism or elimination.

Thus, for example, the system can be implemented as part of a regime for managing a disease or other physical condition. In this instance, measurable attributes of the patient and/or disease, form the system data. This can include information such as the subject's physiological parameters, such as temperature, blood pressure, blood glucose levels, gene or protein expression profile, or the like, as well as attributes of the condition, such as a degree of infection, or the like, with values of these variables being used together with a generic mathematical model of the condition, in order to personalise the model for the particular patient. In this instance, the model ca be refined by tracking changes in the system data over time, so that the model is modified to more accurately reflect the behaviour of the patient. At this point, model parameters can represent system data the clinician is not otherwise able to measure, which can provide useful feedback for the clinician in treating the patient.

Additionally, the system can be used to monitor control variables, such as diet, administered drugs, or the like and ascertain values of these that are likely to result in improvement or reduced impact of the condition.

Thus, in the case of the artificial pancreas referenced above, the system was used to track blood glucose levels in patients, in response to changes in diet, activity and administration of insulin. This allows the system to derive a model that accurately reflect the changes in blood glucose levels within the subject, in turn allowing the model to be used to determine the dose and timing at which insulin should be administered, for example depending on recent diet and activity. Thus, it will be appreciated that this can form part of an artificial pancreas, allowing the model to be used to control the automatic administration of insulin, taking into account current blood glucose levels, as well as other information, such as recent diet or activity, thereby optimising the effectiveness of treatment.

In a further mode of operation, the system can be used in diagnosing one or more conditions, such as diseases, suffered by a patient. In this instance, if the patient presents with an unknown condition, the system can select models corresponding to a range of different conditions. Each of these can then be optimised based on available system data, and in particular physiological parameters, and responses of these to treatment or intervention. The model that leads to the closest match to patient behaviour is then indicative of the condition(s) suffered by the patient, allowing a diagnosis to be performed.

The system can be used for the modelling, Identification and partial control (e.g. via modified culling or fishing policies) of ecological systems, including fisheries.

The system can be used for the modelling, Identification, control, optimisation and prediction of dynamic industrial processes (including analysis and prediction of potential failure of such processes and/or their component parts), including chemical, electrical and/or mechanical engineering processes or engines or motors and/or power plants or generators including thermodynamics and heat transfer or dynamic impedance-matching and/or load-balancing across a power network or grid.

This includes using the system for the modelling, Identification, adaptive control and optimisation of chemical reactions and processes.

This includes using the system for modelling, Identification and control of turbine and reciprocating engines, including their use for propulsion, pumping and energy-generation. Such uses include aviation engines (civil and military) and propulsion engines in shipping (civil and military) and submarines. It includes industrial engines such as turbines and reciprocating engines, including engines used for compressor (pumping) stations in pipelines for oil, natural gas, water and other fluids. It also includes automotive engines, including high-performance engines used in Formula 1 racing and similar. It includes the use of engines and machinery for energy-generation, including turbines for generating electrical power for land-based electrical grids, in ships and in submarines.

For example, the system can be used to model and hence monitor and control physical equipment, such as engines, pumps or the like, which are subject to internal stresses and forces, which are difficult to measure in practical use. In this instance, the modelling system uses a differential equation model indicative of operation and interaction of individual components (either via physical dynamics or thermodynamics), together with system data in the form of values of measurable variables, such as fuel consumption, operating efficiency, vibrations, noise or the like. This information is used to develop a customised model specific to the particular equipment, and its current behaviour. The model will include model parameters corresponding to aspects of the system that cannot be practically measured, such as a stress level and/or deflection in a turbine blade of a jet engine. This allows the system to predict when failures are imminent, for example by examining past behaviour and using the model to predict future behaviour, to determine when the behaviour reaches or will reach a threshold condition, such as a maximum safe stress or deflection. Additionally, this allows control processes to be developed, for example, by altering the operation of the equipment so as to mitigate the issue, for example by reducing the maximum power or rate of change in power that can be applied to the engine. It will be appreciated that this allows the system to extend operating life of the equipment, and ensure the equipment is safely decommissioned prior to failure.

This also includes using the system for enhanced predictive scheduling, risk analysis and adaptive control of networks and network loads, including power distribution grids, telecommunications networks, computer server networks and railway or other transport networks (e.g. load scheduling and routing of railcars carrying commodities such as coal, mineral ores etc.; or enhanced routing of city traffic comprising passenger vehicles, trucks etc.) It includes using such logistical information for enhanced commodities modelling or other financial or logistical modelling.

The system can be used for reverse-engineering of "black box" dynamical systems, including electronic circuits and/or computer programs, including reverse-engineering the operation of software operating across a network. This can include analysis of the dynamics of propagation of a computer virus or worm, bot attacks, distributed-denial-of-service attacks and similar, as well as analysis and optimisation of network routing protocols for the Internet or intranets or other networks. Relevant dynamics include the propagation of signals, information packets, files or computational load within electronic circuits, among processors or servers or across networks.

The system can be used for enhanced evolutionary design of Evolvable Hardware (EH) (including adaptive and self-repairing designs, including diagnostics and failure prediction), e.g. Greenwood and Tyrell (2006); Yao and Higuchi (1997); Thompson (1996). This can include electronic and electrical circuits, including: the design of close-packed electronic circuits, balancing compact packing with transient thermodynamics during computations; the analysis, design or operation of analogue or digital electronic systems, including associated power and thermodynamic management; dynamic distribution of power load over an electrical network or grid; or allocation of computational load or file routing over a network of servers.

The system can be used for design and/or estimation of nonlinear aerodynamic and/or hydrodynamic attributes and associated control surfaces for manned and unmanned vehicles, including their interactions with their nonlinear dynamical environments, including analysis of hydrodynamic or aerodynamic flow over the body and control surfaces of the vehicle, including thermodynamics and heat transfer; for one or more vehicles, estimation of the nonlinear flow of air or water across the vehicles (including control surfaces) and in their local environment, to optimise "vortex surfing" or other nonlinear effects, such as drag optimisation; and generation of relevant controller programs, including guidance and autopilot software and/or software to advise a human pilot, including to optimise a vehicle configuration with respect to any of the above.

The system can be applied to human-controlled or autonomous vehicles or machines, including design, modelling, Identification, control, optimisation, diagnostics (including potential component failure prediction, and adaptive feedback compensation either before or after the failure occurs) and prediction (typically using noise-polluted incomplete information) of the dynamics (including sensor performance, control dynamics, guidance law and/or response logic) of one or more of:

Unmanned Aerial Vehicles, including missiles, and of piloted aircraft;
Exo-atmospheric vehicles (piloted or unmanned);
Other autonomous vehicles, such as Unmanned Submersible Vehicles and torpedoes, and of piloted submarines;
Industrial robots, autonomously-mobile robots and other autonomous machines;
Countermeasures and defensive Fire Control Systems;
Subsystems of any of the above.

In the instances where coordination (cooperative or hostile) between two or more vehicles is required, the system can be used for constrained optimisation of the specifications, configuration or trajectory of the second vehicle, given knowledge (either partial or complete, obtained either directly or via Identification from partial information) of the specifications of the first vehicle; and extension of this principle to multiple vehicles.

The system can be used for integration of these capabilities into other hardware or software to enhance the capabilities of sensor, counter-measures, Fire Control Systems, UAVs/missiles, other autonomous machines, piloted vehicles and/or systems of systems, including Simulator implementation for threat-assessment and/or training and/or programming of systems; and/or
Software-based mapping of strategies and associated asset placement, including location of platforms and supporting resources, (for instance, launch platforms for air-defence missiles and associated support equipment to service those launch platforms); and/or
Construction, implementation and exploitation of databases of such strategies; and/or
Onboard machine-intelligent autonomous guidance and control software, including implementing or exploiting any of the above; and/or
Onboard implementation of the vehicle's guidance and control law in an electronic dynamically-reprogrammable format, including Field Programmable Gate Array and/or Field Programmable Analogue Array computing.

The system can be used for algorithm optimisation, including optimisation of source code and/or optimisation of compiled code and associated hardware computing platforms (e.g. optimal allocation of algorithms and associated computational load over heterogeneous computing platforms, such as a combination of multi-core CPUs and GPU cards, including over a network of such heterogeneous platforms).

The system can be used for modelling, Identification, control, optimisation and prediction of foreign exchange, commodity and other financial market transactions, for the purpose of reducing trading risk and/or maximising profit on trades. This includes analysis of the dynamics of commodity-based markets and derivatives; analysis of foreign exchange dynamics, including capital flows in and out of currencies; the use of models that reject the Efficient Markets Hypothesis; and the modelling of transient trading dynamics ("market sentiment") and its effects on trading strategies currently being implemented in the market. It includes analysis of dynamic risks affecting financial markets, including financial failure of banks and other trading entities. It includes validation of existing quantitative models of financial market dynamics and generation of new models and tools based on available time-series data. This also includes all applications of current quantitative modelling of dynamical processes in financial markets, including those either modelled by stochastic differential equations (e.g. Wilmott, Howison and Dewynn (1995)) or for which neural networks or fuzzy logic are currently being used as analytical tools.

The system can be used for geological/geodynamic modelling of oil, natural gas and other hydrocarbon fluids for purposes of exploration, extraction and production (e.g. Monteiro (2012)). This includes estimation of hydrocarbon fluid dynamics passing through geological strata as a result of pumping or other human-induced intervention, based on response to seismic imaging or other imaging modalities, including changes in these dynamics due to feedback control of the physical parameters of these hydrocarbons (such as viscosity and friction) and/or of the geological strata (such as permeability) caused by reinjection of carbon dioxide, hydraulic fracturing fluids ('fracking compounds'), fines or similar (e.g. Zeinijahromi (2012)).

This includes adaptive feedback control of oil or natural gas pumps, based on these estimates of dynamics and associated physical attributes (volume, density, viscosity, $CO_2$ content etc.).

More generally the system can be used for modelling, Identification and control of the flow of fluids (fluid dynamics, transport of fluids) and transport of fluids and particulate solids with fluid characteristics (e.g. dynamics of discrete-element models of particulate solid flow and particle transport systems, including analysis and transport of slurries, soil, rock or mined ores), including optimisation of pipe design and closed-loop pump controllers.

The system can also be used for modelling, Identification and adaptive control of the dynamics of plasma behaviour and plasma confinement, including for the purposes of power generation through fusion, for example based on the Vlasov equation, which is a differential equation describing time evolution of the distribution function of plasma consisting of charged particles with long-range interactions, as well as models derived therefrom.

For any and all of the applications of the system listed above, the application includes using the system to optimise the placement and allocation of (typically constrained) sensors and associated sensing or signal-processing resources to generate the time-series measurements to be used for the modelling, Identification and feedback control of the underlying dynamics.

For any and all of the applications of the system listed above, the application typically includes implementations either for human decision-support (e.g. human-in-the-loop control) or for independent autonomous closed-loop action.

The system can be used for other applications for which any one of a conventional GA, neural networks or fuzzy logic is known to be suitable.

The above described system utilises a DE formulation, which is relevant to dynamical systems that are:

Already expressed in DE format;
Expressed as well-recognised alternative formulations convertible to DE format (e.g. ODEs, suitably-behaved PDEs, etc.); or
Not initially expressed in a DE formulation but convertible to such (or have their key processes or features reducible to such), e.g.
Dynamical processes (such as agent-based systems) navigating through a network of nodes and arcs;
Algorithms executing via one or more logic trees,
Combinatorial processes,
Cellular automata, etc.

The Model Identifier

Examples of the Identification Mechanisms used by the Model Identifier, and in particular the Evolving Identification using φ-Textured Evolutionary Algorithms (φ-TEA) and Circuits Constructed therefrom will now be described in more detail.

As previously described the system uses φ-Textured Evolutionary Algorithms (φ-TEA) and Modified Genetic Algorithms (MGA) for Identification of complex systems using partial (i.e. incomplete, typically noise-polluted) information. Identifiers built on these algorithms shall be referred to as Evolving Identifiers for the purpose of description.

Some of the key features of the Model Identifier are described below.

EA Interpretation

The Model Identifier uses an interpretation of evolutionary algorithms when reconstructing real-world (physical or biological) dynamical systems from incomplete and/or noise-polluted information. In effect, the Model Identifier uses evolutionary algorithms to reconstruct dynamical systems from incomplete and/or noise-polluted information, which is an exercise analogous to classical mathematical analysis, using heuristic methods to approximate the Inverse Function Theorem (IFT).

In the case of sufficiently limited or polluted information, it is generally understood that reconstructed dynamical structures (by any methods) will be non-unique. Many of these non-unique candidates will be false: i.e. if used, they will correctly match $\{u(t_i)\}_{i=0}^{P}$ with $\{y(t_i)\}_{i=0}^{Q}$, but do not correspond with actual values of the physical or biological system being studied. However, the Model Identifier asserts and exploits the fact that non-chaotic real-world dynamical systems must enjoy an additional feature, namely stability within at least small local neighbourhoods of their actual parameter values, given that parameters actually typically undergo some variation in value (with the notable exception of fundamental constants such as the reduced Planck constant $\hbar$, $\pi$, the speed of light c etc.). When modelling dynamical systems, parameters are typically designated as such, not because they are absolutely constant, but because these variations are much smaller in scale and/or happen on a very different timescale than the behaviour associated with variables.

Consequently, one way of distinguishing between estimates of parameter values that are likely to be physically realistic versus unrealistic ones, for dynamical systems that are far from a stability transition threshold (e.g. transition from non-chaotic to chaotic behaviour) is to look for clustering of estimated vectors in stable sets. If, in parameter space Λ, estimates of a particular combination of parameter values (called here a configuration) are dynamically stable within a finite neighbourhood of those values, then this will be emphasised by a heuristic system such as a GA, which will cause clusters of estimates to form gradually around such stable configurations. For a sufficiently large number of chromosomes evolving over a sufficiently large number of generations, this approach causes finite approximations of what classical analysis calls points of accumulation to form around stable configuration vectors in $\Lambda$.

Compared with conventional methods this phenomenon is weakest in linear systems, where unknown parts of underdetermined dynamical systems resolve as contiguous segments of linear parameterisations. The more nonlinear the dynamical system, the more the inverse-mapped domains under the IFT become topologically disconnected, and hence the more effectively the $\varphi$-TEA technique operates, generating clusters of points around isolated stable configuration vectors. In contrast, conventional methods of linearised Identification are most effective in linear or quasi-linear systems and rapidly become ineffective as the dynamics become increasingly nonlinear.

Consequently, the Model Identifier operates in a fundamentally different way to conventional quasi-linear techniques. In particular, given that actual physical or biological dynamical systems are typically nonlinear, conventional Identification processes rely on linear or near-linear approximation in modelling the system. These approximations are typically valid for some local domain(s) $\Delta_{lin} \times \Lambda_{lin} \subset \Delta \times \Lambda$ (the Cartesian product of state-space and parameter space). Identification is then performed, constructing the appropriate parameter values for this near-linear model within $\Delta_{lin} \times \Lambda_{lin}$. Stability analysis is then required outside $\Delta_{lin} \times \Lambda_{lin}$, to explore how rapidly this near-linear model becomes invalid or linear control of it becomes unstable. In contrast, the Model Identifier embraces nonlinearity: the presence of nonlinear terms and highly-coupled dynamics assists the operation of the $\varphi$-TEA process. Consequently when $\varphi$-TEA Identification is performed on physical or biological systems, linear or near-linear approximations are actively shunned wherever possible. Increasingly-accurate nonlinear models of nonlinear systems enhance the effectiveness of the Identification process, enabling a novel, constructive feedback process between Identification and construction of increasingly complex models $\mathfrak{M}$.

Combined with the system's use of Lyapunov methods to generate nonlinear control laws, this approach provides a stable, robust framework for nonlinear adaptive Identification and Control, typically over much larger domains than $\Delta_{lin} \times \Lambda_{lin}$.

This clustering behaviour can be exploited in two main ways, including by searching for where such clustering occurs, identifying promising configurations for further analysis and, when no such clustering occurs, using this as a machine-decidable criterion. The criterion can be used to change the specifications of the parameter hypercube $\Lambda$ (which is formed by the search intervals for each parameter), as the existing search intervals have been ineffective in generating physically-plausible behaviour (even when non-empty candidates have been found). Performed repeatedly, this constitutes the basis of a search algorithm for such clusters. Alternatively, in the event that no or inadequate clustering behaviour is observed using a nonlinear model $\mathfrak{M}$ despite repeated changes to $\Lambda$ as above, the criterion can be used to decide to change the specifications for the model, as the existing $\mathfrak{M}$ is not generating physically-plausible behaviour.

Computational Machines

The Model Identifier asserts the proposition that real-world biological ecosystems are effectively computational machines for optimisation of complex systems, but conventional GAs only describe a small subset of the machinery. In this regard, although conventional GAs base their processes of heuristic optimisation on mimicking the behaviour of DNA in natural evolution, in fact the heuristic optimisation processes of actual biological evolution in vertebrates involve much more than describing the inter-generational behaviour of chromosomes. The current system aims to incorporate the other important aspects of ecosystems that enable efficient adaptive optimisation to take place.

These other aspects can include animal behaviour, of individual animals and communities of animals during the evolutionary process; the sometime existence of predators, to cull weaker animals above and beyond their inherent lack of evolutionary optimality for reproduction; and/or the structure of the environment. In this regard, conventional GAs treat the environment as simply providing the static specification against which Fitness is measured to optimise the system, whereas the current system regards the environment (more formally, the Environment, being the set of those structured aspects that affect the spatial distribution across multiple populations, transport between populations, survival, relative Fitness and reproduction of individual chromosomes and the wider populations to which they belong) as not just the eventual benchmark of success or failure but an intrinsic part of the optimisation dynamics; it is part of the algorithm, beyond the simple determination of death/survival.

A further aspect can include speciation, which utilises the emergence of patterns of difference (speciation: the emergence of patterns—on the pelt, in plumage, or other distinguishing features of a creature—that define new species and set them apart in a previously-homogenous population), and the consequent constraints imposed on breeding, as a fundamental attribute of efficient evolutionary processes. In the current system, speciation is employed to reduce the information loss associated with genetic drift in evolving populations and the effects of speciation can take one of a number of forms, such as: Speciation-imposed (gene-by-gene) constraints on heterogeneous breeding; and Speciation-imposed (whole-of-chromosome) constraints on heterogeneous breeding, imposed either by: the divergence of solution trajectories through state-space over time; and/or the spontaneous emergence of patterns across the population, caused by a pattern-generating equation.

In summary, the above described feature, in an $\varphi$-TEA typically involves at least one of the following attributes:

- One or more ecological spatial networks of multiple contemporary populations of chromosomes;
- Transfer protocols linking some of these populations, dictating the passage of chromosomes (and/or predators, in some schemes) between populations, typically based on some sort of behavioural archetype;
- Predators (either represented implicitly or explicitly) present in a population, providing an additional culling mechanism apart from that of reproductive penalties for uncompetitive Fitness;
- Modification of the geometrical and algorithmic structure of these populations and transfer protocols to maximise the efficiency of the evolutionary processes they embody; and,
- Imposition of speciation-based constraints on heterogeneous breeding (either by imposing constraints on particular genes on each chromosome, or associating values or symbols with each chromosome that constrain heterogeneous breeding).

Texturing

The system asserts that one cause of conventional GAs suffering from stagnation and instability when used to optimise complex dynamical systems is the lack of sufficient structure in the associated Fitness landscape. To address this, the system can use texturing of the Fitness landscape using concepts taken from differential game theory, creating additional structure and modifying the concept of Fitness so it is typically also dependent on the paths taken through local regions of state space by the associated solution trajectories of the dynamics being studied, rather than simply being a function of the chromosomes in parameter space (as in conventional GAs).

The use of texturing in an evolutionary context means that the basic building block of the evolutionary algorithm ceases to be simply the chromosome, and instead is the Trinity, being a combination of a mathematical model (typically with all its numerical attributes expressed in algebraic form), a chromosome (typically specifying some or all of the numerical information required to generate one or more solution trajectories from this model) and the set of solution trajectories generated from this combination of the model, the chromosome and whatever other information (e.g. noise vector) is provided for trajectory generation.

Texturing uses a number of supporting processes that are also themselves additions to standard GA, including the Event History and Event Predicates. These supporting processes can also be used in non-textured GA.

Sequential Networks

Extension of the above to sequential networks with various topological structures (simple chain, torus etc.), where these networks can represent different kinds of sequential analysis of the system being studied.

Meta Optimisation

Introduction of an additional layer of meta-optimising algorithms, above the basic ("Base") optimising layer of φ-TEA, to improve performance and "tune" this Base Layer.

Recursion

Realising that the same processes and structures used in the φ-TEA Base Layer can also be repeated recursively in this Meta-Optimising Layer (MOL) to improve structural choices for computational efficiency. Thus the system typically has multiple layers of evolving algorithm: the chromosomes evolve within a population; the parameter values by which they evolve within populations also evolve; the rules dictating the algorithmic structure of networked populations and the way chromosomes move among them evolve. With adequate computing power, even the structure of the meta-optimising layer can be made to evolve, with another meta-optimising layer above it. Even this additional MOL can be made to evolve recursively; and so on.

Although that may appear to suggest this sequence would be infinite, a further design feature of the system is the allocation of modifiable information in each layer, so that there is typically less modifiable information in each successive MOL than in the layer beneath it. More formally: given K+1 layers in a φ-TEA, viz. one Base Layer and $K \in \mathbb{N}$ Meta-Optimising Layers, then there exists some layer η, $1 \leq \eta \leq K$, such that each layer above this layer typically contains less modifiable information than does the layer immediately beneath it. This imposes a finite termination to this algorithmic structure, so the system is closed. In actual implementation, constraints on available computational resources also impose a practical limit on the recursive structure.)

The design, construction and placement of Texture sets (including target sets, anti-target sets, Lyapunov functions and general patterning contours in state space) are algorithmic, hence are typically encoded in the MOL as machine-executable processes and heuristically optimised.

The MOL is typically used, not only for algorithm optimisation, but also to inform placement and use of physical assets required to generate the data sets used by the Identifier. This includes optimising the placement of constrained sensor resources required for generating time-series data for Identification, that is in some sense optimal (including Identification resulting in least-error between observed and predicted data; or least-time to perform Identification to within an acceptable accuracy; or least-cost, where different combinations of sensors have different costs; or Identification that generates the most valuable information in terms of reducing operating costs or risks). In this context modifying the sensor resources is typically performed to optimise at least one of (a) explicit parameter estimation, (b) observing changes in configurations of combinations of parameter gene values (where individual parameter values can't be reliably estimated, but combinations can, as the actual values of these underlying parameters change), or (c) choosing sensors that enable best information for the computation of control strategies. This includes scenarios where sensors resources are constrained by number or are mutually-exclusive (e.g. can have a limited number of RF-transmitting sensors without mutual interference of signal).

Model Library

As well as invoking a library of existing mathematical models $\mathfrak{M}_j$, $j \in \{1, \ldots, M\}$, additional features in the system alternatively use distributed machine intelligence to generate new models.

This is done using a variant of Ant Logic using sub-models, combined with φ-TEA or MGA or GA, in what is dubbed Textured Evolutionary Ant (TEa) Programming, to construct new models from known sub-models; or encoding model components as genes again in a chromosome format, called "model chromosomes" (M-chromosomes) and using a further implementation of φ-TEA, MGA or GA to find the best-fitting candidate models from these M-chromosomes.

Accordingly, the above described features can be used to construct complex EAs. In this regard, any form of evolutionary algorithm that uses texturing and uses mathematical interpretation of evolutionary algorithms when reconstructing real-world (physical or biological) dynamical systems from incomplete and/or noise-polluted information is described as a φ-Textured Evolutionary Algorithm (φ-TEA). Other forms of modified GA are referred to as a Modified Genetic Algorithm (MGA).

The system uses a self-evolving algorithm tasked to achieve efficient Identification of complex dynamical systems when running on an appropriate computing architecture. It forms part of a larger novel machine-intelligent algorithmic structure, including being interfaced to other algorithms (the Game against Nature) in order to handle residual uncertainties (including abandoning the need for unique solutions) when controlling a complex system in the presence of significant uncertainty and a possible hostile adversary. This larger machine-intelligent structure can itself be described in terms of an encoding of φ-TEA chromosomes, and so the recursive evolutionary processes can again be applied at the largest scales of the algorithm to optimise it.

Building the necessary mathematical concepts step-by-step requires taking these points in a different order to the list given above.

Baseline: Conventional Genetic Algorithm (GA) Theory as Applied to Identification The following begins by outlining the basic theory of conventional genetic algorithms (GAs) as demonstrated when applied to our task of performing Identification of a set of ODEs, using incomplete information, and then explain the novel and inventive features we have added to this concept, transforming it into a new form of heuristic evolutionary algorithm.

Given the complex system described above, composed of a set of (unknown) ODEs with a natural noise vector:

$$\dot{x}_i = f_i(x(t), \beta, u(t), w(t));$$

This system possibly also has additional constraints that it must obey:

$$\phi_l(x(t), \beta) \leq k_l, l \in \{1, \ldots, S\},$$

for some integer S; some constants $k_l \in \mathbb{R}$. The parameter vector $\beta = (\beta_1, \ldots, \beta_m)^T$ includes not only the parameters that appear explicitly in the ODEs but also initial conditions $x_i(0)$ for the state variables $x_i(t)$ if not:
i. Otherwise known or externally imposed, or
ii. Specified by other parameter values in the equations.

This system is approximated by a known model $\dot{\xi} = f_{\mathfrak{M}}(\xi(t), \lambda, u(t), \lambda, \omega(t), t)$, where $\omega(t)$ denotes the bounded model noise $(0 \leq \|\omega(t)\| < w_\delta < \infty)$.

This system is to undergo the Identification process as specified in the previous section: some or all of the components $\beta_j$ are unknown; some of the state variables $x_i(t)$ may not be directly observable. Using the known system inputs (written as a sequence of values of control variables $\{u(t_i)\}_{i=0}^P$) and measured system outputs (thus measurements of the system "output" are being used as part of the Identifier "input") $\{y(t_i)\}_{i=0}^Q$ as input data for the Identifier, there is a need to reconstruct one or more parameter estimates $\lambda$ for the entire parameter vector $\beta = (\beta_1, \ldots, \beta_m)^T$ and reconstruct state variable estimates $\xi_i(t)$ for the unobserved $x_i(t)$, so that successful Identification is achieved. The optimal solution is a set of estimates $\{\lambda, \xi(t)\}$ such that Identification is achieved for extremely small $\varepsilon_{track} > 0$.

It should be noted that although this general specification of the φ-TEA Evolving Identifier describes taking the observable outputs of a dynamical system $\{y(t_i)\}_{i=0}^Q$ and comparing them to a sequence of known values of the system inputs—control variables $\{u(t_i)\}_{i=0}^P$—in fact the φ-TEA Evolving Identifier can operate under circumstances where one or more of the system input sequences are initially completely unknown or are poorly-known (i.e. are extremely noise-polluted).

Without loss of generality, it is assumed for the sake of elucidation that a single system input $\{u(t_i)\}_{i=0}^P$ is unknown or poorly-known. Depending on the structure of this unknown system input, under this circumstance this input would be removed from the vector-valued sequence $\{u(t_i)\}_{i=0}^P$ and either:

Be modelled as an unknown state variable $x_0(t)$ of the system dynamics, where) $\dot{x}_0 = f_0(x_0(t), \beta, u(t), w(t), t)$, the dimension of x(t) I s increased by one and the dimensions of β and λ are enlarged to include parameters for the dynamics of this initially-unknown variable, or else Be modelled as a sequence of unknown parameters $\{\beta_{0i}\}_{i=0}^P$, where each parameter lies within a known interval $\beta_{0i} \in [\beta_{0i}^-, \beta_{0i}^+]$.

Such an approach would generate significant residual uncertainties in the Identification process. These uncertainties can be handled by a number of available methods, typically including at least one of the components of the system, including:
Downstream disambiguation through Active Modulation and/or
The Game against Nature.

A Genetic Algorithm (GA) is a well-known heuristic technique for numerically finding the optimum (or approximate optimum) configuration of a constrained but complicated system, where that system typically has a large number of combinations of possible values for its component parts.

Figure 9A:
FIG. 9A is a schematic diagram of an example of a Genetic Algorithm (GA) chromosome.

GAs work by mimicking evolution at a chromosomal scale. Each parameter of a system being studied is expressed using a string of symbols (typically, although not always, a binary encoding using bits), corresponding to a "gene". These m genes are concatenated to form "chromosomes", an example of which is shown in FIG. 9A. A given chromosome $\bar{c}$ is in effect a sequence of genes $\{\gamma_j\}_{j=1}^m$, each gene corresponding to a particular estimate for the value of each component parameter; so the $j^{th}$ gene on $\bar{c}$ corresponds to a real number $\gamma_j$ that is a candidate value for a parameter in the system being studied.

A GA typically comprises a population $N > 0$ of distinct chromosomes, $\{\bar{c}_1, \ldots, \bar{c}_N\}$. These chromosomes are trying to survive in an Environment. Given that it is not known a priori the optimal (or approximately optimal) configuration values of the constrained but complicated system being studied, this is dealt with as follows: the Environment is defined in such a way that it will reward near-optimal configurations with survival in the next generation; the closer to optimality, the better the reward (the stronger the configuration's representation in the next generation). The GA then tries to evolve appropriate chromosomes that flourish in this Environment.

This is one of the strengths of GAs, namely that if it is known what optimal configurations of a complex system do, but not know what the values of such optimal configurations are, a GA can be used to exploit the knowledge of how optimal solutions behave to try to find some. For example, in trying to find the complicated combinations of parameters of a carbon lattice so that it forms a diamond: it is not known what all the combinations of parameter values are that are required to turn carbon into diamond, but it is known that a diamond is a transparent crystal. By rewarding transparency, a GA uses this fact to try to modify the parameter values of simulated carbon lattices in various ways in an effort to find combinations leading to a transparent crystal being formed. These successful final combinations are good candidates for being diamonds.

The way this aspect of a GA works: associated with each chromosome is the concept of Fitness (i.e. a quantitative measure of how well that particular combination of genes $\{\gamma_j\}_{j=1}^m$ produces behaviour adapted to the Environment's constraints and hence approximating the behaviour of our desired solution). Fitness is written as a function imposed on each chromosome, $F: \bar{c} \mapsto [0, \infty)$. The better the Fitness of a chromosome, the more likely it is to survive to the next generation and propagate its genes into the future, so high-Fitness chromosomes gradually dominate the gene pool.

When two GA chromosomes combine to produce the next generation, this is typically done by cutting each chromosome somewhere along its length and swapping the remaining genetic material with its partner to produce a new pair of chromosomes. The likely position of this cutting point along the chromosomes is determined using the Crossover Probability $P_C \in [0, 1]$ associated with the Environment). Genes may also randomly mutate (due to a Mutation Probability $P_M \in [0, 1]$ associated with the Environment).

This method of mimicking evolution is actually a fairly efficient method of seeking suitable solutions of complex mathematical systems (not surprisingly, given that the real world has been using it to evolve appropriate life forms to match environments for billions of years).

Applying a conventional GA approach to the Identifier example above and assuming the structure for the model dynamics $f_{\mathfrak{M}}$ is known, then finding the optimal solution to the constrained system corresponds to estimating sufficiently closely the (effectively) constant vector $\beta = (\beta_1, \ldots, \beta_m)^T$ of parameter values. This will also enable estimation of the associated state vector $\xi(t)$ for the solution trajectory generated by the dynamics of $f_{\mathfrak{M}}$ under the parameters $\beta$.

In this case, each chromosome has its sequence of gene values $\{\gamma_j\}_{j=1}^m$ made equivalent to a vector $\lambda = (\lambda_1, \ldots, \lambda_m)^T$, $\lambda_j \equiv \gamma_j \forall_j$, where each gene value has some specified range, $\lambda_j \in [\lambda_j^-, \lambda_j^+]$, corresponding to the range of possible values that can be carried by that gene. (To avoid confusion, for the rest of this specification the gene notation $\{\gamma_j\}_{j=1}^m$ will be suppressed in favour of the parameter vector $\lambda = (\lambda_1, \ldots, \lambda_m)^T$). The chromosome structure is designed to ensure that the range $[\lambda_j^-, \lambda_j^+]$ describable for each gene is sufficiently wide that each (initially unknown) value $\beta_j \in [\lambda_j^-, \lambda_j^+]$, $j \in \{1, \ldots m\}$, i.e. the correct value can be represented on the gene interval. (In real-world applications this plausible interval is typically easy to determine, even when the actual parameter value is unknown.) Then each $\lambda_j$ estimates $\beta_j$, $j \in \{1, \ldots m\}$ and each chromosome's $\lambda$ is used to estimate $\beta$.

The Fitness of each chromosome $\bar{c}_i$ is high when the solution trajectories $\xi(t) = \varphi_{\mathfrak{M}}(\xi(0), \lambda_i, \omega(t), t) | t \in [t_0, t_f]$ generated by the $\lambda_i (\equiv \bar{c})$ have a low tracking error $\varepsilon_{track}$ with respect to the measured data $\{y(t_i)\}_{i=0}^Q$, and the Fitness is low when these solution trajectories have a high tracking error $\varepsilon_{track}$ with respect to the measured data $\{y(t_i)\}_{i=0}^Q$.

Given that each chromosome $\bar{c}_i$ is equivalent to a vector $\lambda_i \in \Lambda = [\lambda_1^-, \lambda_1^+] \times \ldots \times [\lambda_1^-, \lambda_1^+]$ the Fitness can be written as $F: \lambda \mapsto [0, \infty)$ or $F(\lambda)$.

Figure 9B:
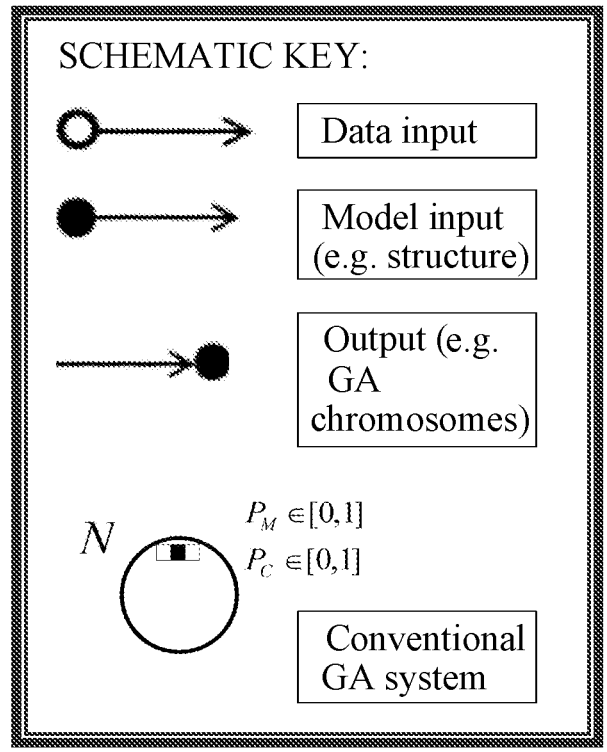
FIG. 9B is a schematic diagram of an example of a basic key for symbols of subsequent Figures.

For the ease of explanation, particularly when describing the construction of networks of populations of Trinities as part of more sophisticated structures, schematic diagrams will be used. More formally, these are not merely networks, but in the language of Graph Theory they are directed graphs, composed of components operating sequentially on sets of chromosomes; referred to as chromosome circuits. Given that the concepts to be discussed should not be confused with those in conventional systems theory flowcharts, new symbols are adopted and a key of the symbols is shown in FIG. 9B.

Figures 9C, 9D:
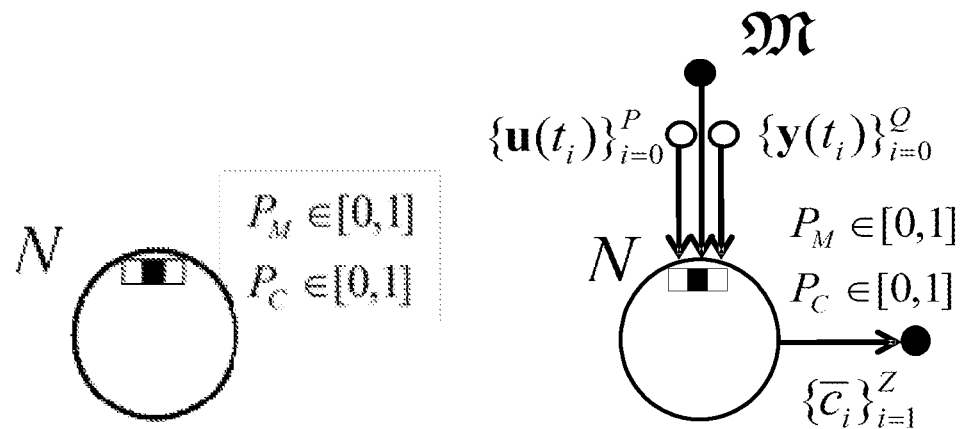
FIG. 9C is a schematic diagram of an example of a symbol to denote a system analogous to a conventional GA system.
FIG. 9D is a schematic diagram of an example of a symbol to denote a system analogous to a conventional GA as applied to an Identification problem.

A population of Trinities undergoing an evolutionary process resembling a conventional GA system is depicted as shown in FIG. 9C, with a population of N chromosomes, Mutation Probability $P_M$ and Crossover Probability $P_C$.

Applying a conventional GA to the problem of Identification using some model $\mathfrak{M}$, the data input and the output of the resulting final generation of acceptable chromosomes $\{\bar{c}_i\}_{i=1}^Z$ corresponding with solution estimates ($\lambda$, approximating $\beta$) is depicted as shown in FIG. 9D, where $Z \leq N$.

Telomeres

A feature of the current system which is distinct from conventional GAs is that Identification-relevant performance data can be appended to the end of the relevant chromosome $\bar{c}_i(g)$ in the form of inert additional "genes" that are not susceptible to mutation, are not involved in breeding and their values are not typically passed on to the next generation. For the purpose of explanation, these genes are referred to as "telomeres", denoted $\tau_1, \ldots, \tau_{m_\tau}$, some $m_\tau \in \mathbb{N}$. The telomeres are appended to the end of each chromosome, with the values of the telomere genes being specific to each individual chromosome and being recalculated in each generation.

Such performance data typically includes an error, the associated Fitness $F(\lambda)$ and other relevant performance data, as desired, such as the component errors $\varepsilon_j > 0$ for variables of particular interest.

The error $\varepsilon_{track}$ is associated with how the associated model solution trajectory $\xi(t) = \varphi_{\mathfrak{M}}(\xi(0), \lambda_i, w(t), t) | t \in [t_0, t_f]$ tracks the measured data $\{y(t_k)\}_{k=0}^Q$. This is defined to be $$\varepsilon_{track} \triangleq \max_j \varepsilon_j,$$

where each component error $\varepsilon_j > 0$ for the $j^{th}$ measured variable $y_j(t)$ is defined such that:

$$\|y_j(t_k) - \xi_j(t_k)\| < \varepsilon_j \forall k \in \{0, \ldots, Q\}$$

where the measured variable $y_j(t)$ corresponds directly with a predicted state variable $\xi_j(t)$, and/or $$\|y_j(t_k) - \lambda_j(t_k)\| < \varepsilon_j \forall k \in \{0, \ldots, Q\}$$

where the measured variable $y_j(t)$ corresponds directly with a predicted parameter value $\lambda_j(t)$, and/or $$\|y_j(t_k) - g_j(\xi(t_k), \eta, u(t_k), \omega(t_k) t_k)\| < \varepsilon_j \forall k \in \{0, \ldots, Q\}, \|\omega(t)\| < w_\delta < \infty$$

where the measured variable $y_j(t)$ corresponds with some function of the predicted state vector $\xi(t)$ and $\eta$ is a parametric vector associated with the function $g_j$, such that $g_j(\xi(t_k), \eta, u(t_k), \omega(t_k), t_k)$ is intended to predict $y_j(t_k)$ (subject to the simulated noise $\omega(t_k)$).

Each piece of data is typically encoded onto its own specific telomere gene $\tau_1, \ldots, \tau_{m_\tau}$. The values of the telomere genes report relevant performance data associated with each chromosome for the purposes of computational efficiency and are not otherwise involved in the evolutionary processes of the evolutionary algorithms. Consequently in the context of an evolutionary algorithm it is possible to write $\bar{c}_i(g) \equiv \lambda_i$ (the equivalence of a chromosome and the parameter vector encoded on it) despite the presence on the chromosome of these additional non-parametric genes.

Gene-Based Speciation Constraint

In conventional GAs, mutation and other genetic variations among chromosomes typically do not constrain the ability of chromosomes to breed; the only constraint on breeding is typically competitive Fitness. This is in stark contrast to biological reality, where the phenomenon of speciation (the spontaneous emergence of distinct, divers species from a hitherto-homogenous population) constrains the ability of such species (represented by sufficiently-distinct chromosomes) to breed heterogeneously.

In biological populations, such constraints on heterogeneous breeding are typically analogue rather than binary. Provided key genes are sufficiently similar, other genes may be significantly different without forbidding breeding (although the probability of successful breeding producing viable offspring may be diminished). For example, the modern polar bear appears to be the result of heterogeneous breeding between the ancestral polar bear and the Irish brown bear in the last Ice Age, under conditions of adversity. However if these key genes are sufficiently distant, heterogeneous breeding is impossible (e.g. polar bears and seagulls will never breed, regardless of adversity).

In the current system, constraints imposed by such speciation can be expressed using a speciation vector $\Sigma \triangleq [\sigma_1, \ldots, \sigma_m]^T$, where $\sigma_k \in [0, 1] \forall k \in \{1, \ldots, m\}$ are speciation weights, one corresponding to each gene on the chromosome.

Assuming that all genes have as their values elements of compact intervals, such that the parameter vector associated with the chromosome is given by $\bar{c} \equiv \lambda \in \Lambda = [\lambda_1^-, \lambda_1^+] \times \ldots \times [\lambda_m^-, \lambda_m^+]$, then the speciation weights are interpreted as follows. Given the chromosomes $\bar{c}_i = (\lambda_{i1}, \ldots, \lambda_{im})^T$, $\bar{c}_j = (\lambda_{j1}, \ldots, \lambda_{jm})^T$, then a necessary (although typically, not sufficient) condition for these chromosomes to breed is the gene-based speciation constraint, namely $$\|\lambda_{jk} - \lambda_{ik}\| \leq \sigma_k \|\lambda_k^+ - \lambda_k^-\| \forall k \in \{1, \ldots, m\}.$$

Then it follows that a speciation vector composed entirely of unity-valued speciation weights $$\Sigma = [\underbrace{1, \ldots, 1}_{m}]^T = 1$$

refers to the case where speciation constraints impose no effective additional constraints on the evolutionary algorithm; breeding is as per a conventional GA on $\Lambda$.

Conversely, a speciation vector composed entirely of zero-valued speciation weights $$\Sigma = [\underbrace{0, \ldots, 0}_{m}]^T = 0$$

refers to me case where speciation constraints impose the requirement that only identical chromosomes can breed.

Typically a speciation vector will have its component weights take divers values, so for heterogeneous chromosomes to breed, these weights may specify that the genes on some positions along the chromosomes may need to be almost identical, while other genes on the chromosome may have no effective speciation constraint, or must satisfy some speciation constraint between these two extremes, i.e. for some genes, the values need to lie within some neighbourhood of each other:

$$\|\lambda_{jk} - \lambda_{ik}\| \leq \sigma_k \|\lambda_k^+ - \lambda_k^-\|, \sigma_k \in (0,1).$$

The above represents the deterministic gene-based speciation constraint. An alternative form is the stochastic gene-based speciation constraint, which imposes an envelope on the probability of heterogeneous breeding. In the case of $\|\lambda_{jk} - \lambda_{ik}\| \leq \sigma_k \|\lambda_k^+ - \lambda_k^-\|$, the probability of heterogeneous breeding is simply that of the chromosomes without any gene-based speciation constraint; however, in the case of $\|\lambda_{jk} - \lambda_{ik}\| > \sigma_k \|\lambda_k^+ - \lambda_k^-\|$ this probability is significantly reduced.

Implementation of a speciation vector, when used in the current system $\|\lambda_{jk} - \lambda_{ik}\| \leq \sigma_k \|\lambda_k^+ - \lambda_k^-\|$, $\sigma_k \in (0,1)$, typically involves $\Sigma \triangleq [\sigma_1, \ldots, \sigma_m]^T$ being designed for a population either manually or algorithmically.

When performed manually, the weights $\sigma_k \in [0,1] \forall k \in \{1, \ldots, m\}$ are manually specified for each gene position on the chromosome for the evolutionary algorithm. In contrast, when performed algorithmically, a process is applied to calculate a speciation vector $\Sigma \triangleq [\sigma_1, \ldots, \sigma_m]^T$ that is in some sense computationally optimal for the evolutionary algorithm across its generations. In this regard, optimal is taken to enable at least one of:

Successful performance of the Identification task to the desired accuracy in least time;
Successful performance of the Identification task to the desired accuracy with minimum computational resources;
Maximally stable evolutionary algorithm computations while performing the Identification task;
Minimized information loss associated with genetic drift in the evolutionary algorithm across generations while performing the Identification task; etc.

In the case where the speciation vector is designed algorithmically, this is typically performed using a patterning algorithm to generate a pattern or waveform of values on the unit interval [0,1]. Typically a pattern-forming equation or equations of one of the following types is used to generate a pattern under specified parameter values (initially either manually or randomly chosen):

Reaction-diffusion equations, e.g. applying the equation associated with any one of the following one-component systems: the Kolmogorov-Petrovsky-Piskounov equation, Fisher's equation, the Newell-Whitehead-Segel equation, Fick's second law of diffusion, the Zeldovitch equation, or similar; or Applying the equations associated with a two-component system, such as those associated with Turing's own study on the chemical basis of morphogenesis, or the Fitzhugh-Nagumo equations or similar, or Applying related published articles in patterning equations, e.g. applying the Swift Hohenberg equation.

Following this the pattern is mapped to one dimension, typically by either restricting the diffusion equations to one dimension, or by taking a linear cross-section of a higher-dimensional pattern. This one-dimensional form of the pattern is then sampled at m uniformly-spaced locations, so that each $\sigma_k \in [0,1]$, $k \in \{1, \ldots, m\}$ takes a value sampled from its corresponding $k^{th}$ location along this line.

The evolutionary algorithm proceeds to operate, under this speciation vector $\Sigma \triangleq [\sigma_1, \ldots, \sigma_m]^T$ imposing the gene-based speciation constraint upon heterogeneous breeding in each generation. In the case of a time-varying pattern, the time variable with respect to the pattern can be mapped to the generations $\{1, \ldots, g^+\}$ and this sampling can be repeated for each generation, so $\Sigma = \Sigma(g)$.

The structure, terms and parameter values of such pattern-forming equations are then optimised, either sequentially over successive generations within a single evolutionary algorithm population; or in parallel among evolutionary algorithm populations; as above, but using a Meta-Optimising Layer (introduced later); or to achieve a computationally optimal outcome as above.

Endowing an Evolutionary Algorithm with Memory: The Event History

The system also includes an Event History, denoted E. The event history is a memory structure, administered by a subroutine or script in the algorithm running during the evolutionary algorithm's evolutionary process, that endows the evolutionary algorithm with a memory of current and previous data (other than is encoded by the current chromosomes and Fitness) generated during the evolution. This is in contrast to conventional GAs, for which all relevant information is typically encoded in the chromosomes (and which are typically otherwise memoryless).

The Event History's attributes are that it typically records:
In the present generation g=g*, the current chromosomes $\{\bar{c}_1(g^*), \ldots, \bar{c}_N(g^*)\}$;
In the present generation g=g*, the paths of the solution trajectories $\xi(t) = \mathscr{P}_{\mathfrak{M}}(\xi(0), \lambda_i, \omega(t), t) | t \in [t_0, t_f]$ corresponding with these chromosomes of the current generation $\{\bar{c}_1(g^*), \ldots, \bar{c}_N(g^*)\}$ where $\lambda_i \equiv \bar{c}_i(g^*)$; and
Interactions such trajectories have with designated sets (targets, anti-targets, avoidance sets and level sets/ contours) in state space Δ, and the individual chromosome $\bar{c}_i(g^*)$ corresponding with the trajectory that has the interaction.

The Event History may also record other events of a population, such as whether the previous generation's solution trajectories interacted with designated sets (targets, anti-targets, avoidance sets and level sets/contours, discussed below) in state space, and what proportion of these trajectories had this interaction; the actual chromosomes $\bar{c}_i(g^*-1)$ corresponding with the trajectories that had these interactions; the summed Fitness (including the Textured Fitness discussed below) across all chromosomes of a generation, for each generation $g \in [1, g^*]$; or other events in generations in the history interval $[1, g^*]$, including introduction of new target/anti-target sets, introduction of predation schemes, re-scaling or deformation of target sets or contours of Lyapunov functions, extinction events, etc.

The Event History continues to record events until the final generation $g=g^+$ is reached, so by the time the evolutionary algorithm concludes its computation, the Event History has typically recorded relevant events for all generations $g \in [1, g^+]$.

Figure 9E:
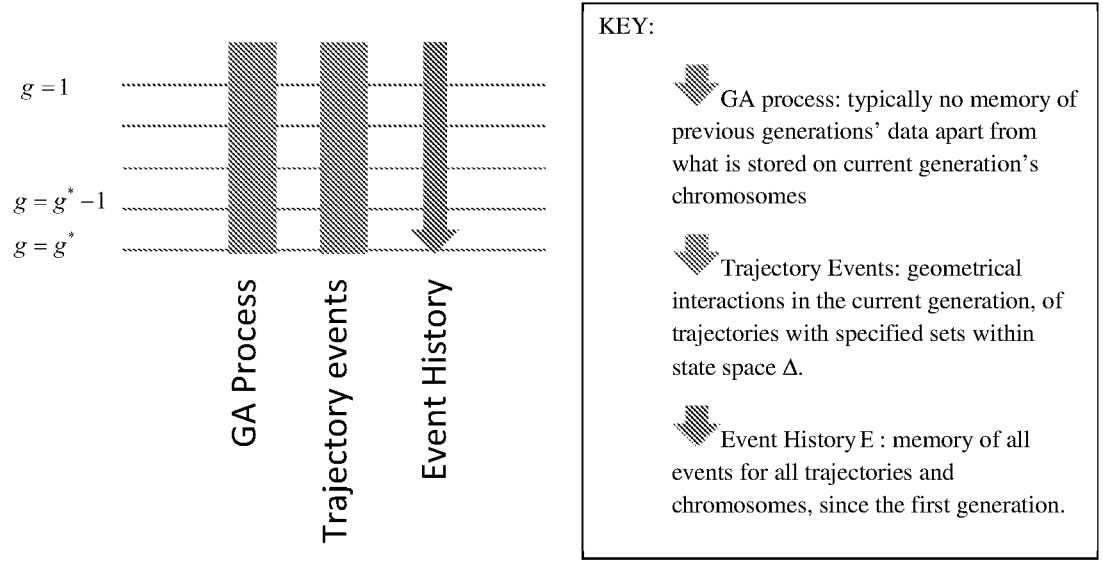
FIG. 9E is a schematic diagram of an example of three component processes across generations that are used to construct textured Fitness.

A diagram showing the three component processes across the generations that are used by the Evolving Identifier to construct textured Fitness: the Genetic Algorithm (green), that typically has no memory apart from what is stored in the current generation's chromosomes; the associated Trajectory Events (orange), where, given the trajectories flowing through state space Δ, each corresponding with a chromosome in the current generation, these events are the geometrical interactions these trajectories have with specified sets in Δ; and the Event History (pink), that records all events in the other two processes across the generations, is shown in FIG. 9E.

Acting Upon Memory: The Event Predicates

The system also uses a script or subroutine, running throughout the execution of the evolutionary algorithm, which externally modifies the Fitness of specific chromosomes (referred to as "textures the Fitness") based on a logical analysis of its history, in a way that is distinct from a GA's usual calculations of Fitness.

In this regard, the Event Predicates $\mathfrak{E}$ is an ordered set composed of logical propositions and set theory, typically expressed in terms of combinations of possible events in the Event History that may befall a solution trajectory. The actual Event History E records what events have actually occurred for each trajectory corresponding with each chromosome $\bar{c}_i(g)$. By passing any given generation of chromosomes $\{\bar{c}_i(g)\}_{i=1}^N$ and Event History through the Event Predicates, the Fitness of each individual chromosome may be externally modified depending on whether its solution trajectory's history satisfies one or more predicates in $\mathfrak{E}$.

The motivation for doing this is explained below. In the rest of this description $\mathfrak{E}$ and E will seldom be referred to explicitly, although they provide the mechanism whereby Fitness is textured for a chromosome based on the behaviour of its trajectory.

As well as being used for texturing, $\mathfrak{E}$ is also used for deciding whether to impose constraints on breeding, typically as an alternative to applying Texture when the summed Fitness (defined later) is stagnating.

Augmenting Fitness with Texture

In the context of the Identification task, the Fitness function of a GA can be viewed as imposing contour maps (or level sets) on the parametric hypercube $\Lambda = [\lambda_1^-, \lambda_1^+] \times \ldots \times [\lambda_m^-, \lambda_m^+]$; for any parameter vector $\lambda \in \Lambda$ corresponding with a chromosome $\bar{c}$ we can write $F(\lambda) \in [0, \infty)$. A key problem encountered with applying conventional GAs to the Identification task is that on models above a certain threshold of complexity, Fitness typically does not continue to improve indefinitely; stagnation emerges, whereby chromosomes survive without improving (and in fact typically deteriorate).

One solution to this issue is to transform the concept of Fitness. In conventional GAs the Fitness is purely a function of the chromosome $\bar{c}$, which is equivalent to some $\lambda \in \Lambda$. In contrast, in the current system, the concept of Fitness is typically modified to become also a function (implicitly or explicitly) of the local behaviour of a solution trajectory in state space associated with this chromosome, i.e. of $\xi(t) = \varphi_\mathfrak{M}(\xi(0), \lambda, \omega(t), t)$ as it passes through $\Delta \subset \mathbb{R}^n$. This modification of Fitness based on the behaviour of the solution trajectory through Δ will be referred to as Texture and this modified Fitness the Textured Fitness $F^\triangleleft$. This modification is achieved through use of the Event History and Event Predicates.

The purpose of introducing the concept of Texture is to give the evolutionary algorithm a "sense of direction" additional to the implied gradient of the Fitness, improving the way the evolutionary algorithm navigates regions of the Fitness landscape for complex dynamical systems and hence altering the rate of change of Fitness across generations. This additional sense of direction is typically defined by the behaviour of the solution trajectories flowing through local neighbourhoods within $\Delta \subset \mathbb{R}^n$.

It should be noted that this is distinct to any consideration of behaviour of the solution trajectories that might be made in calculating the initial value of the Fitness of a chromosome $\bar{c}$ and hence be used in the mapping $F: \bar{c} \mapsto [0, \infty)$. Texture on Fitness is calculated based on the interactions between trajectories (that are typically only partly determined by $\bar{c}$) and sets in Δ that are not described by $\bar{c}$ and hence are not encompassed by some mapping $F: \bar{c} \mapsto [0, \infty)$.

The use of Textured Fitness means that, in contrast to conventional GA formulations, the most general form of $F^\triangleleft$ is typically a function of the estimated state vector $\xi(t)$ and its path-dependent history (i.e. its associated solution trajectory $\varphi_\mathfrak{M}$ over $t \in [0, \infty)$) as well as of the parameter vector λ corresponding to the chromosome $\bar{c}$. Consequently the same chromosome may have different values for Textured Fitness within the same generation, if the associated solution trajectories pass through different regions of state space due to different initial conditions or effects of noise, and over successive generations, as relevant sets in Δ move and change.

In the most general case initial conditions for the solution trajectory $\xi(0)$ are not entirely determined by $\lambda \in \Lambda$ and the state equations are not autonomous over the time interval $[t_0, t_f]$, hence the Textured Fitness is defined over the domains $F^\triangleleft: \Delta \times \Lambda \times [t_0, t_f] \to \mathbb{C}_+$ (non-autonomous systems) or $F^\triangleleft: \Delta \times \Lambda \to \mathbb{C}_+$ (autonomous systems).

It should also be noted that Textured Fitness is mapped onto the positive Complex half-plane $\mathbb{C}_+$ (or similar, e.g. quaternions such that $\text{Re}(F^\triangleleft) \in [0, \infty)$) whereas conventional Fitness is typically only defined over the positive Real interval $[0, \infty)$. The meaning of the Imaginary component of Textured Fitness, $\text{Im}(F^\triangleleft)$, will be explained later.

For brevity, subsequent equations presented here will typically assume the underlying system has autonomous dynamics; extension of the equations to the non-autonomous case is straightforward.

Accordingly, in a conventional GA, Fitness, however implemented, involves a global comparison between some specified criterion and each of the chromosomes of a generation, performed in a uniform, consistent way. How well chromosomes perform in this comparison determines the probabilities of their breeding and influencing the next generation. Similarly, conventional re-scaling of Fitness among chromosomes is done by consistently applying some transformation across all chromosomes in the generation, that modifies them based on a relative ranking of the Fitness of the chromosome $\bar{c}$ with respect to the Fitness of all the other chromosomes in that generation. Thus, to a conventional GA architect it would make no sense to make further, non-global changes to the Fitness of some individual chromosomes that affect this evolutionary process, as this would interfere with optimising evolution with respect to the specified criterion.

In contrast, in the current system texture is imposed by doing precisely this: typically by further modifying the Fitness of some chromosomes differently to others, based on at least one of: local transformations typically applied to some chromosomes differently to others in the generation, and/or transformations typically applied to all chromosomes in the generation, but which are modified by external criteria other than that criterion specified for determining Fitness, and using additional information other than the parameter vectors $\lambda$ corresponding to the chromosomes $\bar{c}$, and/or the Fitness of the chromosomes. Consequently, their effects on Fitness differ across the set of all possible chromosomes.

Accordingly, although Fitness rescaling and similar transformations are already performed in conventional GAs, there is a basic difference between such transformations and the texturing of Fitness. In particular, given any pair of distinct chromosomes $\{\bar{c}_1, \bar{c}_2\}, \bar{c}_1 \neq \bar{c}_2$, such that they have equal Fitness, i.e. $F(\bar{c}_1)=F(\bar{c}_2)$, then any conventional transformation on Fitness (e.g. re-scaling) done in a conventional GA must affect these chromosomes the same way, so their transformed Fitnesses will remain equal. However, in a TEA, the fact these chromosomes are distinct means their parameter vectors occupy different neighbourhoods in $\Lambda$ and hence texturing can produce $F^{\triangleleft}(\bar{c}_1) \neq F^{\triangleleft}(\bar{c}_2)$.

More formally: there exists at least one pair of possible parameter vectors in parameter space, $\{\lambda_1, \lambda_2\} \subset \Lambda$, $\lambda_1 \neq \lambda_2$ such that for the equivalent chromosomes $\bar{c}_i \equiv \lambda_i$, $F(\bar{c}_1)=F(\bar{c}_2)$ but $F^{\triangleleft}(\bar{c}_1) \neq F^{\triangleleft}(\bar{c}_2)$, which never happens under Fitness transformations in a conventional GA. In fact, typically there exist a very large number of such pairs of possible parameter vectors $\{\lambda_1, \lambda_2\} \subset \Lambda$, $\lambda_1 \neq \lambda_2$ where for $\bar{c}_i \equiv \lambda_i$, $F(\bar{c}_1)=F(\bar{c}_2)$ but $F^{\triangleleft}(\bar{c}_1) \neq F^{\triangleleft}(\bar{c}_2)$, such that real-world implementations of TEA are functionally distinct from, and can be readily distinguished from, conventional GA.

Further specification of this: in texturing the Fitness of a chromosome $\bar{c}$, the additional information used is typically obtained from observing the behaviour of its solution trajectories $\xi(t)=\varphi_{\mathfrak{M}}(\xi(0),\lambda,\omega(t),t)$ flowing through local neighbourhoods within $\Delta \subset \mathbb{R}^n$, and the external criteria are typically how these trajectories interact with specified sets in $\Delta$. Hence further unlike Fitness in a conventional GA, the same chromosome $\bar{c}$ typically has various different values for Textured Fitness $F^{\triangleleft}(\bar{c})$, both within the same generation, if the associated solution trajectories pass through different regions of state space due to different initial conditions (where these are not wholly specified by $\bar{c}$) or effects of noise, and/or over successive generations, as relevant sets in $\Delta$ move and change.

The underlying Fitness is typically modified into Textured Fitness in a number of ways.

In a first example, this is achieved through $\varphi_{\mathfrak{M}}(\xi(0),\lambda,\omega(t),t)$ achieving one or more discretely-distributed qualitative objectives in state space, defined in terms of collision, capture or avoidance with, by, or of one or more specified sets. Qualitative behaviour by $\varphi_{\mathfrak{M}}(\xi(0),\lambda,\omega(t),t)$ with respect to specified sets in state-space is described in terms of three component forms of trajectory behaviour: collision, capture and avoidance, defined here consistent with Janislaw Skowronski (1991).

Collision: a solution trajectory is said to achieve collision at time $T_C$ with a target set $T \subset \Delta$, if $\xi(0) \in (\Delta \backslash T)$ (i.e. the complement of T in $\Delta$) and $\exists T_C \in (0,\infty)$, $\xi(T_C)=\varphi_{\mathfrak{M}}(\xi(0),\lambda,\omega(t),T_C)$ such that $\xi(T_C) \cap T \neq \emptyset$;

Capture: a solution trajectory is said to achieve capture after time $T_{CC}$ with a target set $T \subset \Delta$, if $\xi(0) \in (\Delta \backslash T)$ and $\exists T_{CC} \in (0,\infty)$, such that $\varphi_{\mathfrak{M}}(\xi(0),\lambda,\omega(t),t) \subset T \subset \Delta \forall t > T_{CC}$;

Avoidance: a solution trajectory is said to achieve avoidance before time $T_A$ of an anti-target $T' \subset \Delta$ if there exists an avoidance set $\mathbf{A} \subset \Delta$ such that $T' \subseteq \mathbf{A}$, $\xi(0) \in (\Delta \dagger \mathbf{A})$ and $\varphi_{\mathfrak{M}}(\xi(0),\lambda,\omega(t),t) \cap \mathbf{A} = \emptyset \forall t < T_A$.

These definitions are extensible to phase space and more generally to other vector spaces via some mapping $\rho$, such that $\rho(\varphi_{\mathfrak{M}}(\xi(0),\lambda,\omega(t),t))$ achieves collision, capture or avoidance with the image of the relevant set, $\rho(T)$ or $\rho(\mathbf{A})$.

These component forms of behaviour are modular and can be combined: e.g. one can have distinct non-intersecting sets $T_1 \subset \Delta$, $T_2 \subset \Delta$, $T_3 \subset \Delta$ such that $\varphi_{\mathfrak{M}}(\xi(0),\lambda,\omega(t),t)$ achieves sequential collision with $T_1$, avoidance of $T_2$ and capture of $T_3$. One can also have distinct, modular qualitative objectives, e.g. if we define (in $\mathfrak{E}$):

$Q_1$="$\varphi_m(\xi(0),\lambda,\omega(t),t)$ achieves collision with $T_1$"
$Q_2$="$\varphi_m(\xi(0),\lambda,\omega(t),t)$ achieves avoidance of $T_2$" and
$Q_3$="$\varphi_m(\xi(0),\lambda,\omega(t),t)$ achieves capture of $T_3$",
then we can define (in $\mathfrak{E}$):
$Q_{123}$="$\varphi_m(\xi(0),\lambda,\omega(t),t)$ achieves sequential collision with $T_1$, avoidance of $T_2$ and capture of $T_3$"
and $Q_{123} \in Q_1 \cap Q_2 \cap Q_3$.

Given an underlying Fitness function $F: \Lambda \to [0,\infty)$ and non-empty target sets $\{T_1, \ldots, T_a\} \in \Delta$, the Textured Fitness $F^{\triangleleft}$ encourages or penalises chromosomes $\bar{c}$ corresponding with parameter vectors $\lambda \in \Lambda$, based on whether the solution trajectory interacts with the target sets in accordance with the desired qualitative objective(s).

For example, if there exist possible targets $\{T_1, \ldots, T_a\} \subset \Delta$ and the desired qualitative objective Q in $\mathfrak{E}$ is "The solution trajectory achieves collision with a target", then:

$$G(\xi(0), \lambda, w(t)) = \begin{cases} C_T, & \text{if } Q \text{ true on } \varphi_{\mathfrak{M}}(\xi(0), \lambda, \omega(t), t) \\ \delta_T, & \text{if } Q \text{ false on } \varphi_{\mathfrak{M}}(\xi(0), \lambda, \omega(t), t) \end{cases}$$

for some weights $C_T \in (1,\infty)$, $\delta_T \in [0,1)$, and implementations of this would include:

i. $F^{\triangleleft}(\xi(0),\lambda)=G(\xi(0),\lambda,\omega(t)) \cdot F(\lambda)$; or
ii. By constructing a function such that $$F^{\triangleleft}(\xi(0), \lambda) = \begin{cases} F(\lambda), & G(\xi(0), \lambda, \omega(t)) > \varepsilon(\xi(0), \lambda), \\ \delta(\xi(0), \lambda), & \text{otherwise,} \end{cases}$$

for some functions $\varepsilon: \Delta \times \Lambda \to [0,\infty)$, $\delta: \Delta \times \Lambda \to [0,\infty)$; or iii. $F^{\triangleleft}(\xi(0),\lambda)=G(\xi(0),\lambda,\omega(t)) * F(\lambda)$, where * denotes the convolution operator. Conversely, if the desired qualitative objective were "The solution trajectory avoids a target" then these weights in $G(\xi(0),\lambda,\omega(t))$ would be reversed in order compared with collision events.

These sets in $\Delta$ can either be fixed throughout the evolutionary process, or change their structure intermittently over successive generations g of the evolutionary process, based on the behaviour of the solution trajectories $\{\pmb{\mathscr{P}}_{\mathfrak{M}}(\xi(0),\lambda_i,\cap(t),t)\}_{i=1}^Z$, $\lambda_i \equiv \bar{c}_i$ in the previous generation g−1.

An example of a target set that changes its structure intermittently over successive generations is a target $T \subset \Delta$ combined with a contraction mapping operator $\bar{\rho}$ and a criterion to apply the operator to the target. Let $\partial T$ be initially defined by the level set of a positive-definite quadratic function $V(z):\mathbb{R}^{n_\tau} \to \mathbb{R}$ for some $n_\tau \leq n$ such that for some $C_\tau > 0$, $T \triangleq \{z \in \Delta | V(z) \leq C_T\}$, $\partial T = \{z \in \Delta | V(z) = C_T\}$. Define an external level set $S_C \triangleq \{z \in \Delta | V(z) = C\}$ for some $C > C_T > 0$, such that $\xi(0) \in \{z \in \Delta | V(z) > C\}$. If in some generation g at least some specified proportion $K_\varphi(g) \in [0,1]$ of the total population of solution trajectories $\{\pmb{\mathscr{P}}_{\mathfrak{M}}(\xi(0),\lambda_i,\omega(t),t)\}_{i=1}^Z$, $\lambda_i \equiv \bar{c}_i(g)$ crosses this contour $S_C$, then for generation g+1 the contraction mapping is applied using some $\rho \in (0,1]$, so that the target set becomes $T \triangleq \{z \in \Delta | V(z) \leq \rho C_T\}$ for generation g+1 onwards (until the criterion is satisfied again, at which point the process is repeated).

The above example is a simple re-scaling of the target. It should be apparent to the reader that the same approach could be used to apply a deformation to the target geometry by applying a mapping to only some of the components of $V(z)$, enabling the geometry of the target set to change adaptively in response to trajectory behaviour in the previous generation. It should also be apparent that the target set can be designed to move through $\Delta$ as an explicit function of generation.

Let $\partial T$ be initially defined by the level set of a positive-definite quadratic function $V(z,g):\mathbb{R}^{n_\tau} \times [1,g^+] \to \mathbb{R}$ for some $\eta_\tau \leq n$ such that for some $C_T > 0$, $T \triangleq \{z \in \Delta | V(z,g) \leq C_T\}$, $\partial T = \{z \in \Delta | V(z,g) = C_T\}$. For example, $V(z,g)$ can be defined to be symmetrical about some point $z_c(g)$, where $z_c(1)=0$ and $z_c(g) = z_c(g-1) + v(g)$, some generation-dependent vector $v(g)$. Then over the generations $V(z,g)$ moves through $\Delta$ and $T$ moves accordingly. The qualitative objective $Q$ is said to texture the Fitness $F$ and we write $F^q = Q \triangleleft F$.

Obvious examples in the context of Identification include nested target sets in $\Delta$ and Avoidance of Identifier-relevant anti-target sets in $\Delta$.

For nested target sets, given a specified error margin $\varepsilon > 0$ for successful Identification using directly-observable state variables $y_j(t)$, define $\varepsilon_3 > \varepsilon_2 > \varepsilon \geq \varepsilon_1 > 0$ and nested target sets $T_i \triangleq \{\xi \in \Delta | \|y_j(t) - \xi_j(t)\| < \varepsilon_i\}$, $i \in \{1,2,3\}$, $\forall j$. Then if we define $Q_i = ``\pmb{\mathscr{P}}_{\mathfrak{M}}(\xi(0),\lambda,0,t)$ achieves collision with $T_i$'' and wish to structure the Textured Fitness around the noiseless scenario, then for some constants $C_T$ and $\delta_T$ define:

$$G_i(\xi(0), \lambda, 0) = \begin{cases} C_T > 1, & \text{if } Q_i \text{ true on } \pmb{\mathscr{P}}_{\mathfrak{M}}(\xi(0), \lambda, 0, t) \\ \delta_T \ll 1, & \text{if } Q_i \text{ false on } \pmb{\mathscr{P}}_{\mathfrak{M}}(\xi(0), \lambda, 0, t) \end{cases}.$$

Then $F^q(\xi(0),\lambda) = (\xi(0),\lambda) = G_1(\xi(0),\lambda,0)G_2(\xi(0),\lambda,0)G_3(\xi(0),\lambda,0) \cdot F(\lambda)$.

For avoidance of Identifier-relevant anti-target sets in $\Delta$, consider an initial condition $\xi(0)$ for a dynamical system being studied, such that the dynamics are not at equilibrium. For dynamical systems that have one or more equilibria in $\Delta$, the set of equilibrium points for state variables under some equilibrium-inducing control law $u^*(t) = p^*(\xi,t)$ is denoted $\{\xi^*\} \triangleq \{\xi \in \Delta | \mathbf{f}_{\mathfrak{M}}(\xi(t),\lambda,u^*(t),0,t) = 0\}$. (For dissipative systems the most obvious equilibrium-inducing control law is null: $u^*(t) = p^*(\xi,t) = 0$.)

Identification using incomplete information will typically generate multiple distinct candidate vectors $\lambda \in \Lambda$, each producing somewhat different dynamical behaviour and equilibria. By observing the equilibria associated with these $\lambda$, and the model dynamics moving from $\xi(0)$ under $u^*(t) = p^*(\xi,t)$ and $\lambda$, and comparing with actual equilibria $\{x^*\}$ and dynamics experienced by the actual system under $u^*(t) = p^*(x,t)$ and $\beta$, physically implausible regions of $\Delta$ for equilibria can be mapped.

By specifying these implausible regions as one or more anti-targets $T' \subset \Delta$, candidate vectors $\lambda \in \Lambda$ that would generate values of $\xi^* \in T'$ such that noiseless model dynamics acting under $u^*(t) = p^*(x,t)$ and $\lambda$ would enter this anti-target (i.e. $\pmb{\mathscr{P}}_{\mathfrak{M}}(\xi(0),\lambda,0,t) \cap T' \neq \emptyset$) are penalised. This is done by ensuring chromosomes associated with these $\lambda$ have their Fitness reduced to discourage survival. This is achieved by defining an avoidance set $\mathbf{A} \subset \Delta$ such that $T' \subseteq \mathbf{A}$, $\xi(0) \in (\Delta \setminus \mathbf{A})$. If the undesirable qualitative objective (expressed as a logical proposition) is $Q = (\pmb{\mathscr{P}}_{\mathfrak{M}}(\xi(0),\lambda,0,t) \cap \mathbf{A} \neq \emptyset)$, then define:

$$G(\xi(0), \lambda, w(t)) = \begin{cases} C_T > 1, & \text{if } Q \text{ false on } \pmb{\mathscr{P}}_{\mathfrak{M}}(\xi(0), \lambda, 0, t) \\ \delta_T \ll 1, & \text{if } Q \text{ true on } \pmb{\mathscr{P}}_{\mathfrak{M}}(\xi(0), \lambda, 0, t) \end{cases},$$

and set $F^q(\xi(0),\lambda) = G(\xi(0),\lambda,0) \cdot F(\lambda) \forall w(t)$. Then chromosomes generating both implausible equilibria and model dynamics that would interact with these equilibria are effectively forced out of the population.

In a second example, this is achieved through $\pmb{\mathscr{P}}_{\mathfrak{M}}(\xi(0),\lambda,\omega(t),t)$ exhibiting specified behaviour re qualitative objectives in state space described by a continuously-distributed function.

Using the definitions of collision, avoidance and capture stipulated above, some non-void time interval $[t_1,t_2] \subseteq [t_0,\infty)$ and given some non-empty closed set $T \subset \Delta$ with surface $\partial T$, one can use any valid metric $\|\cdot\|$ on $\Delta$ to define two continuously-distributed functions:

$$\rho_{min}(\partial T, \pmb{\mathscr{P}}_{\mathfrak{M}}, \xi(0), \lambda, \omega(t)) = \min_{x \in \partial T} \|x, \pmb{\mathscr{P}}_{\mathfrak{M}}(\xi(0), \lambda, \omega(t), [t_1, t_2])\|;$$

$$\rho_{max}(\partial T, \pmb{\mathscr{P}}_{\mathfrak{M}}, \xi(0), \lambda, \omega(t)) = \begin{cases} \max_{x \in \partial T \cap \pmb{\mathscr{P}}_{\mathfrak{M}}(\xi(0),\lambda,\omega(t),[t_1,t_2])} \|x, \pmb{\mathscr{P}}_{\mathfrak{M}}(\xi(0), \lambda, \omega(t), [t_1, t_2])\|, \\ \quad \text{for } \pmb{\mathscr{P}}_{\mathfrak{M}}(\xi(0), \lambda, \omega(t), [t_1, t_2]) \subseteq (T \cup \partial T) \\ 0, \quad \text{otherwise.} \end{cases}$$

The interval $[t_1,t_2] \subseteq [t_0,\infty)$ may be explicitly stipulated, or be implicitly based on the performance by $\pmb{\mathscr{P}}_{\mathfrak{M}}(\xi(0),\lambda,\omega(t),t)$ of some qualitative objective $Q$ (e.g. collision with the interior of $T$). Given some continuous function $G:\mathbb{R}^2 \to \mathbb{R}$ (a weighting function to encourage solution trajectories to engage in complex behaviour, e.g. encouraging collision with $T$ while at the same time discouraging capture with $T$), it is possible to write $F^q = G(\rho_{min},\rho_{max}) \triangleleft F$ and $G(\rho_{min},\rho_{max})$ is again said to texture $F$, where, for example, this may take the forms:

$$F^q(\xi(0),\lambda) = G(\rho_{min}(\partial T, \pmb{\mathscr{P}}_{\mathfrak{M}}, \xi(0), \lambda, \omega(t)), \rho_{max}(\partial T, \pmb{\mathscr{P}}_{\mathfrak{M}}, \xi(0), \lambda, \omega(t))) \cdot F(\lambda);$$

or by constructing a function such that $$F^{\triangleleft}(\xi(0),\lambda) = \begin{cases} F(\lambda), & G\begin{pmatrix} \rho_{min}(\partial T, \pmb{\varphi_{\mathfrak{M}}}, \xi(0), \lambda, \omega(t)), \\ \rho_{max}(\partial T, \pmb{\varphi_{\mathfrak{M}}}, \xi(0), \lambda, \omega(t)) \end{pmatrix} > \varepsilon(\xi(0),\lambda), \\ \delta(\xi(0),\lambda), & \text{otherwise,} \end{cases}$$

for some functions $\varepsilon:\Delta\times\Lambda\to[0,\infty)$, $\delta:\Delta\times\Lambda\to[0,\infty)$.

The condition that G be continuous may be relaxed to stepwise-continuous functions.

In a third example, this is achieved through $\pmb{\varphi_{\mathfrak{M}}}$ ($\xi(0),\lambda,\omega(t),t$) exhibiting specified continuously-distributed quantitative behaviour (or at least stepwise continuously-distributed quantitative behaviour). We will permeate $\Delta\times\Lambda$ (state space formulation) or $\Delta\times\Lambda\times\dot\Delta\times\dot\Lambda$ (phase space formulation, with some violence to notation) with at least one more distinct set of contours or level sets, associated with Lyapunov functions $V_i: \Delta\times\Lambda\to[0,\infty)$ (or $V_i: \Delta\times\Lambda\times[1,g^+]\to[0,\infty)$, discussed below) or their derivatives $\dot V_i$, to modify the rate of change of Fitness across generations. This is done by imposing a descent condition; the Fitness of each chromosome is modified based on whether the solution trajectory generated by that chromosome obeys or disobeys that descent condition.

In practical terms, this relationship typically involves the use of some stepwise-continuous Real-valued function G to combine the Lyapunov level sets $\{(\xi,\lambda):V(\xi,\lambda)=k,$ some $k\geq 0\}$ (or the level sets of the Lyapunov derivatives, $\{(\xi,\lambda): \dot V(\xi,\lambda)=k,$ some $k\in\mathbb{R}\}$ with the Fitness F to produce $F^{\triangleleft}(\xi,\lambda)$.

These functions are defined so that they are at least one of: fixed as $V:\Delta\times\Lambda\to[0,\infty)$ throughout the evolutionary process, or changing their structure continuously across the evolutionary process, i.e. are defined over the generations as $V_i:\Delta\times\Lambda\times[1,g^+]\to[0,\infty)$, or changing their structure intermittently over successive generations g of the evolutionary process, based on the behaviour of the solution trajectories $\{\pmb{\varphi_{\mathfrak{M}}}(\xi(0),\lambda_i,\omega(t),t)\}_{i=1}^Z, \lambda_i\equiv\bar c_i$ in the previous generation g-1.

The design of Lyapunov functions is addressed in the mathematical literature, where it is recognised that typically multiple Lyapunov functions can be constructed for any given dynamical system. Common practice is to begin by constructing one or more positive-definite quadratic functions that have some physical meaning, and then modifying the structure of the function to optimise its usefulness for the specific system.

It should be noted that concepts of gradient descent employed here, including gradient descent down a Lyapunov function and/or gradient descent down the Fitness function, also encompass related concepts of stochastic gradient descent, stochastic sub-gradient descent and sub-gradient methods as described in the literature.

In the present Invention, Lyapunov functions are typically designed analogously to methods used in the Product State Space Technique (PSST) and its components, discussed in the literature, including Leitmann and Skowronski (1977); Corless, Leitmann and Ryan (1984, 1985, 1987); Corless, Leitmann and Skowronski (1987); Skowronski (1990, 1991), Kang, Horowitz and Leitmann (1998) and more recent studies (including Stipanovic et al.). In particular, the Lyapunov functions used for texturing Fitness are constructed analogously to $V_\eta$ in the PSST. As such they are constructed from at least one of the following: from one or more components $\xi_i(t)$ of the model state vector $\xi(t)$; from one or more components $x_i(t)-\xi_i(t)$ of the error vector between system and model state vectors; or from one or more terms $y_j(t_k)-g_j(\xi(t_k),\eta,u(t_k),\omega(t_k),t_k)$, the difference between components of the observed measurements and some function of the model's state vector intended to predict the values of those measurements, as previously discussed. Instances of both of the latter two cases shall be compendiously described as "error terms".

Typically the Lyapunov functions used for texturing Fitness are designed such that they are either positive definite or positive semidefinite with respect to error terms. In the latter case, additional structure is typically required to ensure the overall function satisfies the criteria of a Lyapunov function.

In designing Lyapunov functions, candidates can include functions of the scalar physical or chemical properties of either the model dynamics, or of the error vector, or of the error between the observed measurements and some function of the model's state vector intended to predict the values of those measurements, or a combination thereof. This can include functions that are inversely proportional to some power of: Entropy (typically such that achieving conditions associated with maximum entropy corresponds with reaching the minimum of the function); Probability density or probability distribution functions (depending on the shape of the density or distribution curves; in either case, typically such that achieving conditions of maximum likelihood corresponds with reaching the minimum of the function); some other scalar property such that its maximum corresponds with the desired target and hence the minimum of the Lyapunov function. This can also include other scalar properties as appropriate, including the thermodynamic potentials (internal energy, enthalpy, Helmholtz free energy, Gibbs free energy); Hamiltonian; work; power; energy loss; power loss; density; flux density; electrostatic charge; pressure; heat; or temperature.

Candidates can also include scalar functions of vector-valued properties, including the modulus of momentum, applied force or acceleration; the modulus of elements of a vector-valued field, including force, flux or momentum; or the path integral of work done through a vector-valued force field.

Candidates can also include the properties of an algorithmic search for best-estimate, e.g. root sum of squares of error variables, root mean square error, mean absolute error, mean squared error, mean absolute percentage error.

Candidates can also include artificial properties associated with enhancing the search algorithm, including: For the specific purpose of imposing a sense of convergence direction, to amplify or encourage evolutionary drift of trajectories towards observed data or desired sets in state space, from regions where the gradient of the Fitness function is too weak for genetic drift to be otherwise effective in progressing evolution, or to encourage or discourage the passing of trajectories through specified regions of state space.

Typically the structure of the Lyapunov function is encoded in the Meta-Optimising Layer, enabling it to be optimised heuristically.

As an example of an intermittently-changing function, consider the Lyapunov function $V:\Delta\times\Lambda\to[0,\infty)$, the contraction mapping operator $\rho$ and the level set $S_C \triangleq \{\xi\in\Delta|V(\xi)=C\}$ for some $C>0$.

If in some generation g at least some specified proportion $K_\phi(g)\in[0,1]$ of the total population of solution trajectories $\{\pmb{\varphi_{\mathfrak{M}}}(\xi(0),\lambda_i,\omega(t),t)\}_{i=1}^Z,\lambda_i\equiv\bar c_i(g)$ crosses this contour $S_C$ then the mapping $\rho:V\mapsto\rho V$ is applied. Hence if in generation g, $$V(\xi) = \sum_{i=1}^{n} \vartheta_i \xi_i^2,$$

some $\vartheta > 0$, then under the mapping described above, the relevant Lyapunov function would become $$V(\xi) = \rho \sum_{i=1}^{n} \vartheta_i \xi_i^2,$$

for some $\rho > 0$, for the subsequent generation g+1 onwards (until the criterion is satisfied again, at which point the process is repeated).

Again it should be noted that the above example is a simple re-scaling of the Lyapunov function. It should be apparent to the reader that the same approach could be used to apply a deformation to $V(\xi)$, by applying a mapping to only some of the components of $V(\xi)$ in response to the behaviour of trajectories in the previous generation, while preserving the function's Lyapunov attributes.

The extension of the above to functions $V_i : \Delta \times \Lambda \times [1, g^+] \to [0, \infty)$ that change their structure continuously over the generations (and hence across the evolutionary process), as described earlier.

It should be noted that a single Lyapunov function $V : \Delta \times \Lambda \to [0, \infty)$ or multiple Lyapunov functions $V_i : \Delta \times \Lambda \to [0, \infty)$ may be used to impose one or more descent conditions. In the case of multiple Lyapunov functions and/or their derivatives (i.e. v>1) being simultaneously imposed (as distinct from sequentially imposed in a circuit, later) on the same playing set of state space $\Delta \subset \mathbb{R}^n$ for texturing Fitness, it is assumed that $\Delta$ is partitioned into v non-empty subsets $\{\Delta_1, \ldots, \Delta_v\}$ such that $$\bigcup_{i=1}^{v} \Delta_i = \Delta$$

and $(\Delta_i \backslash \partial \Delta_i) \cap (\Delta_j \backslash \partial \Delta_j) = 0 \; \forall j \neq i$. Under these conditions each Lyapunov function $V_i$ and its higher derivatives would then be restricted to the relevant subset $\Delta_i$, so that the symbol $V_i$ will be used to denote $$V_i|_{\Delta_i}$$

etc. and the associated descent conditions will be similarly restricted.

Again the Lyapunov functions $V_i$ (or higher-order derivatives $\dot{V}_i$, etc., depending on the condition) is said to texture the Fitness F, creating the Textured Fitness function $F^\triangleleft(\xi, \lambda)$ and we write $F^\triangleleft = G(V_i) \triangleleft F$ (or $F^\triangleleft = G(\dot{V}_i) \triangleleft F$, or more generally $F^\triangleleft = G(V_i, \dot{V}_i) \triangleleft F$, depending on the condition).

Simple examples of $F^\triangleleft = G(V_i) \triangleleft F$ are as follows: Consider some Lyapunov function $V : \Delta \times \Lambda \to [0, \infty)$, some Fitness function $F : \Lambda \to [0, \infty)$ and denote the discrete Heaviside function by H, where $$H(x) \triangleq \begin{cases} 1, & x \geq 0 \\ 0, & x < 0 \end{cases}.$$

Then if the chromosome $\bar{c}$ corresponds with the parameter vector $\lambda \in \Lambda$ and hence with the model dynamics $$\frac{d\xi}{dt} = f_{\mathfrak{M}}(\xi(t), \lambda, u(t), \omega(t), t),$$

generating the solution trajectories $\xi(t) = \varphi_{\mathfrak{M}}(\xi(0), \lambda, \omega(t), t)$ over the time interval $t \in [t_0, t_f]$, we can write $V(\xi(t_j), \lambda)$ to denote the value of the Lyapunov function for this chromosome at the state vector value $\xi(t_j) = \varphi_{\mathfrak{M}}(\xi(0), \lambda, \omega(t), t_j)$ at some moment $t_j \in [t_0, t_f]$.

Then if the surfaces defined by the level sets for $F(\lambda)$ and $V(\xi, \lambda)$ on $\Delta \times \Lambda$ are not parallel or coincident within any relevant local subsets of $\Delta \times \Lambda$; and given $k_{11} > 0$ is a value corresponding to a contour of interest for the Lyapunov function, $k_{12} \in \mathbb{R}$ is a weight, $k_1 \triangleq (k_{11}, k_{12})^T$ and $\mu \neq 0$ is a vector of weights, some function can be defined $G(\xi(t), \lambda, \omega(t), V, k_1, \mu) : \Delta \times \Lambda \times \mathbb{R}^n \times C^1 \times \mathbb{R}^2 \times \mathbb{R}^J \to \mathbb{R}$, such that for most $\lambda \in \Lambda$ the surfaces defined by the level sets for $F(\lambda)$ and $G(\xi, \lambda, \omega(t), V, k_1, \mu)$ on $\Delta \times \Lambda$ are not parallel or coincident within relevant local subsets of $\Delta \times \Lambda$.

Examples of $G(\xi, \lambda, \omega(t), V, k_1, \mu)$ include:

$$G(\xi(t), \lambda, \omega(t), V, k_1, \mu) = \prod_{j=1}^{J} \mu_j H(k_{11} - k_{12} V(\xi(t_j), \lambda)),$$

$$t_1, \ldots, t_J \in [t_0, t_f], \text{ or}$$

$$G(\xi(t), \lambda, \omega(t), V, k_1, \mu) = \prod_{j=1}^{J} \mu_j H(k_{11} - k_{12} V(\xi(t_j), \lambda)),$$

$$t_1, \ldots, t_J \in [t_0, t_f].$$

Then examples of Textured Fitness using the above components would include $F^\triangleleft(\xi(t_j), \lambda) \triangleq F(\lambda) \cdot G(\xi(t_j), \lambda, \omega(t), V, k_1, \mu) + \delta$ for some bounded function $\delta : \Delta \times \Lambda \to [0, K]$, some $K < \infty$, where $G(\xi(t), \lambda, \omega(t), V, k_1, \mu)$ takes any of the forms listed above.

It should be apparent to the reader that various constructions analogous to this example can also be applied using higher-order derivatives of a Lyapunov function; examples of $F^\triangleleft = \dot{V} \triangleleft F$ include (for some $k_{21} \in \mathbb{R}$, $k_{22} \in \mathbb{R}$, $k_2 \triangleq (k_{21}, k_{22})^T$):

$$F^\triangleleft(\xi(t), \lambda) = F(\lambda) \cdot G(\xi(t), \lambda, \omega(t), \dot{V}, k_2, \mu) + \delta, \text{ where}$$

$$G(\xi(t), \lambda, \omega(t), \dot{V}, k_2, \mu) = \prod_{j=1}^{J} \mu_j H(k_{21} - k_{22} \dot{V}(\xi(t_j), \lambda)), \text{ or}$$

$$G(\xi(t), \lambda, \omega(t), \dot{V}, k_2, \mu) = \sum_{j=1}^{J} \mu_j H(k_{21} - k_{22} \dot{V}(\xi(t_j), \lambda)), \text{ or}$$

$$G(\xi(t), \lambda, \omega(t), \dot{V}, k_2, \mu) =$$

$$\prod_{j=1}^{J} \mu_j H(k_{21} - k_{22} \nabla V^T(\xi(t_j), \lambda) \cdot f_m(\xi(t_j), \lambda, u(t_j), \omega(t), t_j)), \text{ or}$$

-continued $$G(\xi(t), \lambda, \omega(t), \dot{V}, k_2, \mu) =$$

$$\sum_{j=1}^{J} \mu_j H(k_{21} - k_{22} \nabla V^T(\xi(t_j), \lambda) \cdot f_m(\xi(t_j), \lambda, u(t_j), \omega(t), t_j)) \text{ etc.}$$

where · denotes the scalar inner product.

The constant $k_{12}$ may be replaced by some $C^1$ function of the norm of the Lyapunov function across the time-series, $k_{12} \mapsto (\{\|V(\xi(t_j),\lambda)\|\}_{j=1}^{J})$; similarly the constant $k_{22}$ may be replaced by some $C^1$ function of the sign and norm of the derivative across the time-series, $k_{22} \mapsto h_2(\{\text{sgn}[\dot{V}(\xi(t_j),\lambda)]\}_{j=1}^{J}, \{\|\dot{V}(\xi(t_j),\lambda)\|\}_{j=1}^{J})$, for some functions $h_1: \mathbb{R}^J \to \mathbb{R}$, $h_2: \mathbb{R}^{2J} \to \mathbb{R}$.

It should also be clear to the reader that the above examples, where a Real-valued function G of the Lyapunov function or derivatives is imposed as a simple envelope on the Fitness F, is not the only way of using the interaction between the dynamics associated with a chromosome and the Lyapunov function or its derivative to modify the rate of change of the Fitness function across generations.

Writing a Real-valued function of the Lyapunov function or derivatives in its most general form as $G(\xi(t),\lambda,\omega(t),V,\dot{V},k,\mu,\eta)$ for some vectors of constants k, $\eta \in \mathbb{R}^K$, $K \geq 1$, (e.g. some linear combination $\eta_1 G(\xi(t),\lambda,\omega(t),V,k_1,\mu) + \eta_2 G(\xi(t),\lambda,\omega(t),\dot{V},k_2,\mu)$).

From the examples above, where $\eta$ is a vector of the coefficients for each component and k is a vector constructed from the $k_j$), then other candidates for $F^\triangleleft(\xi(t),\lambda)$ include:

Constructing composite mappings of Fitness F and $G(\xi(t),\lambda,\omega(t),V,\dot{V},k,\mu,\eta)$, i.e. given $\xi(t) = \varphi_{\mathfrak{M}}(\xi(0),\lambda,\omega(t),t)$, $F^\triangleleft(\xi(t),\lambda) = F \circ G(\xi(t),\lambda,\omega(t),V,\dot{V},k,\mu,\eta)$.

Constructing a function such that $$F^\triangleleft(\xi(t), \lambda) = \begin{cases} F(\lambda), & G(\xi(t), \lambda, \omega(t), V, \dot{V}, k, \mu, \eta) > \varepsilon(\xi(t), \lambda), \\ \delta(\xi(t), \lambda), & \text{otherwise,} \end{cases}$$

for some functions $\varepsilon: \Delta \times \Lambda \to [0,\infty)$, $\delta: \Delta \times \Lambda \to [0,\infty)$.

Constructing more complicated geometrical combinations of the functions, e.g. weighting the Fitness F by the inner product of the spatial gradient vectors of $F(\lambda)$ and $G(\xi(t),\lambda,\omega(t),V,\dot{V},k,\mu,\eta)$.

Again these functions $G(\xi(t),\lambda,\omega(t),V,\dot{V},k,\mu,\eta)$ can be defined so that they are either fixed throughout the evolutionary process, or change their structure continuously across the evolutionary process, i.e. are defined as explicit functions of generation $g \in [1,g^+]$, and/or change their structure intermittently over successive generations $g \in [1,g^+]$ of the evolutionary process, based on the behaviour of the solution trajectories $\{\varphi_{\mathfrak{M}}(\xi(0),\lambda_i,\omega(t),t)\}_{i=1}^{Z}, \lambda_i \equiv \bar{c}_i$ in the previous generation g−1, with respect to contours of V, $\dot{V}$ or $G(\xi(t),\lambda,\omega(t), V,\dot{V},k, \mu, \eta)$.

Following the earlier example, an example of a function that changes its structure is as follows. Given:

(A) The mapping operator $\hat{\rho}$ associated with some vector $\rho = (\rho_1, \ldots, \rho_{dim(\mu)})$ such that $\rho_j > 0 \forall j$, and (B) The level set $S_C \triangleq \{z \in \Delta | G(\xi(t),\omega(t),V,\dot{V},k,\mu,\eta) = C\}$ for some C>0 and (C) In generation g at least some specified proportion $K_\varphi(g) \in [0,1]$ of the total population of solution trajectories $\{\varphi_{\mathfrak{M}}(\xi(0),\lambda_i, \omega(t),t)\}_{i=1}^{Z}, \lambda_i \equiv \bar{c}_i(g)$ crosses this contour $S_C$, The mapping $\hat{\rho}$: $G(\xi(t),\omega(t),V,\dot{V},k,\mu,\eta) \mapsto G(\xi(t),\lambda,\omega(t),V,\dot{V},k,\rho \cdot \mu,\eta)$ is applied for generation g+1 and $G(\xi(t),\lambda,\omega(t),V,\dot{V},k,\rho \cdot \mu,\eta)$ is the new form of the function for subsequent generations (until the criterion is met again and the mapping is repeated).

Alternatively and following analogous logic to the above, a mapping $\hat{\rho}$ associated with some vector $\rho = (\rho_1, \ldots, \rho_{dim(k)})$ such that $\rho_j \geq 0 \forall j$ could be implemented:

i. To modify the vector k as follows:
$\hat{\rho}$: $G(\xi(t),\lambda,\omega(t),V,\dot{V},k,\mu,\rho) \mapsto G(\xi(t),\lambda,\omega(t),V,\dot{V},\rho \cdot k,\mu,\eta)$ for generation g+1 and $G(\xi(t),\lambda,\omega(t),V,\dot{V},\rho \cdot k,\mu,\eta)$ is the new form of the function for subsequent generations (until the criterion is met again and the mapping is repeated); or ii. To modify the vector $\eta$ as follows:
$\hat{\rho}$: $G(\xi(t),\lambda,\omega(t),V,\dot{V},k,\mu,\eta) \mapsto G(\xi(t),\lambda, \omega(t),V,\dot{V},k,\mu,\rho \cdot \eta)$ and $G(\xi(t),\lambda,\omega(t),V,\dot{V},k,\mu,\rho \cdot \eta)$ is similarly the new form.

The optimal design for $F^\triangleleft(\xi,\lambda)$ will depend on the specific dynamical system being Identified, and may typically involve various candidates being explored before a final design is chosen.

A fourth example is through divergence-based speciation, based on the divergence of solution trajectories $\xi(t) = \varphi_{\mathfrak{M}}(\xi(0),\lambda,\omega(t),t)$ across $\Delta$. In contrast with the previous three methods, which modify the Real-valued Fitness $F(\lambda)$ by mapping it to a Real-valued Textured Fitness $F^\triangleleft(\xi,\lambda) \in \mathbb{R}$, this method represents a mapping $\Psi: F(\lambda) \mapsto F^\triangleleft(\xi,\lambda)$ in a more complex mathematical structure, typically the Complex half-plane $\mathbb{C}_+$ or similar.

A set of distinct chromosomes $\{\bar{c}_i\}_{i=1}^{Z}$ will produce a set of distinct solution trajectories $\{\varphi_{\mathfrak{M}}(\xi(0),\lambda_i, \omega(t),t)\}_{i=1}^{Z}$, $\lambda_i \equiv \bar{c}_i$ emanating out of the initial conditions $\xi(0)$. This set of trajectories will typically diverge across $\Delta$ over the fixed time interval $t \in [t_0,t_f]$. To each member of $\{\varphi_{\mathfrak{M}}(\xi(0),\lambda_i,\omega(t),t)\}_{i=1}^{Z}$ an additional number $\psi_i \in \mathbb{R}$ is assigned, such that solution trajectories which remain close together in $\Delta$ over $t \in [t_0,t_f]$ have closely values of $\psi$, trajectories that diverge over $t \in [t_0,t_f]$ have values of $\psi$ that are further apart and trajectories that are the furthest apart over $t \in [t_0,t_f]$ have associated values of $\psi$ that are far apart.

This proximity among trajectories can be measured using any one of a number of methods, including:

The divergence operator of vector calculus ($\nabla \cdot$) applied to this set of trajectories; and/or The relative distances among trajectories at the end of the interval $\varphi_{\mathfrak{M}}(\xi(0),\lambda_i,\omega(t),t_f)$ under some metric $\|\bullet\|$; and/or The relative distances among trajectories as measured using path integrals over the time interval $t \in [t_0,t_f]$ under some metric $\|\bullet\|$, and/or Some spatial orientation scheme across $\Delta$, e.g. to distinguish between trajectories that are each equidistant from a reference trajectory but are on opposite sides of that reference trajectory.

Each of these trajectories has its $\psi_i$ associated with its Fitness, typically in such a way that it does not directly affect the value of $F(\lambda)$. The simplest typical implementation is to set $\mathbf{F}^\triangleleft(\xi,\lambda_i) = F(\lambda_i) + i\psi_i$ (where $i = \sqrt{-1}$, written in bold here to distinguish it from the index i), so $\text{Re}(\mathbf{F}^\triangleleft(\xi,\lambda_i)) = F(\lambda_i)$; $\text{Im}(\mathbf{F}^\triangleleft(\xi,\lambda_i)) = \psi_i$.

Then, using some metric $\|\bullet\|$:

Under deterministic breeding schemes, a pair of chromosomes $\{\bar{c}_i,\bar{c}_j\}$ can breed if and only if $\|\text{Im}(\mathbf{F}^\triangleleft(\xi,\lambda_i) - \mathbf{F}^\triangleleft(\xi,\lambda_j))\| = \|\psi_i - \psi_j\| < K_\psi$, some specified $K_\psi > 0$, with the Fitness of the parents being given by Re($F^{\triangleleft}(\xi,\lambda_i)$) and Re($F^{\triangleleft}(\xi,\lambda_j)$) respectively; or Under stochastic breeding schemes, the probability of a pair of chromosomes $\{\bar{c}_i,\bar{c}_j\}$ breeding is:
(a) Low where $\|\text{Im}(F^{\triangleleft}(\xi,\lambda_i)-F^{\triangleleft}(\xi,\lambda_j))\|=\|\psi_i-\psi_j\|$ is large, and
(b) High where $\|\text{Im}(F^{\triangleleft}(\xi,\lambda_i)-F^{\triangleleft}(\xi,\lambda_j))\|=\|\psi_i-\psi_j\|$ is small.

This approach can be further fine-tuned, for example, given the deterministic breeding scheme described above, consider the situation where any pair of chromosomes $\{\bar{c}_i, \bar{c}_j\}$ is such that $\|\text{Im}(F^{\triangleleft}(\xi,\lambda_i)-F^{\triangleleft}(\xi,\lambda_j))\|=\|\psi_i-\psi_j\|<K_\psi$, some specified $K_\psi>0$, so breeding can occur.

Then, using some breeding scheme (such as Roulette selection), the first chromosome $\bar{c}_i$ is chosen based on its Fitness Re ($F^{\triangleleft}(\xi, \lambda_i)$). However, instead of choosing the second chromosome $\bar{c}_j$ based simply on its Fitness Re($F^{\triangleleft}(\xi,\lambda_j)$), a relative Textured Fitness $F^{\triangleleft}(\xi,\lambda_j)|\lambda_i$ is calculated for all chromosomes, using a penalty based on the relative distances of their solution trajectories from that generated by $\bar{c}_i$. For example, one such relative Fitness would be $$\text{Re}(F^{\triangleleft}(\xi,\lambda_j)|\lambda_i) \triangleq \text{Re}(F^{\triangleleft}(\xi,\lambda_j))-k_\psi\|\psi_i-\psi_j\|^{C_\psi};$$
$$\text{Im}(F^{\triangleleft}(\xi,\lambda_j)|\lambda_i) \triangleq (F^{\triangleleft}(\xi,\lambda_j)),$$

using some metric $\|\bullet\|$, $k_\psi \geq 0$, $C_\psi \geq 1$ (where $k_\psi=0$ delivers the simple cut-off scheme).

Then a Roulette selection process is applied on all $\bar{c}_j$, using the relative Fitness Re($F^{\triangleleft}(\xi,\lambda_j)|\lambda_i$) substituted for each chromosome instead of the Fitness, to find the second chromosome in the breeding scheme.

Thus the distance between the solution trajectories associated with chromosomes is used to influence the probability of their breeding.

More mathematically-complicated formulations for $\psi_i$ to describe divergence of trajectories can be readily deduced from the above: for example, vector spaces over the Complex field, or quaternions or other forms of hypercomplex structure. $\Psi$ is said to texture the Fitness F, creating the Textured Fitness function $F^{\triangleleft}(\xi,\lambda)$ and we write $F^{\triangleleft}=\Psi \triangleleft F$.

A fifth example is through surface-based speciation. A patterning algorithm is used to generate a pattern of values over some surface S. Typically a pattern-forming equation or equations of one of the following types is used to generate a pattern under specified parameter values (initially either manually or randomly chosen). This can include, reaction-diffusion equations, e.g. applying the equation associated with any one of the following one-component systems: the Kolmogorov-Petrovsky-Piskounov equation, Fisher's equation, the Newell-Whitehead-Segel equation, Fick's second law of diffusion, the Zeldovitch equation, or applying the equations associated with a two-component system, such as those associated with Turing's own study on the chemical basis of morphogenesis, or the Fitzhugh-Nagumo equations or similar, or applying related published work in patterning equations, e.g. applying the Swift-Hohenberg equation.

This pattern is then mapped to S, typically by either adjusting the dimensionality of the patterning equations to the dimensionality of S, or using S to take a cross-section of a higher-dimensional pattern.

The numbers associated with the pattern on S are then mapped to the Complex plane. This is typically done simply by mapping these numbers to Imaginary counterparts. (For example, some pattern number $\alpha \in \mathbb{R}$, corresponding with some colour in the pattern, is mapped $\alpha \mapsto \alpha i$.) More complicated schemes could be used here, and these are also encompassed.

S is then mapped or inserted into the state space $\Delta$, such that the trajectories cross it. Where the trajectories $\varphi_{\mathfrak{M}}(\xi(0),\lambda_i,\omega(t),t)$ intersect S, the Fitness of their chromosomes $\bar{c}_i$ acquires the local Imaginary value of the pattern, i.e. $F^{\triangleleft}(\xi,\lambda_i)=F(\lambda_i)+i\alpha_i$, some $\alpha_i$.

The breeding rules then follow those of divergence-based speciation, above.

This method represents a mapping $\Upsilon: F(\lambda) \mapsto F^{\triangleleft}(\xi,\lambda)$. $\Upsilon$ is said to texture the Fitness F, creating the Textured Fitness function $F^{\triangleleft}(\xi,\lambda)$ and we write $F^{\triangleleft}=\Upsilon \triangleleft F$.

The various sets in $\Delta$ used to texture Fitness are compendiously referred to as texture sets. Depending on the behaviour of one or more solution trajectories in a previous chromosome generation, these texture sets may be introduced into state space, moved through state space, enlarged, compressed, deformed, subdivided or deleted from state space.

Various Forms of φ-Textured Evolutionary Algorithm

Any evolutionary algorithm employing a Textured Fitness function is described as a φ-Textured Evolutionary Algorithm (φ-TEA). The purpose of the Textured Fitness function $F^{\triangleleft}(\xi,\lambda)$ is to replace the conventional Fitness in all evolutionary algorithm computations.

In a conventional GA the chromosomes live, reproduce and die in generations. The chromosomes $\{\bar{c}_1(g),\ldots,\bar{c}_N(g)\}$ for each generation $g \in \{1, \ldots, g^+\}$, (where $g^+ \in \mathbb{N}$ is the GA's final generation) each have a Fitness value associated with them, $\{F(\bar{c}_1(g)), \ldots, F(\bar{c}_N(g))\}$. The higher a chromosome's Fitness value relative to other chromosomes, the more likely it is that this chromosome will find a mate (also with a high relative Fitness value) and reproduce, ensuring the genes are passed on to the next generation. Chromosomes with low relative Fitness are unsuccessful in reproducing and their gene combinations become extinct.

The literature describes multiple ways of using Fitness to influence the likelihood of a chromosome mating and passing on genes. The most common is the Roulette method, whereby the Fitness across a generation is summed and pairs of chromosomes are chosen randomly based on Fitness. This means those chromosomes whose individual Fitness values make up most of this summed total Fitness are the most likely to reproduce. (Conversely, those chromosomes with relatively low Fitness values are unlikely to reproduce, but it is still possible.)

Another approach is to combine this Roulette concept with an absolute threshold: any chromosome with a Fitness value below some specified threshold value $C_{fit}(g)>0$ is deemed inherently defective and is forbidden to reproduce at all.

A third approach is a one-sided Roulette process, whereby each chromosome in the population reproduces, but chooses its mate based on the Roulette method.

A fourth approach is to combine Fitness with the local geometry of $\Lambda$, whereby there exists some non-empty set $V \subset \Lambda$ such that given $\bar{c}_i \in V$, it can only breed with other chromosomes $\bar{c}_j \in V$; given that there exists at least one such chromosome $\bar{c}_j$, then the Roulette process or one of its variants above is applied.

Once $F^{\triangleleft}(\xi,\lambda)$ has been designed, there are multiple ways of implementing it in a φ-TEA. Some of these implementations have been assigned a schematic symbol as will now be described.

Figure 9F:
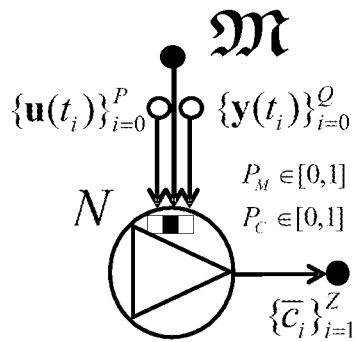
FIG. 9F is a schematic diagram of an example of a symbol to denote a "Weak" Textured Evolutionary Algorithm (TEA)

An example of weak TEA is shown in FIG. 9F. In each generation a "Weak" TEA applies the Textured Fitness $F^{\triangleleft}(\xi, \lambda)$ to each of the chromosomes, producing a set of values $\{F^\triangleleft(\xi,\bar{c}_1(g)), \ldots, F^\triangleleft(\xi,\bar{c}_N(g))\}$ (not distinguishing in notation between an encoded chromosome $\bar{c}_i(g)$ and its equivalent parameter vector $\lambda_i$). Then a Weak TEA proceeds as if it were a conventional GA, i.e. uses the Roulette method or similar to generate the chromosomes of the following generation. In other respects the Weak TEA behaves like a conventional GA.

Figure 9G:
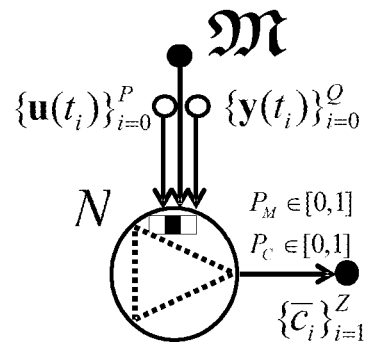
FIG. 9G is a schematic diagram of an example of a symbol to denote a "Stochastic Weak" TEA.

An example of Stochastic Weak TEA is shown in FIG. 9G. Implementation of a "Stochastic Weak" TEA involves replacing deterministic certainty over whether the Textured Fitness conditions are met with probability thresholds. If the parent chromosomes $\{\bar{c}_i(g),\bar{c}_j(g)\}$ each have probability $P_{Str}(i,g),P_{Str}(j,g)\in(0,1]$ respectively of satisfying the conditions $F^\triangleleft(\xi,\bar{c}_i(g))\geq C_{fit}(g)$, $F^\triangleleft(\xi,\bar{c}_j(g))\geq C_{fit}(g)$, and both $P_{Str}(i,g)\geq C_{Str}(g)$, $P_{Str}(j,g)\geq C_{Str}(g)$, for some specified threshold $C_{Str}(g)>0$, then this mating is permitted and offspring are produced; otherwise this particular mating is rejected.

Figure 9H:
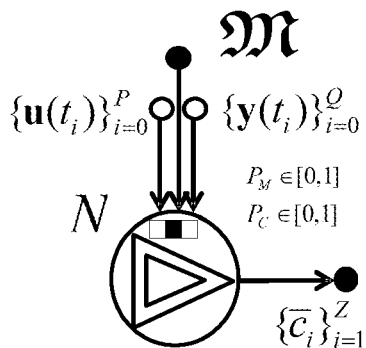
FIG. 9H is a schematic diagram of an example of a symbol to denote a "Strong" TEA.

An example of Strong TEA is shown in FIG. 9H. There are five "flavours" of Strong TEA: "Basic", "Mild", "Steep", "Shallow", "Deep".

"Basic Strong TEA": In each generation a Basic Strong TEA applies the Textured Fitness $F^\triangleleft(\xi,\lambda)$ to each of the chromosomes, producing a set of values $\{F^\triangleleft(\xi,\bar{c}_1(g)), \ldots, F^\triangleleft(\xi,\bar{c}_N(g))\}$. It then forecasts the reproduction process and only allows it for each pair of parent chromosomes if both the parents and the offspring have a sufficiently high Textured Fitness relative to some absolute threshold value $C_{fit}(g)>0$.

For example, consider the instance where each pair of parent chromosomes (say, $\{\bar{c}_i(g),\bar{c}_j(g)\}$ produces a single pair of offspring chromosomes $\{\bar{c}_i(g+1),\bar{c}_j(g+1)\}$. Under the Basic Strong TEA, these parents are only allowed to reproduce if the parents' Textured Fitness values satisfy $F^\triangleleft(\xi,\bar{c}_i(g))\geq C_{fit}(g)$, $F^\triangleleft(\xi,\bar{c}_j(g))\geq C_{fit}(g)$ and their offspring's Textured Fitness values satisfy $F^\triangleleft(\xi,\bar{c}_i(g+1))\geq C_{fit}(g+1)$, $F^\triangleleft(\xi,\bar{c}_j(g+1))\geq C_{fit}(g+1)$ for some specified thresholds $C_{fit}(g)>0$, $C_{fit}(g+1)>0$.

The other four forms of Strong TEA, "Mild", "Steep", "Shallow", "Deep" are specific to the use of Lyapunov functions for texturing Fitness.

"Mild Strong TEA": In each generation Mild Strong TEA requires each "child" Trinity to have its trajectory descend down the Lyapunov contours (i.e. have negative Lyapunov derivative across the trajectory), where the mildest (i.e. least-negative derivative) instance of contour descent in the child is steeper (i.e. more negative in its derivative) than the mildest instance of contour descent in either parent.

"Steep Strong TEA": In each generation Steep Strong TEA requires each "child" Trinity to have its trajectory descend down the Lyapunov contours (i.e. have negative Lyapunov derivative across the trajectory), where the steepest (i.e. most-negative derivative) instance of contour descent in the child is steeper (i.e. more negative in its derivative) than the steepest instance of contour descent in either parent.

"Shallow Strong TEA": In each generation Shallow Strong TEA requires each "child" Trinity to have its trajectory descend overall down the Lyapunov contours (but not necessarily monotonically), whereby the shallowest contour (i.e. furthest from the global minimum) reached by the child is deeper (i.e. closer to the global minimum) than the shallowest contour reached by either parent.

"Deep Strong TEA": In each generation Deep Strong TEA requires each "child" Trinity to have its trajectory descend overall down the Lyapunov contours (but not necessarily monotonically), whereby the deepest contour (i.e. closest to the global minimum) reached by the child is deeper (i.e. closer to the global minimum) than the deepest contour reached by either parent.

It should be apparent that some of these attributes can be combined in a Block, e.g. Basic Deep Strong TEA.

Given that the Crossover Probability $P_C \in (0,1)$ means that repeated attempts by a single pair of parents will produce different pairs of offspring, the Strong TEA typically permits a finite number of attempts by any pair of parent chromosomes to achieve acceptable offspring, before forbidding that pairing of parents. Alternatively, if generating a viable number of acceptable offspring appear heuristically impossible across the population, a Strong TEA Block may attempt a finite number of attempts before downgrading itself to a Weak TEA Block and generating offspring under Weak TEA rules.

It should be noted that the Strong TEA can also be used to implement a set of relative thresholds, e.g. $C_{fit}(g+1) \triangleq C_{fit}(g)+\varepsilon_{fit}$, for some $\varepsilon_{fit}>0$.

Figure 9I:
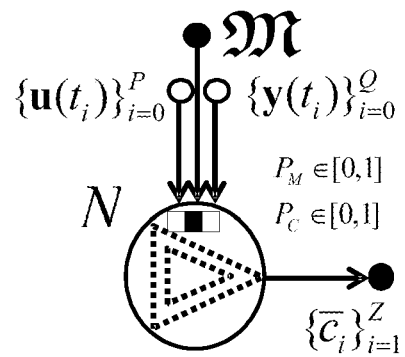
FIG. 9I is a schematic diagram of an example of a symbol to denote a "Stochastic Strong" TEA.

An example of Stochastic Strong TEA is shown in FIG. 9I. Implementation of a "Stochastic Strong" TEA is more complex. Ignoring possible mutation, denote the mating of two parent chromosomes $\{\bar{c}_i(g),\bar{c}_j(g)\}$ to produce two child chromosomes $\{\bar{c}_i(g+1),\bar{c}_j(g+1)\}$ under the Crossover Probability $P_C$ by writing $\{\bar{c}_i(b+1),\bar{c}_j(g+1)\}=\langle\bar{c}_i(g)|P_C|\bar{c}_j(g)\rangle$.

Let the parent chromosomes each have probability $P_{Str}(i,g),P_{Str}(j,g)\in(0,1]$ of satisfying the conditions $F^\triangleleft(\xi,\bar{c}_i(g))\geq C_{fit}(g)$, $F^\triangleleft(\xi,\bar{c}_j(g))\geq C_{fit}(g)$. Then if $P_{Str}(i,g)>C_{Str}(g)$, $P_{Str}(j,g)>C_{Str}(g)$, for some $C_{Str}(g)>0$ and $\langle\bar{c}_i(g)|P_C|\bar{c}_j(g)\rangle$ has probability $P_{Str}(g+1)\in(0,1]$ of producing $\{\bar{c}_i(g+1),\bar{c}_j(g+1)\}$ such that at least one of the following conditions is satisfied:

$F^\triangleleft(\xi,\bar{c}_i(g+1))\leq C_{fit}(g+1)$ or $F^\triangleleft(\xi,\bar{c}_j(g+1))\geq C_{fit}(g+1)$, and $P_{Str}(g+1)\geq C_{Str}(g+1)$, some specified threshold $C_{Str}(g+1)>0$, then this mating is permitted and offspring are produced; otherwise this particular mating is rejected.

Stochastic Strong TEA can be further strengthened to insist that the probability that both of the conditions $F^\triangleleft(\xi,\bar{c}_i(g+1))\geq C_{fit}(g+1)$ and $F^\triangleleft(\xi,\bar{c}_j(g+1))\geq C_{fit}(g+1)$ occur be above a certain threshold value before mating is permitted; this is described as a Stochastic Uniformly-Strong TEA, and currently uses the same schematic symbol as the Stochastic Strong TEA.

Composite Textures—Augmenting Textured Fitness with Other Textures

A more sophisticated version of the above is when the Textured Fitness is itself augmented with another texturing function, typically through reference to the Event History E.

For example, consistent with the earlier discussion, the question of when to apply Texture to the Textured Fitness of chromosomes is predicated on logical conditions applied to solution trajectories corresponding with chromosomes, during the evolutionary process. These logical conditions are contained in the ordered set called the Event Predicates, denoted $\mathfrak{E}$ (E). They analyse events recorded in the Event History.

Any logical condition can be placed in $\mathfrak{E}$(E) and used as the trigger to apply further Texture to the Textured Fitness of chromosomes, including the elapsing of a specified number of generations, the failure of the existing Textured Fitness to discriminate adequately among diverse chromosomes in a generation, etc.

One such method of deciding whether to apply Texture to the Textured Fitness of chromosomes is resolved by the Event Predicates referring to time-series values of the summed Fitness $\Sigma F^\triangleleft(g)$, where this is defined across the φ-TEA population at generation g* as:

$$\sum F^\triangleleft(g^*) \triangleq \sum_{i=1}^{N} \mathrm{Re}(F^\triangleleft(\xi(0), \overline{c}_i(g^*))) \text{ where } \overline{c}_i(g^*) \equiv \lambda_i,$$

some $\lambda_i \in \Lambda$.

Under these circumstances, the Event History has recorded $\Sigma F^\triangleleft(g) \forall g \in [1, g^*]$.

Examples of its use include where: if there exists a discrete interval of preceding generations $\{g^* - n_{stagnate}, \ldots, g^* - 1\}$, for some $n_{stagnate} \in \mathbb{N}$, such that given any generation $g_i \in \{g^* - n_{stagnate}, \ldots, g^* - 1\}$, either a dynamic equilibrium has temporarily occurred, $$\max_{g_j \in \{g^* - n_{stagnate}, \ldots, g^* - 1\}} \left| \sum F^\triangleleft(g_i) - \sum F^\triangleleft(g_j) \right| < \varepsilon_{stagnate},$$

for some specified small error value $\varepsilon_{stagnate} > 0$, but $\Sigma F^\triangleleft(g_i) - \Sigma F^\triangleleft(g^*) \gg \varepsilon_{stagnate}$ (i.e. a sudden plunge in the summed Fitness occurs in the current generation); or else no such plunge occurs:

$$\max_{g_j \in \{g^* - n_{stagnate}, \ldots, g^*\}} \left| \sum F^\triangleleft(g_i) - \sum F^\triangleleft(g_j) \right| < \varepsilon_{stagnate},$$

but $n_{stagnate}$ has grown above some specified trigger value, i.e. summed Fitness is stagnating, then $\mathfrak{E}(E)$ decides to apply Texture to the Textured Fitness of all chromosomes in the generation g*.

The initial Textured Fitness function $F^\triangleleft(\xi, \lambda)$ has been constructed such that given a solution trajectory $\xi(t) = \varphi_{\mathfrak{M}}(\xi(0), \lambda, \omega(t), t)$ associated with a parameter vector $\lambda \in \Lambda$, the value for $F^\triangleleft(\xi, \lambda)$ is defined in terms of the behaviour of this solution trajectory. These methods of texturing Fitness are also available as a further texturing function, the relevant trajectory behaviour being: Interacting with one or more sets $T \subset \Delta$, and/or passing across the level sets of some Lyapunov function $V: \Delta \times \Lambda \to [0, \infty)$ or its higher derivatives, and/or diverging from the solution trajectories associated with other distinct chromosomes, and/or passing through a patterned surface inserted into $\Delta$.

Alternatively, it should be noted that this capacity to apply Texture, based on logical conditions being satisfied during the evolutionary process, can also be used to convert algorithms analogous to a conventional GA being executed on Trinities, or an MGA, into a φ-TEA during the evolutionary process, rather than the Textured Fitness being stipulated at the outset as was done earlier.

Typically the application of additional Texture is imposed using some adjunct Fitness function $F_a: \Delta \times \Lambda \times \mathbb{R} \to [0, \infty)$, which is defined such that for most $\lambda \in \Lambda$ the surfaces defined by the level sets for $F^\triangleleft(\xi, \lambda)$ and $F_a(\xi, \lambda, t)$ are not parallel or coincident within any relevant local subsets of $\Delta \times \Lambda$.

Typical instances of Textured Fitness for solution trajectories $\xi(t) = \varphi_{\mathfrak{M}}(\xi(0), \lambda, \omega(t), t)$ include mapping:

$$\begin{cases} \mathrm{Re}(F^{\triangleleft\triangleleft}(\xi(t), \lambda, t)) = \mathrm{Re}(F^\triangleleft(\xi(t), \lambda)) \cdot F_a(\xi(t), \lambda, t) + \delta \\ \mathrm{Im}(F^{\triangleleft\triangleleft}(\xi(t), \lambda, t)) = \mathrm{Im}(F^\triangleleft(\xi(t), \lambda)) \end{cases}$$

for some constant $\delta \geq 0$ or bounded function $\delta: \Delta \times \Lambda \to [0, K]$, some $K < \infty$; or else $$\begin{cases} \mathrm{Re}(F^{\triangleleft\triangleleft}(\xi(t), \lambda, t)) = \mathrm{Re}(F^\triangleleft(\xi(t), \lambda)) * F_a(\xi(t), \lambda, t) \\ \mathrm{Im}(F^{\triangleleft\triangleleft}(\xi(t), \lambda, t)) = \mathrm{Im}(F^\triangleleft(\xi(t), \lambda)) \end{cases},$$

where *denotes the convolution operator; or else setting $$\begin{cases} \mathrm{Re}(F^{\triangleleft\triangleleft}(\xi(t), \lambda, t)) = \begin{cases} \mathrm{Re}(F^\triangleleft(\xi(t), \lambda)), & F_a(\xi(t), \lambda, t) > \varepsilon(\xi(t), \lambda), \\ \delta(\xi(t), \lambda), & \text{otherwise,} \end{cases} \\ \mathrm{Im}(F^{\triangleleft\triangleleft}(\xi(t), \lambda, t)) = \mathrm{Im}(F^\triangleleft(\xi(t), \lambda)) \end{cases}$$

for some functions $\varepsilon: \Delta \times \Lambda \to [0, \infty)$, $\delta: \Delta \times \Lambda \to [0, \infty)$.

As in the case of $F^\triangleleft = G(V_i, \dot{V}_i) \triangleleft F$, other more complicated candidates for $F^{\triangleleft\triangleleft}(\xi(t), \lambda)$ (such that $F^{\triangleleft\triangleleft} = F_a \triangleleft F^\triangleleft$) include composite mappings of $F_a(\xi, \lambda, t)$ and $F^\triangleleft(\xi, \lambda)$, or geometrical combinations of $F_a(\xi, \lambda, t)$ and its derivatives and $F^\triangleleft(\xi, \lambda)$ and its derivatives.

A particular instance occurs where there is some local subset $\Delta_\theta \subseteq \Delta$ of state-space and subset $\Lambda_\theta \in \Lambda$ of parameter space (where at least one of these subsets is non-empty) such that for $\xi \in \Delta_\theta$ and/or $\lambda \in \Lambda_\theta$, $F^\triangleleft(\xi, \lambda) \gg 1$ but chromosomes $\overline{c}_i(g)$, $g < g^+$ corresponding with $\lambda \in \Lambda_\theta$ are undesirable solutions for the Identification task for that evolutionary algorithm. (Typically this happens when they are found to exhibit unrealistic attributes, e.g. the physical system being modelled by $\overline{c}_i(g)$ violates specified constraints.) In this situation, let an adjunct Fitness function $F_a: \Delta \times \Lambda \times \mathbb{R} \to [0, \infty)$ be defined such that the surfaces defined by the level sets for $F^\triangleleft(\xi, \lambda)$ and $F_a(\xi, \lambda, t)$ are not parallel or coincident within any relevant local subsets of $\Delta \times \Lambda$ containing $\lambda \in \Lambda_\theta$; $\mathrm{Re}(F_a(\xi, \lambda, t)) \in [0, 1)$ $\forall \xi \in \Lambda_\theta$, $\forall \lambda \in \Lambda_\theta$; $\mathrm{Re}(F_a(\xi, \lambda, t)) \in [1, \infty)$ $\forall \lambda \notin \Lambda_\theta$. We will say that $F_a$ textures $F^\triangleleft(\xi, \lambda)$, abbreviated $F^{\triangleleft\triangleleft} = F_a \triangleleft F^\triangleleft$.

The schematic diagrams previously introduced to denote various forms of TEA (e.g. Weak, Stochastic Weak, Strong, Stochastic Strong) under $F^\triangleleft = Q \triangleleft F$, $F^\triangleleft G(\rho_{min}, \rho_{max}) \triangleleft F$ or $F^\triangleleft = G(V_i, \dot{V}_i) \triangleleft F$ will again be used to denote the equivalent forms of TEA under $F^{\triangleleft\triangleleft} = F_a \triangleleft F^\triangleleft$.

It will be apparent that the same processes outlined above can be again repeated to generate more complex forms of Textured Fitness function, for instance, including but not limited to:

$$\left. \begin{aligned} F^{\triangleleft\triangleleft}(\xi, \lambda) &= F_a \triangleleft (G(V_i, \dot{V}_i) \triangleleft F) \\ F^{\triangleleft\triangleleft}(\xi, \lambda) &= Q \triangleleft (G(V_i, \dot{V}_i) \triangleleft F) \\ F^{\triangleleft\triangleleft}(\xi, \lambda) &= Q_1 \triangleleft (Q_2 \triangleleft F) \\ F^{\triangleleft\triangleleft}(\xi, \lambda) &= F_a \triangleleft (Q \triangleleft F) \\ F^{\triangleleft\triangleleft}(\xi, \lambda) &= G(\rho_{min}, \rho_{max}) \triangleleft (Q \triangleleft F) \\ F^{\triangleleft\triangleleft}(\xi, \lambda) &= F_a \triangleleft (\Psi \triangleleft F) \\ F^{\triangleleft\triangleleft}(\xi, \lambda) &= Q \triangleleft (\Upsilon \triangleleft F) \end{aligned} \right\} \text{etc.}$$

A further modification of this is when Textured Fitness has additional Texture intermittently added and removed over generations: writing the Textured Fitness of a chromosome $\bar{c} \equiv \lambda$ in some specific generation g as $F^{\triangleleft}(\xi,\lambda,g)$, then the process of reversibly alternating the chromosome's Textured Fitness across intervals of generations, which can be written: $F^{\triangleleft}(\xi,\lambda,1), \ldots, F^{\triangleleft}(\xi,\lambda,1-n_1) \mapsto F^{\triangleleft}(\xi,\lambda,1+n_1), \ldots, F^{\triangleleft}(\xi,\lambda,1+n_2) \mapsto F^{\triangleleft}(\xi,\lambda,1+n_2), \ldots, F^{\triangleleft}(\xi,\lambda,1+n_3) \mapsto F^{\triangleleft}(\xi,\lambda,1+n_3), \ldots$, where $0 < n_1 < n_2 < n_3 < \ldots$; $n_i \in \mathbb{N}$, is called a Texture Ratchet.

A particular example is the intermittent imposition and removal of Texture on a conventional GA: writing the Fitness of a chromosome $\bar{c} \equiv \lambda$ in some specific generation g as $F(\lambda, g)$, then this process becomes:

$$F(\lambda,1), \ldots, F(\lambda,1+n_1) \mapsto F^{\triangleleft}(\xi,\lambda,1+n_1), \ldots, F^{\triangleleft}(\xi,\lambda,1+n_2) \mapsto F(\lambda,1+n_2), \ldots$$

Typically the Texture Ratchet is applied across either an entire population of chromosomes, or else a subset of a population, and its mappings are applied based on some trigger criteria specified by $\mathfrak{E}(E)$.

More complex sequences are encompassed by the Texture Ratchet, including switching among two or more different, unrelated forms of Textured Fitness: in the instance of two such forms, $F^{\triangleleft 1}$ and $F^{\triangleleft 2}$, where this is obviously extensible to a larger number of $F^{\triangleleft j}$. (A return to $F(\lambda,1+n_i)$ is shown here for clarity as part of each switch; it should be clear that switching between $F^{\triangleleft 1}$ and $F^{\triangleleft 2}$ need not necessarily involve such a return, if one Textured Fitness can be directly mapped from the other.)

$$F^{\triangleleft 1}(\xi,\lambda,1), \ldots, F^{\triangleleft 1}(\xi,\lambda,1+n_1) \mapsto$$
$$F(\lambda,1+n_1) \mapsto F^{\triangleleft 2}(\xi,\lambda,1+n_1), \ldots, F^{\triangleleft 2}(\xi,\lambda,1+n_2) \mapsto F(\lambda,1+n_2) \mapsto F^{\triangleleft 1}(\xi,\lambda,1+n_2), \ldots, F^{\triangleleft 1}(\xi,\lambda,1+n_3) \mapsto F(\lambda,1+n_3) \mapsto \ldots,$$

Predation

Predation can be used within an evolutionary algorithm to augment the passive culling of inferior chromosomes represented by conventional Fitness-favouring reproduction (e.g. Roulette method or similar). An evolutionary algorithm with static predation constitutes a basic building-block for analogue Cellular Automata (ACA), which are used as computational structures within the system as will be described in more detail below.

Predation is a Fitness-related concept, although its implementation depends on whether the φ-TEA is currently an otherwise-conventional GA (with a conventional Fitness function) or already a TEA (with a Textured Fitness function). Without loss of generality the symbol $\text{Re}(F^{\triangleleft}(\xi,\lambda))$ will be used to denote the Fitness function relevant to the particular φ-TEA. If the φ-TEA is not Textured, then $\text{Re}(F^{\triangleleft}(\xi,\lambda))$ defaults to $F(\lambda)$.

In the current system predation within an φ-TEA takes one of four forms (different predation types may be present in combination in a population), namely no predation, static predation, implicit predation and dynamic predation.

Static predation has a Genesis condition. In this regard, the summed Fitness at generation g, $\Sigma F^{\triangleleft}(g)$, is defined across the φ-TEA population as:

$$\Sigma F^{\triangleleft}(g) \triangleq \sum_{i=1}^{N} \text{Re}(F^{\triangleleft}(\xi(0), \bar{c}_i(g^*)))$$

where $\bar{c}_i(g) \equiv \lambda_i$, some $\lambda_i \in \Lambda$;

Static predation does not become an active feature in the φ-TEA from its genesis (g=1) until a generation is reached whereby the summed Fitness satisfies a threshold condition: $\Sigma F^{\triangleleft}(g) > K_{genesis}$, some $K_{genesis} > 0$.

Once static predation is active, chromosomes below some generation-specific survival threshold of Fitness are killed within each generation before the reproduction process is invoked. This is a deterministic process.

If the φ-TEA has a maximum population of N chromosomes, typically referred to as the carrying capacity, then denoting the mortality (number of killed chromosomes) as $N_\theta(g) \geq 0$, the surviving population $N_\tau(g) = N - N_\theta(g)$ is then used by the reproduction algorithm to generate the subsequent generation. In determining the Fitness associated with chromosomes being killed, this survival threshold is either "absolute", or "relative", defined respectively by:

$\text{Re}(F^{\triangleleft}(\xi,\lambda)) < C_{abs}^{prey}(g)$, some $C_{abs}^{prey}(g) > 0$; or $\langle \text{Re}(F^{\triangleleft}(\xi,\lambda)) \rangle (g-g_{lag}) - \text{Re}(F^{\triangleleft}(\xi,\lambda)) > C_{rel}^{prey}(g)$, some $C_{rel}^{prey}(g) > 0$ (where $\langle \text{Re}(F^{\triangleleft}(\xi,\lambda)) \rangle (g-g_{lag}^{stat})$ denotes the mean value for the population's Fitness in the generation $g-g_{lag}^{stat}$, where $g_{lag}^{stat}$ denotes some fixed offset value, $g_{lag}^{stat} \in \{0,1, 2, \ldots\}$);

If $N-N_\theta(g)=0$, we say that extinction has occurred in the φ-TEA, with the survivor population $N_\tau(g)=0$. In a non-networked φ-TEA this extinction is permanent until another run of the evolutionary process is begun afresh. However, in spatially-networked φ-TEA other ways for a new population to re-start can be implemented, as will be explained in more detail below.

If extinction occurs in the φ-TEA at some generation $g^\dagger$, then there exists a period of time (the "extinction decay period" $T^\dagger \in \mathbb{N}$) such that for every $T^\dagger$ generations that elapse after $g=g^\dagger$ for which the φ-TEA is not continually populated (i.e. there exists at least one generation $g \in [g^\dagger, g^\dagger+T^\dagger]$ for which $N_\tau(g)=0$), the survival threshold decays by some proportion $K^\dagger \in (0,1]$, the "extinction decay rate".

If an absolute survival threshold $C_{abs}^{prey}$ is implemented, given $\exists g \in [g^\dagger, g^\dagger+T^\dagger]$ such that $N_\tau(g)=0$, this means that $C_{abs}^{prey}(g+1) = K^\dagger \cdot C_{abs}^{prey}(g)$. If a relative survival threshold $C_{rel}^{prey}$ is implemented, given $\exists g \in [g^\dagger, g^\dagger+T^\dagger]$ such that $N_\tau(g)=0$, this means that $$C_{rel}^{prey}(g+1) = \frac{C_{rel}^{prey}(g)}{K^\dagger}.$$

It should be noted that in contrast with the other two forms of predation below, static predation does not become extinct when the underlying chromosomes become extinct. Instead it undergoes the decay process outlined above, and becomes active again at the new (decayed) survival threshold if a new population is introduced (via a spatially-networked φ-TEA, later).

For Implicit predation a number of chromosomes in each generation are killed before the reproduction algorithm recruits the remaining members to generate the subsequent generation. Again, implementation of implicit predation in an φ-TEA has a Genesis condition, as above. The predation scheme is first activated in some generation $g=g^* > 1$.

If at any generation the population suffers extinction, then this predation scheme also becomes extinct. If the population is subsequently re-started (under a spatially-networked φ-TEA, discussed later), this predation scheme is no longer present (unless also externally re-introduced by the spatially-networked φ-TEA; this will be discussed later).

A first implementation of implicit predation uses different equations in which the number of chromosomes within a generation, N(g), follows a model of population dynamics, expressed as a difference equation, where the existence of predators is implicit, such as the Logistic Equation or the Ricker Model. The maximum population of chromosomes N now effectively specifies the carrying capacity of the φ-TEA: $N(g) \le N$. Under these population models, the number of members of the successor generation $N(g+1)$ is dictated from $N(g)$. This means a number $N_\theta(g) \ge 0$ of members of $N(g)$ will die early: $N_\theta(g) = \max\{N(g) - N(g+1), 0\}$. There are $N_\tau(g) = N(g) - N_\theta(g)$ breeding survivors, who will then produce $N(g+1)$ offspring. In each generation, the $N_\theta(g)$ are chosen from the members of the population with the lowest Fitness; the members of $N_\tau(g)$ are recruited from the chromosomes with the highest Fitness.

A second implementation is in the form of digital Cellular Automata ("Game of Life") analogy. Digital Cellular Automata (CA) in the literature represent a well-established stand-alone approach of modelling ecosystem dynamics through establishment of a grid of binary-valued cells, whereby each cell being "on" denotes a creature occupying territory, while being "off" denotes vacant territory. Generation-based rules are established whereby a cell's proximity to adjacent "on" or "off" cells in one generation dictates its own value in the next generation. (More sophisticated variations of this are discussed later in this Invention.)

In this system CA is implemented within the φ-TEA, where the notional distribution of members of N(g) on a grid is used in conjunction with CA rules to generate the value for $N(g+1)$. (The distribution of $N(1)$ on the grid is either random or uses some specified pattern.) Survivors in generation g for reproduction to fill this quota are the $N_\tau(g)$ Fittest members. This is a deterministic approach that for some parameter values can generate mathematical chaos in the population dynamics.

In the case of dynamic predation a generation-dependent population of predators $N_p(g) \ge 0$ exists within the φ-TEA. Again, implementation of implicit predation in an φ-TEA has a Genesis condition, as above. When the predation scheme is first activated in some generation $g = g^* > 1$, the original population of predators is small: $N_p(g^*) \ll N(g^*)$ where $N(g^*)$ is the number of chromosomes in that generation. If at any generation the chromosome population suffers extinction, then this predation scheme also becomes extinct. If the population is subsequently re-started (under a spatially-networked φ-TEA, discussed later), this predation scheme is no longer present (unless also externally re-introduced by the spatially-networked φ-TEA). Unlike implicit predation, here the predator population can become extinct ($N_p(g) = 0$) while the underlying chromosome population survives ($N(g) > 0$). In this instance, this predation scheme also becomes extinct and ceases to be present (unless externally re-introduced by the networked φ-TEA).

Dynamic predation is stochastic. The probability of any given chromosome $\bar{c}(g)$ being killed, $P_\theta(\bar{c}(g))$, is proportional to $N_p(g)$. In an "absolute" scheme, $P_\theta(\bar{c}(g))$ is low where $\mathrm{Re}(F^\triangleleft(\xi,\lambda))$ associated with $\bar{c}(g)$ is high and high where $\mathrm{Re}(F^\triangleleft(\xi,\lambda))$ associated with $\bar{c}(g)$ is low. In a "relative" scheme, $P_\theta(\bar{c}(g))$ is low where $\mathrm{Re}(F^\triangleleft(\xi,\lambda))$ associated with $\bar{c}(g)$ is high compared with $\langle \mathrm{Re}(F^\triangleleft(\xi,\lambda)) \rangle (g - g_{lag})$ and high where $\mathrm{Re}(F^\triangleleft(\xi,\lambda))$ associated with $\bar{c}(g)$ is low compared with $\langle \mathrm{Re}(F^\triangleleft(\xi,\lambda)) \rangle (g - g_{lag}^{dyn})$, again where $g_{lag}^{dyn}$ denotes some fixed offset value, $g_{lag}^{dyn} \in \{0, 1, 2, \ldots\}$).

A first implementation of dynamic predation uses difference equations. Again denoting the mortality within a generation as $N_\theta(g)$, then $N_\theta(g)$ is generated stochastically as follows: $N_\theta(g) = 0$; $N_p(g)$ specimens of prey (chromosomes) are chosen randomly from the herd (i.e. assume the predators are ideally hunting for a maximum of one carcass per predator). For each specimen $\bar{c}_j(g)$, $P_\theta(\bar{c}_j(g))$ is calculated using $N_p(g)$ and $\mathrm{Re}(F^\triangleleft(\xi,\lambda))$ (and $\langle \mathrm{Re}(F^\triangleleft(\xi,\lambda)) \rangle (g - g_{lag}^{dyn})$, in the case of a relative scheme). A random variable is generated and compared with $P_\theta(\bar{c}_j(g))$ to see whether the kill is successful or not. If the kill is successful, $N_\theta(g) \mapsto N_\theta(g) + 1$; else the tally for $N_\theta(g)$ is unchanged. An example of implementation of predator-prey equations is as follows:

$$N_\tau(g) = N(g) - N_\theta(g);$$

$$N(g+1) = \max([N(g)[1+\alpha] - N_\theta(g)], 0)$$

$$N_p(g+1) = \max([N_p(g)[1-\gamma + N_\theta(g)]], 0)$$

in a modified version of the Lotka-Volterra equation, where $\alpha, \gamma \in [0, \infty)$ are the usual parameters and $\lceil x \rceil$ denotes the ceiling integer of $x \in [0, \infty)$.

Reproduction for the next generation is done by the $N_\tau(g)$ most Fit members of the chromosome population. This approach can also be modified to accommodate alternative predator-prey models.

In a second example, dynamic predation can be implemented as Cellular Automata analogy. The digital Cellular Automata approach, when modified to include explicit stochastic predation in the literature, generates generation-by-generation estimates of predator and prey populations known to be broadly analogous to the Lotka-Volterra model and its variants (e.g. the classic "fox and rabbit" formulation).

In the current system, it has a modified implementation within the φ-TEA. The distribution of $N(1)$ on the grid is either random or uses some specified pattern. Predators are activated in generation $g = g^* > 1$, where $N_p(g^*)$ predators are placed on the grid. The CA generates values for $N(g+1)$ and $N_p(g+1)$ by applying rules to the grid. This also generates the mortality $N_\theta(g)$, which is taken from among the least Fit members of that generation. $N(g+1)$ is treated as a quota. The actual chromosomes that constitute this population are generated by breeding pairs taken from $N_\tau(g) = N(g) - N_\theta(g)$. This approach can be extended to more complex implementations of Cellular Automata and such extensions are encompassed within the system.

Multiple different predation schemes may be present in a φ-TEA population. Where more than one predation scheme is present, there is a rule of precedence analogous to operator precedence in arithmetic, to ensure computationally-consistent results when calculating $N_\theta(g)$. Any given set of rules establishing precedence among predation schemes, and/or ways the various predation schemes interact is called a "multi-predator rule set" (MPRS). Multi-predator rule sets can be formally encoded as part of the φ-TEA. It will be appreciated that not all multi-predator rule sets in a φ-TEA use all the forms of predation specified here (i.e. for some implementations, some forms of predation may remain unused); Multi-predator rule sets can be modified and optimised by the Meta-Optimising Layer, as will be described in more detail below.

Examples of a multi-predator rule set will now be described. In this regard, in the situation where a φ-TEA population initially has some predator scheme (labelled 1) then has a second predator scheme introduced (labelled 2). Then a tabulated multi-predator rule set to handle this is laid out, as shown in Table 1 below.

In detail, denoting the relevant coefficients $C_{abs}^{prey}(1; g)$, $C_{rel}^{prey}(1; g)$ for scheme 1 (depending on whether the scheme is Absolute or Relative) and similarly for scheme 2. Then, without loss of generality assume that $C_{abs}^{prey}(2; g) > C_{abs}^{prey}(1; g)$ and $C_{abs}^{prey}(2; g) < C_{rel}^{prey}(2; g) < C_{abs}^{prey}(2; g)$, so the criteria of scheme 2 will dominate those of scheme 1. Denoting the number of chromosomes to be killed under scheme in isolation as $\{\bar{c}_{\theta j}(g)\}$ and the cardinality of that set as $\#\{\bar{c}_{\theta j}(g)\}$, and denoting the predator population of scheme j to be $N_{pj}(g)$.

Predation schemes under this multi-predator rule set are typically additive (i.e. predators are commensal on chromosomes, as indicated below in Table 1 by the word "Additive":

$$\{\bar{c}_\theta(g)\} = \{\bar{c}_{\theta 1}(g)\} \cup \{\bar{c}_{\theta 2}(g)\}, N_\theta(g) = \#\{\bar{c}_{\theta 1}(g)\} + \#\{\bar{c}_{\theta 2}(g)\} - \#\{\bar{c}_{\theta 1}(g) \cap \bar{c}_{\theta 2}(g)\}).$$

The exception to that rule is where there are two dynamic predation schemes present in a φ-TEA. In that instance the second predator population $N_{p2}(g)$ represents a super-predator population, which preys on the first predator population $N_{p1}(g)$ in an analogous manner to the first predator population preying on the chromosome population N(g). The obvious objection to this is that the concept of chromosome Fitness does not apply to predators.

Predator Fitness values for members of the first predator population are typically generated by a probability distribution (e.g. Normal distribution, uniform interval distribution, etc.). The shape of this distribution will influence the effectiveness of the Relative or Absolute predation scheme used by the second population. Optimisation of the design of the Predator "Fitness" distribution, for computational purposes, is typically performed by the Meta-Optimising Layer. Then predation is performed first, followed by implicit predation, followed last by static predation; and Relative schemes are performed before Absolute schemes.

Other examples of multi-predator rule sets could be used. For example, rule sets can be implemented where there is only ever one predator in each population, so any one of the following can be implemented as a multi-predator rule set: when a new predation scheme is introduced to a population that already has one, one of the following mechanisms can be used. In one example, the new predator simply replaces the former predator. In another example, the predation scheme with precedence survives; for example, using the precedence rules of the previous multi-predator rule set. For example, when a population which has static predation, and dynamic predation is introduced to change the scheme to dynamic predation. Alternatively, when a population which has dynamic predation, and a static predation scheme is introduced, the population keeps the dynamic predation scheme and the static predation scheme is not established. In another example, the predator with the dominant coefficients replaces the other predator; for example, given $C_{abs}^{prey}(2; g) > C_{abs}^{prey}(1;g)$ and $C_{rel}^{prey}(2;g) < C_{rel}^{prey}(1;g)$, predator scheme 2 replaces predator scheme 1; or the predator with the larger expected number of "kills" in the generation $g = g^*$ when the new predator attempts to enter the population, survives and the other dies: i.e. the $j^{th}$ predation scheme survives, where $$j = \arg\max_{i \in \{1,2\}} \{\#\{\bar{c}_{\theta i}(g^*)\}\}.$$

In a further example a random variable decides which predation scheme survives.

Figures 9J, 9K:
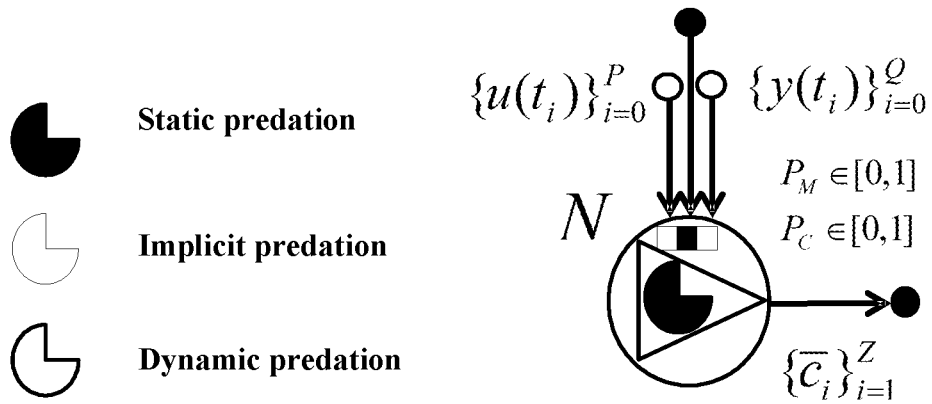
FIG. 9J is a schematic diagram of an example of symbols used to denote different forms of predation.
FIG. 9K is a schematic diagram of an example of symbols used to denote Weak TEA, Static Predation.

An example of symbols used to denote different forms of predation is shown in FIG. 9J, with an example of use of predation in Weak TEA, Static Predation is shown in FIG. 9K.

TABLE 1

|  | No predators | A2 ● | R2 ● | 2 ○ | A2 ◐ | R2 ◐ |
|---|---|---|---|---|---|---|
| No predators | $N_\theta(g) = 0$ | $N_\theta(g) = \#\{\bar{c}_{\theta 2}(g)\}$ | $N_\theta(g) = \#\{\bar{c}_{\theta 2}(g)\}$ | $N_\theta(g) = \#\{\bar{c}_{\theta 2}(g)\}$ | $N_\theta(g) = \#\{\bar{c}_{\theta 2}(g)\}$ | $N_\theta(g) = \#\{\bar{c}_{\theta 2}(g)\}$ |
| A1 ● | $N_\theta(g) = \#\{\bar{c}_{\theta 1}(g)\}$ | Superposition $N_\theta(g) = \#\{\bar{c}_{\theta 2}(g)\}$ | Additive | Additive | Additive | Additive |
| R1 ● | $N_\theta(g) = \#\{\bar{c}_{\theta 1}(g)\}$ | Additive | Additive | Additive | Additive | Additive |
| 1 ○ | $N_\theta(g) = \#\{\bar{c}_{\theta 1}(g)\}$ | Additive | Additive | Additive | Additive | Additive |
| A1 ◐ | $N_\theta(g) = \#\{\bar{c}_{\theta 1}(g)\}$ | Additive | Additive | Additive | Vector $[N_\theta(g), N_{p1\theta}(g)]^T [N_\theta(g), N_{p1\theta}(g)]^T$ | Vector $[N_\theta(g), N_{p1\theta}(g)]^T [N_\theta(g), N_{p1\theta}(g)]^T$ |
| R1 ◐ | $N_\theta(g) = \#\{\bar{c}_{\theta 1}(g)\}$ | Additive | Additive | Additive | Vector $[N_\theta(g), N_{p1\theta}(g)]^T [N_\theta(g), N_{p1\theta}(g)]^T$ | Vector $[N_\theta(g), N_{p1\theta}(g)]^T [N_\theta(g), N_{p1\theta}(g)]^T$ |

$N_\theta(g)$ will typically be reduced when $N_{p2}(g) > 0$, with mortality for chromosomes and predators forming a vector $[N_\theta(g), N_{p1\theta}(g)]^T$.

Under this multi-predator rule set, when performing predation under multiple schemes, in each generation dynamic predation is performed first, followed by implicit predation, followed last by static predation; and Relative schemes are performed before Absolute schemes.

One feature of predation schemes is that they create free room in populations constrained by a carrying capacity, $N(g) \leq N$, enabling reproductive processes to favour more Fit members in the next generation. More formally, let N denote the carrying capacity of some population of chromosomes.

Given a generation $g^* < g^+ - 1$, let $N_\theta(g^*) > 0$ denote the mortality of that generation, taken from the least-Fit members of the population. Then members of the surviving population $N_\tau(g^*) = N - N_\theta(g^*)$ each have a higher expected Fitness than if predation did not occur.

Reproduction typically benefits from predation in at least one of three ways, depending on implementation of the reproductive algorithm to exploit this additional room, to increase the chance of improving population Fitness in the next generation. The first way is that multiple pairings are performed by the surviving population, i.e. the Fittest members of the population can couple with more than one partner while still satisfying the carrying capacity constraint in the next generation, $N(g^*+1) \leq N$. The second way is that single pairings are performed by the surviving population (i.e. each chromosome pairs up at most once with a partner to become a parent), but the Fittest parents can have multiple offspring, using crossover and mutation to explore different combinations of the parent chromosomes. The third way is that single pairings are done by the surviving population, but the Fittest parents can have multiple offspring, where at least one child is cloned from a parent.

Forming Circuits of φ-TEA/MGAs

The evolutionary algorithms can be combined into circuits, including one or more a Modified GA or a φ-TEA.

Figure 9L:
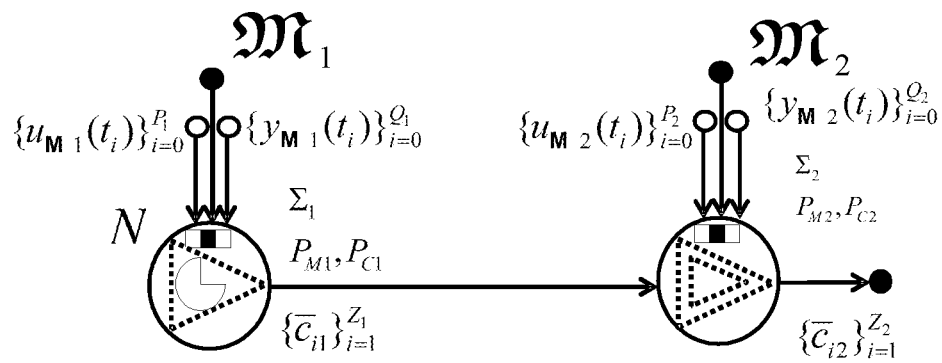
FIG. 9L is a schematic diagram of an example of a circuit of φ-TEA, in the form of a chain.

An illustrative example, is shown in FIG. 9L, in which a Stochastic Weak TEA with Implicit Predation and Stochastic Strong TEA are shown in a circuit in the form of a chain. Denoting the known time-series data (the system inputs and measured system outputs), relevant to the model/sub-model $\mathfrak{M}_j$ as $\{u_{\mathfrak{M}j}(t_i)\}_{i=0}^{P_j}$ and $\{y_{\mathfrak{M}j}(t_i)\}_{i=0}^{Q_j}$, the output of the final generation of acceptable chromosomes fitting the time-series data to the model/sub-model $\mathfrak{M}_j$ is $\{\bar{c}_i\}_{i=1}^{Z_j}$, $Z_j \leq N$.

In all schematic diagrams the population of chromosomes is initially formed in the first (left-hand-most) evolutionary algorithm, to estimate versions of the first model $\mathfrak{M}_1$, in response to the time-series data sets. This is then passed to the next evolutionary algorithm, where it is used to form the first generation of chromosomes for Identification of the subsequent model $\mathfrak{M}_2$ under its associated time-series data, with the final result of this second Identification being the set of chromosomes $\{\bar{c}_i\}_{i=1}^{Z_j}$, $Z_2 \leq N$, etc. In the two-population circuit shown in FIG. 9L, this is also the final result of the overall circuit.

Because each component Block in the circuit typically represents a heuristic process (either an evolutionary algorithm or a Block processing the results of a previous evolutionary algorithm) rather than a deterministic one, it is not guaranteed that each component will necessarily terminate execution with a successful outcome (generation of a non-empty set of suitable candidate chromosomes). In these diagrams, if a component does not terminate with a successful outcome, then it is typically assumed that either that component or its predecessors (as required) will repeat its execution of the relevant heuristic process until a non-empty set of suitable candidate chromosomes is generated, at which point the circuit will resume with the flow of chromosomes to the next Block.

Figure 9M:
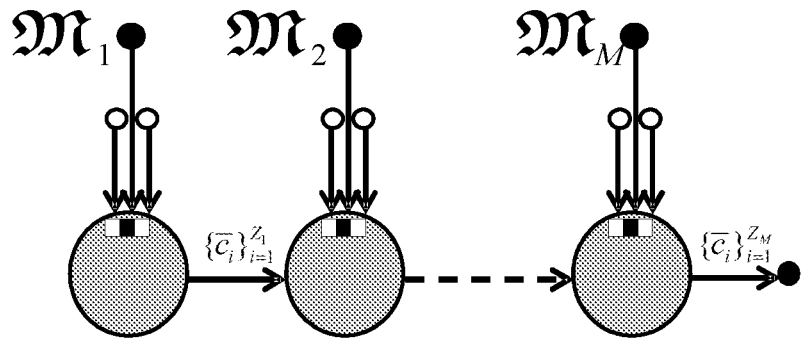
FIG. 9M is a schematic diagram of an example of an open network (chain) of "unspecified" Evolutionary Algorithms (EAs)

Different Implementations of a Circuit Algorithm Under the Same Circuit Topology In a schematic denoting a circuit of evolutionary algorithms, such as that shown in FIG. 9M, which is an example of open network (chain) of "unspecified" EA executing sequentially, at least one of which is a φ-TEA or an MGA, in the absence of further specifications the models $\mathfrak{M}_j$ and associated time-series datasets $\{u_{\mathfrak{M}j}(t_i)\}_{i=0}^{P_j}$ and $\{y_{\mathfrak{M}j}(t_i)\}_{i=0}^{Q_j}$ in each evolutionary algorithm, $j \in \{1, \ldots, M\}$ may refer to a number of different methods of solving a complex Identification problem, the solution in each case being expressed by the final-generation set of chromosomes $\{\bar{c}_i\}_{i=1}^{Z_M}$, $Z_M \leq N$. A number of typical examples will now be described.

The same model on same regions of state space, different control regimes, estimating values of same parameters/state variables or different parameters/state variables:

$$\mathfrak{M}_1 = \mathfrak{M}_2 = \ldots = \mathfrak{M}_M = \mathfrak{M};$$

$$\{u_{\mathfrak{M}1}(t_i)\}_{i=0}^{P_1} \neq \{u_{\mathfrak{M}2}(t_i)\}_{i=0}^{P_2} \neq \ldots \neq \{u_{\mathfrak{M}M}(t_i)\}_{i=0}^{P_M};$$

Same model on same regions of state space, $\mathfrak{M}_1 = \mathfrak{M}_2 = \ldots = \mathfrak{M}_M = \mathfrak{M}$;

Each using different measured output time-series;

$$\{y_{\mathfrak{M}1}(t_i)\}_{i=0}^{Q_1} \neq \{y_{\mathfrak{M}2}(t_i)\}_{i=0}^{Q_2} \neq \ldots \neq \{y_{\mathfrak{M}M}(t_i)\}_{i=0}^{Q_M};$$

Each estimating values of either the same parameters/state variables or of different parameters/state variables.

Same model on different regions of state space:

$$\mathfrak{M} = \mathfrak{M}|_{\Delta_1 \subset \Delta}, \mathfrak{M} = \mathfrak{M}|_{\Delta_2 \subset \Delta}, \ldots, \mathfrak{M}|_{\Delta_M \subset \Delta};$$

$$\Delta_1 \neq \Delta_2 \neq \ldots \neq \Delta_M;$$

Each using either the same control law or different control laws;

Each estimating values of either the same parameters/state variables or different parameters/state variables.

Different models on either the same or different regions of state space, $$\mathfrak{M}_1 \neq \mathfrak{M}_2 \neq \ldots \mathfrak{M}_M;$$

Each model either uses the same control law or different control laws;

Each model is to be used either estimating values of the same parameters/state variables or of different parameters/state variables.

This is typically for at least one of three reasons, namely that the dynamical system being Identified undergoes one or more fundamental changes in dynamical behaviour during the period of time being studied, requiring multiple models to describe the global dynamical behaviour fully, or the dynamical system being Identified has a single set of dynamical behaviour during the period of time being studied, but the complexity of the final model is such that one or more simpler interim approximations is required to enable effective or efficient reconstruction of the final model, or as above, the dynamical system being Identified has a single set of dynamical behaviour during the period of time being studied, but the complexity of the final model is such that the model has to be broken up into sub-models and each sub-model is individually reconstructed (i.e. on the one chromosome, different sets of genes are active for optimisation in each block), after which point the model is effectively reconstructed from the sub-models, possibly with one or more subsequent blocks to fine-tune the parameters by allowing global optimisation of the chromosomes.

In discussing circuit topologies, it is useful to have a symbol for an "unspecified" evolutionary algorithm in a circuit, where an "unspecified" evolutionary algorithm is any one of a (conventional) GA analogy, executing on a population of Trinities, or a Modified GA or a φ-TEA (including Weak, Stochastic Weak, Strong, Stochastic Strong).

The symbol chosen for an "unspecified" evolutionary algorithm is the symbol for a conventional GA with its interior greyed-out and extraneous detail stripped away, as shown in FIG. 9M. Where this notation is used, it is assumed that at least one such "unspecified" evolutionary algorithm has novel structure (i.e. is a Modified GA or a φ-TEA).

A straightforward topology for networked evolutionary algorithms is that of an open chain, as shown in FIG. 9M. The first generation of chromosomes is initially generated in the left hand-most population, and the evolutionary Identification proceeds. The set of suitable candidates from the final generation of these chromosomes, $\{\overline{c}_i\}_{i=1}^{Z_1}$, $Z_1 \leq N$ is then passed to the second EA in the chain where it is used to construct the first generation of this second EA, which eventually evolves the final generation of these chromosomes. The set of suitable candidates from this final generation is $\{\overline{c}_i\}_{i=1}^{Z_2}$, $Z_2 \leq N$, which in turn is passed to the third EA etc. Execution is sequential and concludes when the final generation $g_M^+$ of the final EA has been reached, leading to the output of the final EA's solution set of chromosomes $\{\overline{c}_i\}_{i=1}^{Z_M}$.

Figure 9N:
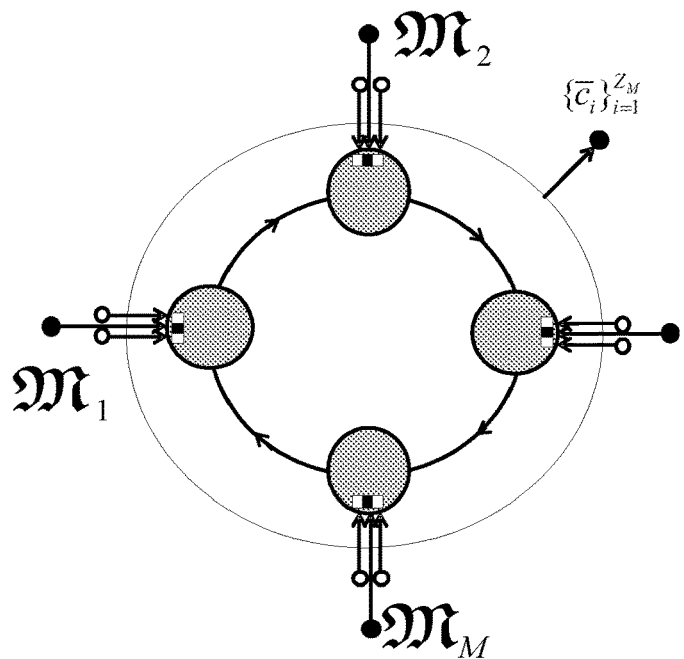
FIG. 9N is a schematic diagram of an example of a closed network (torus) of EAs.

An alternative topology is that of a closed torus, an example of which is shown in FIG. 9N, where execution cycles sequentially among the EA until a specified condition is satisfied, such as when a tracking error between predicted and measured data for all models is below a specified threshold; or tracking error between predicted and measured data for the $M^{th}$ model in the loop is below a specified threshold. In this example, once the condition is met, execution ends and the chromosomes are output as the solution set from this process.

More topologically-complex geometries can be constructed from these building blocks.

Conditional (IF . . . ELSE or WHILE . . . ELSE) Branching Blocks

The system can also implement conditional branching within circuits. In its simplest form a Conditional Branching Block is implemented which typically consists of one input and two or more outputs. The Conditional Branching Block is inserted into the circuit, and uses sets of chromosomes (including the empty set, as appropriate) as input and outputs. Given an input set $\{\overline{c}_i\}_{i=1}^{Z_j}$ of chromosomes, the Conditional Branching Block tests whether these chromosomes fulfil some criterion $\mathfrak{C}$, which (depending on the criterion) can be tested either by being applied once to the entire set, $\mathfrak{C}(\{\overline{c}_i\}_{i=1}^{Z_j})$, or else by being applied separately to each element in the set, $\mathfrak{C}(\overline{c}_1), \mathfrak{C}(\overline{c}_2), \ldots$ . Examples of switching criteria include the testing criteria listed for the Comparison Block, below.

Figure 9O:
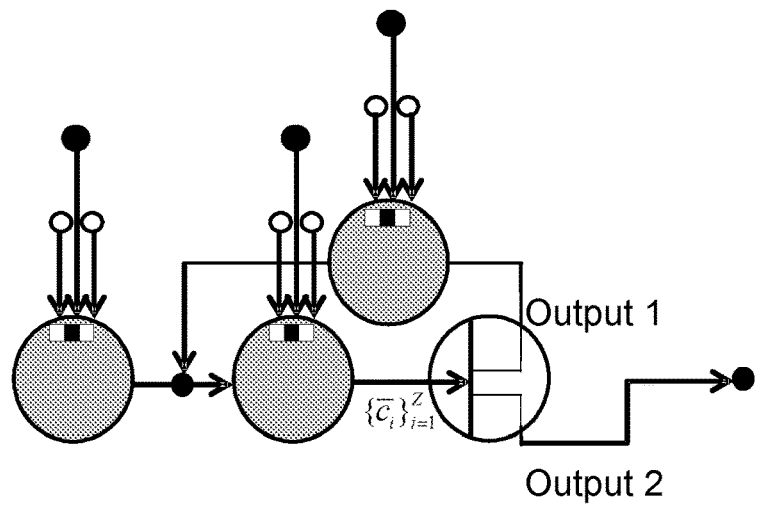
FIG. 9O is a schematic diagram of an example of "unspecified" EAs executing sequentially, with a Conditional Branching Block deciding whether the chromosome set should be passed through to the circuit's output or sent back through a loop for further processing.

An example of this is shown in FIG. 9O, in which "unspecified" EAs are executing sequentially. A Conditional Branching Block having two outputs, named Output 1 and Output 2, is provided for deciding whether the chromosome set $\{\overline{c}_i\}_{i=1}^{Z}$ or its individual elements should be passed through to the network's output or sent back through a loop for further processing. Although two outputs are shown, in practice any number of outputs could be used.

Comparison Blocks

Comparison Blocks typically include two or more inputs and one output. The Comparison Block is inserted into the circuit, and uses sets of chromosomes (including the empty set, as appropriate) as input and outputs. Each Input j carries an input set $\{\overline{c}_i\}_{i=1}^{Z_j}$ of chromosomes, either empty or non-empty. The Comparison Block compares these input sets by testing whether these chromosomes fulfil some criterion $\mathfrak{C}$, which (depending on the criterion) can be tested either by being applied once to the entire set on each input, $\mathfrak{C}(\{\overline{c}_i\}_{i=1}^{Z_j})$, or else by being applied separately to each element in each input set, $\mathfrak{C}(\overline{c}_{1j}), \mathfrak{C}(\overline{c}_{2j}), \ldots$ , or else by being applied to some combination of the two input sets. Such a criterion typically consists of determining at least one of the following:

Comparison of element chromosomes (i.e. whether the input sets share common elements or not);

Whether one or more specified genes (possibly including telomeres) on a chromosome have values that lie within or outside some specified interval, or whether some function of these specified genes takes a value that lies within or outside some specified interval;

Whether the values of one or more specified genes on the chromosomes form clusters;

Whether some function of these specified genes takes values that form clusters or not;

Whether the chromosomes have a Fitness or Textured Fitness with a specified attribute (e.g. Real or Complex; and/or has a specified component whose value is above or below some specified threshold);

Whether one or more specified genes (possibly including telomeres) on the chromosomes take distinct values or not;

Whether the chromosomes are the result of a specified number of generations;

Cardinality of sets;

A combination of some of the above.

The comparison Block then performs a set-valued operation or operations on the input sets or their elements, typically including at least one or more of the following:

Union $$\bigcup_{j=1}$$

Union with repeated elements (i.e. multiset union)

$$\biguplus_{j=1}^{\omega}$$

Intersection $$\bigcap_{j=1}$$

Disjunction (or "set minus").

These operations are performed using either the entire chromosome or else are restricted to specified gene positions (e.g. generate a union of chromosomes for which values on one or more specified genes lie within or outside a specified interval). This leads to the construction of a single set $\{\overline{c}_i\}_{i=1}^{Z}$ (which may be either non-empty or empty) of chromosomes, which is carried on the output.

Figure 9P:
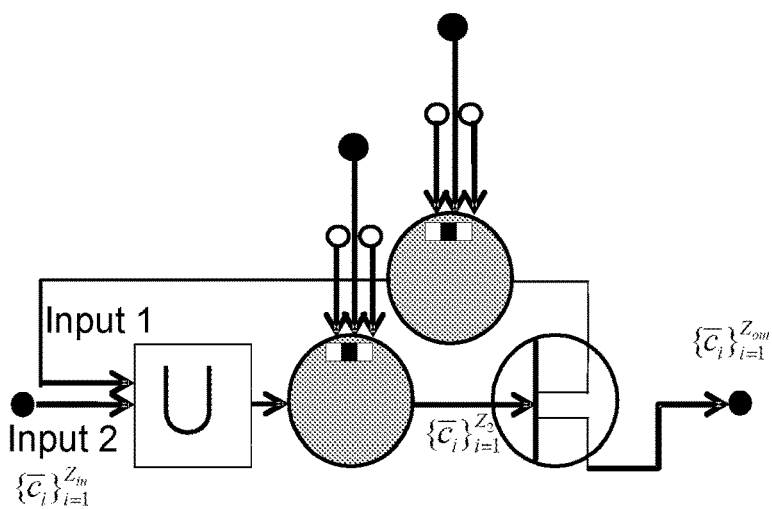
FIG. 9P is a schematic diagram of an example of a circuit with a Conditional Branching Block and a Comparison Block.

An example of a comparison Block is shown in FIG. 9P, with the comparison Block having two inputs, named Input 1 and Input 2. In this example, a Conditional Branching Block decides whether the members of the chromosome set $\{\overline{c}_i\}_{i=1}^{Z_2}$ should be passed through to the network's output or sent back through a loop for further processing. If passed through the loop, they are sent to a Comparison Block that finds the union of the two inputs. This circuit assumes the external input is repeatedly inserting chromosome sets $\{\overline{c}_i\}_{i=1}^{Z_{in}}$ over time; if the external input only sent a chromosome set once then this Comparison Block could be replaced by a simple Junction as in FIG. 9O.

Alternative Blocks

A number of other forms of Block can be derived which can in turn be combined into logical circuits. Examples of these include transistors which can be combined into logical circuits, enabling more complex decision-making regarding the routing of sets of chromosomes, Multi-Input Switching Blocks, combining one or more Comparison Blocks with one or more Conditional Branching Blocks, e.g. for determining an appropriate union of inputs before routing resulting chromosomes, and Ground Blocks that acts as a null sink, mapping any inputs to $\emptyset$ and removing them from the circuit.

Selection/Construction of Chromosomes

Once the circuit of EA has completed execution, the result is the final EA's solution set $\{\overline{c}_i\}_{i=1}^{Z_M}$. This needs to be interpreted (or transformed) by the algorithm to decide which chromosomes $\{\overline{c}_i\}_{i=1}^{Z_{final}}$ will be used as final estimates for $\beta$. Identifying the chromosomes $\overline{c}_k$ with their equivalent parameter vectors $\lambda_k$, let $\overline{C} = \{\overline{c}_i\}_{i=1}^{Z_K}$, $K \leq M$, then this set maps to the set of equivalent parameter vectors, $\overline{C} \mapsto \{\lambda_i\}_{i=1}^{Z_K} \subset \Lambda$.

Then selection or construction of the final chromosomes is done by using one or more suitable mechanisms.

One example mechanism includes selection from $\{\overline{c}_i\}_{i=1}^{Z_M}$: define one or more non-zero sets $\overline{\overline{C}} \subseteq \{\overline{c}_i\}_{i=1}^{Z_M}$, constructed from selected elements of $\{\overline{c}_i\}_{i=1}^{Z_M}$. The selection criterion for elements of $\overline{C}$ are typically composed of at least one of physical plausibility of $\lambda_k | \lambda_k \equiv \overline{c}_k \in \overline{C}$ compared with pre-expected values; or "Best tracking" of chromosome behaviour, including at least one of least-error and/or bounded-error: given bounded simulated noise $\|\omega(t)\| < \omega_\delta$, some specified $\omega_\delta \in [0, \infty)$, some controller program $\{u(t_i)\}_{i=0}^P$ and measured system response $\{y(t_i)\}_{i=0}^Q$, least-error gives $\overline{c} \in \overline{C}$ where $$\overline{c} = \arg\min_{\overline{c}_k \in \{\overline{c}_i\}_{i=1}^{Z_M}} \|g(\xi(t), \eta, \{u(t_i)\}_{i=0}^P, \omega(t), t) - \{y(t_i)\}_{i=0}^Q\| \,|\, \lambda_k \equiv \overline{c}_k,$$

$$\xi(t) = \varphi_m(\xi(0), \lambda_k, \omega(t), t)$$

while bounded-error gives, for some error $\varepsilon > 0$, $$\overline{C} = \{\overline{c}_k | \|g(\xi(t), \eta, \{u(t_i)\}_{i=0}^P, \omega(t), t) - \{y(t_i)\}_{i=0}^Q\| < \varepsilon, \lambda_k \equiv \overline{c}_k, \xi(t) = \varphi_m(\xi(0), \lambda_k, \omega(t), t)\};$$

This could be based on clustering of elements within subsets of $\Lambda$ (including existing cluster analysis techniques used in statistics and conventional machine learning); or in an apparent phase-change of the dynamics of the underlying system, as suggested by the distribution of elements across $\Lambda$, collection of elements within the same phase; or by random selection as part of a wider heuristic or statistical scheme; or using an identity transformation, in which all chromosomes are used, $\overline{C} = \{\overline{c}_i\}_{i=1}^{Z_M}$.

Another example mechanism includes weighting. If performed, this involves mapping $\overline{C}$ to an (initially isomorphic) multiset, denoted $\widehat{\overline{C}}$, and then populating $\widehat{\overline{C}}$ with additional copies of some elements. If this is done, then where subsequent processes discuss performing analysis or transformations on $\overline{C}$ or its elements, read such analysis or transformations as being performed on $\widehat{\overline{C}}$ or its elements.

Subsequent processes can include tracking-weighted analysis in which $\widehat{\overline{C}}$ is constructed: $\overline{C} \mapsto \widehat{\overline{C}}$ such that $\widehat{\overline{C}} \sim \overline{C}$ (isomorphism). Then the initial distribution of chromosomes in $\widehat{\overline{C}}$ is modified as follows: multiple copies of $\overline{c} \in \widehat{\overline{C}}$ are generated based on how closely the trajectory $\xi(t) = \varphi_m(\xi(0), \lambda, \omega(t), t) | \lambda \equiv \overline{c}$ tracks (either directly or in the form of the function $g(\xi(t), \eta, \{u(t_i)\}_{i=0}^P, \omega(t), t))$ the measured data $\{y(t_i)\}_{i=0}^Q$ (assuming bounded simulated noise $\|\omega(t)\| < w_\delta$, some specified $w_\delta \in [0, \infty)$).

Alternatively, externally-weighted analysis can be used in which $\widehat{\overline{C}}$ is constructed: $\overline{C} \mapsto \widehat{\overline{C}}$ such that $\widehat{\overline{C}} \sim \overline{C}$ (isomorphism). Then the initial distribution of chromosomes in C is modified as follows: use of externally-obtained data (for instance, medical, engineering, scientific or financial studies—depending on application—using other forms of analysis) is used to weight $\overline{c} \in \widehat{\overline{C}}$ by generating more copies of more likely elements, or excising elements as being physically untenable.

A combination of the above techniques can also be used.

Another example mechanism is statistical analysis. In this example, given that for any parameter vector $\lambda_k = (\lambda_{k1}, \ldots, \lambda_{km})^T \forall k \in \{1, \ldots, Z_K\}$, then the set of vectors $\{\lambda_i\}_{i=1}^{Z_K}$ can be decomposed to m sets of corresponding gene values $\{\lambda_{11}, \ldots, \lambda_{Z_K 1}\}, \ldots, \{\lambda_{1m}, \ldots, \lambda_{Z_K m}\}$. Writing $\{\lambda_{ij}\}_{i=1}^{Z_K} = \{\lambda_{1j}, \ldots, \lambda_{Z_K j}\}$, then at least one of the following is true:

a. $\lambda \triangleq (\langle\{\lambda_{i1}\}_{i=1}^{Z_K}\rangle, \ldots, \langle\{\lambda_{im}\}_{i=1}^{Z_K}\rangle)^T \Rightarrow \overline{c} \in \{\overline{c}_i\}_{i=1}^{Z_{final}}$ where $\overline{c} \equiv \lambda$ (where brackets $\langle\rangle$ denote the statistical mean of a set);

b. Given some $\varepsilon > 0$ define the vectors $\zeta_1, \ldots, \zeta_w \in \Lambda$, m-dimensional hyperspheres $N(\zeta_1, \varepsilon), \ldots, N(\zeta_\omega, \varepsilon)$ and closed sets $\Omega_1, \ldots, \Omega_\omega$ defined by $\Omega_j = \{\lambda_k \in \{\lambda_i\}_{i=1}^{Z_K} | \lambda_k \in N(\zeta_j, \varepsilon) \cup \partial N(\zeta_j, \varepsilon)\}$ for some $\omega \in \mathbb{N}$, such that $\text{int}(\Omega_i) \cap \text{int}(\Omega_j) = \emptyset$ for $i \neq j$;

$$\{\lambda_i\}_{i=1}^{Z_K} \subseteq \bigcup_{j=1}^\omega \Omega_j, \text{ and } \left(\bigcup_{j=1}^\omega \Omega_j\right) \setminus \{\lambda_i\}_{i=1}^{Z_K} = \emptyset.$$

For each $\Omega_j$ define a corresponding multi-set $\widehat{\Omega}_j$ as follows:

$$\Omega_j = \emptyset \Rightarrow \widehat{\Omega}_j = \emptyset;$$

Given a $\Omega_j$ that is non-empty, map $\Omega_j \mapsto \widehat{\Omega}$ as follows: given $\lambda_k \in \Omega_j$, $\lambda_l \in \Omega_j$ such that $\lambda_k \neq \lambda_l$, impose a mapping $\lambda_k \mapsto \widehat{\lambda}, \in \widehat{\Omega}, \lambda_l \mapsto \widehat{\lambda} \in \widehat{\Omega}$ (repeated element in multi-set) for some $\lambda_k \in N(\zeta_j, \varepsilon) \cup \partial N(\zeta_j, \varepsilon)$.

Then $$\lambda \triangleq \left(\biguplus_{j=1}^\omega \widehat{\Omega}_j\right) \Rightarrow \overline{c} \in \{\overline{c}_i\}_{i=1}^{Z_{final}}$$

where $\overline{c} \equiv \lambda$;

c. As above, except that $$\lambda \triangleq \text{mode}\left[\left(\biguplus_{j=1}^{\omega} \hat{\Omega}_j\right)\right] \Rightarrow \bar{c} \in \{\bar{c}_i\}_{i=1}^{Z_{final}}$$

where $\bar{c} \equiv \lambda$;

d. As above, except that instead of a single global mode, multiple local peaks (i.e. the modes of local neighbourhoods, typically subject to a minimum magnitude requirement) in the distribution $$\left(\biguplus_{j=1}^{\omega} \hat{\Omega}_j\right)$$

are located, corresponding with clusters of promising candidates; the chromosomes of these candidates are included in $\{\bar{c}_i\}_{i=1}^{Z_{final}}$;

e. As above, except that instead of searching for multiple peaks in $$\left(\biguplus_{j=1}^{\omega} \hat{\Omega}_j\right),$$

the chromosomes belonging to peaks (modes of local neighbourhoods, as above) in any one of the component distributions $\{\lambda_{i1}\}_{i=1}^{Z_K}, \ldots, \{\lambda_{im}\}_{i=1}^{Z_K}$ are included in $\{\bar{c}_i\}_{i=1}^{Z_{final}}$.

Another example mechanism involving statistical analysis is, in choosing the final choice for one or more candidate parameter values among the candidates in the final set $\{\bar{c}_i\}_{i=1}^{Z_{final}}$, implementation of the Neyman-Pearson Theorem for choosing among discrete hypotheses (here, represented by parameter vectors $\lambda_i \in \Lambda$ and their associated chromosomes) through use of what the literature calls "rejection regions". Here this is typically performed through generating paths of solution trajectories $\xi(t) = \varphi_m(\xi(0), \lambda_i, \omega(t), t) = t \in [t_0, t_f]$ as the random variable to be assessed, using at least one of (a) random selection of initial conditions $\xi(0)$ within a specified set in state space, for a specified controller program; (b) random selection of a random permissible controller program within specified constraints, for a specified initial conditions vector $\xi(0)$, or (c) a combination of the above.

Another example mechanism is Transform-based analysis, which involves determining dominant values for genes in chromosomes in $\overline{C}$ (and hence deciding relevant elements $\bar{c} \in \{\bar{c}_i\}_{i=1}^{Z_{final}}$) by applying transforms on the chromosome sets. These include:

a. Convolution transforms on decompositions of $\{\lambda_i\}_{i=1}^{Z_K}$, by applying the convolution of some specified waveform to the $\{\lambda_{ij}\}_{i=1}^{Z_K}$ for specified $j \in \{1, \ldots, m\}$;

b. Fourier Transforms (including Discrete and/or Fast Fourier Transforms) on $\{\lambda_{ij}\}_{i=1}^{Z_K}$;

c. An Inverse Fourier Transform on decompositions of $\{\lambda_i\}_{i=1}^{Z_K}$, e.g. on $\{\lambda_{ij}\}_{i=1}^{Z_K}$, for some j.

Other example mechanisms include a range of other processes, such as attractor geometry, (Finite) cluster points or identity. For example, in attractor geometry values for candidate vectors $\lambda$ are constructed based on the geometry of Attractor dynamics as suggested by members of $\overline{C}$ and the behaviour of their associated trajectories $\xi(t) = \varphi_m(\xi(0), \lambda_k, \omega(t), t)|\lambda_k = \bar{c}_k \in \overline{C}$ in state space or phase space, then the equivalent chromosomes $\bar{c} \equiv \lambda$ are constructed and inserted into the final chromosome set, $\bar{c} \in \{\bar{c}_i\}_{i=1}^{Z_{final}}$. For (Finite) Cluster points, values for candidate vectors $\lambda$ are constructed based on being points within a set formed by $\lambda_k = \bar{c}_k \in \overline{C}$, then the equivalent chromosomes $\bar{c} \equiv \lambda$ are constructed and inserted into the final chromosome set, $\bar{c} \in \{\bar{c}_i\}_{i=1}^{Z_{final}}$. It should be noted that this is using the term "cluster" not in the formal mathematical sense, which would require an infinite number of points, but in its more general sense as a tightly-grouped finite set of points. Finally, for Identity, $\{\bar{c}_i\}_{i=1}^{Z_{final}} = \overline{C}$.

Another implementation involves the Block operating on the trajectory component of Trinities rather than on chromosome component, treating the trajectory associated with a chromosome as a signal and performing standard signal-processing operations, processing time-domain or frequency-domain behaviour: e.g. for any trajectory's specified component variable, takes that variable's time-series and imposes high/low pass filters, also de-spiking (spike artefacts in trajectories replaced by NaN) or performing convolution/deconvolution transforms or Fourier Transforms and/or Inverse Fourier Transforms on the trajectory. Given a Trinity as input, output from that Block is the Trinity with its trajectory's specified variables' time-series processed in this way, thus effectively modifying the trajectory associated with each chromosome.

It will be appreciated that the Selection/Construction Block can also be introduced earlier within a circuit, to modify chromosomes at that point within the circuit (i.e. convert $\{\bar{c}_i\}_{i=1}^{Z_K}$ to $\{\bar{c}_i\}_{i=1}^{Z_{k+1}}$), rather than being only restricted to modifying the penultimate chromosome set $\{\bar{c}_i\}_{i=1}^{Z_M}$ to $\{\bar{c}_i\}_{i=1}^{Z_{final}}$.

Figure 9Q:
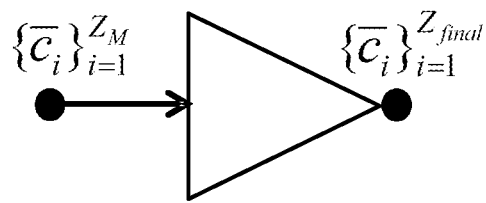
FIG. 9Q is a schematic diagram of an example of a symbol to denote a generic block diagram for selection/construction of chromosomes.

A generic block diagram for selection/construction of chromosomes is shown in FIG. 9Q.

Optimising these Structures in the Base Layer

Circuit architectures involving MGA or φ-TEA as defined thus far comprise a single layer of algorithm Blocks (what shall be called the Base Layer), containing within them all the relevant structures, parameter values, threshold criteria etc.

The design of a Base Layer (comprising a single φ-TEA or MGA, or comprised of one or more circuits constructed from multiple Blocks, including at least one φ-TEA or MGA) to solve a specified Identification problem is typically non-unique; there is usually a multitude of different architectures that will perform the same task, although to different degrees of efficiency.

Criteria for the efficiency of a Base Layer for Identification typically include at least one or more of tracking accuracy, the time taken for tracking convergence, time taken for execution of the overall algorithm or specific tasks, use of computational resources, minimisation of false candidates, or the like.

For example, in the case of tracking accuracy, for a specified circuit architecture and either a specified number of generations or a specified clock time for algorithm execution, the criterion how big does $\varepsilon > 0$ have to be to expect $\overline{C}$ has at least a specified number of members can be used to assess accuracy given the equation below. This for can be used to establish a benchmark for tracking accuracy, either for the output chromosomes from the overall circuit or for the output chromosomes of a component EA:

$$\overline{C} = \{\bar{c}_k \| g(\xi(t), \eta, \{u(t_i)\}_{i=0}^P, \omega(t), t) - \{y(t_i)\}_{i=0}^Q \| < \varepsilon, \lambda_k = \bar{c}_k, \xi(t) = \varphi_m(\xi(0), \lambda_k, \omega(t), t)\};$$

In the case of the time taken for tracking convergence, for a specified circuit architecture and specified ε>0, this examines "What is either the clock time and/or the number of generations of chromosomes required so that $\overline{C}$ (as defined in the previous point) can be typically expected to have at least a specified number of members?"

The system can examine the time taken for overall algorithm execution, or taken for execution of specified tasks or component algorithms within the circuit and/or the use of computational resources used for overall task execution, or used for execution of specified components of circuit. Thus this could example whether the circuit architecture or individual algorithm component configured in such a way as to use the available computing resources— multi-threaded CPUs, parallel throughput GPUs, different kinds of memory etc.—in the most efficient way?

Finally, the system can operate to minimise the number of false candidates in a specified chromosome set $\{\overline{c}_i\}_{i=1}^{Z_j}$ within the circuit, some $j \in \{1, \ldots, M\}$.

Given the non-uniqueness of architectures, the question then becomes how to optimise the Base Layer design, so it achieves an optimal value of at least one of the efficiency criteria above? In this regard, it will be apparent that, to a limited extent, it is possible to improve the performance of a single Base Layer design, by manually executing the circuit on data, measuring the efficiency criteria above, modifying the circuit structure and/or parameter values and re-running, either sequentially or in parallel, to improve the circuit design. However, the complexity of the various stages outlined above is such that rigorous optimisation is typically impossible to perform manually.

Figure 9R:
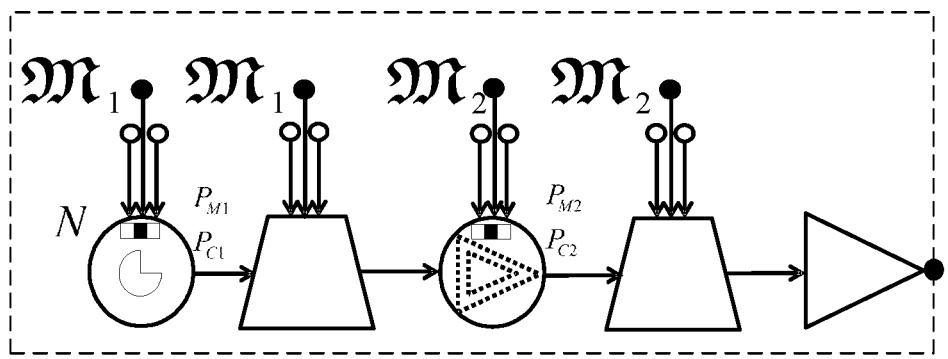
FIG. 9R is a schematic diagram of an example of two distinct circuits for solving an Identification task.
Figure 9R:
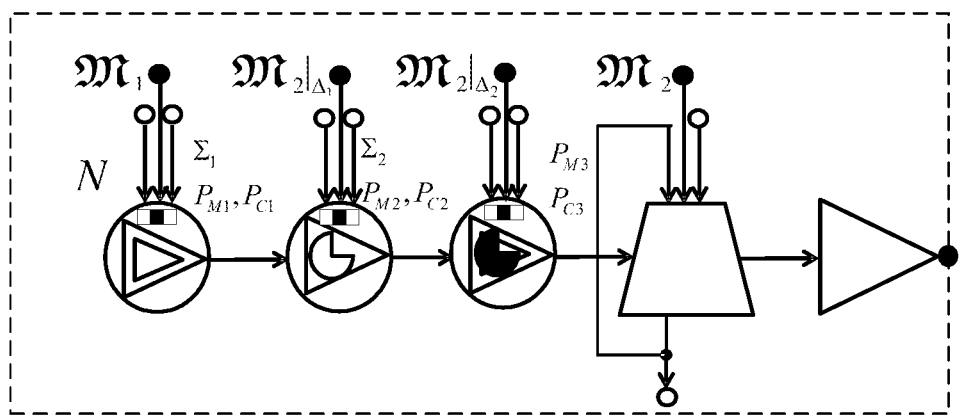

FIG. 9R shows two distinct circuits for solving the same Identification task, fitting data to dynamics involving a phase-change over time, modelled using two distinct models $\mathfrak{M}_1$ and $\mathfrak{M}_2$. Dotted lines around the networks denote the Meta-Optimising Layer on each network, to handle (and typically optimise) the actual fragments of data to be analysed from available raw time-series data, and/or the specifications for the processes of analysis to be done, by each component. Such specifications include mutation and crossover probabilities, "locked" genes (explained in more detail below), criteria thresholds (explained in more detail below), Textured Fitness and φ-TEA specifications, predation, model constraints, and final chromosome selection or construction processes. This also includes the values of weights in transforms, tracking criteria or statistical analysis; and window size and choice of function waveform used in convolutions or other forms of transform.

Further Structural Specifications that can be Encoded on a Chromosome

As a further alternative, this system recognises that information regarding the design of a Base Layer can be reduced into a specification that can also be quantitatively encoded into chromosomes for the purpose of optimisation. This can include encoding information for each circuit component ("Block"), such as:

a. Specifications on the actual fragments of data to be analysed by that Block from available raw time-series data, e.g. variables and lengths of time-series to be analysed;
b. Models, restrictions of models to subsets of state space Δ and/or subsets of parameter space Λ and restrictions on the time-series data to be analysed in that Block;
c. Mutation and crossover probabilities in that Block, including rules for changing these probabilities adaptively over generations;
d. Gene-by-gene speciation constraints;
e. Genes that are "locked" in chromosomes undergoing evolution within that Block (i.e. some genes will be made unable to mutate or be split during crossover, so those gene values on all chromosomes remain fixed in this Block during this evolution);
f. Criteria and associated numerical thresholds for decision-trees, including criteria for Conditional Branching Blocks and Multi-Input Switching Blocks (if used) and rules for adaptive modification of these criteria, depending upon Block or circuit performance;
g. Textured Fitness specifications (if used), e.g. qualitative objectives (initial locations, sizes and rules associated with target, anti-target and avoidance sets), Lyapunov functions, parameters and rules associated with divergence-based speciation or surface-based speciation, etc.;
h. φ-TEA specifications (if used), e.g. rules and thresholds for implementing Textured Fitness in the φ-TEA;
i. Decision whether to implement predation, and if so, predation type(s), associated specifications, Multi-Predator Rule Sets and Predator Transfer Protocols (discussed later);
j. Individual criteria to be used in each Comparison Block (if used);
k. Criteria for imposing local geometry constraints on breeding and applying Turbulent Stirring (if used);
l. Method and criteria for final chromosome selection or construction (if relevant Block being specified);
m. If used, the values of weights in transforms, tracking criteria or statistical analysis; and window size and choice of function waveform used in convolutions or other forms of transform.

Then one method of optimising these structural specifications is to lengthen the chromosomes being used in the Base Layer, introducing additional genes to carry further information. Specifications are then encoded into these genes, which shall be referred to as "structure genes". One or more additional Blocks ("structure Blocks") are then introduced for modifying the values encoded in these genes, in accordance with the criteria for optimising efficiency, based on criteria for optimising efficiency above, typically including at least one Conditional Branching Block and/or Multi-Input Switching Block and/or a Comparison Block, enabling optimising loops to be constructed. Each structure gene is typically unlocked for at least one of these "structure" Blocks, and typically locked for all Blocks that are not "structure" Blocks. As each chromosome interacts with a Block that is at least partly specified by genes on the chromosome, it interacts with that Block in accordance with that specification embodied by its gene values.

Adding a Meta-Optimising Layer (MOL)

As an alternative to optimising structures in the base layer, only some, or none, of the structural information described previously is encoded in the Base Layer. Instead a single circuit design, such as the individual circuits in FIG. 9R, which shows two different architectures to solve the same problem, is optimised according to criteria described above by introducing an additional, Meta-Optimising Layer (MOL) over it, as shown by dotted lines. It should be note the additional circuit Block symbols in FIG. 9R can simply be taken to denote additional processes, or combinations of processes. This MOL typically contains the structural and quantitative specifications of the underlying circuit design, described earlier. It should be clear that the allocation between information to be stored in the MOL and information to be encoded on chromosomes in the Base Layer is itself a design specification that can be optimised.

As well as the encodable structural information already listed previously, construction of the MOL as a separate layer also enables easier optimisation of local circuit topology (this is otherwise difficult to achieve using the previous formulation using only the Base Layer). This can include optimising the design of loops and branches (and more complex switching circuits constructed therefrom) built using switching Blocks, including Conditional Branching Blocks and/or Multi-Input Switching Blocks, and the associated specifications, threshold values etc. pertaining to those Blocks; and/or whether that Block will form part of an open chain, a torus or a more complex structure.

Following this, some of this encoded data in the MOL will be "locked" (analogously to the locking of genes on chromosomes within Blocks, above) to forbid modification during the evolutionary process. Operating on the unlocked segments of this encoded data is an optimisation method implemented in the MOL, whereby sequential or parallel execution of one or more candidate circuits has performance measured against one or more criteria for the efficiency of the circuit's performance.

Apart from using evolutionary optimisation, other methods available to the MOL include using traditional methods currently in the literature suited to Identifier optimisation, such as: neural networks; stochastic methods; simulated annealing; regression trees; linear/nonlinear regression, linear discriminant analysis, logistic regression, principal component analysis and fuzzy logic. Such optimisation methods are typically stored in a library $\mathbb{L}_I$, for example in a database or computer memory, and accessed by the Identifier Module. The performance benchmarks are then used by the optimisation method to improve the circuit's design by modifying the specifications in the meta-optimising layer and hence modifying the circuit accordingly.

Depending on implementation, the MOL can be regarded as a single contiguous layer overlaying the Base Layer, or as a set of smaller, distinct MOL sets, each overlaying a single component in an φ-TEA circuit in the Base Layer.

Typically, as part of the optimisation method used in the MOL, the system employs an implementation of MGA and/or φ-TEA again within the MOL, using "meta-chromosomes" $\bar{c}^\circ$ composed of "meta-genes", each meta-gene equivalent to some meta-parameter value $\lambda_j^\circ$. These meta-chromosomes are then processed by Blocks or circuits of Blocks running in the MOL, analogously to those processes, Blocks and circuits already described for the Base Layer. All of the structures, processes, Blocks and circuits described in the system for the Base Layer have counterparts in the MOL.

The way the MOL encodes the specification for each Block is by allocating a fragment of meta-chromosome to each Block and describing its specifications in terms of meta-gene values. An example of this is shown in Table 2 below, which outlines examples of meta-genes on a meta-chromosome in the MOL.

TABLE 2

| Meta-Genes | $\lambda_1^\circ$ to $\lambda_{1+k_1}^\circ$: Block Structure | $\lambda_{1+k_1+1}^\circ$ to $\lambda_{1+k_1+k_2}^\circ$: Parameters associated with Block Structure | $\lambda_{1+k_1+k_2+1}^\circ$ to $\lambda_{1+k_1+k_2+k_3}^\circ$: Textured Fitness (may be repeated genes if Texture is composite) | $\lambda_{1+k_1+k_2+k_3+1}^\circ$ to $\lambda_{1+k_1+k_2+k_3+k_4}^\circ$: Parameters associated with Textured Fitness | $\lambda_{1+k_1+k_2+k_3+k_4+1}^\circ$ to $\lambda_{1+k_1+k_2+k_3+k_4+k_5}^\circ$: Predation |
|---|---|---|---|---|---|
| Meta-Gene values: | Conventional GA TEA Weak Stochastic Weak Strong Stochastic Strong Stochastic Uniformly-Strong Disambiguation Passive External Passive Internal Active Selection/ Construction Other | Parameter and threshold values associated with the structure in the preceding genes. | None (conventional Fitness) Single Texture Discrete Qualitative Discrete Quantitative Continuous Quantitative Divergence-based Speciation Surface-based Speciation Composite Textures [Permutations of the above specified.] | Parameter and threshold values associated with the structure in the preceding genes. | None Static, Absolute Static, Relative Implicit Dynamic, Absolute Dynamic, Relative Combinations of predation types Rules of Multi-Predator Rule Sets (if relevant) Predator Transfer Protocols (if relevant) |

Figure 9S:
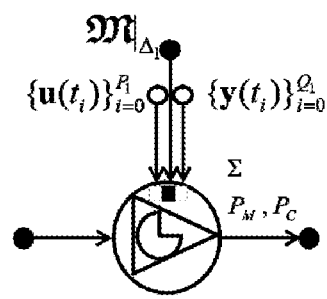
FIG. 9S is a schematic diagram of an example of an φ-TEA component, with its specifications encoded in a meta-chromosome beneath.

Table 2 highlights that any Block can be completely specified by meta-genes on a meta-chromosome. By concatenating these meta-genes, any GA-, MGA- or φ-TEA circuit (or component of such circuit) can be completely described by a corresponding meta-chromosome in the MOL, as illustrated in FIGS. 9R and 9S, which shows an example of an φ-TEA component, being itself expressed as a meta-chromosome in the Meta-Optimising Layer (MOL). Every gene on the meta-chromosome corresponds with one of the pieces of information in the MOL pertaining to that Block; the value of each meta-gene (expressed in some form of gene encoding) describes the current value of that piece of information. The circle notation denotes meta-chromosomes in the MOL, to distinguish from chromosomes within the φ-TEA in the Base Layer. Denoting such a meta-chromosome as $\bar{c}^\circ$, each of the meta-genes $\lambda_1^\circ, \ldots, \lambda_m^\circ$ embodies a feature of one of the component Blocks in the circuit, e.g. whether it is analogous to an ordinary GA, or is an MGA or a φ-TEA; if a φ-TEA, the structure of the Textured Fitness; whether predation is present or not; etc. Different meta-gene values correspond to different options for that feature.

It should be noted that the lists in Table 2 are not intended to imply that those list's options are equally likely (i.e. have uniform Hamming distance in their encoding on meta-genes). In fact they are typically skewed, so that mutation is more likely to produce some options than others.

The meta-chromosomes are used to encode algorithmic changes and criteria for algorithmic changes to a Block algorithm, including adaptive changes in specifications such as probabilities and switching thresholds which may be algorithmically altered during execution of the Block, depending upon the Block's performance over generations (e.g. if evolution stagnates in the population being modified by the Block, or it fails to generate a usable result).

One or more additional meta-genes on the meta-chromosome (here $\lambda_{m^\circ+1}{}^\circ$) specify the relevant computational configuration on the underlying computing platform, for example whether the circuit or component intended to run on a multi-threaded CPU, or on a GPU card, and associated parameters. Modification of the values of meta-genes in $\bar{c}^\circ$ leads to (typically instantaneous) corresponding modification in the specifications of the underlying circuit or component. Each meta-chromosome $\bar{c}^\circ$ can then be linked to executable scripts on the computing platform, enabling the performance of the circuit or component to be evaluated.

In implementations of the system where the criteria for efficiency include the efficient use of computational resources, each meta-chromosome $\bar{c}^\circ$ is linked to a compiler (where the language in use requires one for execution), enabling the algorithm described by $\bar{c}^\circ$ to be compiled in real time during the evolutionary process and run on the computing platform using the specified architecture (e.g. GPU vs. CPU), and its efficiency assessed.

Recursive Structures in the Meta-Optimising Layer

As a consequence of the above, the system is able to implement GA, MGA or φ-TEA structures in the MOL to enable enhanced evolution of the underlying algorithmic structure. Using the criteria of computational efficiency outlined above, a (possibly Textured) Fitness function is created such that meta-chromosomes describing an algorithmic structure evolve to optimise their Fitness, and thus generate a computationally efficient configuration.

Figure 9T:
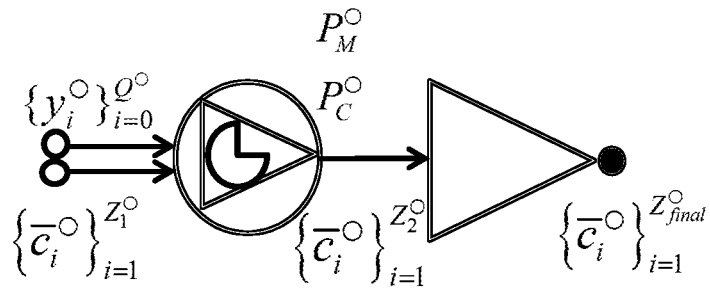
FIG. 9T is a schematic diagram of a first example of an φ-TEA network in a Meta-Optimising Layer.
Figure 9U:
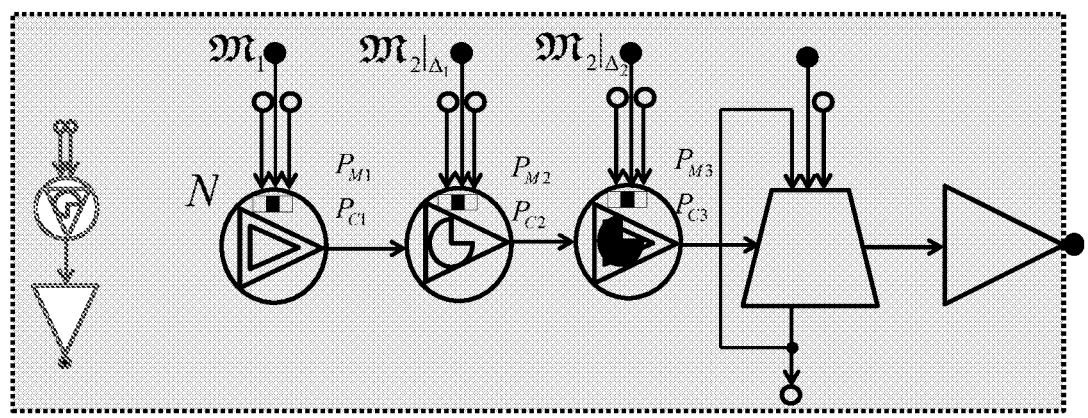
FIG. 9U is a schematic diagram of a second example of an φ-TEA network.

FIG. 9T shows a simple example of an φ-TEA network in the Meta-Optimising Layer, to optimise the algorithmic structure of a φ-TEA network in the Base Layer. For the purpose of illustration, similar symbols are used as for the Base Layer, except with a double-line instead of a solid line, to avoid confusion. FIG. 9U shows both an original configuration of φ-TEA network in the Base Layer for Identification (black), the Meta-Optimising Layer (dotted lines) and a simple φ-TEA network in the MOL (pale grey) to optimise the design of the Base Layer's φ-TEA network. In FIG. 9T, $$\{\bar{c}_i{}^\circ\}_{i=0}^{Z_1^\circ}$$

represents the meta-chromosomes initially describing possible configurations for the underlying Base Layer circuit in FIG. 9U. At least one of them corresponds with the actual φ-TEA circuit as originally configured, while the remaining meta-chromosomes describe alternatives.

If all the meta-chromosomes in the MOL are initially encoded to have the same configuration of Base Layer φ-TEA network, and the relevant genes that carry the specifications for this configuration are locked, then this configuration's structural specifications [Strong TEA with no predation analysing $\mathfrak{M}_1$, followed by Weak TEA with dynamic predation analysing $\mathfrak{M}_2|_{A_1}$, followed by Strong TEA with static predation analysing $\mathfrak{M}_2|_{A_2}$, followed by downstream disambiguation via active modulation and a final chromosome selection/construction Block] are locked and cannot be changed, but whatever parameters of the BL-φ-TEA network remain unlocked (e.g. Blocks' mutation and crossover probabilities, static and dynamic predation thresholds etc.) can be optimised by the MOL-φ-TEA network [a Weak TEA with dynamic predation and a final chromosome selection/construction Block] to produce final meta-chromosomes $$\{\bar{c}_i{}^\circ\}_{i=0}^{Z_{final}^\circ}$$

with the optimal values for these BL-φ-TEA parameters.

Rather than representing actual observations, as in the Base Layer, $\{y_i{}^\circ\}_{i=0}^{Q^\circ}$ represents desired specifications for computational performance, so the evolutionary Identification process, rather than modifying chromosomes to match measured data as in the Base Layer, is here modifying meta-chromosomes to match computational performance specifications as closely as possible. These meta-chromosomes then evolve accordingly and pass through a final meta-chromosome selection/construction Block; the best element in $$\{\bar{c}_i{}^\circ\}_{i=0}^{Z_{final}^\circ}$$

is then used to construct the final algorithmic configuration in the Base layer for future Identification tasks.

Depending on the circuit design for the MGA or φ-TEA in the MOL ("MOL-φ-TEA"), it can seek to optimise the configuration of the MGA circuit or φ-TEA circuit in the Base Layer ("BL-φ-TEA") either globally, such that all features of all the Blocks in the BL-φ-TEA circuit can be made to evolve simultaneously, or locally, such that Block features in the BL-φ-TEA circuit are made to evolve sequentially and gradually within each Block, and this process is done block-by-block (including, although not restricted to, a block sequence that is left-to-right or right-to-left). This means there exist a significant number of different possible configurations for the MOL-φ-TEA circuit.

Figure 9V:
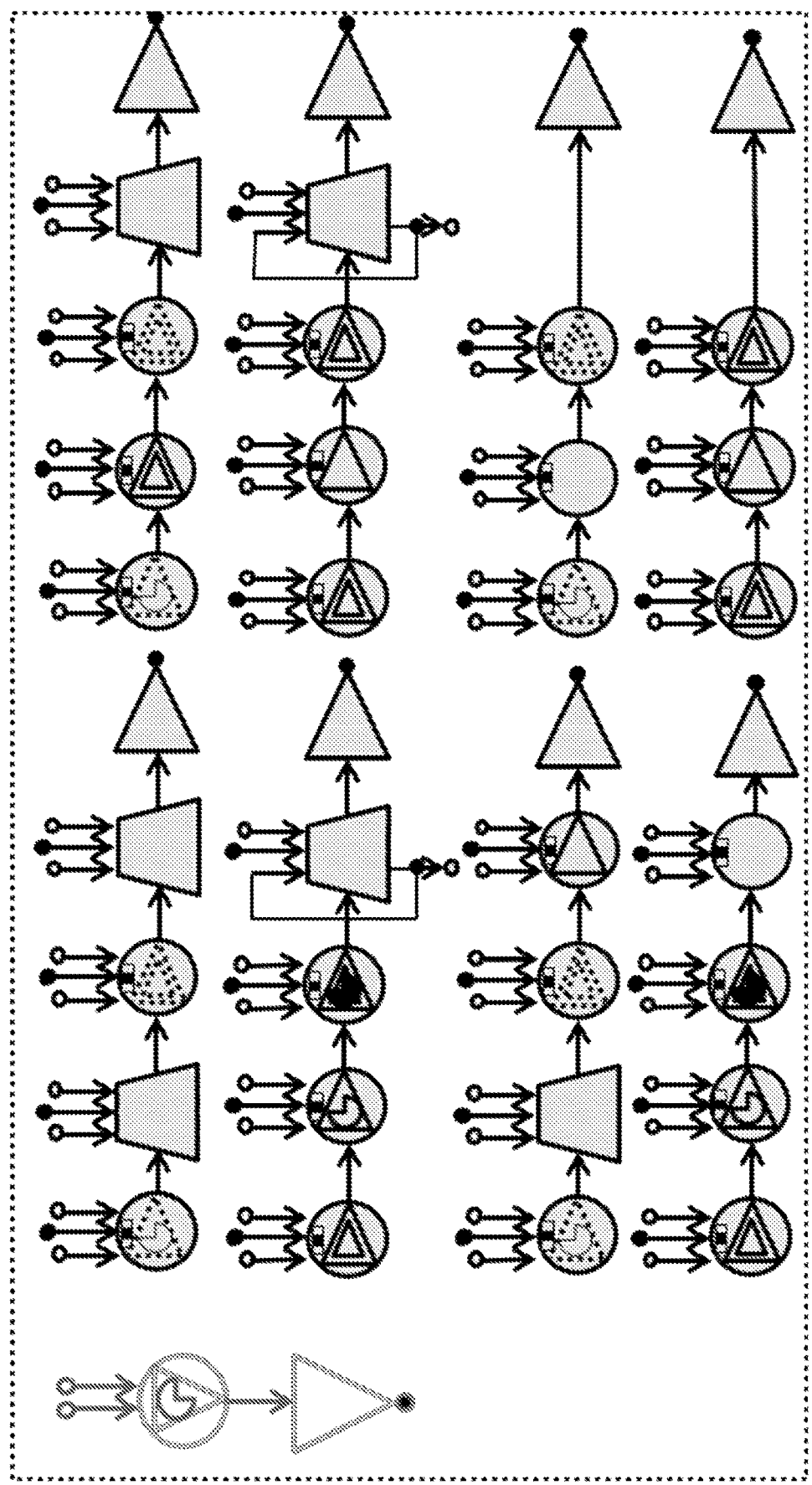
FIG. 9V is a schematic diagram of an example of genes in a Meta-Optimising Layer specifying the structural configuration for an underlying φ-TEA network, showing various configurations.

FIG. 9V is a schematic diagram showing an example of what happens when the genes specifying the structural configuration for Base Layer φ-TEA network are unlocked and hence can be optimised. Diagram shows eight initial, different network structures (black), each one encoded in a distinct meta-chromosome. The MOL-φ-TEA applies evolutionary optimisation on these meta-chromosomes, using a Weak TEA with dynamic predation and a final chromosome selection/construction Block, to generate one or more final structures (described by $$\{\bar{c}_i{}^\circ\}_{i=0}^{Z_{final}^\circ})$$

that best comply with the computational specifications $\{y_i{}^\circ\}_{i=0}^{Q^\circ}$.

Configuration design in the MOL-φ-TEA circuit (including constraints on $\{y_i{}^\circ\}_{i=0}^{Q^\circ}$) is in turn optimised using the same methods and processes outlined above to optimise the BL-φ-TEA circuit, by applying an additional Meta-Optimising Layer (MOL$^2$) to the MOL and repeating the MOL optimising features listed above, including possibly reducing the MOL-φ-TEA circuit to meta-chromosomes and implementing another φ-TEA circuit in the MOL$^2$ to optimise this (i.e. a MOL$^2$-φ-TEA circuit).

Although this sequence could be infinite, the system can allocate modifiable information in each layer, so that there is typically less modifiable information in each successive MOL$^i$-φ-TEA circuit than in the layer beneath it (MOL$^{i-1}$-φ-TEA or Base Layer). Thus, given K+1 layers in a φ-TEA, viz. one Base Layer and K∈ℕ Meta-Optimizing Layers, then there exists some layer η, 1≤η≤K, such that each layer above this layer typically contains less modifiable information than does the layer immediately beneath it. This imposes a finite termination to this algorithmic structure and a finite upper bound on the computational complexity for the overall entity, so the system is closed. Constraints on available computational resources also typically impose practical constraints on the complexity of higher MOLs.

Inter-Layer Information Exchange During Base-Layer Evolution

The above section primarily discussed interactions between the Base Layer and MOL that occur once the Base Layer Block or circuit has entirely completed its execution, including any evolutionary processes. At that point the performance of the Base Layer Block or circuit demonstrated in that execution would typically be used to inform the Fitness of the corresponding meta-chromosome $\bar{c}^\circ$, for subsequent optimisation (typically then modifying the specifications for the Base Layer Block or circuit for some future execution).

However it is also useful for a Base Layer Block or circuit to communicate information to the MOL during execution, including during evolutionary processes. This data communication among layers enables more computationally efficient processing, rather than waiting until overall execution has completed, in that it enables modifications to be made "on the fly" instead of waiting for manifestly inefficient or dysfunctional Base Layer Blocks or circuits to complete their execution.

Such inter-layer communication from the Base Layer to the MOL is typically intermittent, rather than continuous. Modifications made to meta-chromosomes $$\{\bar{c}_i^\circ\}_{i=1}^{Z^\circ}$$

in the MOL are typically deemed to have immediate effect on the specifications of the Blocks and/or circuits in the underlying Base Layer. There are a number of situations in which such information is useful.

For example, if the population of a Block becomes extinct during evolution and this is reported to the MOL then it enables the generation to be reset to g=1 and a new population is generated, to attempt the computation again and/or if such extinctions keep repeating, either: modification of the meta-chromosome $\bar{c}^\circ$ is needed to reduce the risk of further extinctions in the Block or circuit, or else the Block or circuit is dysfunctional and hence the associated meta-chromosome $\bar{c}^\circ$ is unfit, in which case the entire circuit is shut down and $\bar{c}^\circ$ is "killed", to conserve computational resources for other, better-performing candidate circuits and associated $\bar{c}^\circ$.

In another example, the switching criteria of a Block (including Multi-Input Switching Blocks) are such that appropriate switching of chromosomes to other Blocks in the circuit, necessary for circuit operation, is not happening. If this is reported to the MOL then $\bar{c}^\circ$ is typically modified to alter the switching specifications until appropriate switching ensues.

In another example, Blocks/circuits specified by a small subset of meta-chromosomes $$\{\bar{c}_i^\circ\}_{i=1}^{Z^\circ_{sub}} \subset \{\bar{c}_i^\circ\}_{i=0}^{Z^\circ}$$

may prove significantly more successful at performing their tasks than are those specified by the rest of the meta-chromosome population. For instance, all members of this subset have achieved much higher levels of Fitness during execution and/or successfully completed execution, while the other candidate Blocks/circuits have demonstrated inferior performance. This is communicated if all Blocks pass interim performance information to the MOL during execution, typically including at least one of: the number of Base Layer chromosomes currently within the Block; the current Fitness of each of these Base Layer chromosomes; their summed Fitness; or the Block's current value for $$\frac{g}{g^+}$$

(i.e. execution of their evolutionary process is reported as being x % complete). Under these conditions the MOL may decide to force the next generation of evolution among the meta-chromosomes, based on the interim performance information of this small subset $$\{\bar{c}_i^\circ\}_{i=1}^{Z^\circ_{sub}},$$

without waiting for the circuits corresponding with the rest of the population $$\{\bar{c}_i^\circ\}_{i=Z^\circ_{sub}+1}^{Z^\circ}$$

to complete execution. Typically then an inferior Fitness is then allocated to the still-executing circuits, including some penalty based on inferior performance.

A number of further refinements to φ-TEA/MGA circuits will now be described.

Ecological Spatial Networks of Contemporary φ-TEA/MGA Populations in the Circuit A key problem with conventional GAs is that their populations can suddenly collapse into global extinction during the process of trying to evolve a solution to the optimisation task, losing the information that had been assembled in the generations prior to the extinction event and potentially destroying the entire process.

Conventional solutions to this problem have included simple repetition, in which the process of GA evolutionary computations is repeated enough times so that the GA eventually reaches a conclusion without suffering an extinction event, and re-scaling fitness values across the population of chromosomes in each generation.

However, neither of these solutions is particularly satisfactory. Accordingly, the current system stabilises the evolutionary process by transforming the conception and scope of EA. In this regard, the orthodox concept of GAs views evolution as a purely reactive process in which chromosomes respond to Environment-imposed constraints (described by the Fitness function), by evolving appropriate chromosome structures that have a high Fitness value. Optimisation is one-sided, performed by the GA on the chromosomes in response to the Environment.

In contrast, the current system considers Environment-imposed constraints as an intrinsic part of the optimisation dynamics. This is done by including ecological dynamics at entirely different scales to that of conventional GAs: by copying the ecology and behaviour of vertebrate species in the wild (at both single-creature and herd scales), to design semi-isolated networks of populations under different mutation and crossover probabilities and different Fitness functions. Limited numbers of chromosomes can pass from one population to another, depending on a chromosome "transfer protocol", which is a set of rules governing who can cross between populations and when.

Chromosome transfer protocols can enable transfers to occur "in some generations", including, but not limited to periodically, i.e. every T generations, where $T \in \{1, 2, \ldots\}$; or sporadically, i.e. the timing of the transfers is itself an heuristic event; or based on Event-triggers, for example, an influx of "foreign" chromosomes from another population is permitted following an extinction event within a EA population.

The first role of these networks of populations is to enable evolution to continue, and information from previous generations to be at least partially preserved, despite the occurrence of extinction events from time to time within individual populations. The second role of these networks of populations is that it has been determined that, with suitable choice of different crossover and mutation probabilities and transfer protocol parameters (number of chromosomes to transfer; criteria for transfer; timing of transfer events) the network achieves significantly more efficient generation of optimal or near-optimal solutions than conventional GAs.

Optimisation of these network parameters can be used to protect most efficiently against extinction, and/or to produce the most efficient computation and generation of solutions, will be discussed later, where a meta-optimising layer will be added.

Figure 10A:
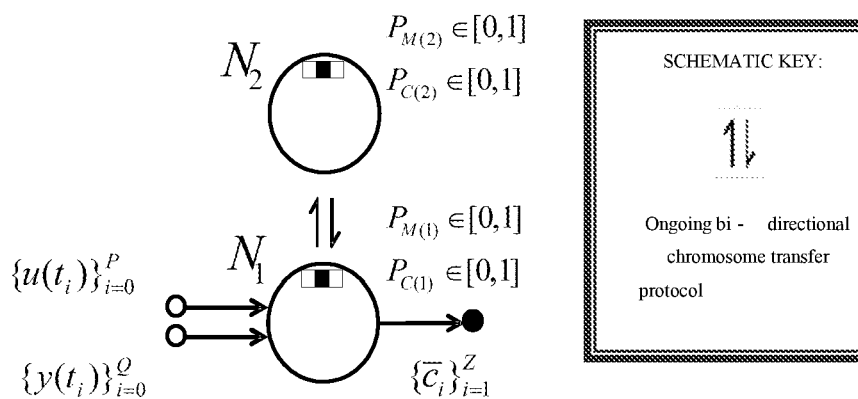
FIG. 10A is a schematic diagram of a first example of a "building block" for ecological circuit (EC) archetypes.

Simple archetypes for these different ecologically-inspired networks and associated transfer protocols are listed below. It should be noted that these simple archetypes can be combined in the system to construct more complex switching rules among φ-TEA populations. In each case for the simple archetype, the corresponding schematic can be depicted as shown in FIG. 10A, with the differences among the archetypes are in the design of the relevant chromosome transfer protocol.

In each simple archetype, two populations of EA exist, denoted Population (1) and Population (2), each with its own crossover and mutation probabilities and Fitness functions. Typically, control input and measurement output time-series directly influence the chromosomes of Population (1): running the Identifier problem, Population (1)'s Fitness function $\text{Re}(F_1^{\triangleleft}(\xi,\lambda)):(\xi(0),\bar{c}) \mapsto [0,\infty)$ rewards chromosomes composed of genes that successfully match input and output, so that solution trajectories $\xi(t)=\varphi_{\mathfrak{M}}(\xi(0),\lambda,\omega(t),t)$ to the model equations $\dot{\xi}=f_{\mathfrak{M}}(\xi(t),\lambda,u(t),\omega(t),t)$ track the measured output $\{y(t_i)\}_{i=0}^{Q}$ to within some accuracy ε. Population (2) represents a distinct population of chromosomes that interacts with Population (1) from time to time, including repopulation in times of extinction. By the end of the final generation, the network has eventually generated the penultimate solution chromosomes, denoted $\{\bar{c}_i\}_{i=1}^{Z}$, which then pass through a Selection/Construction Block.

Ecological Archetype 1: "Archaic Species"

In ecological history, species that are rendered "obsolete" (in terms of Fitness with respect to prevalent conditions) do not always become immediately extinct. Instead they disperse spatially away from their more Fit competitors, forming colonies elsewhere (e.g. Neanderthals versus modern *Homo sapiens* in Europe) creating what is known in ecology as a "Lost World" (e.g. monotremes and marsupials surviving in Australia). If the competitors become extinct, or the criteria for Fitness with respect to the environment changes (e.g. another Ice Age occurs), then these archaic species can flourish again, re-seeding the extinct host population or at least returning to it and improving its fitness with respect to the new conditions.

As new, more Fit chromosomes emerge in each next generation in Population (1), some or all members of a previous generation in Population (1) ("archaic" chromosomes) are transferred by the chromosome transfer protocol to Population (2), where they may either displace the current member chromosomes there or interbreed with them subject to the crossover and mutation probabilities $P_{C(2)} \in [0,1]$, $P_{M(2)} \in [0,1]$ and Fitness function $F_2^{\triangleleft}:(\xi(0),\bar{c}) \mapsto \mathbb{C}_+$ of Population (2).

In the case of only some members of the previous generation being transferred, the typical criterion is relative Fitness with respect to other members of that generation. In the case of these chromosomes displacing others already in Population (2), then if this two-population archetype is scaled up to more complex systems, some or all members of the former generation of Population (2) may themselves be transferred to a third population, Population (3), etc.

In the event of extinction in Population (1), large numbers of copies of "archaic" chromosomes or their descendants may be returned to re-seed this population; alternatively, if the sum of the Fitness of the chromosomes in subsequent generations in Population (1) declines, then the most Fit of the archaic chromosomes or their descendants can return to Population (1) to improve its overall Fitness.

The above archetype concentrates on continual or periodic displacement of archaic chromosomes from a central population into outlying populations. An alternative archetype involves two semi-independent populations with occasional interactions.

Ecological Archetype 2: "Isolated Valleys"

The rainforests of Papua New Guinea grow in valleys divided by steep mountain ridges that are difficult to cross. Each valley can have a micro-climate distinct to its neighbours. Consequently adjacent valleys have distinct species evolved under different constraints, although they have some cross-population among the hardier species.

In some generations, particularly Fit chromosomes from Population (1) are able to transfer via the chromosome transfer protocol to Population (2), where they interbreed with the indigenous population. Similarly, in some generations particularly Fit chromosomes from Population (2) are able to transfer across into Population (1) and interbreed. Extinction events (where the sum of fitness of all the chromosomes of a generation of a population drops below some specified threshold value) enable a larger-scale migration of copies of Fit chromosomes from the other population to be brought across by the transfer protocol and re-seed the extinct population.

Ecological Archetype 3: "Waterhole"

In the Australian Bush and African savannah, ability to flourish is contingent on availability of water. Survival hardship increases proportional to radial distance from water. Typically the Fittest species seize the proximate territory surrounding the waterhole, forcing weaker species to cope with harsher conditions further away, where any given ecological niche can support only a relatively small number of occupants. If they become sufficiently Fit, they can force their way into the population closest to the waterhole, creating survival advantage for their offspring.

Population (1) "has the waterhole" and is able to reproduce in the usual manner. In some generations, chromosomes with modest fitness (i.e. not necessarily among the Fittest members of the population, but not disastrously weak; the demarcation lines for choosing this set are part of the parameters of the transfer protocol, and can be optimised, as discussed later) from Population (1) are able to transfer via the chromosome transfer protocol to Population (2), where they interbreed with the indigenous population under a different Fitness function and mutation and crossover probabilities from those of Population (1), typically limiting the number of copies of any single distinct chromosome, or any distinct set of values on a specified subset of genes on a chromosome (equivalent to an ecological niche becoming full).

In some generations the most Fit chromosomes from Population (2) are able to transfer across into Population (1) and interbreed. Extinction events (where the sum of Fitness of all the chromosomes of a generation of a population drops below some specified threshold value) enable a larger-scale migration of copies of Fit chromosomes from the other population to be brought across by the transfer protocol and re-seed the extinct population. This is a way of enabling useful information embodied in moderately-Fit chromosomes to survive unstable boom-and-bust evolutionary processes that lead to extinction events in the parent population.

Ecological Archetype 4: "Lone Bulls"

A common ecological phenomenon is that when a generation of a species generates a large number of Fit male members, they are expected to leave the parent population and go elsewhere. Versions of this phenomenon appear in multiple archetypes (e.g. returning species in "Waterhole") which concentrate on the aspect of Fit chromosomes improving the gene-pool of the population they join. In "Lone Bulls", an alternative aspect is emphasised: the spatial dispersal of extremely Fit chromosomes, improving their survival in the event of an extinction event occurring in the parent population.

Population (1) is the parent population. In any generation, copies of the Fittest chromosomes are taken by the transfer protocol and placed elsewhere (in Population (2), with its own mutation and crossover probabilities). In some generations, descendants of some of these are permitted to return to Population (1) as a standard diffusion (unlike "Isolated Valleys" or "Waterhole", this can be regardless of whether or not they are particularly good examples of Population (2), depending on choice of Fitness threshold in the transfer protocol; again, this is a parameter that can be optimised); in the case of extinction events in Population (1), the transfer protocol allows a much larger influx of copies of members of Population (2) to re-seed Population (1).

Ecological Archetype 5: "Repopulating Desolation"

A common component of all of the above archetypes is the scenario whereby a catastrophe in an ecosystem, forcing extinction, represents an opportunity for large-scale migration and re-population by previously obscure creatures. This migration may be geographical, or it may be a marginal but robust species suddenly diversifying in a population explosion to fill suddenly-vacated ecological niches. Examples include the small arboreal mammals after the Cretaceous extinction. From a computational perspective this process should have a distinct identity, isolated from the more complex ecological archetypes above that also incorporate it.

There are two populations, Population (1) and Population (2). Under this transfer protocol, there is no transfer between them while both populations are viable. Without loss of generality, assume Population (2) either suffers a collapse in Fitness across the population and has a predation scheme that translates such a collapse into an absolute extinction event; or suffers a collapse in Fitness across the population such that the summed Fitness $\Sigma F^{-1}$ (g) of the population is many orders of magnitude (typically 10 or more) lower than that of the neighbouring Population (1). Following such events, Population (2) is deemed extinct, its population is set to zero and copies of the next generation of Population (1) are transferred across to repopulate Population (2), to continue evolution under its conditions.

Predator Transfer Protocols

The above ecological archetypes for transfer protocols are to move chromosomes from one Population to another based on criteria of Fitness. Such transfer protocols help minimise the adverse computational effects of extinction events on information retention and stability.

Predation schemes also suffer extinction events. For example, both Implicit and Dynamic Predation schemes will become extinct if the underlying chromosome population becomes extinct, $N(g)=0$. Dynamic Predation schemes will become extinct if at any stage the predator population drops to zero, $N_p(g)=0$, regardless of whether the chromosome population survives, $N(g)>0$. Static Predation schemes do not suffer extinction events, but suffer decay if the underlying chromosome population remains zero for prolonged periods of time.

Consequently in a spatially-networked set of Populations with predation schemes, there are Predator Transfer Protocols (PTP). In contrast to the ordinary chromosome transfer protocols described previously, which are essentially analogue, the Predator Transfer Protocols operate between Populations according to digital logic, albeit with a stochastic flavour: when predators move, they cross from Population i to Population j in any given generation with probability $P_{p(ij)} \in [0,1]$ as described below.

Figure 10B:
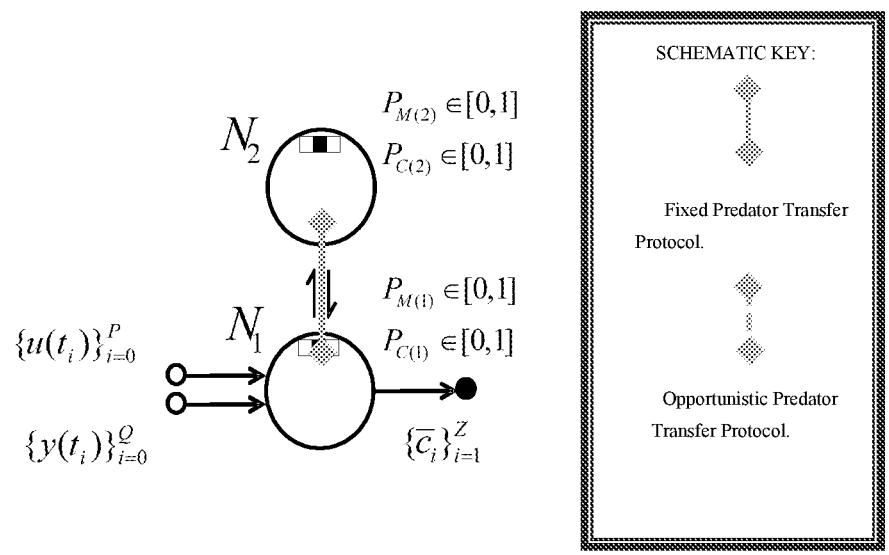
FIG. 10B is a schematic diagram of a second example of a "building block" for ecological circuit (EC) archetypes.

A schematic diagram for simple "building block" Ecological Circuit archetypes, showing Predator Transfer Protocol is shown in FIG. 10B, showing two types of predator transfer protocol namely, Fixed and Opportunistic, as will be described in more detail below.

Table 3 shows a logic table for Predator Transfer Protocols, single-species predator. Numbers "1" and "2" denote Populations. Symbols as follows: "p": predators are present; "c": chromosomes are present; "¬p": no predators are present; "¬" no chromosomes are present. "Ø" means that no transfer occurs;

$$i \xrightarrow{P_{p(ij)}} j$$

means that predator transfer occurs from Population i to Population j with probability $P_{p(ij)}$ per generation.

TABLE 3

| | 2: ¬p¬c | 2: ¬p c | 2: p¬c | 2: p c |
|---|---|---|---|---|
| 1: ¬p¬c | ∅ | ∅ | ∅ | ∅ |
| 1: ¬p c | ∅ | ∅ | $2 \xrightarrow{P_{p(21)}} 1$ | $2 \xrightarrow{P_{p(21)}} 1$ |
| 1: p¬c | ∅ | $1 \xrightarrow{P_{p(12)}} 2$ | ∅ | ∅ |
| 1: p c | ∅ | $1 \xrightarrow{P_{p(12)}} 2$ | ∅ | ∅ |

Table 4 is a logic table for Predator Transfer Protocols, two species of predator. Symbols are as in previous table, except that subscripts are used to denote species of predator. When a transfer occurs, placing one species of predator into a Population already occupied by the other predator, the outcome is dictated by a Multi-Predator Rule Set (MPRS).

TABLE 4

| | $N_2$: ¬$p_2$¬c | $N_2$: ¬$p_2$ c | $N_2$: $p_2$¬c | $N_2$: $p_2$ c |
|---|---|---|---|---|
| $N_1$: ¬$p_1$¬c | ∅ | ∅ | ∅ | ∅ |
| $N_1$: ¬$p_1$ c | ∅ | ∅ | $2 \xrightarrow{P_{p(21)}} 1$ | $2 \xrightarrow{P_{p(21)}} 1$ |
| $N_1$: $p_1$¬c | ∅ | $1 \xrightarrow{P_{p(12)}} 2$ | ∅ | $1 \xrightarrow{P_{p(12)}} 2$ |
| $N_1$: $p_1$ c | ∅ | $1 \xrightarrow{P_{p(12)}} 2$ | $2 \xrightarrow{P_{p(21)}} 1$ | $1 \xrightarrow{P_{p(12)}} 2$; $2 \xrightarrow{P_{p(21)}} 1$ |

As mentioned above, there are two types of Predator Transfer Protocols: Fixed and Opportunistic. The Fixed Predator Transfer Protocol (FPTP) is permanently anchored between two specified Populations, analogous to chromosome transfer protocols, whereas in opportunistic protocols, given a predator initially exists in a Population, and that Population is linked to other Populations via one or more chromosome transfer protocols, there is a probability $P_{Op(ij)} \in [0,1]$ (a generalisation of the concept of $P_{p(ij)} \in [0,1]$ between specified Populations) that predators will cross over any one of these chromosome transfer protocols to the adjacent Population in any given generation. Thus, the Opportunistic Predator Transfer Protocol (OPTP) behaves the same way as the FPTP, except that the FPTP is explicitly placed between some Populations as a specification, whereas the OPTP finds its own crossings between Populations.

Construction of More Complex Spatial Network Geometries

Figure 10C:
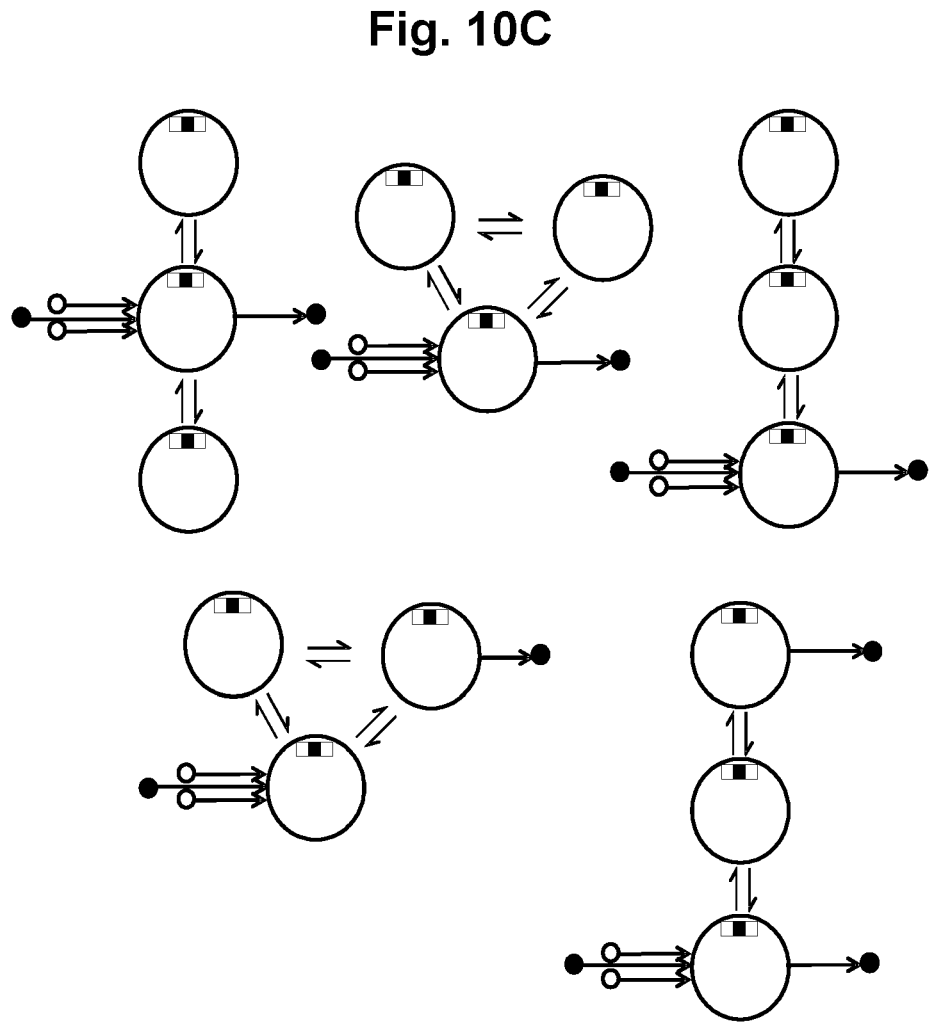
FIG. 10C is a schematic diagram of an example of basic ecological spatial network geometries, as building-blocks.

These spatial networks described above can be combined to form more complex geometries, and an example of this is shown in FIG. 10C.

Associate each Population in the spatial network in each generation g with a single number, the summed Fitness $\Sigma F^{\triangleleft}(k,g)$, where this summed Fitness across the $k^{th}$ φ-TEA Population at generation g is written $$\sum F^{\triangleleft}(k, g) \triangleq \sum_{i=1}^{N_k} \text{Re}(F^{\triangleleft}(\xi(0), \bar{c}_i(g)))$$

where $\bar{c}_i(g) \equiv \lambda$, some $\lambda_i \in \Lambda$.

Then the spatial network and its associated transfer protocols form an analogue counterpart to a digital Cellular Automaton, where the φ-TEA Populations form the counterpart to CA "tiles" or "cells" and $\Sigma F^{\triangleleft}(k,g)$ forms the analogue counterpart to the digital "on" or "off" (shades of grey, in contrast to the black and white of CA). In this example, a sufficiently low $\Sigma F^{\triangleleft}(k,g)$ for a Population (typically 10 orders of magnitude or lower relative to those of neighbouring populations) is treated by transfer protocols that link the $k^{th}$ population with its neighbours as an extinction event and hence the Population is treated as "off" for that generation with respect to its neighbours. Alternatively, if static predation is active and has an appropriate threshold, sub-threshold values for $\Sigma F^{\triangleleft}(k,g)$ automatically force actual extinction (regardless of neighbours) and sets the Population to zero ("off") for that generation. The transfer protocols form local rules, in counterpart to the global rules in a digital CA.

Given that is the case, it should also be clear that the number of Populations in a spatial network can be huge. Relatively few Populations are shown in the diagrams of spatial networks in this specification, for sake of clarity.

Figure 10D:
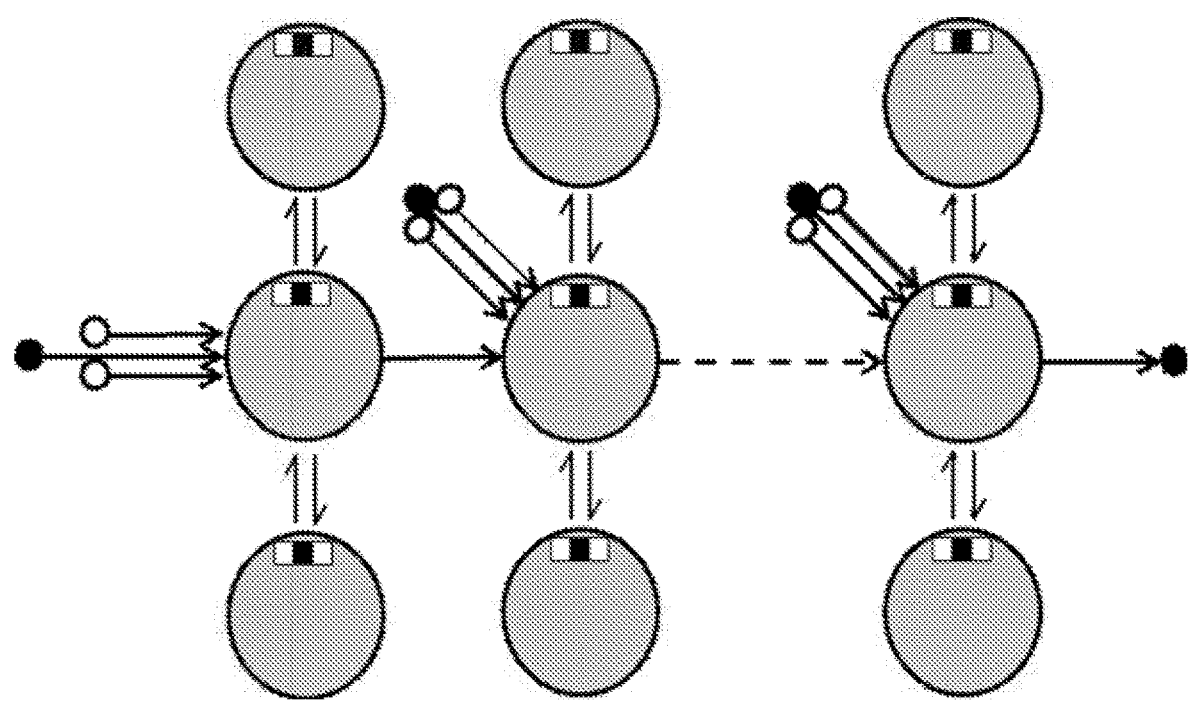
FIG. 10D is a schematic diagram of an example of ecological spatial networks forming a sequential circuit.
Figure 10E:
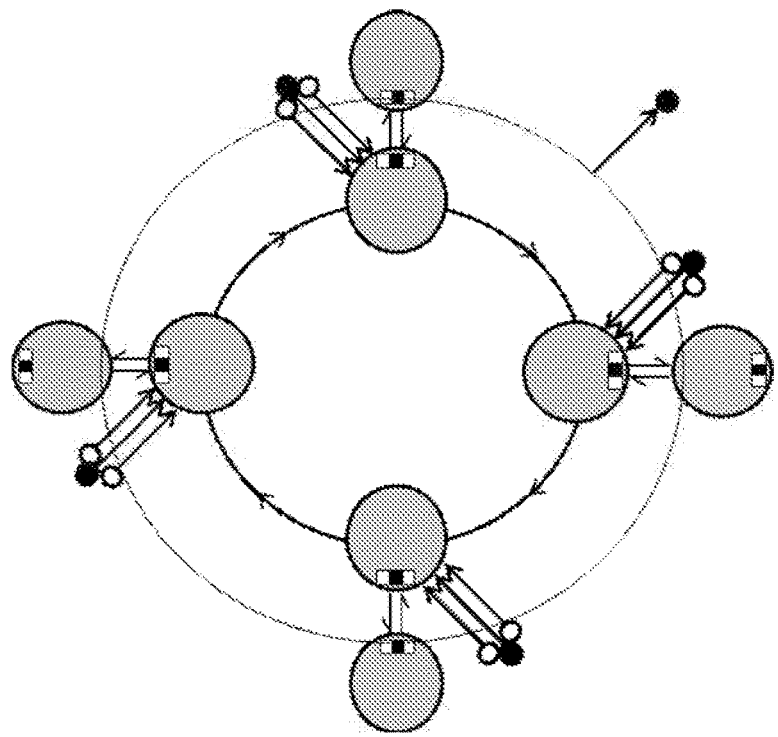
FIG. 10E is a schematic diagram of an example of a closed circuit (torus) of sequentially-executed sets of ecological spatial networks.

Constructing Sequential Circuits from Ecological Spatial Networks of Contemporary Populations This follows the same logic as the previously-introduced circuits of φ-TEA/MGAs, to be interpreted using the same reasoning. The spatial networks of contemporary populations can be arranged into sequential circuits of Blocks, for sequential computation. Analogously to circuits previously described, these circuits can have a simple open chain topology, as shown for example in FIG. 10C or a torus as shown in FIG. 10D. These are relatively simple examples, but more complex circuits can be constructed, e.g. by further incorporating the previous example structures, or combining the structures of FIGS. 10D and 10E, as shown for example in FIG. 10F.

φ-TEA circuits with both spatial and sequential aspects are described as Ecological Circuits ("φ-TEA-EC"). The same φ-TEA-EC structure can have different data sets and models applied to it.

Additional Blocks in the Ecological Circuit

Figure 10F:
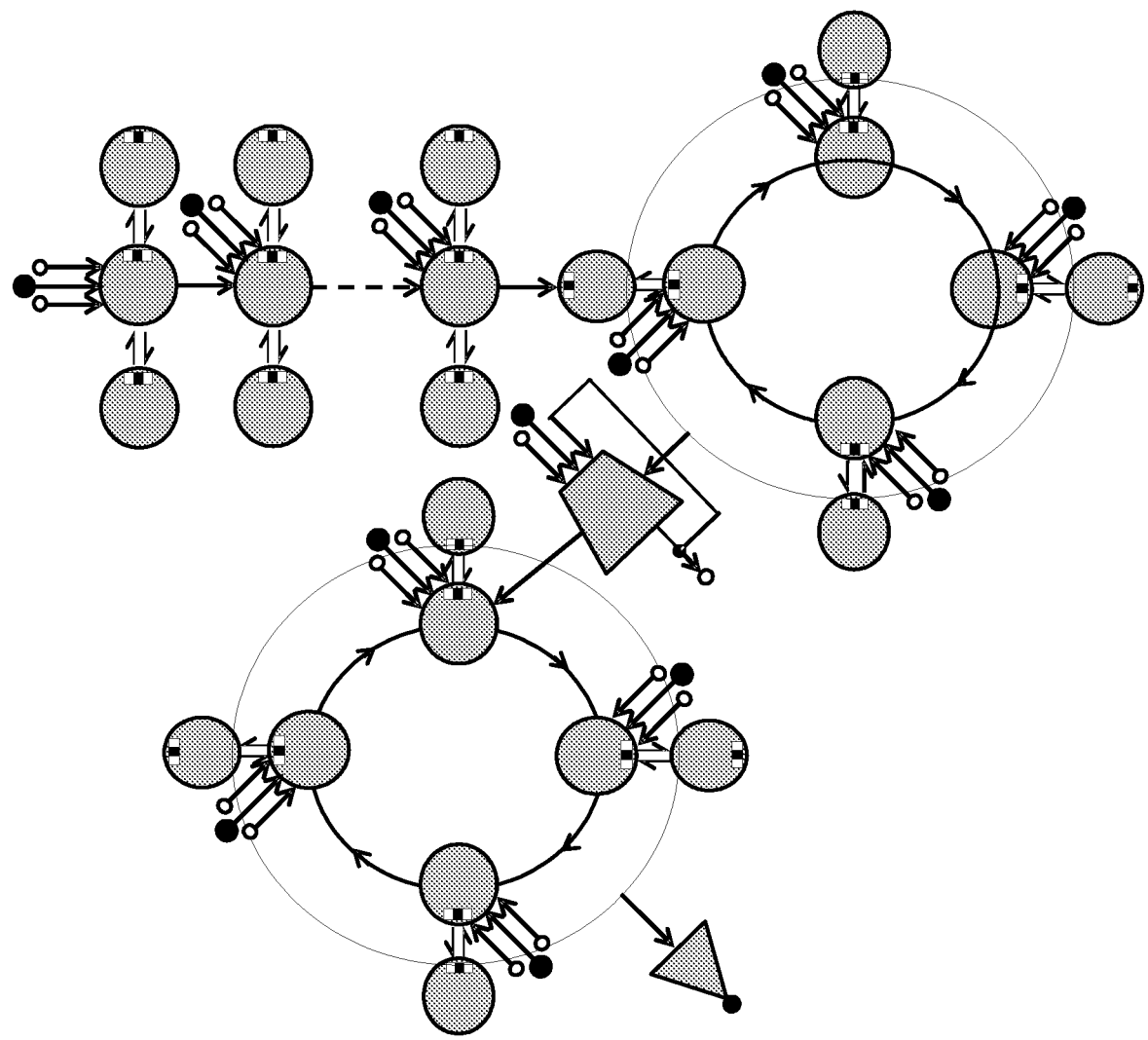
FIG. 10F is a schematic diagram of an example of a more complex φ-TEA-EC combining chain and torus topologies.

The ecological circuits can also include additional Blocks; for example, Blocks for chromosome selection/construction can be inserted into the φ-TEA Ecological Circuit. In the example of FIG. 10F, a selection/construction Block can be placed between the major network sub-geometries (between the two tori and at the termination). It will also be appreciated that this could be inserted within these network sub-geometries as well (e.g. within the chain or within the tori).

The Meta-Optimising Layer and its Recursive Structures for Ecological Circuits

The Meta-Optimising Layer and its recursive structures, can again be applied here on φ-TEA Ecological Circuits. Due to the additional complexity of φ-TEA-EC, further features are added to the Meta-Optimising Layer for an Ecological Circuit ("MOL-EC").

As well as optimising the φ-TEA-EC in the Base Layer ("BL-φ-TEA-EC") the MOL-EC has to be aware of and disrupt limit cycles if and as they form in the dynamics of the transfer protocols between contemporary populations. This can happen if the specification of timing and criteria for chromosome transfer causes the same set of chromosomes to keep shuttling backwards and forwards between two populations. When such limit cycles emerge, at least one of the timing or the criteria for chromosome transfer must be altered in the transfer protocol by the MOL-EC to disrupt the cycle.

Transfer protocol archetypes are reduced to specifications that are included in the MOL-EC, enabling them to be manipulated by conventional optimising algorithms in the MOL-EC, including using neural networks, regression trees, fuzzy logic, simulated annealing etc. as listed in the earlier implementation of a MOL, to enable transfer protocols to be constructed from rules taken from one or more archetypes; or encoded as genes on a meta-chromosome, in such a way that mutation or crossover occurring on those genes in a GA or φ-TEA allows composite transfer protocols to be created, i.e. combining features from multiple archetypes (e.g. "Waterhole" with "Archaic Species" etc.).

Transfer protocols' parameter values are expressed as MOL-EC specifications distinct from those MOL-EC specifications stipulating the protocols' rule structure. This allows the specification stipulating the rules of the protocols (a single archetype or mixture of archetypes) to be locked while still enabling the actual parameter numbers (e.g. Fitness thresholds, timing of transfers, how low the summed Fitness of one population has to fall before another population regards it as effectively extinct and invades, etc.) to be optimised for the rules that the protocols implement. This also includes the distinct encoding of the transfer protocols' rule structure and parameter values in meta-genes on MOL-EC meta-chromosomes.

Geometries for ecological spatial networks are reduced to specifications enabling them to be manipulated by optimising algorithms in the MOL-EC, including neural networks, regression trees, fuzzy logic, simulated annealing etc. as listed in the earlier implementation of a MOL, to enable the number of populations in the ecological spatial network, their specifications and geometrical relationships with one another to be altered. Additionally and/or alternatively, these can be encoded on the meta-chromosome, enabling mutation or crossover on the relevant meta-genes to alter the number of populations in the ecological spatial network, their specifications and geometrical relationships with one another. For example, the fact that Population (1) and Population (2) are linked by a transfer protocol is due to a meta-gene value specifying that a transfer protocol exists; modification of that gene value can sever that link, isolating one of the populations completely for at least the next generation. Alternatively it may establish multiple links between the two populations using distinct transfer protocols, or create a new transfer protocol linking to a different population.

Just as in previous examples, the basic MOL typically uses a GA or φ-TEA to optimise meta-chromosomes describing the structure of the φ-TEA-BL, here the MOL-EC also typically has a GA, φ-TEA or φ-TEA-EC running in this layer to optimise the BL-φ-TEA-EC in the layer beneath. The GA, φ-TEA or φ-TEA-EC running in the MOL-EC shall be denoted the MOL-φ-TEA-EC.

The same recursion can be applied here: the algorithmic structure of the φ-TEA-EC-MOL can itself be optimised, by imposing another MOL-EC over the top, named $MOL^2$-EN, containing both the specifications for the algorithmic structure of the MOL-φ-TEA-EC; possibly including other optimising algorithms from the literature, e.g. neural networks, regression trees, fuzzy logic, simulated annealing, etc., and/ or placing another GA, φ-TEA or φ-TEA-EC in $MOL^2$-EN; call it $MOL^2$-φ-TEA-EC and use it to optimise the MOL-φ-TEA-EC via evolution.

The recursive structure again typically has a finite computational complexity (with each $MOL^i$-HGA-EN being typically designed to carry less modifiable information than the one beneath) and so is able to be run on a parallel computing platform.

For purposes of brevity, the terms φ-TEA-EC, BL-φ-TEA-EC and MOL-φ-TEA-EC will be assumed from now on to encompass also the corresponding simpler structures of φ-TEA, BL-φ-TEA and MOL-φ-TEA where the spatial networks are not present (which is equivalent to a spatial network being formally present but extinct and isolated with permanently null transfer protocols).

Also, the fact this Invention uses structures repeated in the Base Layer and in Meta-Optimising Layers mean that the cumbersome terminology of meta-chromosomes and meta-genes can be discarded: from now on the term "chromosome" will encompass both chromosomes in the Base Layer and meta-chromosomes in the MOL(s) while "genes" will encompass genes on chromosomes and meta-genes on meta-chromosomes.

Inclusion of Conventional Identifiers in Library

The Identifier Module in the current system can also utilise other published Identification techniques known to practitioners in the field. These are typically stored in an Identifier algorithm library $\mathbb{L}_I$ in a database or computer memory, and are typically employed by the Identifier MOL to optimise the computational processes of Identification.

For instance, $\mathbb{L}_I$ includes the linear and extended Kalman Filters. If the model $\mathfrak{M}$ to be used for Identification is linear or sufficiently-close to linear, with sufficiently low levels of uncertainty that a nonlinear Evolving Identifier is unnecessary, the Identifier MOL may conclude that such conventional methods are preferable. In this case the final (typically single) output from the conventional Identifier would then be encoded into a chromosome and passed to the other modules as $\{\bar{c}_i\}_{i=1}^1$. It should be noted that the process of coming to this conclusion typically involves the running of φ-TEA circuits or φ-TEA-EC in the MOL, hence retains novelty over the conventional Identifiers stored in $\mathbb{L}_I$.

"Orphan" Evolving Identifiers (OEI), Re-Tasked

Up to this point the Evolving Identifier has been specified in order to perform a particular task, namely to Identify a dynamical system. However the features of the Evolving Identifier constitute a powerful tool for tasks other than Identification.

In this regard, an orphan Evolving Identifier (OEI) is defined as one where there is no system to be Identified, simply a model $\mathfrak{M}$ and model equations $\dot{\xi} = f_{\mathfrak{M}}(\xi(t), \lambda, u(t), \omega(t), t)$ with the associated state, parameter, controller and noise vectors. Where conditions of complete information do not apply, the concepts of an output variable and output time-series $\{y(t_i)\}_{i=0}^Q$ are applied to the model state and parameters, not the system state and parameters. The concept of tracking error $\varepsilon_{track}$, previously associated with how the model solution trajectory $\xi(t) = \varphi_{\mathfrak{M}}(\xi(0), \lambda_i, \omega(t), t) | t \in [t_0, t_j]$ tracks the measured data $\{y(t_k)\}_{k=0}^Q$, is discarded. The tracking criteria previously employed, whereby the Fitness of a chromosome $F: \bar{c} \mapsto [0, \infty)$ was a function of the tracking error $\varepsilon_{track}$ of its associated trajectory, is discarded. Instead a performance function $I(\bullet)$ is introduced so that the Fitness of a chromosome $F: \bar{c} \mapsto [0, \infty)$ is a function of $I(\bullet)$. Under conditions of complete information this takes the form $I:\{\boldsymbol{\varphi}_{\mathfrak{M}}(\xi(0),\lambda_i,\omega(t),t)|t\in[t_0,t_f]\}\to\mathbb{R}$, whereas under incomplete information it becomes $I:(\{y(t_i)\}_{i=0}^{Q}|\{\boldsymbol{\varphi}_{\mathfrak{M}}(\xi(0),\lambda_i,\omega(t),t)|t\in[t_0,t_f]\})\to\mathbb{R}$.

This performance function measures how well the trajectories associated with chromosomes fulfil some specified objectives within state space.

The other features of the Orphan Evolving Identifier are those of the typical Evolving Identifier, such as texturing of Fitness, circuits, ecological spatial networks, MOL etc.

Thus the Orphan Evolving Identifier is a sophisticated tool for heuristic optimisation of complex dynamical systems, generating multiple solutions that can then be used by machine-intelligent algorithms. Typically where other modules in the Modular modelling system perform optimisation in their MOLs, it is performed by an Orphan Evolving Identifier.

As an example of its wider application, consider the task of constructing electronic circuits, either in two dimensions on a microchip, or in three dimensions, filling space. A payoff is typically sought, between closest-packing of a circuit capable of performing specified operations and physical constraints such as the need to limit the effects of heat generation by components, including separation constraints required for cooling processes such as fan-forced air. The components within an electronic circuit are specified as nodes of a connected network, typically as part of the model specification $\mathfrak{M}$ with spatial locations for each node specified by parameters encoded as genes. Geometrical constraints on the relative positions of nodes are imposed to reflect physical constraints in connecting components. These are typically imposed by penalising the Fitness of chromosomes corresponding with infeasible combinations of node positions. Electronic processes corresponding with circuit operation are modelled using differential or difference equations, with the thermodynamics associated with operation of the circuit and its cooling being modelled using partial differential equations. The Textured Fitness of chromosomes rewards minimum area/volume occupied by the circuit and compliance with thermal and geometrical specifications, whilst the performance function reflects a combination of the minimum areas/volumes and the most desirable thermal specifications achieved by the circuits, subject to other constraints being obeyed.

Summary and Export to Other Modules

At a fundamental mathematical level, the techniques of φ-TEA circuits and associated Blocks, predation, ecological spatial networks and transfer protocols (for both chromosomes and predators) represent a new kind of heuristic analogue symbolic logic, manipulating chromosome-based data structures for machine-intelligent interrogation of complex systems. The existence of the meta-optimising layers means that the architecture best-suited for the task at hand is, literally, evolved from a unified set of building-blocks.

In particular what has been described here is the use of one or more autonomous, recursively-evolving φ-Textured Genetic Algorithm(s)/Modified Genetic Algorithm(s) for the purpose of nonlinear Identification or optimisation of a complex system using noise-polluted partial information.

The end result is a set of one or more chromosomes $\{\bar{c}_i\}_{i=1}^{Z_{final}}$ corresponding with parameter vectors $\{\lambda_{i,j}\}_{i=1}^{Z_{final}}$ such that, under the model $\mathfrak{M}$, the model equations $\dot{\xi}= f_{\mathfrak{M}}(\xi(t),\lambda,u(t),\omega(t),t)$ will track, either directly, or some function $g(\xi(t),\eta,\{u(t_i)\}_{i=0}^{P},\omega(t),t)$, the measured system behaviour $\{y(t_i)\}_{i=0}^{Q}$ as well as is computationally possible. Here bounded simulated noise is assumed: $\|\omega(t)\|<w_\delta$, some specified $w_\delta\in[0,\infty)$.

Apart from the specific application of Identification, it should be apparent that the structures, processes and features described for the Evolving Identifier have much broader application, as exemplified in the Orphan Evolving Identifier (OEI). The other modules all have the OEI and its component features included within their own structures to help them achieve their own objectives.

The Controller

The next component to consider is the Controller, which examines how the system implements identified models to control the dynamical system being studied. Furthermore, assuming the model $\mathfrak{M}$ is (approximately) correct, how does the system modify controller laws adaptively, to overcome the initial effects of residual uncertainty in $\mathfrak{M}$ or $\{\lambda_i\}_{i=0}^{Z_{final}}$ on those controller laws, and/or minimise any damaging effects of residual uncertainty in $\{\lambda_i\}_{i=1}^{Z_{final}}$ or elsewhere in the system dynamics, which propagate through the controller laws, as well as exploiting the known information on $\mathfrak{M}$ and $\{\lambda_i\}_{i=1}^{Z_{final}}$ to minimise any subsequent external threats.

Multiple kinds of closed-loop controller method are encompassed by the system in the Controller Module, which typically uses at least one, selected by the MOL based on the Identified model $\mathfrak{M}(\{\lambda_i\}_{i=1}^{Z_{final}})$, $Z_{final}\geq 1$ and how closely it tracks the measured output $\{y(t_i)\}_{i=0}^{Q}$, to steer the dynamical system. These different kinds of controller method are typically stored in a library $\mathbb{L}_C$, typically stored in a database or computer memory, accessible to the Controller Module.

The Controller Module also typically implements numerical and analytical techniques to estimate Regions of Controllability and Regions of Strong Controllability associated with controller methods. Such techniques are well-established in the technical literature (Control Theory and Differential Game Theory); here Regions of Strong Controllability are typically calculated against a combination of actual adversaries (where they exist) and Nature. Some controller methods, such as control using Lyapunov functions, have specific techniques associated with them for estimating these regions. Techniques are also provided to allow use of the information provided by these estimated Regions to inform high-level Controller decisions, typically performed in the Controller Module's MOL.

The Region of Controllability of a specified controller law can be denoted by the symbol $\Delta_q$, where $\Delta_q\subset\Delta$, to steer the state vector $x(t)\in\Delta$ along a trajectory to a designated target T. Similarly (where they exist) denote the Region of Strong Controllability for that same controller law by the symbol $\Delta_Q$ and the Guaranteed Winning Region (a desired subset within $\Delta_Q$) as $\Delta_{GWR}$, where $\Delta_{GWR}\subset\Delta_Q\subset\Delta_q\subset\Delta$.

The MOL typically uses the existence, location and relative volume of these regions for various controller methods to decide which method to employ to steer the system to target; and decide, if needed, which controller method to employ as an interim measure if $x(0)\notin\Delta_q$, to steer the system to within the sets $\Delta_q\subset\Delta$. In the case of $x(0)\in\Delta_q$ but $x(0)\notin\Delta_Q\subset\Delta_q$, the Region of Strong Controllability associated with the preferred controller method, the MOL decides whether to activate the preferred controller method selected to steer the system to target, or to employ an interim method to steer the system to a state within $\Delta_Q\subset\Delta_q$ prior to activating the controller method to steer the system to target. Similarly, in the case of $x(0)\in\Delta_Q\subset\Delta_q$ but $x(0)\notin\Delta_{GWR}\subset\Delta_Q$ associated with the preferred controller method, prior to activating the preferred controller method.

Given that the controller vector is typically constrained within compact sets $$u(t)=(u_1(t), \ldots, u_p(t))^T \in U \triangleq [u_1^-, u_1^+] \times \ldots \times [u_p^-, u_p^+],$$

typically a smaller hypercube is designated by the MOL within this control set:

$$U^\square = [u_1^{\square-}, u_1^{\square+}] \times \ldots \times [u_p^{\square-}, u_p^{\square+}]$$

where $[u_i^{\square-}, u_i^{\square+}] \subseteq [u_i^-, u_i^+]$.

If the form of control being undertaken permits either repetition on a system and/or repetition with parallel implementation on multiple systems then the MOL typically optimises this controller method. Examples of this implementation include industrial robots, where the one robot may have a control task such as Model Reference Adaptive Control (MRAC) rehearsed on it repeatedly, or multiple new identical robots on a factory floor may have the same MRAC task rehearsed on them both in parallel and sequentially; or multiple possible dynamical systems to be controlled are used to train the controller method, to be robust across the entire set of possible systems; or simulations of one or more dynamical possible systems to be controlled are used to train the controller method to be robust across the entire set of possible systems.

Typically each controller method has various parameters or other structures (e.g. Lyapunov functions) associated with it, which are to be optimised, including the upper and lower bounds on each component of the controller variable in the restricted hypercube, $[u_i^{\square-}, u_i^{\square+}] \forall i \in \{1, \ldots, p\}$. Similarly the decisions whether to activate a preferred controller method to steer the system to target or exploit an interim controller to reach regions of higher-confidence controllability (where they exist) before activating the preferred controller can be represented as an adjustable set of parameters, including numerical labels for various controller methods, plus switches and thresholds for decision-making, plus parameter values associated with each controller method.

Similarly there are multiple numerical and analytical methods in the literature by which the Regions of Controllability, Strong Controllability and Guaranteed Winning Regions can be computed. The decision to choose a particular method and the assumptions that method employs are again represented as an adjustable set of parameters, including switches, thresholds and other associated parameters.

Writing the vector of these parameters as $\lambda^\circ$, then either this or a higher MOL optimises the controller method and associated decisions by optimising this vector using one or both of qualitative or quantitative methods. Qualitative methods include that the confidence associated with the applied controller is high over the maximal set of likely initial conditions, typically through maximising the Guaranteed Winning Regions or Regions of Strong Controllability, whereas quantitative methods include the controller being optimised to achieve its objectives most efficiently in some manner, including in least time, or using least resources, or with least disruption to the system, and/or over the maximal number of distinct plausible dynamical systems to be controlled.

To do this, typically the MOL encodes $\lambda^\circ$ into chromosome form and uses a φ-TEA circuit or φ-TEA-EC to optimise the chromosomes through sequential or parallel-sequential repetitions of control of the system or repetitions of rehearsals of control of the simulated system by the controller. These circuits may themselves be optimised by a higher MOL.

The Controller Module typically retains the ability to apply different controller methods sequentially. This may be used because the Identified model $\mathfrak{M}(\lambda)$ indicates that the system dynamics may change, or other reasons exist requiring a change in controller method (for instance the state vector x(t) may have moved outside the Region of Controllability for the controller method previously used). Alternatively, this may be used if the existing controller method is failing to achieve the specified objectives, based on the lack of convergence to target of one or more of the measured output $\{y(t_i)\}_{i=0}^Q$ and the expected trajectories $\xi(t)=\varphi_\mathfrak{M}(\xi(0),\lambda_i,\omega(t),t)|t\in[t_0,t_f]$.

The Controller Module also typically uses its MOL to look for apparent anomalies or errors during closed-loop control, such as anomalous isolated data from measured system output $\{y(t_i)\}_{i=0}^Q$; sustained divergence between $\{y(t_i)\}_{i=0}^Q$ and expected trajectories $\xi(t)=\varphi_\mathfrak{M}(\xi(0),\lambda_i,\omega(t),t)|t\in[t_0,t_f]$, indicating model error or controller failure, and/or erroneous controller output in terms of prescribed control values u(t).

Such anomalies and errors are typically discovered by comparing observed data with expected/predicted trajectories, to determine if the observed data lies significantly outside the reduced dynamic envelope, or the observed data lies within the reduced dynamic envelope, but are inconsistent with the geometries of all candidate solution trajectories represented there (e.g. time series multivariate data where the relationship among measured data variables is inconsistent with the candidate relationships postulated by the trajectories). Alternatively, anomalies and errors can be determined by confirming prescribed control values satisfy $u(t) \in U^\square \subseteq U$ and/or predicting the behaviour of trajectories under $u(t)=p(\xi,t)$ from reliable past data and discovering inconsistencies with the observed data at the relevant times.

The MOL of the Controller Module typically then decides whether to ignore such anomalies or errors, or whether to engage in processes to reduce or minimise the effects of such anomalies and errors. Such processes typically include instructing the system or human user to re-sample the measured output $\{y(t_i)\}_{i=0}^Q$ to confirm the anomalous data; and/or modifying the Controller intervals $U^\square \subseteq U$ to enable the Controller to compensate; and/or using other Modules to re-assess either the choice of model $\mathfrak{M}$, and/or the parameter set $\{\lambda_i\}_{i=1}^{Z_{final}}$ associated with the Identified model. Additionally, and/or alternatively, this can include activating a MRAC process (described below) to compensate for the anomaly; and/or activating a Game against Nature (described below), or, if one is already running, revising its associated intervals of uncertainty to include the apparent anomaly or error; and/or disregarding the anomaly as an error and deleting it from $\{y(t_i)\}_{i=0}^Q$.

Identification-Related Controller Algorithms

Identification-related Controller algorithms are typically employed to perturb the system being studied to improve the accuracy of the model describing it. A number of mechanisms for achieving this will now be described.

Downstream Disambiguation Among Candidate Trajectories Through Active Modulation Controller Aspect Here the system is typically formally under-determined, i.e. the available measurable data is insufficient to produce a unique (within the constraints of noise) numerical model of the system using Identification methods. Instead multiple candidate trajectories exist.

In this case the controller vector would typically be manipulated using one or more algorithms, such as "downstream disambiguation" algorithms (defined below), to change the dynamical conditions under which the system was being observed, with a view to generating further information about the system. The controller law is typically calculated such that it forces candidate trajectories to diverge in state-space Δ over time. From the perspective of the Controller, the most effective way of achieving this is through "active modulation".

In active modulation, instead of relying on a suitably-different controller input being externally provided, a control sequence $\{u^{disamb}(t_i)\}_{i=0}^{P}$, $u_l^{disamb}(t_i) \in [u_l^-, u_l^+]$, $l \in \{1, \ldots, p\}$ is generated by this algorithm based on the dynamics of the model $\mathfrak{M}$ and administered to the dynamical system being studied such that it forces the expected measurable behaviour $g(\xi(t), \eta, \{u^{disamb}(t_i)\}_{i=0}^{P}, \omega(t), t)$ of trajectories $\xi(t) = \varphi_{\mathfrak{M}}(\xi(0), \lambda_i, \omega(t), t) | t \in [t_0, t_f]$ corresponding with distinct $\lambda_k | \lambda_k \equiv \bar{c}_k \in \{\bar{c}_i\}_{i=1}^{Z}$ to diverge under the model $\mathfrak{M}$.

One way of generating the controller sequence $\{u^{disamb}(t_i)\}_{i=0}^{P}$ is to define a compact Avoidance Set A in terms of the distance between trajectories as they travel through state space Δ and then use a Lyapunov-based controller law to force them to diverge. Level sets of the Lyapunov function $V_A$ are defined in terms of this distance between trajectories. Then, for each pair of distinct trajectories, or each pair of representative trajectories, a (possibly non-uniform) time interval $\Delta t_{jk}$ is prescribed over which their divergence will be forced; if $\Delta t_A$ denotes the overall period of time assigned to downstream disambiguation through active modulation, then $$\Delta t_A = \sum_{j=1}^{Z} \sum_{k=1}^{Z} \Delta t_{jk}$$

where $\Delta t_{jj} \equiv 0$. Then on $(\xi, t) \in A \times \Delta t_A$ design the control law $u^{disamb}(t) = p(\xi, t)$ by imposing a necessary condition: the function $p(\xi, t)$ must achieve $\dot{V}_A(\xi(t), t) \geq C_A > 0$ $\forall t \leq \Delta t_A$, for some positive constant $C_A$. If a discrete-valued controller sequence $\{u^{disamb}(t_i)\}_{i=0}^{P}$ is required, then this is obtained by discrete sampling of $u^{disamb}(t) = p(\xi, t)$ over the time interval $t \in [0, \Delta t_A]$.

Variations on this are possible. For example, instead of explicit specification of sequential time intervals $\Delta t_{jk}$, these can be implicitly defined to last until such time as $(\varphi_{\mathfrak{M}}(\xi(0), \lambda_j, 0, t) - \varphi_{\mathfrak{M}}(\xi(0), \lambda_k, 0, t))^2 > \delta_{jk}^2$, some separation distance $\delta_{jk} > 0$ that is sufficiently large as to be visible despite background noise. Furthermore, instead of defining $V_A$ in terms of distance between trajectories, it can be defined in terms of distance between other measurable behaviour $g(\varphi_{\mathfrak{M}}(\xi(0), \lambda_1, 0, t), \eta, \{u(t_i)\}_{i=0}^{P}, \omega(t), t)$ of trajectories $\xi(t) = \varphi_{\mathfrak{M}}(\xi(0), \lambda_i, \omega(t), t)$.

It should be noted that while engaged in downstream disambiguation among candidate trajectories through active modulation, all elements of this set of trajectories corresponding with distinct $\lambda_k | \lambda_k \equiv \bar{c}_k \in \{\bar{c}_i\}_{i=1}^{Z}$ are also typically steered through state-space so that they also remain within some desired flow constraints (tube) $\lambda_{tube}(t) \subset \Delta$ and, where possible, are ultimately steered to and kept within preferred constraints $T_{tube}(t) \subset \Delta_{tube}(t)$. This is typically achieved using a second $C^1$ Lyapunov function $V_{tube}$ such that a target set defining the preferred constraints is given by $$T_{tube} \triangleq \{(\xi, t) \subset \Delta \times [0, \Delta t_A] | V_{tube}(\xi, t) < C_{tube}\} \text{ for some } C_{tube} > 0.$$

Following the concept and theorems of Lyapunov-based controllability for capture in the literature, the closure of the complement of $T_{tube}(t)$ in Δ can be denoted by $cl(\Delta \setminus T_{tube}(t))$ and some open set D defined such that $cl(\Delta \setminus T_{tube}(t)) \subset D$ and $V_{tube}: D \times [0, \Delta t_A] \to \mathbb{R}_+$. Define some initial playing set $\Delta_0$ by $\Delta_0 \subseteq (\Delta_{tube}(t) \setminus T_{tube}(t))$ with $\xi(0) \in \Delta_0$, and the following constants:

$$\begin{cases} v_T^- \triangleq \inf V_{tube}(\xi, t) | \xi \in \partial T_{tube} \\ v_0^- \triangleq \inf V_{tube}(\xi, t) | \xi \in \partial \Delta_0 \end{cases}$$

Given $$\left. \begin{array}{l} V_{tube}(\xi, t) > v_T^- \\ V_{tube}(\xi, t) \leq v_0^- \end{array} \right\} \forall \xi \in \Delta \setminus T_{tube}(t),$$

then further constraints are placed on $u^{disamb}(t) = p(\xi, t)$, namely
a. The values for $u^{disamb}(t)$ are chosen $\forall t \in [0, \Delta t_A]$ such that there exists some constant $C_{tube} > 0$ satisfying $\dot{V}_{tube}(\xi(t), t) \leq -C_{tube} < 0$ $\forall t \leq \Delta t_A$, and
b. Where possible, the values for $u^{disamb}(t)$ are chosen $\forall t \in [0, \Delta t_A]$ such that there exists $T_{tube} \in (0, \Delta t_A)$ such that $$\dot{V}_{tube}(\xi(t), t) \leq -\frac{v_0^- - v_T^-}{T_{tube}}.$$

An example is the analysis of the pharmacokinetics ('PK') parameters for infused insulin in humans from fasting blood samples. Insulin is infused subcutaneously from an external source using a pump; the control input is the specified rate of infusion $u_I(t)$. Once subcutaneous, an accepted model (call it $\mathfrak{M}_{lin}$) of insulin PK states that two distinct types (monomeric and non-monomeric) of insulin become apparent, each with different PK parameter values:

$$\left. \begin{array}{l} \dot{\xi}_{21}(t) = -(\lambda_{18} + \lambda_{16})\xi_{21}(t) + u_I(t) \\ \dot{\xi}_{22}(t) = \lambda_{16}\xi_{21}(t) - \lambda_{19}\xi_{22}(t) \\ \dot{\xi}_{20}(t) = -(\lambda_{22} + \lambda_{24})\xi_{20}(t) + \frac{1}{\lambda_{20}}\left(\lambda_{21}\xi_{26}(t) + \frac{\lambda_{18}}{\eta}\xi_{21}(t) + \frac{\lambda_{19}}{\eta}\xi_{22}(t)\right) \end{array} \right\}$$

Here $u_I(t)$ denotes infused insulin; $\xi_{21}(t)$ denotes the amount of the first type of insulin (in pmol); $\xi_{22}(t)$ denotes the amount of the second type of insulin (in pmol); $\xi_{20}(t)$ denotes the plasma concentration of insulin; $\eta$ denotes body mass (easily measured accurately).

From a past time-series obtained from a medical history, matching the insulin infusion time-series $\{u(t_i)\}_{i=0}^{P}$ with time-series measurements of insulin concentration in plasma $\{y(t_i)\}_{i=0}^{Q}$, the Identifier extracts distinct candidate parameter vectors that all generate trajectories that track $\{y(t_i)\}_{i=1}^{Q}$ under $\{u(t_i)\}_{i=0}^{P}$ to within a specified accuracy.

Given that these $\lambda_i$ are distinct, another controller sequence of infused insulin exists, $u_I^{disamb}(t)$, such that these trajectories $\{\varphi_{\mathfrak{M}}(\xi(0), \lambda_i, 0, t)\}$, can be forced to diverge under $u_I^{disamb}(t)$. Such a $u_I^{disamb}(t)$ can be computed by using a Lyapunov function $V_A$ constructed as described above. For safety reasons, these diverging trajectories are typically constrained within a specified tube by using $V_{tube}$ to apply constraints that modify $u_I^{disamb}(t)$, forcing $\xi_{20}(t)$ to remain within a specified interval for all time.

It will be appreciated that other methods also exist for ensuring all elements of this set of trajectories corresponding with distinct $\lambda_k | \lambda_k \equiv \bar{c}_k \in \{\bar{c}_i\}_{i=1}^Z$ are also typically steered through state-space so that they also remain within desired flow constraints, such as imposing constraints on $u^{disamb}(t) = p(\xi, t)$ so that the trajectories do not cross specified geometrical surfaces within $\Delta$. These methods are also encompassed in the current system.

Controller Response Triggered by Identifier Failure

Typically a Controller algorithm is triggered by failure of the Identifier to achieve satisfactory convergence. When activated, typically the Controller translates the state of the system in $\Delta$ to a new state in $\Delta$, where Identification may have better results in generating $\{\lambda_i\}_{i=1}^{Z_{final}}$, based on knowledge of the model $\mathfrak{M}$. Note that either $\{\lambda_i\}_{i=1}^{Z_{final}} \subset \Lambda$ or else the expected parameter space is also modified, so $\{\lambda_i\}_{i=1}^{Z_{final}} \subset \tilde{\Lambda}$, where $\tilde{\Lambda} \neq \Lambda$ (i.e. the two sets are distinct, although possibly $\tilde{\Lambda} \cap \Lambda \neq \emptyset$).

For example if attempted Identification on a dynamical system fails to generate consistent results and suggests that the system is actually in a chaotic state, an external Controller is applied to modify the system until chaotic behaviour ceases. This Controller also transforms at least one system parameter, so its value now lies in a different interval of expected values than previously. Identification is then repeated on the now non-chaotic system.

A less extreme example is where a dynamical system (e.g. an industrial robot) is observed to suffer from erratic behaviour when it overheats performing pick-and-place chores over time. Due to this erratic behaviour, Identification is impossible as the associated noise overwhelms the underlying dynamics. The robot controller is then modified to stop pick-and-place behaviour for an hour, allowing the machinery to cool down, prior to the dynamical behaviour resuming and the Identification being repeated. Here again some parameter values may change, depending on whether the robot's lubricant is such that its viscosity alters over the temperature range.

Translation of State Vector to Map System Dynamics Across State Space

The control variable is modified by the Controller to translate the system's initial conditions from place to place within state-space. This can be performed to search for equilibrium conditions, regions of attraction and/or limit cycles by studying trajectory behaviour in state-space.

Alternatively, this might be performed because a Poincaré surface-of-section map analysis on the trajectories generated by the set of candidate chromosomes in the model, $\mathfrak{M}(\{\bar{c}_i\}_{i=1}^Z)$, suggest that multiple domains with different stability attributes exist under physically-relevant conditions, and/or the system changes behaviour autonomously (i.e. in a manner that is not explicitly time-dependent) across two or more subsets in state space: for instance, as the system trajectory travels across state-space, onset of instability and/or period-doubling and/or mathematical chaos are observed. In these cases, the control variable would typically be modified by the Controller to translate the initial conditions of the systems across various locations in state space, to enable detailed mapping of this dynamical behaviour of the system, including its transitions.

Single-Objective Controller Algorithms

Single-objective Controller algorithms can include control methods published in the literature, including, but not limited to linear or quasi-linear control methods, including $H_\infty$ control; stochastic control; optimal control methods based on the Euler-Lagrange equation; fuzzy logic controllers; neural network controllers; or control of chaotic or otherwise unstable systems (including perturbation or modification of parameter values and state variables to translate the system to a non-chaotic and/or otherwise stable state, prior to use other non-chaotic controllers).

In the current system such controller algorithms typically rely on the fact that the system dynamics are tracked by the Identified model dynamics, comprising one or more elements of $\{\lambda_i\}_{i=1}^{Z_{final}}$, to within an acceptable margin of error. In this case, it is possible to construct a closed-loop controller law based on these Identified model dynamics to manipulate the system within an acceptable margin of error.

The set of single-objective Controller algorithms can also include control methods using a single Lyapunov function and associated Control Theory and Game Theory concepts, for instance as outlined in a medical context in WO2004/027674. This typically comprises the use of $\{\lambda_i\}_{i=1}^{Z_{final}}$ with Lyapunov functions to generate controller laws to steer the system trajectories into one or more desired (target) sets in state space; generate controller laws to steer the system trajectories to avoid one or more undesired (anti-target) sets in state space, possibly by enclosing them singly or collectively with a larger set(s) in state space, to be avoided by system trajectories (one or more avoidance set(s)), or a combination of the two. It will be appreciated that this can be achieved in conjunction with or using techniques outlined in WO2004/027674.

Model Reference Adaptive Control Algorithms

Model Reference Adaptive Control (MRAC) algorithms operate where the system retains significant dynamical uncertainties (in terms of structural uncertainty, as well as uncertain values of parameters and/or state variables). A dynamical reference model $\mathfrak{M}(\lambda)$ exists, with an associated reference trajectory path in state space that we desire the system to follow. The objective in MRAC is to generate a controller that steers the reference model along the reference trajectory while at the same time modifying the values of parameters and state variables in the reference model, so that the dynamics of the system and the reference model converge, pulling the poorly-known system into controlled convergence along the reference trajectory.

The Controller Module in the current system can utilise multiple MRAC methods. Its MOL decides which MRAC method to employ, based on the structure of $\mathfrak{M}(\lambda)$ compatible with the expected dynamics of the system (for instance, whether they are linear or highly nonlinear).

This can include the use of linear or quasi-linear forms of MRAC, which are well-known in the literature and are incorporated in Modular modelling systems.

This can also include the use of a Product State Space Technique involving nonlinear MRAC using Lyapunov functions, described in WO2007/104093.

In broad terms the product state space technique involves finding suitable $\dot{\mu}(t)$ such that $\dot{V}_\eta \leq -h(\|[X_m(t), \alpha(t)]^T\|) < 0$ without compromising the effectiveness of bounded $u(t) = p(X_m, t)$ in forcing $\dot{V}_s < 0$, steering the system to T. Expressed in terms of difference equations, given for some time increment $\delta t > 0$, $\mu(t+\delta t) = \mu(t) + \delta\mu(t)$, this challenge is then to find suitable $\delta\mu(t)$ at each increment such that:

$$V_\eta(t+\delta t) - V_\eta(t) \leq -h(\|[X_m(t), \alpha(t)]^T\|) < 0 \text{ and}$$

$$V_s(t+\delta t) < V_s(t) \text{ for bounded } u(t) = p(X_m, t) \in U.$$

These two criteria are referred to as the Product State Space convergence criteria. The traditional way of achieving the Product State Space convergence criteria is to use local search methods from $\mu(t)$, such as steepest-descent algorithms, to find the next value for this adjustable parameter vector. An alternative, global way used by the current system to achieve this is to establish a local set $\Lambda^\square \subset \Lambda_0$ as a search hypercube around $\mu(t) \in \Lambda_0$, defined by $\Lambda^\square \triangleq [\mu_1 - \Delta\mu_1, \mu_1 + \Delta\mu_1] \times \ldots \times [\mu_m - \Delta\mu_m, \mu_m + \Delta\mu_m]$, for some non-negative increments $\Delta\mu_1, \ldots, \Delta\mu_m \geq 0$. Then an evolutionary algorithm (EA, such as a φ-TEA, MGA or conventional GA) is applied to $\Lambda^\square$ to find sets of (positive or negative) increments $\delta\mu = [\delta\mu_1, \ldots, \delta\mu_m]^T$ such that $\mu(t) + \delta\mu \in \Lambda^\square$ and $V_\eta(t+\delta t) - V_\eta(t) \leq -h(\|[X_m(t), \alpha(t)]^T\|) < 0$ and $V_s(t+\delta t) < V_s(t)$ for $u(t) = p(X_m, t) \in U$.

Typically this is done by encoding $\mu(t) + \delta\mu \in \Lambda^\square$ as chromosomes, typically with a gene allocated to each component $\mu_i(t) + \mu_i$, and endowing significantly higher values of Fitness to chromosomes satisfying $V_\eta(t+\delta t) - V_\eta(t) \leq -h(\|[X_m(t), \alpha(t)]^T\|) < 0$ and $V_s(t+\delta t) < V_s(t)$ for $u(t) = p(X_m, t) \in U$.

The advantage of using an EA is that a large number of candidates for $\mu(t) + \delta\mu$ can be computed and tested in parallel, allowing multiple solutions to be explored rapidly. One of these is then chosen for this iteration $t+\delta t$ and the MRAC process continues.

An alternative method that can be used instead of applying a EA to $\Lambda^\square$, is to use simulated annealing or other known non-evolutionary heuristic method as a global search on $\Lambda^\square$ to find the "best" candidate.

Evolving MRAC

Another, alternative way to achieve MRAC, is referred to as "Evolving MRAC". It shares the same structure as the Product State Space Technique until the stage is reached of needing to find suitable $\delta\mu$ at each increment to satisfy the Product State Space convergence criteria. This technique again establishes $\Lambda^\square \subset \Lambda_0$ and encodes $\mu(t) + \delta\mu \in \Lambda^\square$ as chromosomes, typically with a gene allocated to each component $\mu_i(t) + \delta\mu_i$.

However, instead of using a conventional GA, simulated annealing or other known heuristic method, it employs at least a modified form of Evolving Identifier (referred to as an Evolving MRAC Engine), typically running a φ-TEA circuit or φ-TEA-EC. The Evolving MRAC Engine has similar features to the Evolving Identifier. However, whereas an Evolving Identifier forces the model trajectories associated with chromosomes to converge with the observed system behaviour, in an Evolving MRAC Engine the direction of convergence is reversed: the system behaviour is forced to converge with the model trajectory as it is adaptively controlled. Additionally, whilst a typical Evolving Identifier forces chromosomes to track measured data and rewards good tracking with increased Fitness (further Textured to encourage other independent traits), the Evolving MRAC Engine uses Textured Fitness to reward chromosomes corresponding with $\mu(t) + \delta\mu \in \Lambda^\square$ that fulfil the Product State Space convergence criteria.

In one example implementation fitness rewards chromosomes for which the corresponding trajectories achieve $V_\eta(t+\delta t) - V_\eta(t) \leq -h(\|[X_m(t), \alpha(t)]^T\|) < 0$. This is then Textured to reward those chromosomes that also generate trajectories for which $V_s(t+\delta t) < V_s(t)$ for some $u(t) = p(X_m, t) \in U$. The Fitness is possibly further Textured, for instance to encourage more physically plausible/desirable variations $\mu(t) + \delta\mu$, and/or encourage variations $\mu(t) + \delta\mu$ that are more amenable to control the system for collision or capture with T, or enable a more desirable T to be specified for collision or capture.

In another example, the Fitness rewards those chromosomes for which the corresponding trajectories achieve $V_s(t+\delta t) < V_s(t)$ for some $u(t) = p(X_m, t) \in U$; this is then Textured to reward those chromosomes that also generate trajectories for which $V_\eta(t+\delta t) - V_\eta(t) \leq -h(\|[X_m(t), \alpha(t)]^T\|) < 0$. Again the Fitness is possibly further Textured, for instance to encourage more physically plausible/desirable variations $\mu(t) + \delta\mu$, and/or encourage variations $\mu(t) + \delta\mu$ that are more amenable to control the system for collision or capture with T, or enable a more desirable T to be specified for collision or capture.

Again, as in the EA above, the use of φ-TEA means that a large number of candidates for $\mu(t) + \delta\mu$ can be computed and tested in parallel, allowing multiple solutions to be explored globally, rapidly. One of these is then chosen for this iteration $t+\delta t$ and the MRAC process continues.

One advantage of this approach over using the EA previously discussed above includes improved stability and efficiency in the search algorithm, especially for complex dynamical models. Additionally, the Event Predicates of the Evolving MRAC Engine can be used to monitor sequential values of $\mu(t) + \delta\mu$ generated and tested by this algorithm, to detect (and typically remove) inefficient limit cycles that may emerge and repeat, and remember values for $\mu(t) + \delta\mu$ from which the Product State Space convergence criteria have already been found to subsequently fail within a local neighbourhood of $[X_m(t), \alpha(t)]^T$, and hence represent known dead-ends to be ignored in future.

The MOL of the Evolving MRAC Engine enables evolutionary optimisation, including improving the design of the φ-TEA circuit or φ-TEA-EC used by the Engine; the Lyapunov functions $V_s(X_m(t), \alpha(t), t)$ and $V_\eta(X_m(t), \alpha(t), t)$; the function $h(\|[X_m(t), \alpha(t)]^T\|)$ and/or the target T.

In some implementations, the Evolving MRAC Engine also includes a Model Selection module. In the event of suboptimal MRAC performance due to an inadequate model $\mathfrak{M}$, the structure of $\mathfrak{M}$ can then be modified by this module until convergence between system and model is observed to within an acceptable margin, as will be described in more detail below.

The Game Against Nature Controller Algorithms

Game against Nature ('GaN') algorithms typically seek to compensate for large-scale uncertainties in the system dynamics, including noise, external perturbations or unknown values for state variables, parameters or dynamics, that may interfere with Controller objectives or prevent them from being met. This compensation is done using a form of machine intelligence.

The Game Against Nature: Single Lyapunov Function

Typically, under the single Lyapunov function method the GaN algorithm collects these ambiguities or uncertainties into a second Controller vector, $u_2(t) \in U_2$, where $U_2$ is typically a compact set of possible values. The GaN algorithm then assumes $u_2(t)$ has its values chosen by a hostile intelligence (Nature) to manipulate the reduced dynamic envelope and computes control programs $p_1^*(\xi, t) \in U_1$ robust against unknown choices for $u_2(t)$, typically by assuming these choices for $u_2(t)$ are chosen intelligently by Nature to deliver the worst-possible outcomes for trajectories in the reduced dynamic envelope and then computing counter-strategies for $u_1(t) = p_1^*(\xi, t)$ that are also robust against variations in $u_2(t)$, to endeavour to prevent such worst-possible outcomes from happening.

Typically there are one or more undesirable sets in state space, denoted $T_i^\blacksquare \subset \Delta$, $i = 1, \ldots, B$, corresponding with physically lethal, dangerous, unstable or uncontrollable conditions. Where they exist, the GaN algorithm typically assumes Nature is trying to steer the system (as represented by one or more trajectories in the reduced dynamic envelope) to one of these sets, described as anti-targets.

The following sets are defined, including a desired target set $T \subset \Delta$, with its state-space complement written $\complement T \triangleq \Delta \backslash T$; and an open set $D \subset \Delta$ such that $cl\,(\complement T) \subset D$ (where "cl" denotes closure). A Lyapunov function $V_1: D \to \mathbb{R}$ is introduced such that it encloses $T$ within a level set: $\exists C_1 > 0$ such that $T \subset \{x \in \Delta | V_1(x) < C_1\}$.

Then if $u_2(t)$ does not include significant uncertainty in $\{\lambda_i\}_{i=1}^Z$, i.e. for some acceptable error margin $\varepsilon_A > 0$ related to the maximum divergence of associated trajectories across state space over some finite time interval, $\|\lambda_j - \lambda_j\| < \varepsilon_A | \forall \lambda_j, \lambda_k \in \{\lambda_i\}_{i=1}^Z$ then some representative $\lambda \in \{\lambda_i\}_{i=1}^Z$ is selected, and a GaN controller law that is strongly-controllable for asymptotically-stable control of trajectories towards the desired target is generated by choosing $$u_1 \in U_1 \left| \sup_{u_2 \in U_2} \frac{\partial V_1}{\partial t} + \nabla V_1^T \cdot f_m(\xi(t), \lambda, u_1, u_2, t) \leq -h(\|\xi(t)\|) < 0 \right.$$

where $h(\|\xi\|)$ is some continuous, monotonically increasing function of $\|\xi(t)\| | \forall \xi \in \Delta$; or Alternatively an asymptotically-stable GaN controller law for steering trajectories towards the desired target is generated using a weaker condition, choosing $$u_1 \in U_1 \left| \sup_{u_2 \in U_2} \frac{\partial V_1}{\partial t} + \nabla V_1^T \cdot f_m(\xi(t), \lambda, u_1, u_2, t) < 0 \right.$$

As a further alternative, a stable GaN controller law for steering trajectories towards the desired target is generated using a weaker condition, choosing $$u_1 \in U_1 \left| \sup_{u_2 \in U_2} \frac{\partial V_1}{\partial t} + \nabla V_1^T \cdot f_m(\xi(t), \lambda, u_1, u_2, t) \leq 0 \right.$$

An important example of the Game against Nature using a single Lyapunov function is provided by Identification of an underdetermined dynamical system, resulting in multiple distinct parameter vectors $\{\lambda_i\}_{i=1}^Z$ that all generate equivalent behaviour under a designated input $\{u(t_i)\}_{i=1}^P$, in producing trajectories that all track measured output within the specified margin of error. The set $\{\lambda_i\}_{i=1}^Z$ is scattered across a significant distance in $\Lambda$, $\exists \lambda_j, \lambda_k \in \{\lambda_i\}_{i=1}^Z$ such that $\|\lambda_j - \lambda_k\| > \varepsilon_A$, possibly with multiple clusters of candidate values.

Given that these chromosomes are distinct, their trajectories are expected to exhibit significantly diverse behaviour under other inputs. For a sufficiently large number of chromosomes, this diverse behaviour generated by these trajectories through state space is expected to impose an envelope on the actual (incompletely-known) system behaviour, namely the reduced dynamic envelope. It is assumed that Downstream Disambiguation is either not available or not effective under the practical constraints of the current scenario and accordingly, a Game against Nature is then employed such that the choice of worst-possible $\lambda \in \{\lambda_i\}_{i=1}^Z$ is included in Nature's choice of $u_2 \in U_2$. This can be written by choosing one fixed vector $\{\lambda_i\}_{i=1}^Z$ (without loss of generality $\lambda_1$ is chosen) and the other elements in $\{\lambda_i\}_{i=1}^Z$ are considered as variations of this vector: $\lambda_i = \lambda_1 + \delta\lambda_i$, some $\delta\lambda_i \in \Lambda_0$, $\forall i=1, \ldots, Z$.

Then $U_2$ is augmented by the set $\{\delta\lambda_i\}_{i=1}^Z = \{0, \delta\lambda_2, \ldots, \delta\lambda_Z\}$, so that Nature's choice of $u_2 \in U_2$ specifies the choice of $\lambda = \lambda_1 + \delta\lambda_i$ and the above conditions for GaN controller laws remain valid:

Strong-controllability for asymptotically-stable control:

$$u_1 \in U_1 \left| \sup_{u_2 \in U_2} \frac{\partial V_1}{\partial t} + \nabla V_1^T \cdot f_m(\xi(t), \lambda, u_1, u_2, t) \leq -h(\|\xi(t)\|) < 0, \right.$$

or

Asymptotically-stable control (further weakened to stability if strict inequality becomes non-strict):

$$u_1 \in U_1 \left| \sup_{u_2 \in U_2} \frac{\partial V_1}{\partial t} + \nabla V_1^T \cdot f_m(\xi(t), \lambda, u_1, u_2, t) < 0. \right.$$

Typically, in implementation these conditions are converted to difference equations and Nature re-evaluates its choices at every time increment $\delta t$.

Triage Logic

In the above method, where not all trajectories corresponding with elements in $\{\lambda_i\}_{i=1}^Z$ can be steered to the desired target $T$, a form of "triage logic" (a term adopted from emergency medicine) is applied, whereby the algorithm secures the best (or least-worst) compromise, based on its ability to manipulate membership of a subset $\{\lambda_i\}_{i=1}^Y \subseteq \{\lambda_i\}_{i=1}^Y$:

An ordering $T^\blacksquare(1), \ldots, T^\blacksquare(B)$ is assigned to the $\{T_i^\blacksquare\}_{i=1}^B$ according to the level of undesirability of each set, where $T^\blacksquare(1)$ is the most undesirable and $T^\blacksquare(B)$ is the least undesirable. This is called the "threat ordering".

One or more rules including are then formulated and implemented according to a preference ordering (where that preference ordering is application-specific, i.e. different applications may have different priorities: avoiding anti-targets may under some circumstances be more important than achieving the target, whereas under other circumstances these priorities may change). This preference ordering is used to modify the design of $u_1(t) = p_1(\xi(t), t) \in U_1$.

Preference ordering typically includes the following elements, to be ordered according to a specification typically encoded in the MOL (it should be apparent to the reader that this list is not exhaustive).

i. $u_1(t) = p_1(\xi(t), t) \in U_1$ is chosen such that, in steering trajectories acting under the influence of the controller to the desired target without intersecting $\{T_i^\blacksquare\}_{i=1}^B$, strong controllability for asymptotic stability is achieved for all members of some non-empty subset $\{\lambda_i\}_{i=1}^Y \subseteq \{\lambda_i\}_{i=1}^Z$ where this is the maximal possible such set in $\{\lambda_i\}_{i=1}^Z$;

ii. As above, but with strong controllability for asymptotic stability replaced by controllability for asymptotic stability, or, failing this, controllability for stability;

iii. Given that, at some time $t$ and state $\xi(t)$, there exist chromosomes $\{\lambda_i\}_{i=1}^X \subseteq \{\lambda_i\}_{i=1}^Z$ such that their trajectories $\{\varphi_m(\xi(0), \lambda_i, \omega(t), t)\}_{i=1}^X$ are projected to intercept $\{T_i^\blacksquare\}_{i=1}^B$ if these chromosomes are excluded from the set $\{\lambda_i\}_{i=1}^Y \subseteq \{\lambda_i\}_{i=1}^Z$ used for calculating the controller strategy, then $u_1(t) = p_1(\xi(t), t) \in U_1$ and $\{\lambda_i\}_{i=1}^Y$ are chosen such that:

(a) $\{\lambda_i\}_{i=1}^X \subseteq \{\lambda_i\}_{i=1}^Y$ (i.e. this set is included in the set of chromosomes used for calculating the controller strategy) and all trajectories are steered with strong controllability for asymptotic stability to the desired target without intersecting $\{T_i^\blacksquare\}_{i=1}^B$; or else (b) As above, but with strong controllability for asymptotic stability replaced by controllability for asymptotic stability, or, failing this, controllability for stability; or else (c) $\{\lambda_i\}_{i=1}^X \cap \{\lambda_i\}_{i=1}^Y \neq \emptyset$, where the maximal number of elements in $\{\lambda_i\}_{i=1}^X$ are included in $\{\lambda_i\}_{i=1}^Y$, such that all trajectories corresponding with $\{\lambda_i\}_{i=1}^Y$ are steered with strong controllability for asymptotic stability to the desired target without intersecting $\{T_i^\blacksquare\}_{i=1}^B$; or else (d) As above, but with strong controllability for asymptotic stability replaced by controllability for asymptotic stability, or, failing this, controllability for stability; or else (e) $\{\lambda_i\}_{i=1}^Y \neq \emptyset$, where the maximal number of elements in $\{\lambda_i\}_{i=1}^X$ otherwise intercepting $T^\blacksquare(1)$ are included in $\{\lambda_i\}_{i=1}^Y$, such that all trajectories corresponding with $\{\lambda_i\}_{i=1}^Y$ are steered with strong controllability for asymptotic stability to the desired target without intersecting $\{T_i^\blacksquare\}_{i=1}^B$; or else (f) As above, but with strong controllability for asymptotic stability replaced by controllability for asymptotic stability, or, failing this, controllability for stability; or else (g) $\{\lambda_i\}_{i=1}^X \cap \{\lambda_i\}_{i=1}^Y \neq \emptyset$, where the maximal number of elements in $\{\lambda_i\}_{i=1}^X$ otherwise intercepting the most dangerous anti-targets according to the threat ordering are included in $\{\lambda_i\}_{i=1}^Y$, such that all trajectories corresponding with $\{\lambda_i\}_{i=1}^Y$ are steered with strong controllability for asymptotic stability to the desired target without intersecting $\{T_i^\blacksquare\}_{i=1}^B$; or else
  (i) As above, but where those $\lambda_i \in \{\lambda_i\}_{i=1}^X \setminus \{\lambda_i\}_{i=1}^Y$ also avoid $\{T_i^\blacksquare\}_{i=1}^B$; or else
  (ii) As above, except those $\lambda_i \in \{\lambda_i\}_{i=1}^X \setminus \{\lambda_i\}_{i=1}^Y$ that are permitted to intersect the least-dangerous anti-targets according to the threat ordering; or else (h) As above, but with strong controllability for asymptotic stability replaced by controllability for asymptotic stability, or, failing this, controllability for stability; or else
  (i) As above, but where those $\lambda_i \in \{\lambda_i\}_{i=1}^X \setminus \{\lambda_i\}_{i=1}^Y$ also avoid $\{T_i^\blacksquare\}_{i=1}^B$; or else
  (ii) As above, except those $\lambda_i \in \{\lambda_i\}_{i=1}^X \setminus \{\lambda_i\}_{i=1}^Y$ that are permitted to intersect the least-dangerous anti-targets according to the threat ordering; or else (i) $\{\lambda_i\}_{i=1}^X \cap \{\lambda_i\}_{i=1}^Y \neq \emptyset$, where the maximal number of elements in $\{\lambda_i\}_{i=1}^X$ are also included in $\{\lambda_i\}_{i=1}^Y$ such that $u_1(t)=p_1(\xi(t),t) \in \mathcal{U}$ achieves avoidance of $\{T_i^\blacksquare\}_{i=1}^B$; or else
  (i) As above, but where those $\lambda_i \in \{\lambda_i\}_{i=1}^X \setminus \{\lambda_i\}_{i=1}^Y$ also avoid $\{T_i^\blacksquare\}_{i=1}^B$; or else
  (ii) As above, except those $\lambda_i \in \{\lambda_i\}_{i=1}^X \setminus \{\lambda_i\}_{i=1}^Y$ that are permitted to intersect the least-dangerous anti-targets according to the threat ordering; or else (j) As above, where the maximal number of elements in $\{\lambda_i\}_{i=1}^X$ are included in $\{\lambda_i\}_{i=1}^Y$ such that $u_1(t)=p_1(\xi(t),t) \in U_1$ achieves avoidance of the most dangerous anti-targets according to the threat ordering; or else
  (i) As above, but where those $\lambda_i \in \{\lambda_i\}_{i=1}^X \setminus \{\lambda_i\}_{i=1}^Y$ also avoid $\{T_i^\blacksquare\}_{i=1}^B$; or else
  (ii) As above, except those $\lambda_i \in \{\lambda_i\}_{i=1}^X \setminus \{\lambda_i\}_{i=1}^Y$ that are permitted to intersect the least-dangerous anti-targets according to the threat ordering;

The preference ordering is typically encoded in the MOL, along with the specifications for the compromises apparent in its elements (for instance, there is a payoff between the relative danger of anti-targets as listed in the threat ordering, versus number of chromosomes to be saved from their trajectories intercepting these anti-targets).

Typically, as well as the desired target set T, there are also one or more other highly-desirable sets in state space, denoted $T_i^\square \subset \Delta$, $i=1, \ldots, b$, corresponding with physically advantageous conditions that should be established prior to, or as part of, ultimately steering the trajectory to T. Examples include: in critical-care medicine, ensuring the patient's appropriate vital signs such as blood pressure and oxygen levels are first steered to within desired intervals prior to staging an invasive medical intervention; in aerospace, ensuring a vehicle first has established sufficient specific energy, prior to engaging in high-drag manoeuvres intended ultimately to reach a desired configuration. Where they exist, the GaN algorithm typically assumes Nature is trying to steer the system, as represented by one or more trajectories in the reduced dynamic envelope, to avoid these sets, described as lesser targets.

Again, where not all trajectories corresponding with elements in $\{\lambda_i\}_{i=1}^Z$ can be steered to the desired target T, a form of triage logic is applied, whereby the algorithm secures the best (or least-worst) compromise, based on its ability to manipulate membership of a subset $\{\lambda_i\}_{i=1}^Y \subseteq \{\lambda_i\}_{i=1}^Z$: Again, an ordering $T^\square(1), \ldots, T^\square(b) \subset \Delta$ is assigned to the $\{T_i^\square\}_{i=1}^b$ according to the level of desirability of each set, where $T_i^\square(1)$ is the most desirable and $T_i^\square(b)$ is the least desirable. This is called the "opportunity ordering". To achieve this, one or more rules including the following elements are formulated and implemented, again according to a preference ordering:

i. $u_1(t)=p_1(\xi(t),t) \in U_1$ is chosen such that, in steering trajectories acting under the influence of the controller to the ultimately-desired target T such that they achieve prior collision or capture (depending on application) with $\{T_i^\blacksquare\}_{i=1}^b$, strong controllability for asymptotic stability is achieved for all members of some non-empty subset $\{\lambda_i\}_{i=1}^Y \subseteq \{\lambda_i\}_{i=1}^Z$, where this is the maximal possible such set in $\{\lambda_i\}_{i=1}^Z$;

ii. As above, but with strong controllability for asymptotic stability replaced by controllability for asymptotic stability, or, failing this, controllability for stability;

iii. Given that, at some time t and state $\xi(t)$, there exist chromosomes $\{\lambda_i\}_{i=1}^Z \subseteq \{\lambda_i\}_{i=1}^Z$ such that their trajectories $\{\varphi_m(\xi(0),\lambda_i,\omega(t),t)\}_{i=1}^X$ are projected not to intercept $\{T_i^\blacksquare\}_{i=1}^b$ if these chromosomes are excluded from the set $\{\lambda_i\}_{i=1}^Y \subseteq \{\lambda_i\}_{i=1}^Z$ used for calculating the controller strategy, then $u_1(t)=p_1(\xi(t),t) \in U_1$ and $\{\lambda_i\}_{i=1}^Y$ are chosen such that:

(a) $\{\lambda_i\}_{i=1}^X \subseteq \{\lambda_i\}_{i=1}^Y$ (i.e. this set is included in the set of chromosomes used for calculating the controller strategy) and all trajectories are steered with strong controllability for asymptotic stability to the desired target, with prior collision or capture (depending on application) of $\{T_i^\blacksquare\}_{i=1}^b$; or else
  (b) As above, but with strong controllability for asymptotic stability replaced by controllability for asymptotic stability, or, failing this, controllability for stability; or else
  (c) $\{\lambda_i\}_{i=1}^X \cap \{\lambda_i\}_{i=1}^Y \neq \emptyset$, where the maximal number of elements in $\{\lambda_i\}_{i=1}^X$ are included in $\{\lambda_i\}_{i=1}^Y$, such that all trajectories corresponding with $\{\lambda_i\}_{i=1}^Y$, are steered with strong controllability for asymptotic stability to the desired target with prior collision or capture (depending on application) of $\{T_i^{\blacksquare}\}_{i=1}^b$; or else (d) As above, but with strong controllability for asymptotic stability replaced by controllability for asymptotic stability, or, failing this, controllability for stability; or else (e) $\{\lambda_i\}_{i=1}^X \cap \{\lambda_i\}_{i=1}^Y \neq \emptyset$, where the maximal number of elements in $\{\lambda_i\}_{i=1}^X$ otherwise not intercepting $T^{\square}(1)$ are included in $\{\lambda_i\}_{i=1}^Y$, such that all trajectories corresponding with $\{\lambda_i\}_{i=1}^Y$ are steered with strong controllability for asymptotic stability to the desired target with prior collision/capture of $\{T_i^{\blacksquare}\}_{i=1}^b$; or else (f) As above, but with strong controllability for asymptotic stability replaced by controllability for asymptotic stability, or, failing this, controllability for stability; or else (g) $\{\lambda_i\}_{i=1}^X \cap \{\lambda_i\}_{i=1}^Y \neq \emptyset$, where the maximal number of elements in $\{\lambda_i\}_{i=1}^X$ otherwise not intercepting the most desirable lesser targets according to the opportunity ordering are included in $\{\lambda_i\}_{i=1}^Y$, such that all trajectories corresponding with $\{\lambda_i\}_{i=1}^Y$ are steered with strong controllability for asymptotic stability to the desired target with prior collision/capture of $\{T_i^{\square}\}_{i=1}^b$; or else
  (i) As above, but where those $\lambda_i \in \{\lambda_i\}_{i=1}^X \setminus \{\lambda_i\}_{i=1}^Y$ also achieve prior collision/capture with $\{T_i^{\square}\}_{i=1}^b$; or else
  (ii) As above, except those $\lambda_i \in \{\lambda_i\}_{i=1}^X \setminus \{\lambda_i\}_{i=1}^Y$ that are permitted to miss the least-desirable lesser targets according to the opportunity ordering; or else (h) As above, but with strong controllability for asymptotic stability replaced by controllability for asymptotic stability, or, failing this, controllability for stability;
  (i) As above, but where those $\lambda_i \in \{\lambda_i\}_{i=1}^X \setminus \{\lambda_i\}_{i=1}^Y$ also achieve prior collision/capture with $\{T_i^{\square}\}_{i=1}^b$; or else
  (ii) As above, except those $\lambda_i \in \{\lambda_i\}_{i=1}^X \setminus \{\lambda_i\}_{i=1}^Y$ that are permitted to miss the least-desirable lesser targets according to the opportunity ordering; or else (i) $\{\lambda_i\}_{i=1}^X \cap \{\lambda_i\}_{i=1}^Y \neq \emptyset$, where the maximal number of elements in $\{\lambda_i\}_{i=1}^X$ are also included in $\{\lambda_i\}_{i=1}^Y$ such that $u_1(t)=p_1(\xi(t),t) \in U_1$ achieves prior collision/capture of $\{T_i^{\square}\}_{i=1}^b$;
  (i) As above, but where those $\lambda_i \in \{\lambda_i\}_{i=1}^X \setminus \{\lambda_i\}_{i=1}^Y$ also achieve prior collision/capture with $\{T_i^{\square}\}_{i=1}^b$; or else
  (ii) As above, except those $\lambda_i \in \{\lambda_i\}_{i=1}^X \setminus \{\lambda_i\}_{i=1}^Y$ that are permitted to miss the least-desirable lesser targets according to the opportunity ordering; or else (j) As above, where the maximal number of elements in $\{\lambda_i\}_{i=1}^Y$ are included in $\{\lambda_i\}_{i=1}^Y$ such that $u_1(t)=p_1(\xi(t),t) \in U_1$ achieves prior collision/capture of the most desirable lesser targets according to the opportunity ordering;
  (i) As above, but where those $\lambda_i \in \{\lambda_i\}_{i=1}^X \setminus \{\lambda_i\}_{i=1}^Y$ also achieve prior collision/capture with $\{T_i^{\square}\}_{i=1}^b$; or else
  (ii) As above, but except those $\lambda_i \in \{\lambda_i\}_{i=1}^X \setminus \{\lambda_i\}_{i=1}^Y$ that are permitted to miss the least-desirable lesser targets according to the opportunity ordering.

The preference ordering is typically encoded in the MOL, along with the specifications for the compromises apparent in its elements (for instance, there is typically a payoff between the relative advantage of collision/capture with lesser targets as listed in the opportunity ordering, versus number of chromosomes that can/cannot be improved by their trajectories being steered into these lesser targets before reaching the main target).

Real-world applications typically include both sets of anti-targets and sets of lesser targets. In such cases, these two preference orderings are combined, balancing the relative advantages of avoiding anti-targets and achieving lesser targets prior to reaching the main target, with the numbers of chromosomes that can/cannot be made to benefit from these considerations.

A further version of this form of GaN algorithm is where sequential or parallel-sequential rehearsals are possible to optimise the GaN controller parameters against various responses, effectively training the algorithm, including through the use of simulations. Under these conditions multiple MOLs exist and enable evolutionary optimisation, including improving the design of: the preference ordering and associated specifications for compromises in its elements; the threat ordering and anti-target specifications $\{T_i^{\blacksquare}\}_{i=1}^B$; the opportunity ordering and lesser target specifications $\{T_i^{\square}\}_{i=1}^b$; the Lyapunov function $V_1$; the function $h(\|\xi(t)\|)$, where employed; the target T; the $\varphi$-TEA circuit or $\varphi$-TEA-EC used by the MOL to optimise the other controller parameters; and the counter-strategies employed by Nature.

Additionally, further refinements to the GaN minimax process can be applied. For example this can be performed under conditions where the information set, underlying dynamics and computational resources allow it, statistical methods (including Bayesian analysis and derived techniques, such as particle filters) are typically overlaid onto the dynamic envelope to apply probabilistic weights to various candidate trajectories, weighting the manipulation of the reduced dynamic envelope (and hence the likely strategies used) by both Nature and the first Player. If it is assumed Nature is intelligent and thus understands the threat-ordering, preference-ordering and triage logic of the first Player, then Nature's choice of $u_2 \in U_2$ is typically further refined to incorporate this information consistent with its desire to make $$\frac{dV_1}{dt} \geq 0,$$

and/or to ensure trajectories collide with one or more of the anti-targets, and/or to ensure trajectories fail to achieve collision/capture with the lesser targets prior to reaching their ultimate target, so the first Player's process of strategy computation then typically undergoes multiple iterations to generate the final control law $u_1(t)=p_1(\xi(t),t) \in U_1$.

Game Against Nature: Multiple Lyapunov Functions

Alternatively, the Game against Nature can be implemented using two or more Lyapunov functions, for instance as outlined in WO2004/027674. For the sake of clarity the following discussion will be in terms of Nature and our controller each using a single functions; the extension of this to participants using multiple functions is straightforward.

Again there are typically one or more undesirable sets in state space, denoted $T_i^{\blacksquare} \subset \Delta$, $i=1, \ldots, B$. Typically at least one is used to form the first Player's anti-target, that Nature adopts as its target $T_{Nature}$, i.e. $T_{Nature} \in \{T_i^{\blacksquare}\}_{i=1}^{B}$ or else $$T_{Nature} \subset \bigcup_{i=1}^{B} T_i^{\blacksquare}.$$

Typically Nature also constructs a set of Nature's lesser targets out of elements of $\{T_i^{\blacksquare}\}_{i=1}^{B}$ and an opportunity ordering to attempt to force collision/capture with these.

Where not all trajectories corresponding with elements in $\{\lambda_i\}_{i=1}^{Z}$ can be steered to the desired target T or be made to avoid the one or more anti-targets, a form of triage logic is again applied by the first Player, as in the single Lyapunov function method.

Similarly, again there are typically one or more desirable sets in state space, $T^{\square}(1), \ldots, T^{\square}(b) \subset \Delta$, such that the first Player endeavours to steer trajectories to achieve collision/capture with one or more of these sets prior to reaching the ultimate target by applying a form of triage logic as in the single Lyapunov function method.

Typically at least one element of the set $\{T_i^{\square}\}_{i=1}^{b} \cup T$ is used by Nature to form its own anti-target $$T_{Nature}^{\blacksquare}$$

or set of anti-targets $$\{T_{Nature,i}^{\blacksquare}\}_{i=1}^{B_{Nature}}.$$

Nature endeavours to ensure that trajectories avoid $$T_{Nature}^{\blacksquare} \cup \{T_{Nature,i}^{\blacksquare}\}_{i=1}^{B_{Nature}}$$

and achieve collision/capture with Nature's lesser targets, by implementing its own mirror-image version of triage logic with respect to anti-targets and lesser targets, as already outlined from the first Player's perspective in the case of a single Lyapunov function. Again the Player's preference ordering is typically encoded in the MOL, along with the specifications for the compromises apparent in its elements.

Further refinements to the GaN minimax process can be applied analogously to the Game against Nature using a single Lyapunov function above, encompassing all the features described there. A number of further features can be applied, such as, if it is assumed Nature is intelligent and thus understands the threat-ordering, preference-ordering and triage logic of the first Player, then Nature's choice of $u_2 \subset U_2$ is typically further refined to incorporate this information, consistent with its desire to ensure at least one of: to make $\dot{V}_1 \geq 0$, and/or to make $\dot{V}_2 < 0$, and/or to ensure trajectories collide with one or more elements of $\{T_i^{\blacksquare}\}_{i=1}^{B}$, and/or to ensure trajectories fail to achieve collision/capture with one or more elements of $$T_{Nature}^{\blacksquare} \cup \{T_{Nature,i}^{\blacksquare}\}_{i=1}^{B_{Nature}};$$

so the first Player's process of strategy computation then typically undergoes multiple iterations to generate the final control law $u_1(t) = p_1(\xi(t),t) \in U_1$.

Again, a further version of this form of GaN algorithm is where sequential or parallel-sequential rehearsals are possible to optimise the GaN controller parameters against various responses, effectively training the algorithm, including through the use of simulations. Again, under these conditions multiple MOLs exist and enable evolutionary optimisation, including improving the design of the preference ordering and associated specifications for compromises in its elements; the threat ordering and anti-target specifications for $\{T_i^{\blacksquare}\}_{i=1}^{B}$; the opportunity ordering and lesser target specifications for $\{T_i^{\square}\}_{i=1}^{b}$; Nature's threat ordering and anti-target specifications for $$T_{Nature}^{\blacksquare}, \{T_{Nature,i}^{\blacksquare}\}_{i=1}^{B_{Nature}};$$

Nature's opportunity ordering and lesser target specifications for members of $\{T_i^{\blacksquare}\}_{i=1}^{B}$ and/or other sets; the Lyapunov functions $V_1$ and $V_2$; the functions $h_1(\|\xi(t)\|)$ and $h_2(\|\xi(t)\|)$, where employed; the targets T and $T_{Nature}$; the counter-strategies employed by Nature; and/or the φ-TEA circuit or φ-TEA-EC used by the MOL to optimise the other controller parameters.

Combinations of Controller Algorithms

Different forms of Controller are not necessarily mutually exclusive; for instance, the current system can use a combination of Game against Nature and Model Reference Adaptive Control algorithms.

Game Against Nature Plus Model Reference Adaptive Control

It should be apparent that the situation may arise that the Controller Module needs to apply GaN and MRAC methods simultaneously. In this case, the current system typically combines the Game against Nature using one or multiple Lyapunov functions with either the Product State Space Technique or Evolving MRAC.

A typical instance of this combination is when controlling a system that has substantial dynamical uncertainties in the Identified model $\mathfrak{M}(\{\lambda_i\}_{i=1}^{Z})$, for instance due to being underdetermined using available data $\{y(t_i)\}_{i=0}^{Q}$ responding to $\{u(t_i)\}_{i=0}^{P}$; and appears to have dynamical structure unmodelled by $\mathfrak{M}$, such that $\mathfrak{M}$ is compatible with the system for the purposes of MRAC, but their trajectories might otherwise diverge under a common controller law.

For example, in machine-intelligent control of insulin medication for a diabetic subject, where the subject's medical history has been used for Identification, generating an underdetermined model $\mathfrak{M}(\{\lambda_i\}_{i=1}^{Z})$ where all trajectories associated with these chromosomes successfully track fasting data to within the desired margin, and substantial metabolic or other changes may occur in the fasting subject (e.g. he falls asleep) that the controller needs to handle, and the subject's state (e.g. blood glucose level) needs to be steered adaptively to a desired target interval (typically 80 mg/dl to 140 mg/dl) while avoiding dangerously low blood glucose levels (<70 mg/dl) or high levels (>180 mg/dl). In this case:

a. The parameter set is mapped to adjustable parameters: $\{\lambda_i\}_{i=1}^{Z} \mapsto \{\mu_i(t)\}_{i=1}^{Z} | \mu_i(0) = \lambda_i$; similarly the vector $X_m(t)$ becomes the set $\{X_{mi}(t)\}_{i=1}^{Z}$.

b. The MRAC tasks of achieving $u_1(t) \in p_1(\{X_{mi}(t)\}_{i=1}^{Z}, t)$, $\dot{\mu}_i(t) = -f_a([\{X_{mi}(t)\}_{i=1}^{Z}, \alpha_i(t)]^T, t)$ where $\alpha_i(t) = \beta - \mu_i(t)$ such that $\forall \|w(t)\| < w_\delta < \infty$, ideally become $$\sup_{\mu_i(t)\in\{\mu_i(t)\}_{i=1}^Z} \begin{cases} \dot{V}_s(X_{mi}(t), \alpha_i(t), t) < 0 \\ \dot{V}_\eta(X_{mi}(t), \alpha_i(t), t) \le -h(\|[X_{mi}(t), \alpha_i(t)]^T\|) < 0 \end{cases}.$$

Features associated in the current system with the Game against Nature using one or multiple Lyapunov functions, such as threat-ordered anti-targets and triage logic, are also available here. Threat-ordering of anti-targets is useful: hypoglycaemia (blood glucose <70 mg/dl) is more dangerous than hyperglycaemia (>200 mg/dl), which is more dangerous than high blood glucose levels (>180 mg/dl), which is less desirable than elevated blood glucose levels (>150 mg/dl). Similarly a desired target set exists: T corresponds with 80 mg/dl to 140 mg/d, which is the ideal range for blood glucose.

A further variant of this is when the subject chooses to eat, inducing a poorly-modellable perturbation to the system dynamics (the time-series effect of a meal on blood glucose depends on the carbohydrate, protein and fat content of the meal, which are typically poorly-estimated). This is again handled by the Game against Nature, which attributes to Nature control of the uncertainty around the user's estimate of carbohydrate content and uncertainties about other aspects of the ingestion and digestion process, creating a controller vector $u_2 \in U_2$ that Nature endeavours to use to force hypoglycaemia or hyperglycaemia in the subject.

Then the above formulae become (for clarity, $\mu_i(t) \in \{\mu_i(t)\}_{i=1}^Y$ are kept distinct from other $u_2 \in U_2$):

$$\sup_{\substack{u_2 \in U_2 \\ \{\mu_i(t)\}_{i=1}^Y \subseteq \{\mu_i(t)\}_{i=1}^Z}} \begin{cases} \dot{V}_s(X_{mi}(t), \alpha_i(t), t) < 0 \\ \dot{V}_\eta(X_{mi}(t), \alpha_i(t), t) \le -h(\|[X_{mi}(t), \alpha_i(t)]^T\|) < 0 \end{cases},$$

subject to triage logic if not all $\mu_i(t) \in \{\mu_i(t)\}_{i=1}^Z$ are able to be steered to target.

Typically this would take the form of revising the medication program and adaptive laws such that at least some of the triage objectives (i.e. elements in the preference ordering) are achieved. One example of this would be, in preference ordering:

i. Such that the maximum number of $\mu_i(t)$ corresponding with trajectories that would otherwise experience hypoglycaemia are controlled to avoid it, and are steered to target;
ii. As above, but if controlling to target reduces the number of trajectories that would otherwise be controlled to avoid hypoglycaemia, then this objective of controlling to target is restricted as an objective to those $X_{mi}(t)$ such that this reduction does not occur;
iii. Subject to the above, but if not all trajectories can be controlled to avoid hypoglycaemia, then the maximum number of $\mu_i(t)$ corresponding with trajectories that would otherwise experience the most severe hypoglycaemia are steered to avoid it;
iv. Subject to the above, but such that the maximal number of $\mu_i(t)$ are controlled such that their corresponding trajectories avoid hyperglycaemia;
v. Subject to the above, but such that the maximal number of $\mu_i(t)$ are controlled such that their corresponding trajectories avoid high blood glucose levels;
vi. Subject to the above, but such that the maximal number of $\mu_i(t)$ are controlled such that their corresponding trajectories avoid elevated blood glucose levels.

Note that if additional sources of uncertainty or noise are introduced into the system, then these are typically also incorporated into $u_2 \in U_2$, with their ranges appended to the Nature control set $U_2$.

Model Choice and Refinement

A number of aspects of the Model Selector module will now be described.

A model $\mathfrak{M}$ is typically a set of one or more: in the case of process modelling, ordinary differential equations (including their extension into fractional-order differential equations); or Partial differential equations; or Stochastic differential equations; or Difference equations; or a combination of the above; or in the case of function modelling, a set of one or more candidate functions, expressed in algebraic form, such that under appropriate parameter values the functions provide solution trajectories to a set of differential or difference equations, as described for process modelling above. A model $\mathfrak{M}$ under process modelling can also have other mathematical structure associated with it, including Fuzzy Cognitive Modelling (FCM) and Bayesian probabilities for transitions among models or model components.

Furthermore a model $\mathfrak{M}$ can be a combination of the above features plus components of the model or model equations that have been modelled using numerical techniques such as neural networks.

It should be apparent to the reader that under function modelling, the stipulation that the functions to be modelled are to provide solution trajectories to a set of differential or difference equations can be extended to other parameterizable vector-valued functions that can be expressed in terms of a single parameter, continuous almost everywhere. Typically that parameter is time; however other strictly monotonically-increasing parameters can be used instead.

The following specification will limit itself to describing process modelling, as function modelling is a simpler implementation that follows the same structure, which will be apparent to the reader once process modelling is explained.

If the model $\mathfrak{M}$ is flawed, the current system will typically become "aware" of this due to relatively poor Identifier performance in attempting to achieve tracking of $\{y(t_i)\}_{i=1}^Q$ for bounded noise. This conclusion is typically reached if the Controller Module, using controller response processes triggered by the Identifier fails to try to improve tracking; and/or where an Evolving Identifier is being used, indications that there are flaws in the model can be achieved if tracking does not improve to below a (large) threshold $\varepsilon > 0$ despite the amount of computational resources applied.

Under these circumstances, for simple models it may be possible for a user manually to specify an alternative model, or choose an alternative model from a library. However, in many cases the complexity of these models is such that manual manipulation is too time-consuming or difficult. Consequently the Model Selection Module is adapted to enable automated searches to achieve a better model. To achieve this the Model Selection Module typically includes a library $\mathbb{L}_{M\text{-}alg}$, stored in a database or computer memory, that includes candidate models, in the case that more than one model exists of the system being studied, candidate sub-models and/or model fragments.

In this regard, sub-models exist when one or more candidate models consist of more than one equation. Sub-models consist of one or more such equations, typically pertaining to specific sub-systems, such that the number of equations in a sub-model is less than that in the associated model. In contrast model fragments typically consist of plausible terms for equations within a sub-model or model. They include a finite number of individual terms of Taylor Series expansions, enabling an increasingly nonlinear model to be constructed by "bolting-on" additional terms to the linear approximation until suitable system tracking is achieved.

Typically the library is scaled, in the sense that data is recursively structured to enable initial searching to improve the model is at a coarse scale, choosing among multiple candidate models. If none of these candidate models enables satisfactory tracking to within a desired margin, or otherwise they are all deemed unsatisfactory, then the library provides the candidate structures to assemble one or more models by combining sub-models. If both of the above processes fail, then typically the library provides the sub-model equations plus a set of model fragments, with which to refine the sub-models and hence assemble a model that achieves suitable tracking. Finally, if all of the above processes fail, then typically the library provides the set of model fragments to enable bottom-up model construction.

The Model Selection Module typically also includes a library $\mathbb{L}_M$, containing model-construction and/or model-selection methods. These can include variants of simulated insect search algorithms, using sub-models, combined with $\varphi$-TEA or MGA or GA, to construct new models from known sub-models in what is dubbed Textured Evolutionary Ant (TEa) or other analogous swarm optimisation techniques, or encoding model components as genes in model chromosomes (M-chromosomes) and using a further implementation of $\varphi$-TEA, MGA or GA to find the best-fitting candidate models.

The library $\mathbb{L}_M$ can also include conventional model-construction and model-selection methods, including FCM as applied using fuzzy logic.

At least one method from $\mathbb{L}_M$ operates on the model structures provided by $\mathbb{L}_{M\text{-}alg}$, generating candidate models for the Identifier until such time as at least one or more acceptable Identified models $\mathfrak{M}(\{\lambda_i\}_{i=1}^Z)$ have been found that track $\{y(t_i)\}_{i=0}^Q$ to within an acceptable margin, or else no such model $\mathfrak{M}$ can be found within an acceptable time period.

This process may generate multiple candidate models $\{\mathfrak{M}_1, \ldots \mathfrak{M}_{M_{\mathfrak{M}}}\}$, some $M_{\mathfrak{M}} \in \mathbb{N}$. Typically multiple models are handled by choosing one of these models as the preferred model $\mathfrak{M}$, based on criteria including physical plausibility and/or simplicity; or constructing a composite model $$\mathfrak{M} \triangleq \bigcup_{i=1}^{M_{\mathfrak{M}}} \mathfrak{M}_i,$$

such that by setting the appropriate parameters to zero, $\mathfrak{M}$ can be made equivalent to any of its component models. Alternatively, each candidate model is employed in parallel by the Identifier before a final model is selected and passed to the Controller, or each candidate model is employed in parallel by the Identifier and all are passed to the Controller, where typically Game against Nature techniques are used to accommodate the structural uncertainties associated with using multiple models.

An example of this process is provided by the analysis of the pharmacokinetics ('PK') parameters for infused insulin in humans from fasting blood samples. Insulin is infused subcutaneously from an external source using a pump; the control input is the specified rate of infusion $u_I(t)$. Once subcutaneous, the initial model (call it $\mathfrak{M}_{lin}$) of insulin PK states that two distinct types (monomeric and hexameric) of insulin become apparent, each with different PK parameter values:

$$\left.\begin{aligned}\xi_{21}(t) &= -(\lambda_{18} + \lambda_{16})\xi_{21}(t) + u_I(t) \\ \xi_{22}(t) &= \lambda_{16}\xi_{21}(t) - \lambda_{19}\xi_{22}(t) \\ \xi_{20}(t) &= -(\lambda_{22} + \lambda_{24})\xi_{20}(t) + \frac{1}{\lambda_{20}}\left(\lambda_{21}\xi_{26}(t) + \frac{\lambda_{18}}{\eta}\xi_{21}(t) + \frac{\lambda_{19}}{\eta}\xi_{22}(t)\right)\end{aligned}\right\}.$$

Here $u_I(t)$ denotes infused insulin; $\xi_{21}(t)$ denotes the amount of the first type of insulin (in pmol); $\xi_{22}(t)$ denotes the amount of the second type of insulin (in pmol); $\xi_{20}(t)$ denotes the plasma concentration of insulin; $\eta$ denotes body mass (easily measured accurately).

From a past time-series obtained from a medical history, matching the insulin infusion time-series $\{u(t_i)\}_{i=0}^P$ with time-series measurements of insulin concentration in plasma $\{y(t_i)\}_{i=0}^Q$, the Identifier is unable to extract distinct candidate parameter vectors $\{\lambda_i\}_{i=1}^Z$, that all generate trajectories that track $\{y(t_i)\}_{i=0}^Q$ under $\{u(t_i)\}_{i=0}^P$ to within an acceptable accuracy.

The hypothesised reason is that the above model fails to take into account the nonlinearities associated with the formation of a depot of infused insulin beneath the skin. The fact that some processes may be proportionate to depot volume and others to the depot's surface area, and the fact the depot's volume changes over time, introduces nonlinearities to the dynamics.

Typically the first step is to explore models associated with various plausible, well-behaved geometries for the depot: viz. spherical, lenticular ('[biconvex] lens-shaped'), hemi-lenticular and laminar shapes. This is done by assigning $\mathbb{L}_{M\text{-}alg}$ to models $\mathfrak{M}_{spherical}, \mathfrak{M}_{lenticular}, \ldots$ that modify the equations of $\mathfrak{M}_{lin}$ according to the effects of these various depot geometries. If this fails to produce trajectories that track the measured $\{y(t_i)\}_{i=0}^Q$ to within an acceptable error, then the next steps are to further modify these models to include biologically-plausible irregularities and re-test, or else use sub-models and model fragments to build better-performing subcutaneous insulin PK from the ground up.

The model-selection methods of $\mathbb{L}_M$ will now be described in more detail.

Textured Evolutionary Ant (TEa) Programming

Ant Colony Optimisation (ACO) methods are recognised in the literature (e.g. Dorigo and Stuetzle, 2004) as useful heuristic methods to find paths through graphs, by simulating ants operating in swarm intelligence. The underlying idea is that ants' search for food represents a search algorithm that has evolved over hundreds of millions of years, is efficient, and operates well over complex terrains. Consequently ACO methods use simulated 'ants' engaged in stochastic searches through networks to find 'food' at a geographically fixed point in the network.

Although there are multiple versions of ACO algorithms, these typically have a number of common characteristics, including that once the food is found, the successful ant returns, laying down a stronger 'pheromone' trail to mark the path, which gradually evaporates over time. Other ants are more likely to follow a nearby pheromone path rather than continue in stochastic behaviour, and will in turn lay down pheromone paths if successful at finding the food. The phenomenon of evaporation means that shortest-distance paths are reinforced more effectively than longer paths by ants, optimising the path to food.

Figure 11A:
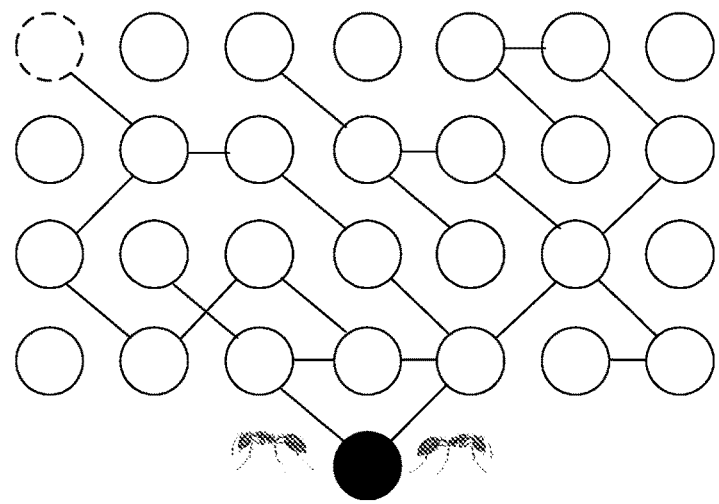
FIG. 11A is a schematic diagram of an example of a typical ant colony optimisation (ACO) search problem.

FIG. 11A is a schematic diagram illustrating a typical ACO search problem, with the initial position of the ant "nest" is marked black and the food location marked in dotted lines. In conventional ACO, the problems are (a) to find the food and (b) to find the least path between the food and the nest.

The Model Selection Module of the current system uses a variant of these methods, dubbed Textured Evolutionary Ant (TEa) Programming and example features of this will now be described. A significant difference compared to traditional ACO techniques is that, instead of a reward ("food") being physically located at any particular physical node in the network, the reward is generated by appropriate combinations of paths traversed by the ants and the circuits carried by the ants.

TEa (accessing $\mathbb{L}_{M\text{-}alg}$ and $\mathbb{L}_M$) is typically running in real time in parallel with the Identifier Module, with data passed in both directions. Computationally less-demanding versions can also be constructed, using repeated sequential operations of the Identifier and Model Selection Modules instead of simultaneous real-time operation; the design of such versions will be apparent to the reader, given the real-time implementation description below.

Each simulated ant is not simply a distributed agent, as in ordinary ACO but is instead a computational entity (typically in a massively-parallel computing architecture) performing its component of the two-way real-time data transfer between the Model Selection Module and the Identifier Module. Such simulated ants are referred to as TEa-bots.

Each TEa-bot in TEa passes a candidate model $\mathfrak{M}$ to the Identifier Module, which attempts to perform Identification on the dataset $\{y(t_i)\}_{i=0}^{Q}$ using $\mathfrak{M}$ to generate $\mathfrak{M}(\{\lambda_i\}_{i=1}^{Z})$ and the associated tracking error $\varepsilon_{track}$ for each chromosome $\lambda_i$, which is typically placed in the telomere of each chromosome before $\mathfrak{M}(\{\lambda_i\}_{i=1}^{Z})$ is returned to TEa and the TEa-bot.

Figure 11B:
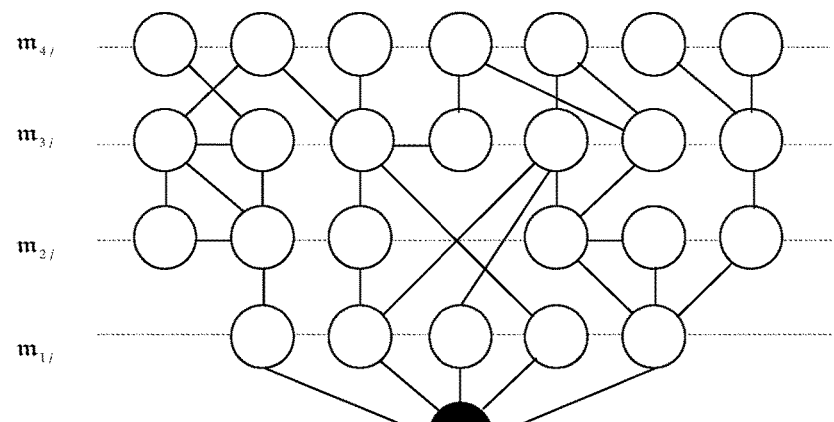
FIG. 11B is a schematic diagram of an example of ant colony network topology.

$\mathbb{L}_{M\text{-}alg}$ is used to generate one or more networks, written $\Upsilon(\mathbb{L}_{M\text{-}alg})$, composed of arcs and nodes, an example of which is shown in FIG. 11B. Depending on the scale currently being used by $\mathbb{L}_{M\text{-}alg}$, typically each node in $\Upsilon(\mathbb{L}_{M\text{-}alg})$ is occupied by a candidate model; candidate sub-model; or a model fragment.

The geometrical shape and topology of the network $\Upsilon(\mathbb{L}_{M\text{-}alg})$ is typically either manually specified by the user, or generated by an algorithm. Such algorithm may include an Orphan Evolving Identifier running in the MOL of the Model Selection Module. In this case, the design of $\Upsilon(\mathbb{L}_{M\text{-}alg})$ for a particular application is typically optimised over repeated Model Selection runs. Each candidate model is constructed by a TEa-bot wandering through $\Upsilon(\mathbb{L}_{M\text{-}alg})$ In the illustrated example of FIG. 11B, sub-model components pertaining to the same subsystem are arranged on horizontal gridlines, while those pertaining to different subsystems are on vertical gridlines. Combination of sub-models can be done using a method we describe as "positive-signed", whereby all sub-models $m_{ij}$ traversed on a path are combined, by having each sub-model $m_{ij}$ multiplied by an associated parameter $\lambda_{ij} \in [-\lambda_{ij}^+, \lambda_{ij}^+]$ (with some upper bound $\lambda_{ij}^+ > 0$) and a sign operator $\pi_{ij} \in \{0, +1\}$ is added to its predecessors traversed on the path, or a variant of this we describe as "negative-signed", whereby all sub-models traversed on a path are combined by adding each sub-model $m_{ij}$ multiplied by an associated parameter $\lambda_{ij} \in [0, \lambda_{ij}^+]$ and a sign operator $\pi_{ij} \in \{-1, 0, \pm 1\}$ to its predecessors on the path. For example, in the "negative-signed" instance, if a TEa-bot traverses the path $\Gamma \subset \Upsilon(\mathbb{L}_{M\text{-}alg})$, then this path defines the model using an ordered set of the nodes traversed by the TEa-bot on $\Gamma$, in the order they were traversed, modified by a parameter $\lambda_{ij}$ and a sign operator $\pi_{ij} \in \{-1, 0, +1\}$ associated with each node. Any pair of sub-model components on neighbouring nodes for the same subsystem that are traversed sequentially (i.e. $\{m_{ij}, m_{ik}\} | k \in \{j-1, j+1\}$) are then combined as $\pi_{ij} \lambda_{ij} m_{ij} + \pi_{ik} \lambda_{ik} m_{ik}$, for some parameters $\lambda_{ij} \in [0, \lambda_{ij}^+]$, $\lambda_{ik} \in [0, \lambda_{ik}^+]$. In this way the model is constructed, $$\mathfrak{M} = \bigoplus_{(i,\cdot) \in \Gamma, (\cdot, j) \in \Gamma} \sum \pi_{ij} \lambda_{ij} m_{ij} \bigg| (i, j) \in \Gamma,$$

where $\oplus$ denotes the sum of vector subspaces. It will be appreciated by the reader that the "positive-signed" implementation is just a simpler version of this, involving Identification over much larger intervals for the $\lambda_{ij}$ in return for removing the option $\pi_{ij} = -1$. The remainder of this specification will restrict itself to the "negative-signed" instance.

Figure 11C:
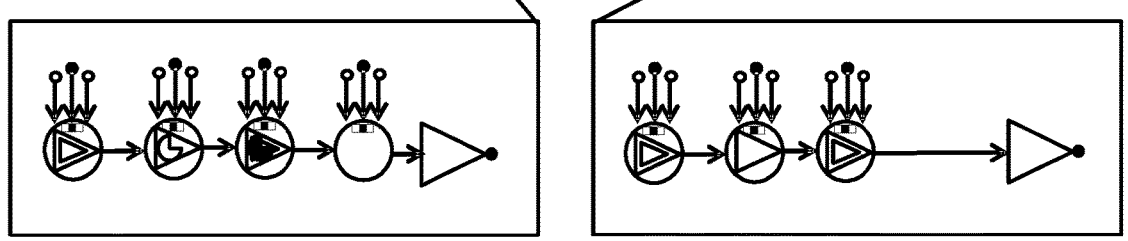
FIG. 11C is a schematic diagram of an example of a cross-section of 3D arcs connecting the nodes.
Figure 11C:
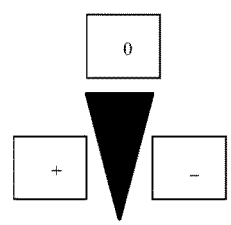
Figure 11D:
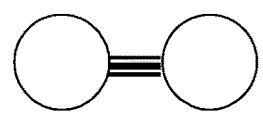
FIG. 11D is a schematic diagram of an example of the branches connecting any two adjacent nodes.

The value for the sign operator $\pi_{ij} \in \{-1, 0, +1\}$ associated with each node is determined by each TEa-bot as it approaches that node. This is done by picturing each arc as a three-dimensional "branch" linking the adjacent nodes. Each branch has a triangular cross-section, as shown in FIG. 11C, so each branch has three facets. Each facet is associated with one of the elements of the set $\{-1, 0, +1\}$. Magnifying the branches connecting any two adjacent nodes, as shown in FIG. 11D means each 3D branch can be regarded as effectively three single-valued 1D arcs connecting the nodes, each 1D arc having exactly one facet value in $\{-1, 0, +1\}$.

Depending on the facet a particular TEa-bot is walking on as it approaches the node, dictates the value for $\pi_{ij} \in \{-1, 0, +1\}$ chosen by that TEa-bot for that node (i.e. the facet a TEa-bot is standing on just before it reaches the node is the one that dictates the final value for $\pi_{ij}$ and is marked in the pheromone return path). The choice of facet is initially determined (for an arc that has not been previously traversed by any TEa-bots) based on a probability distribution $P(\pi_{ij})$ over the possible values of $\pi_{ij}$. Once TEa-bots have traversed the arc, then any pheromone trail laid down on this arc will influence the choices of future TEa-bots regarding which facet they walk on, skewing the probabilities in favour of the path with the prior pheromone trail, consistent with pheromone trails in conventional ACO.

Although in some instances the upper bound $\lambda_{ij}^+$ for the parameter associated with each sub-model can be assigned manually, typically it is assigned algorithmically as part of the process of a TEa-bot approaching a node.

Typically this is done again using the concept of a path, so that a successful combination of choices for the $\lambda_{ij}^+$ is signalled using pheromones and this is incorporated into the overall pheromone-signalled path.

Typically this is done by assigning "gates" to each node, each gate associated with a candidate value for $\lambda_{ij}^+$ for that node. The choice of gate used by a TEa-bot to enter the node is governed by a probability distribution, which alters depending upon the pheromone trail. For example, consider a node with 11 gates, consecutively labelled $\{-5, -4, \ldots, -1, 0, 1, \ldots, 5\}$. If a TEa-bot enters the node via the $n^{th}$ gate, then $\lambda_{ij}^+=10^n$ (so for a TEa-bot that enters via the gate labelled "$-2$", $\lambda_{ij}^+=10^{-2}$, whereas a TEa-bot that enters via the gate labelled "3" has $\lambda_{ij}^+=10^3$). In the absence of any prior pheromone trail (i.e. the node has not been previously visited by a TEa-bot at all, or has been visited by a TEa-bot but not by one sufficiently successful such that it generated a pheromone trail), each of these gates has a probability distribution $P(\lambda_{ij}^+=10^n)$, e.g. a TEa-bot has probability $P(\lambda_{ij}^+=10^{-5})$ that it enters the gate labelled "$-5$", and $$\sum_{k=-5}^{5} P(\lambda_{ij}^+ = 10^k) = 1.$$

These initial probabilities to use various gates need not be uniform; there may be a physical reason initially to guess some orders of magnitude are more plausible than others for the least upper bound. Consider the situation once a few successful TEa-bots have passed through one gate (say, the one labelled "n" for some $n \in \{-5, \ldots, 5\}$): typically the resulting pheromone trail alters the probability distribution asymmetrically across gates, such that the probability distribution across all gates is not uniform; the most successful gate has the single greatest likelihood, i.e.

$$\max_{k \in \{-5,\ldots,5\}} P(\lambda_{ij}^+ = 10^k) = P(\lambda_{ij}^+ = 10^n);$$

the gate with the second greatest likelihood is the gate labelled "n+1", with $P(\lambda_{ij}^+=10^{n+1})$, enabling a search upwards across scales of magnitude until the least upper bound for $\lambda_{ij}^+$ is found (pheromone passing through "n−1" is significantly less than that passing through "n" or "n+1", disproportionate to the effects of the probability distribution alone). At this point the probability distribution is again typically adjusted to encourage "n" as the appropriate node gate to be used for TEa-bots entering the node, as "n+1" is computationally more onerous. (It should be appreciated by the reader that the actual number connoted by the phrase "a few" depends upon the total number of TEa-bots in use and the complexity of the network being traversed.)

Once a TEa-bot finds a 'successful' path through $\Upsilon(\mathbb{L}_{M-alg})$ (where this is defined below), then its pheromone trail back to the nest will specify the path through the network, including each facet traversed, and hence the sequence of values for the $\pi_{ij}|(i,j) \in \Gamma$ and $\lambda_{ij}^+|(i,j) \in \Gamma$ associated with the sub-models $m_{ij}$, enabling the model to be constructed and Identified.

Typically, when the interval $[0, \lambda_{ij}^+]$ is deemed too large for an efficient search, this technique is repeated for each node, constructing a second layer of gates which are entered by the TEa-bots to generate candidates for $\lambda_{ij}^- > 0$ as part of entering the node.

Typically this second layer of gates has the same number of gates as the first layer. Each TEa-bot is then required to pass through two gates to enter the node, the first to generate a value for $\lambda_{ij}^+$ and the second to generate a value for $\lambda_{ij}^-$. An initial probability distribution is generated across this second layer of gates, subject to the Bayesian constraint $P(\lambda_{ij}^-|\lambda_{ij}^+ \leq \lambda_{ij}^-) = 0$, i.e. no TEa-bot can enter a gate that generates a value for $\lambda_{ij}^-$ that violates the condition $0 < \lambda_{ij}^- < \lambda_{ij}^+$. Once a few successful TEa-bots have passed through one gate (say, the one labelled "m") then typically the resulting pheromone trail alters the probability distribution asymmetrically across gates, such that the probability distribution across all gates is not uniform; the most successful gate has the single greatest likelihood; the gate with the second greatest likelihood is the gate labelled "m−1", enabling a search downwards across scales of magnitude until the greatest lower bound for $\Delta_{ij}^-$ is found (pheromone passing through "m+1" is significantly less than that passing through "m" or "m−1", disproportionate to the effects of the probability distribution alone). At this point the probability distribution is again typically adjusted to encourage "m" as the appropriate second-layer node gate to be used for TEa-bots entering the node, as "m+1" is computationally more onerous.

Typically branch facets do not have symmetrical probabilities for being walked on by a TEa-bot, i.e. some branch facets are more likely to be walked upon than others by a TEa-bot when wandering stochastically. These probabilities are typically specified and refined by the MOL. In the case of $N_{facets}$-facetted branches, discussed briefly below, the spatial ordering of the facets around the branch is also specified by the MOL.

This technique can be extended to generate combinations of more complicated operators and sub-model components. For example, let a branch have $N_{facets}$ facets, some $N_{facets} \in \mathbb{N}$. Each facet corresponds with some unary or binary operator, denoted generically $\odot_1, \ldots, \odot_{N_{facets}}$. In this instance, the path taken by a TEa-bot over the nodes $(i,j) \in \Gamma$ constructs the model $$\mathfrak{M} = \bigoplus_{(i,j) \in \Gamma} (\ldots ((\pi_{i1}\lambda_{i1}m_{i1})\pi_{i2}\lambda_{i2}m_{i2}) \ldots \pi_{ik}\lambda_{ik}m_{ik} \mid (i,j) \in \Gamma,$$

where $\pi_{ij} \in \{\odot_1, \ldots, \odot_{N_{facets}}\}$ (without loss of generality, assuming consecutively-numbered nodes along $\Gamma$ for convenience).

These algebraically more complicated structures are also encompassed in the system. However, they make explanations of the system more opaque, so the simpler form of the system using $\pi_{ij} \in \{-1, 0, +1\}$ is usually employed for the rest of this specification.

Unlike ACO, there is no geographically-specific 'food' node in the network. Instead the concept of food reward is implicit in all the network paths, depending on whether a suitable model $\mathfrak{M}$ has been constructed by traversing a particular sequence of nodes in a path.

Consequently each TEa-bot has to possess a termination time $T^{term}$, which is typically a randomly-generated stochastic event generated individually for each TEa-bot as it leaves the Nest, such that at time $t=T^{term}$ that TEa-bot will end its outward journey through $\Upsilon(\mathbb{L}_{M-alg})$ and head back to the Nest.

Each TEa-bot typically carries a circuit with it as it wanders through $\Upsilon(\mathbb{L}_{M-alg})$, supplied by the Evolving Identifier. In the case that the Evolving Identifier is comparing a number of distinct candidate circuits then typically each candidate circuit is issued to multiple TEa-bots, enabling the same circuit to have multiple distinct models constructed for it. Each circuit typically has inputs for a model $\mathfrak{M}$, possibly subdivided into various sub-models for the various circuit Blocks.

The TEa-bot wanders through $\Upsilon(\mathbb{L}_{M\text{-}alg})$, with its historical path $\Gamma$ being used to assemble a model $$\mathfrak{M} = \bigoplus_{(i,\cdot) \in \Gamma} \sum_{(\cdot,j) \in \Gamma} \pi_{ij} \lambda_{ij} \mathfrak{m}_{ij} \bigg| (i,j) \in \Gamma,$$

until all of the model inputs for the TEa-bot's circuit are satisfied. The TEa-bot then halts and uploads its model $\mathfrak{M}$ through TEa to the Identifier Module, which immediately uses this to attempt Identification on $\{y(t_i)\}_{i=0}^Q$, generating $\mathfrak{M}(\{\lambda_i\}_{i=1}^Z)$ and the associated tracking error $\varepsilon_{track}(\mathfrak{M}(\lambda_i))$ for each chromosomes $\lambda_i$. Once computed, these are downloaded back to the relevant TEa-bot.

These tracking errors $\varepsilon_{track}(\mathfrak{M}(\lambda_i))$ are then assessed by the TEa-bot to decide whether or not $\mathfrak{M}$ is an acceptable model for use by the Identifier Module. This is typically done using a threshold criterion to accept or reject the model $\mathfrak{M}$. A threshold value $\delta_{track} > 0$ is specified. If there exists $\lambda_i \in \{\lambda_i\}_{i=1}^Z | 0 \leq \varepsilon_{track}(\mathfrak{M}(\lambda_i)) < \delta_{track}$, then the model $\mathfrak{M}$ is an acceptable model for use by the Identifier Module; else it is rejected.

If the model $\mathfrak{M}$ proves to be an acceptable model, then this is analogous to 'food' being successfully found and one of the following responses is employed.

A first response is immediate return, in which the TEa-bot locks its model choice $\mathfrak{M}$ (i.e. no further changes to this model can be made before the TEa-bot returns to the Nest) evaluates it and, typically using its memory of its path from the Nest, lays down a (slowly evaporating) pheromone trail through the network as it returns to the Nest to report its results, passing through all the nodes corresponding with the construction of $\mathfrak{M}$. In this case, other TEa-bots are then also more likely to follow this pheromone trail, as simulated ants do in conventional ACO tasks. In this example, the strength of the pheromone is typically inversely proportional to some (possibly non-integer) power of the size of $$\min_{\lambda_i \in \{\lambda_i\}_{i=1}^Z} \varepsilon_{track}(\mathfrak{M}(\lambda_i)),$$

so better-tracking models correspond to a TEa-bot laying down a stronger pheromone marker, where "stronger" refers to at least one of: the "amount" of pheromone released, i.e. the increased relative probability that the pheromone influences the behaviour of other TEa-bots on this arc; and/or the reduced rate at which the pheromone evaporates.

Another response is localised optimisation/refinement. A further local search algorithm is undertaken in $\Upsilon(\mathbb{L}_{M\text{-}alg})$ in an effort to improve $\mathfrak{M}$ further before the TEa-bot reports back to the Nest. Multiple relevant techniques that can be used to implement such a localised search algorithm exist in the literature. Alternatively, using the existing novel design of branches outlined above, an example is for the TEa-bot to continue to wander through the $\Upsilon(\mathbb{L}_{M\text{-}alg})$. Each subsequent node it traverses (i.e. walks across) further modifies the TEa-bot's model $\mathfrak{M}$. Subsequent $\pi_{ij} \in \{-1, 0, +1\}$ enable some existing terms in the model to be cancelled out ($\pi_{ij} = -1$) and new terms added. A node will only be traversed if it does not damage the quality of the tracking (i.e. does not increase the best tracking error $$\min_{\lambda_i \in \{\lambda_i\}_{i=1}^Z} \varepsilon_{track}(\mathfrak{M}(\lambda_i))).$$

Such nodes are called "acceptable". If traversing a node would increase the best tracking error $$\min_{\lambda_i \in \{\lambda_i\}_{i=1}^Z} \varepsilon_{track}(\mathfrak{M}(\lambda_i)),$$

then the TEa-bot typically will refuse to traverse that node. Once the local neighbourhood of acceptable nodes has been exhausted, or else a stipulated time period has passed ($t \geq T^{term}$), the TEa-bot then locks the model $\mathfrak{M}$, evaluates it and returns to the Nest to report its final results, laying down pheromone on the return journey. Again, typically the strength of the pheromone is inversely proportional to some (possibly non-integer) power of the size of $$\min_{\lambda_i \in \{\lambda_i\}_{i=1}^Z} \varepsilon_{track}(\mathfrak{M}(\lambda_i)),$$

so better-tracking models correspond to a TEa-bot laying down a stronger pheromone marker.

A third response is a global competitive search, in which case all TEa-bots that set out from the Nest wander through $\Upsilon(\mathbb{L}_{M\text{-}alg})$ and have knowledge of the best-known value of $$\min_{\lambda_i \in \{\lambda_i\}_{i=1}^Z} \varepsilon_{track}(\mathfrak{M}_{good}(\lambda_i))$$

that has already been reported back to the Nest by previous TEa-bots, corresponding with some candidate model $\mathfrak{M}_{good}$. Under this refinement, having found a model $\mathfrak{M}$ that is inferior to $\mathfrak{M}_{good}$, the TEa-bot continues to wander through $\Upsilon(\mathbb{L}_{M\text{-}alg})$ until it generates some model $\mathfrak{M}_{better}$ such that $$\min_{\lambda_i \in \{\lambda_i\}_{i=1}^Z} \varepsilon_{track}(\mathfrak{M}_{better}(\lambda_i)) < \min_{\lambda_i \in \{\lambda_i\}_{i=1}^Z} \varepsilon_{track}(\mathfrak{M}_{good}(\lambda_i))$$

in which case it locks $\mathfrak{M}_{better}$, and lays down a pheromone trail and returns to the Nest to report $\mathfrak{M}_{better}$. This terminates for each TEa-bot once it reaches its individual search time constraint ($t \geq T^{term}$).

Alternatively, this is performed until a specified global search time constraint ($t \leq T^{search}$) elapses, forcing the TEa-bot to abandon the search and return to the Nest anyway. Unlike the localised optimisation/refinement algorithm, here the TEa-bot will typically traverse further nodes that damage the quality of the tracking, if no better node is available; however, typically the least-damaging node will be chosen each time. Again, typically the strength of the pheromone is inversely proportional to some (possibly non-integer) power of the size of $$\min_{\lambda_i \in \{\lambda_i\}_{i=1}^Z} \varepsilon_{track}(\mathfrak{M}_{better}(\lambda_i)),$$

so better-tracking models correspond to a TEa-bot laying down a stronger pheromone marker.

If the model $\mathfrak{M}$ proves to be unacceptable, then the TEa-bot either returns to the nest to start again, or else the TEa-bot resumes moving through $\Upsilon(\mathbb{L}_{M\text{-}alg})$ to achieve further modifications of the model, until either an acceptable model is found, or else the search time constraint is reached, forcing the TEa-bot to return to the Nest.

Theoretically, every time the TEa-bot reaches a new node $(i,j) \in \Gamma$ it should halt again, re-upload its revised model $\mathfrak{M}$ and assess tracking errors $\varepsilon_{track}$ again. In fact, due to computational constraints this is typically performed periodically with a period larger than the time taken to travel to the next node, during subsequent wandering through $\Upsilon(\mathbb{L}_{M\text{-}alg})$.

The threshold criterion $\varepsilon_{track}(\mathfrak{M}(\lambda_i)) < \delta_{track}$ to accept or reject the model $\mathfrak{M}$ is typically modifiable across the TEa-bot population. Such global modifications are typically performed at the Nest, either as TEa-bots bring information in from $\Upsilon(\mathbb{L}_{M\text{-}alg})$ or prior to their return into $\Upsilon(\mathbb{L}_{M\text{-}alg})$.

If too few TEa-bots are finding acceptable models, and this continues over a sufficiently long period of time, then typically the threshold value for $\delta_{track}$ is globally relaxed (i.e. increased) until sufficient candidate models are generated for the Identification Module to operate. In contrast, if too many TEa-bots are finding acceptable models according to the threshold criterion, then typically this value for $\delta_{track}$ is at least temporarily globally tightened (i.e. reduced) across the TEa-bot population to make the model search more rigorous.

In the current system, the evaporating pheromone trail is employed to provide a form of Ockham's Razor. In conventional ACO tasks, evaporating pheromones lead to shortest-path optimisation. However, the current system encourages least-complexity for the model $\mathfrak{M}$, by favouring a suitable model associated with the shortest path through $\Upsilon(\mathbb{L}_{M\text{-}alg})$.

An extension of this concept is to generate multiple sub-networks $\Upsilon_1(\mathbb{L}_{M\text{-}alg}), \ldots, \Upsilon_{N_\Upsilon}(\mathbb{L}_{M\text{-}alg})$ such that each sub-network is typically disjoint from the others, except for a common node at the Nest and the network is the union of the sub-networks, $$\Upsilon(\mathbb{L}_{M-alg}) = \bigcup_{j=1}^{N_\Upsilon} \Upsilon_j(\mathbb{L}_{M-alg}).$$

Each TEa-bot is multi-dimensional, in that it traverses each and every sub-network simultaneously, to construct the candidate model $\mathfrak{M}$ from the vector-valued path $\Gamma = \Gamma_1 \oplus \ldots \oplus \Gamma_{N_\Upsilon} | \Gamma_j \subseteq \mathfrak{t}_j(\mathbb{L}_{M\text{-}alg})$. (This is described as the TEa-bot being the union of "avatars", with typically one active avatar in each sub-network.) The rest of the model construction process then continues as previously.

An example of this, using branch facets composed of complicated binary operators described as "subspace operators", is as follows: Consider a process-modelled model at $\mathfrak{M}$, which comprises n ordinary differential equations $\dot{x}_1 = m_1, \dot{x}_2 = m_2, \ldots, \dot{x}_n = m_n$, where the form of the right hand side terms $m_i$ is initially unknown. Let $\Upsilon(\heartsuit_{M\text{-}alg})$ be constructed from n sub-networks $\Upsilon_i(\mathbb{L}_{M\text{-}alg}), \ldots, \Upsilon_n(\mathbb{L}_{M\text{-}alg})$, that are topologically not connected with one another except for a common node at the Nest, such that the network is the union of these sub-networks. Each sub-network pertains to the ODE of the same index, i.e. $\Upsilon_i(\mathbb{L}_{M\text{-}alg})$ will be used by TEa-bots to build the $m_i$ for the ODE $\dot{x}_i = m_i$. Each TEa-bot is multi-dimensional, in that it traverses each and every sub-network simultaneously and so builds the ODEs in parallel. To do this, each TEa-bot initially has one avatar in each sub-network. Apart from the usual facet operators $\pi_{ij} \in \{-1, 0, +1\}$, two further facet operators, called "subspace facet operators", are introduced as follows: there are two subspace facet operators, the "additive subspace operator" denoted $\bar{\oplus}$ and the multiplicative subspace operator denoted $\bar{\otimes}$. Each of these is assigned a branch facet, so the facet operators become $\pi_{ij} \in \{-1, 0, +1, \bar{\oplus}, \bar{\otimes}\}$. A probability distribution is assigned across these facets, so $P(\pi_{ij} = -1) + P(\pi_{ij} = 0) + P(\pi_{ij} = +1) + P(\pi_{ij} = \bar{\oplus}) + P(\pi_{ij} = \bar{\otimes}) = 1$, where this probability distribution dictates the facet used by a TEa-bot to approach a node, as a stochastic event. This probability distribution is typically non-uniform, so some facets are more likely to be used by a TEa-bot than others.

Consider a TEa-bot walking through the sub-network $\Upsilon_i(\mathbb{L}_{M\text{-}alg})$, on a branch connected to the node containing $m_{ij}$. The TEa-bot has already assembled a partial model for $m_i$; denote this partial model $m_i^{partial}$. Then if the TEa-bot uses any one of the facets $\pi_{ij} \in \{-1, 0, +1\}$ to approach this node, then $m_i^{partial} \mapsto m_i^{partial} + \pi_{ij} \lambda_{ij} m_{ij}$, as already outlined. However, if the TEa-bot uses the facet $\pi_{ij} = \bar{\oplus}$ then the following processes occur.

The node becomes empty ($\emptyset$) for that TEa-bot, i.e. it no longer contains $m_{ij}$ (unless the particular case applies where $\bar{\oplus}$ is mapping from $\Upsilon_i(\mathbb{L}_{M\text{-}alg})$ to $\Upsilon_i(\mathbb{L}_{M\text{-}alg})$, as described below).

The algebraic mapping for the partial model becomes $m_i^{partial} \mapsto m_i^{partial} + \lambda_{ij} (\cdot)^{g_1}$, where $g_1 \in \mathbb{Z}$ is some integer, the value of which is determined by a probability distribution over a set of gates of possible values attached to the node, analogously to the generation of $\lambda_{ij}^+$: there is a finite set of possible values to choose from (typically $\{-4, -3, -2, -1, 0, 1, 2, 3, 4\}$). In the absence of a prior pheromone trail through any of these gates, the choice is dictated by a probability distribution that is typically non-uniform: values $\{-2, -1, 1, 2\}$ typically have high likelihood, while other values have low likelihood. If a choice leads to a useful modelling result, then the TEa-bot will mark this gate with pheromone, increasing the likelihood of future TEa-bots choosing the $\pi_{ij} = \bar{\oplus}$ facet and this gate, at the expense of probabilities for other facets and other gates. The space between parentheses is then populated, below.

The avatar for that TEa-bot in $\Upsilon_i(\mathbb{L}_{M\text{-}alg})$ is divided into two. The first part remains in $\Upsilon_i(\mathbb{L}_{M\text{-}alg})$ but typically halts until the second part (its "shadow") re-joins it.

The second part of that avatar is mapped to a random branch in front of some node (say, containing $m_{kl}$) in some sub-network $\Upsilon_k(\mathbb{L}_{M\text{-}alg})$, using a stochastic process that can be "tagged" by pheromone (i.e. the first mapping to some branch is generated by a random process, but if it leads to successful model-building, this process can be marked by a pheromone trail and be repeated by subsequent TEa-bots, as the pheromone skews the probabilities for subsequent TEa-bots that use the branch facet in the original sub-network $\Upsilon_i(\mathbb{L}_{M\text{-}alg})$).

A future termination time $T_{shadow}^{term}$ is generated for the shadow, again typically initially of random duration but repeatable if a pheromone trail occurs; once the time $t=T_{shadow}^{term}$ is reached, the search in $\Upsilon_k(\mathbb{L}_{M\text{-}alg})$ is ended and the shadow must return to the original avatar in $\Upsilon_i(\mathbb{L}_{M\text{-}alg})$.

While in $\Upsilon_k(\mathbb{L}_{M\text{-}alg})$ the shadow avatar continues to conduct a conventional search to aggregate additional terms. For the purposes of illustration, assume it travels from the node containing $m_{kl}$ to the node for $m_{km}$ and then in $m_{kq}$, at which time the time-limit $t=T_{shadow}^{term}$ is reached and the shadow avatar returns to $\Upsilon_i(\mathbb{L}_{M\text{-}alg})$, where it recombines with the original avatar, carrying the search information from $\Upsilon_k(\mathbb{L}_{M\text{-}alg})$. Then the aggregated model carried by the avatar becomes $m_i^{partial} \mapsto m_i^{partial} + \lambda_{ij}(\pi_{kl}\lambda_{kl}m_{kl}\pi_{km}\lambda_{km}m_{km}\pi_{kq}\lambda_{kq}m_{kq})^{g1}$. After this the recombined avatar resumes its usual process of aggregating model terms in $\Upsilon_i(\mathbb{L}_{M\text{-}alg})$.

It should be noted that subspace operators can also map shadow avatars from $\Upsilon_i(\mathbb{L}_{M\text{-}alg})$ to $\Upsilon_i(\mathbb{L}_{M\text{-}alg})$, i.e. they provide a method of searching through and combining terms from nodes in different neighbourhoods within the one sub-network $\Upsilon_i(\mathbb{L}_{M\text{-}alg})$, as well as searching and combining terms from different sub-networks. This includes mapping shadow avatars back to the original branch, e.g. in the above example, producing $m_i^{partial} \mapsto m_i^{partial} + \lambda_{ij}(\pi_{ij}\lambda_{ij} m_{ij} \ldots )^{g1}$.

The traversing of branches in $\Upsilon_k(\mathbb{L}_{M\text{-}alg})$ may involve traversing one or more additional subspace facets and hence the mapping of additional shadow avatars into further sub-networks, enabling terms to be built of the form $m_i^{partial} \mapsto m_i^{partial} + \lambda_{ij}(\pi_{kl}\lambda_{kl}m_{kl} + \lambda_{km}(\pi_{rs}\lambda_{rs}m_{rs}\pi_{rt}\lambda_{rt} m_{rt})^{g2})^{g1}$, etc.

The original avatar belonging to $\Upsilon_k(\mathbb{L}_{M\text{-}alg})$ typically continues to build its candidate model for $m_k$ while the shadow avatar is also travelling through $\Upsilon_k(\mathbb{L}_{M\text{-}alg})$ building terms for the candidate model for $m_i$. Consequently the pheromone trail generated by each avatar is typically labelled, to avoid confusion if trails cross.

The operation of the multiplicative subspace operator $\pi_{ij} = \otimes$ works analogously to the additive subspace operator $\oplus$, except that the resulting binary operation is multiplication rather than addition. Hence in the above example, $\pi_{ij} = \otimes$ could have produced $m_i^{partial} \mapsto m_i^{partial} \cdot \lambda_{ij}(\pi_{kl}\lambda_{kl}m_{kl}\pi_{km}\lambda_{km}m_{km}\pi_{kq}\lambda_{kq}m_{kq})^{g1}$.

Probability distributions and algorithmic methods of modifying probability distributions based on pheromone signal are typically specified in the MOL, where they can in turn be optimised.

It will be appreciated that various modifications to ACO would be apparent to a reader skilled in the art and all such modifications to TEa are also encompassed by the current system. Other analogous implementations of Swarm Intelligence and Particle Swarm Optimisation in this context should be apparent to the reader and are also encompassed by the current system.

Model Chromosomes (M-Chromosomes)

Instead of using Swarm Intelligence to constructing candidate models, an alternative method that can be used is genetic optimisation of model structure. This method assigns genes to encode members of the library $\mathbb{L}_{M\text{-}alg}$, including models, sub-models and model fragments, onto chromosomes (M-chromosomes). M-chromosomes are not to be confused with the chromosomes used in the Evolving Identifier; analogous concepts and processes of evolutionary optimisation are being re-used here, but the information carried by an M-chromosome is different from that carried by an Identifier chromosome.

Consequently, writing an M-chromosome that specifies the model $\mathfrak{M}_k$ as $\overline{c}^{\mathfrak{M}_k}$, relevant Trinities become $\{(\mathfrak{M}_k, \overline{c}_j, \{\varphi_{\mathfrak{M}}\}(j))\}_{j=1}^Z \mapsto \{(\overline{c}^{\mathfrak{M}_k}, \overline{c}_j, \{\varphi_{\mathfrak{M}}\}(j))\}_{j=1}^Z$.

When model fragments are gene-encoded on an M-chromosome, typically associated with each fragment is another gene, encoding the value for $\pi_{ij} \in \{-1, 0, +1\}$, so again depending on the values of $\pi_{ij}$ along the length of the chromosome, the model can be written as $$\mathfrak{M}_k = \bigoplus_{i=1} \sum_{j=1} \pi_{ij}\lambda_{ij}m_{ij}.$$

The Hamming distances for the encodings of the various values for $\pi_{ij}$ on the genes are typically non-uniform, so some values are more likely to be adopted by the EA than others.

As in the TEa search, this formulation can be extended to a more general algebraic structure, so $\pi_{ij} \in \{\odot_1, \ldots, \odot_{N_{facets}}\}$ (where this is a set of user-defined operators, including a mapping of the $m_{ij}$ to Identity) and the model is:

$$\mathfrak{M} = \bigoplus_{i=1} (\ldots ((\pi_{i1}\lambda_{i1}m_{i1})\pi_{i2}\lambda_{i2}m_{i2}) \ldots \pi_{ik}\lambda_{ik}m_{ik}.$$

Each M-chromosome corresponds with a candidate model; each generation of M-chromosomes is passed to the Identifier Module for these candidate models to be used in computing $\mathfrak{M}_k(\{\lambda_i\}_{i=1}^Z)$ and the associated $\varepsilon_{track}(\mathfrak{M}(\lambda_i))$. More precisely, M-chromosomes exist within the Model Selection Module to: evolve candidate models $\mathfrak{M}_k$, to be passed to the Identifier Module to be fitted to the dataset $\{y(t_i)\}_{i=0}^Q$; generate Identified models $\mathfrak{M}_k(\{\lambda_i\}_{i=1}^Z)$ and associated tracking error $\varepsilon_{track}$ for each chromosome $\lambda_i$; place the relevant $\varepsilon_{track}(\mathfrak{M}(\lambda_i))$ in the telomere of each chromosome; and return $\mathfrak{M}_k(\{\lambda_i\}_{i=1}^Z)$ to the Model Selection Module for assessment.

The Fitness of the consequent Genetic Algorithm is typically inversely proportional to a power of one or more values of $\varepsilon_{track}(\mathfrak{M}(\lambda_i))$ corresponding with elements of $\{\lambda_i\}_{i=1}^Z$ in $\mathfrak{M}(\{\lambda_i\}_{i=1}^Z)$.

All of the concepts, structures and methods introduced elsewhere, to enhance evolutionary optimisation of chromosomes in an Evolving Identifier, are again typically employed here to enhance the evolutionary optimisation of M-chromosomes for Model Selection. Typically the Model Selection Module uses an OEI to optimise these M-chromosomes over generations using the Fitness as described above. The Model Selection Module typically uses a MOL to optimise this process, by optimising structural assumptions and threshold values used for Model Selection.

Typically, where the task of model Identification is broken up across multiple Blocks, the Model Selection Module is analogously broken up and distributed across multiple Blocks, with the relevant part of $\Upsilon(\mathbb{L}_{M\text{-}alg})$ deployed for each Block to reduce computational complexity.

Modular Modelling Systems: Deployment and Applications

Example implementations of the systems will now be described.

The modular modelling system can be installed to run on a single computing platform, or else are distributed across heterogeneous computing architectures, such as multi-core CPUs and massively-parallel GPU cards, and/or distributed across multiple PCs, handheld devices (such as smartphones and medical devices such as insulin pumps), wearable computing devices (such as Google Glass and similar) and servers in an intranet or the Cloud.

Typically the modular modelling systems and/or their distributed components and their computing platforms communicate with external devices and one another using data links that include methods of telephonic data transmission, wires, lasers, Bluetooth and other wireless modes of communication, as well as manual (keyboard or similar) transfer of data.

Modular modelling systems can operate either as fully-automated devices, or as decision-support devices for a human operator. Thus, all of the modules of the system are designed to operate either as entirely autonomous machine-intelligent processes, or else involve a human user exercising an executive discretion. In this latter case, the operator typically chooses the eventual model to be used by the Identifier from among the candidates nominated by the system, approving the priority list to be implemented for triage logic in the Controller, and the like.

In the situation where an operator is interacting with the modular modelling system, the controller module typically generates a user interface including a representation of the solution trajectories and associated information, allowing the operator to use this in selecting the model. In one example, the representation includes one or more of the one or more solution trajectories; the starting points; any chaotic regions (if they exist); regions where the solution trajectories are stable or can be made stable; limit cycles and equilibrium points; target sets and undesired sets; regions of controllability for each of the user and Nature; and "strongly-winning regions", i.e. regions of strong controllability for each of the user and Nature, when they exist. The user is then able to user the interface to select the solution trajectories of interest, allowing the control module to use these in generating a control program. The control program can then be provided to a suitable control system and/or displayed to the operator, allowing the operator to implement the control program.

In one example, multiple modular modelling systems operate in parallel and in conflict. An example of this is shown in FIG. 8B. In this example, two modular modelling systems are operating in parallel and for the purpose of description, these will be referred to as Red and Blue players.

It will be appreciated that conflict always exists in real-world applications. This is true even when both players are trying purely to cooperate, due to noise and system uncertainty. Examples include air-traffic control, with aircraft in holding patterns wishing to avoid one another, but being impeded by partial information. Typically, however, additional conflict exists, either due to partially conflicting objectives (e.g. rival traders in the financial markets) or entirely conflicting objectives—so-called zero-sum conflict (e.g. an anti-shipping missile trying to penetrate the target ship's air-defences).

Each player has a host Modular modelling system (possibly containing further, embedded Modular modelling systems), again labelled Red and Blue respectively. For the purposes of exposition, assume the dynamics of the overall system is divisible into two sub-systems, one of which is Red-controllable and the other is Blue-controllable. These will be referred to as the Red dynamics and Blue dynamics respectively. It will be appreciated that extension to the circumstances where no such separation is possible is straightforward.

In this situation, each host Modular modelling system constructs models of its own and the other's dynamics, Identifies these models as accurately as possible using available information and constructs controller strategies to achieve desired outcomes despite the conflict. Each host Modular modelling system typically also uses this information to construct a Map of the Game of Kind, estimating regions in $\Delta$ from which either it is able to control the system if the adversary plays an appropriate strategy or establish a strongly-winning strategy regardless of the adversary's strategy.

Based on assumptions about the sophistication of the other player, each host Modular modelling system typically also uses this information to construct a Map of the Game of Kind for its adversary, estimating regions in $\Delta$ from which its adversary either is able to control the system if the host player plays an appropriate strategy, or establish a strongly-winning strategy regardless of the host player's strategy. This aggregated Map of the Game of Kind typically helps inform the strategies of the relevant Controller Module, typically using the Game against Nature and threat-ordering.

This architecture is extensible to an arbitrary number of players, each with a Modular modelling system.

Examples of situations in which a single pair of modular modelling systems can be usefully employed will now be described.

One example includes testing athletes for illegal use of performance-enhancing drugs. Such drugs may leave detectable traces of by-products or altered parameters in the athlete's body; as isolated evidence these may be inconclusive to establish illegal use.

In this example, the task of the Blue player is to use time-series measurements of blood samples to reconstruct one or more models of possible metabolic dynamics over the previous interval of time including the period where possible drug abuse may have happened, to establish whether plausible models exist consistent with drug abuse. This reconstruction is typically performed using the Evolving Identifier and the Model Selection Module. The Controller, modulating relevant medication applied to the athlete, is then typically used to improve the confidence levels regarding whether or not drug abuse has happened.

The Red player operates the counter activities, including altering the timing and dosing of performance-enhancing drugs and taking additional medications, to attempt to thwart this proof from being established. The Map of the Game drawn by Blue is used to establish protocols to ensure that Red fails to conceal illegal drug use.

Another example is that of air-defence between a Red anti-shipping missile and a Blue air-defence missile, whereby the Red missile intends to strike and sink a Blue ship and the Blue missile is trying to prevent this.

In this example, the Red player uses available noise-polluted sensor data from previous flights of other Blue air-defence missiles of the same type as is currently deployed, to reconstruct the Blue missile dynamics (aerodynamic model and associated parameters). It then analyses appropriate launch conditions and generates associated guidance law(s) to evade the Blue missile (once launched) and strike the Blue ship.

The Blue player similarly reconstructs the Red missile aerodynamics and likely guidance laws to establish Red's preferred launch conditions. It then computes its own preferred launch conditions and guidance law(s) to minimise the confidence levels associated with the Red attack.

It should be noted that the guidance laws and associated launch strategies for both Red and Blue may be adaptively generated in real time by their respective modular modelling systems.

Another example is non-zero sum games. For example, in financial markets where multiple traders are trying to establish competitive profits against one another, while mutually trying to avoid a market crash or market stagnation. Each trader only ever has partial controllability of the system and limited resources to affect a controller strategy that modifies the market. Time-series data on foreign exchange rates and associated commodity data are used to reconstruct market dynamics, including the transient dynamics of market sentiment. Analysis of other players' strategies (whether aggregated as a single 'Nature' or treated as multiple entities) is then performed to generate strategies that enhance the likelihood of the Blue trader generating a relative profit while avoiding strategies that have a disastrous effect on the overall market.

Modular modelling systems can also be aggregated in large numbers, to generate diverse behaviour useful for analysis by much simpler fuzzy logic or neural network devices. This includes the instance where large-scale computational resources are available at one time but not at another, so large sets of Modular modelling systems are used to generate data that computationally simpler forms of machine intelligence can be trained on to emulate subsequently.

A version of the modular modelling system, where the Identifier Module is running an Evolving Identifier that is in fact an Orphan Evolving Identifier, is called an Orphan Modular modelling system. A typical application of an Orphan Modular modelling system is where the performance function I(•) is chosen to optimise the operation of another Modular modelling system performing Identification and control of a complex dynamical system using partial (i.e. incomplete) information. The performance function is typically to achieve a desired confidence-level of control while minimising resources, such as computational time, computational resources, information required to be extracted from the system, and/or Minimal controller interventions or controller feedstock expenditure (e.g. amount of applied medication) to be imposed on the underlying system.

Optimisation is typically performed sequentially on the one system or in a combination of parallel and sequential actions on multiple dynamical systems (whether actual systems or simulated systems).

An example of this is optimising artificial pancreas software's analysis of meal data, when deciding insulin doses for type-1 diabetes. Modular modelling systems have been tested and successfully applied in simulation prototypes of artificial pancreas software, deciding personalised dosing of insulin for type-1 diabetes.

A key task is handling the uncertainties associated with meals and their effects on blood glucose. Given that the Controller is using a Game against Nature with a single Lyapunov function to handle these uncertainties, three different formulations for describing meal effects are available for the Evolving Identifier in an effort to reduce uncertainty.

Given a sequence of meals the user specifies a time-series of estimates of carbohydrate content of meals provided as an input $\{u(t_i)\}_{i=0}^P$, then published typical parameter values are used by the modular modelling system to project the likely effect on blood glucose.

The user assigns a label to each distinct type of meal ingested and provide a time-series of labelled meals and associated estimates of carbohydrate content for each meal provided as an input $\{u(t_i)\}_{i=0}^P$. The modular modelling system Identifies one or more parameter values for the blood glucose dynamics for each meal label based on observed blood glucose effects $\{y(t_i)\}_{i=0}^Q$, to approximate the predictable blood glucose profile of that meal.

The user also assigns a label to each distinct type of meal ingested and provides a time-series of labelled meals and associated estimates of carbohydrate, protein and fat content for each meal provided as an input $\{u(t_i)\}_{i=0}^P$. The Invention Identifies one or more parameter values for the blood glucose dynamics for each meal label based on observed blood glucose effects $\{y(t_i)\}_{i=0}^Q$, to approximate the predictable blood glucose profile of that meal.

Setting I(•) to reward asymptotically-stable (or failing that, stable) blood glucose control by the Controller within specified bounds, while also rewarding the minimal requirement for information from the diabetic subject and computational time and resources to perform the Identification to achieve that stable blood glucose control, the Orphan Modular modelling system then resolves which of these three formulations is preferable, balancing Controller performance with resource requirements.

Another example of an application for an Orphan Modular modelling system is to optimise the implementation of Evolving MRAC on a specified system.

Given a Modular modelling system's need to operate in real time, to engage in sophisticated behaviour (such as robust control or Evolving MRAC) with a complex dynamical system, one or more other Modular modelling systems may be embedded within a Module of the host Modular modelling system to enhance its efficiency or capabilities.

Typically this embedded machine will be an Orphan Modular modelling system, the purpose of which is real-time heuristic optimisation of various supporting algorithms and functions to be used by the host Module, so that they are ready for use when needed.

Typically this is done by the Orphan Modular modelling system being embedded within the Controller Module and being passed a list of candidate models $\{\mathfrak{M}_1, \ldots, \mathfrak{M}_{M_\mathfrak{M}}\}$ likely to be encountered by the parent Modular modelling system. It then configures optimal forms of the supporting algorithms and functions for each candidate model in turn, so when the Identifier Module and Model Selection Module have decided on the appropriate model to be used, the Controller has these resources immediately available to it.

Specific Example

A specific example taken from the field of systems biology will now be described. It should be appreciated by the reader that the technique is applicable to multiple problems across applied mathematics.

In this example a noise-polluted system was studied (based on a simplified model of glucose-insulin dynamics, with intravenous control inputs), from de Gaetano and Arino (2000) and Palumbo and de Gaetano (2007) with the following ODEs:

$$\dot{x}_1 = -b_1 x_1(t) - b_4 x_1(t) x_2(t) + b_7 + u_G(t) + w_1(t)$$

$$\dot{x}_2 = -b_2 x_2(t) + b_6 x_3(t) + u_1(t) + w_2(t)$$

$$\dot{x}_3 = -\gamma x_3(t) + \gamma^2 x_4(t)$$

$$\dot{x}_4 = x_1(t) - \gamma x_4(t)$$

where: system parameters are denoted by the symbols b, and γ;
 $x_1$ is blood glucose concentration;
 $x_2$ is plasma insulin concentration;
 $x_3$ and $x_4$ are additional state variables required to convert integro-differential equations into ODEs The control inputs are given by:

$$u_1(t) = u_{Ins}(t) + w_1(t)$$

$$u_G(t) \in [0.0, 5.0] \text{ mg/dl/min}$$

$$u_{Ins}(t) \in [0.1, 5.0] \text{ µU/ml/min}.$$

where: $u_G(t)$ assumes blood glucose can be directly increased by intravenous intervention,
 $u_{Ins}(t)$ assumes plasma insulin can again be directly increased; hence $u(t) = [u_G(t), u_{Ins}(t)]^T$.
 $u_{Ins}(t)$ is noise-polluted by some term $w_1(t)$, while for this particular example $u_G(t) = 0$.

It should be noted that the purpose of this example was to test and demonstrate aspects of the φ-TEA algorithm rather than necessarily to be clinically realistic. The coupled non-linearity in $\dot{x}_1$ should also be noted.

Typical system parameter values are given in Table 5, below.

TABLE 5

| Parameter | Healthy | Type-1 | Type-2 | Units |
|---|---|---|---|---|
| $G_b$ | 79 | 180 | 150 | mg/dl |
| $I_b$ | 62.5 | 3 | 40 | µU/ml |
| $b_1$ | 0.018063 | 0.018063 | 0.018063 | min$^{-1}$ |
| $b_2$ | 0.041342 | 0.041342 | 0.041342 | min$^{-1}$ |
| $b_4$ | 1. 10$^{-5}$ | 6.457 10$^{-4}$ | 1.484 10$^{-4}$ | (µU/ml)$^{-1}$min$^{-1}$ |
| $b_6$ | 0.032707 | 6.890 10$^{-4}$ | 0.011 | (µU/ml)(mg/dl)$^{-1}$min$^{-1}$ |
| $b_7$ | 1.4763 | 3.6 | 3.6 | (mg/dl)min$^{-1}$ |
| γ | 0.1022 | 0.1022 | 0.1022 | min$^{-1}$ |

The system is assumed to have the properties of a Type-1 diabetic and has the initial conditions listed below, whereby equilibrium ("basal") conditions in blood glucose concentration $G_b$ and plasma insulin $I_b$ had been artificially perturbed by an unknown glucose bolus $b_0$:

$$\left.\begin{array}{l} x_1(t_0) = G_b + b_0, \\ x_2(t_0) = I_b + b_3 b_0, \\ x_3(t_0) = G_b, \text{ and} \\ x_4(t_0) = \dfrac{G_b}{\gamma}. \end{array}\right\}$$

These basal conditions are given by:

$$\left.\begin{array}{l} G_b = \dfrac{b_2}{2 b_4 b_6}\left(-b_1 + \sqrt{b_1^2 + 4\dfrac{b_4 b_6 b_7}{b_2}}\right), \\ I_b = \dfrac{b_6}{b_2} G_b. \end{array}\right\}$$

In the system equations there are finite noise terms $w_i$, creating noise-polluted dynamics, given by:

$$w_1(t) = 0.02 G_b X_1(t) | X_1 \sim N(0,1),$$

$$w_2(t) = 0.02 I_b X_2(t) | X_2 \sim N(0,1),$$

$$w_i(t) = 0.025 X_3(t) | X_3 \sim N(0,1)$$

where: $X_i(t)$ were random variables obeying the probability distribution N(0,1) (i.e. Normal distribution with zero mean and unit variance).

The model $\mathfrak{M}$ is an example of process modelling, with the following equations $f_\mathfrak{M}$:

$$\dot{\xi}_1 = -\lambda_1 \xi_1(t) - \lambda_4 \xi_1(t) \xi_2(t) + \lambda_7 + u_G(t)$$

$$\dot{\xi}_2 = -\lambda_2 \xi_2(t) + \lambda_6 \xi_3(t) + u_{Ins}(t)$$

$$\dot{\xi}_3 = -\lambda_8 \xi_3(t) + \lambda_8^2 \xi_4(t)$$

$$\dot{\xi}_4 = \xi_1(t) - \lambda_8 \xi_4(t)$$

The solution trajectories for these ODEs are then:

$$\xi(t) = \varphi_\mathfrak{M}(\xi(0), \lambda, \omega(t), t) | t \in [t_0, t_f]$$

In this example the model equations were noiseless: ω(t)=0. However a more usual implementation would be to include simulated noise, to explore formation of limit points within Λ for one or more sets of chromosomes using noise-polluted trajectories.

The only observable variable was $x_1(t)$, which was discretely sampled at times $t_i$, 5 seconds apart over 720 minutes, giving 8641 data points: $y_1(t) = \{x_1(t_i)\}_{i=0}^{8640}$. Measurement was assumed noiseless, the relevant noise being within the system dynamics. The initial combination of basal glucose level and glucose bolus was observable, $y_1(0) = G_b + b_0$, but the proportion of this due to $b_0$ was initially unknown. Hence, in this example there is one state variable for which a time-series exists; three more state variables that cannot be measured and nine parameters that cannot be measured.

The input controller variable $u_G(t)$ is fixed at zero while the commanded values for the input controller variable $u_{Ins}(t)$ were known but the noise-polluted actual values $u_I(t)$ could not be measured by the user.

Simulations were performed as difference equations, with the simulation time increment δt=5 seconds. Values for the random variables $X_i(t)$ were generated at every time increment.

Figure 12A:
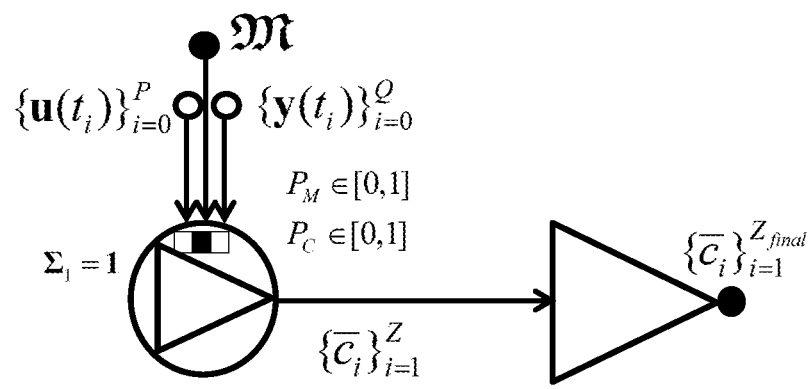
FIG. 12A is a schematic diagram of an example of an Weak TEA circuit used in a specific example.

The Identifier uses a φ-TEA algorithm to interrogate a "medical history", evolving candidate parameter vectors $\{\lambda_i\}_{i=1}^{100}$ and associated initial conditions ξ(0) such that the trajectories $\xi(t) = \varphi_\mathfrak{M}(\xi(0), \lambda_i, \omega(t), t) | t \in [t_0, t_f]$ predict the observed behaviour of the system to within an acceptable margin of accuracy ε, hence each trajectory needed to achieve $\|y_1(t_i) - \xi_1(t_i)\| < \varepsilon$ for all measurement times $t_i$. To do this, a Weak TEA circuit was constructed as shown in FIG. 12A.

A Lyapunov function $V_\eta(\xi, x, \lambda)$ is constructed first, such that its global minimum implied perfect prediction of blood glucose: $V_\eta = 0 \Rightarrow \xi(t_i) = y_1(t_i) \; \forall i \in \{0, \ldots, 8640\}$. In reality this global minimum was assumed unattainable; instead a neighbourhood of this minimum was to be approached through texturing the Fitness.

The Fitness function $F(\lambda)$ was then constructed such that:
1. It rewarded the accurate tracking of candidate trajectories, so $F(\lambda)$ was large when $\|y_1(t_i) - \xi_1(t_i)\|$ was small and vice versa;
2. On a Fitness landscape, contours of $F(\lambda)$ were not locally coincident or parallel with contours of some texturing function $G(V_\eta, \dot{V}_\eta)$ such that $F^\triangleleft(\xi, \lambda) = G(V_\eta, \dot{V}_\eta) \cdot F(\lambda)$.

Here $F(\lambda)$ was taken to be $$F(\lambda) \triangleq \frac{1}{V_\eta + \varepsilon_{Pole}},$$

some $\varepsilon_{Pole} > 0$. (A value of $\varepsilon_{Pole} = 2.22 \times 10^{-16}$ was used, to avoid singularities if $V_\eta = 0$ actually occurred.)

A population of 100 chromosomes was constructed over a search space $\Lambda = [\lambda_1^-, \lambda_1^+] \times \ldots \times [\lambda_8^-, \lambda_8^+]$, intervals for which are shown in Table 6.

TABLE 6

| Model Parameter | Interval for $\Lambda$ | Interval for $\tilde{\Lambda}$ |
| --- | --- | --- |
| $\lambda_{m1}$ | [0.01445, 0.021676] | [0.01445, 0.049403] |
| $\lambda_{m2}$ | [0.033074, 0.049610] | [0.033074, 0.10298] |
| $\lambda_{m4}$ | [1.0 $10^{-5}$, 7.0 $10^{-4}$] | [1.0 $10^{-5}$, 1.71 $10^{-3}$] |
| $\lambda_{m6}$ | [5.0 $10^{-4}$, 5.0 $10^{-3}$] | [5.0 $10^{-4}$, 9.0 $10^{-3}$] |
| $\lambda_{m7}$ | [1.46, 3.6] | [1.46, 8.28] |
| $\lambda_{m8}$ | [0.08176, 0.12264] | [0.08176, 0.30021] |

Model parameters in Table 6 are denoted $\lambda_{mi}$ rather than the terser $\lambda_i$ notation used elsewhere in this specification.

The chromosomes were encoded using Gray code to prevent Hamming walls forming during the mutation process. As a result, the search space $\Lambda$ was enlarged to a larger space $\tilde{\Lambda}$ due to mutations upon Gray-encoded chromosomes. The 100 chromosomes had their genes (corresponding with the parameters $\lambda_0, \ldots, \lambda_8$ to estimate $b_0, \ldots, b_7, \gamma$) randomly generated over $\tilde{\Lambda}$, with $\lambda_0 = y_1(0) - G_b(\lambda)$ being the initial perturbation estimated by each chromosome, given that a basal blood glucose equilibrium $G_b(\lambda)$ was effectively postulated by the values in the rest of each chromosome.

Non-zero mutation and crossover probabilities were imposed, but the speciation vector was set to unity ($\Sigma_1 = 1$) meaning that no speciation constraint was effectively imposed.

Figure 12B:
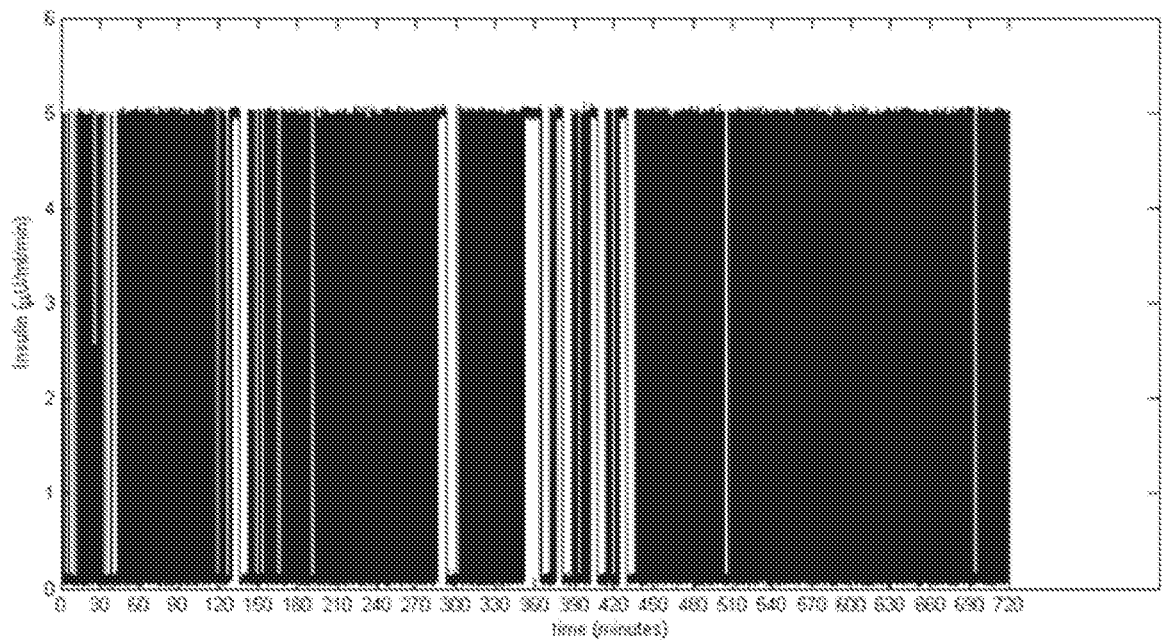
FIG. 12B is a graph illustrating an example of a noise-polluted insulin input signal from a subject's medical history.
Figure 12C:
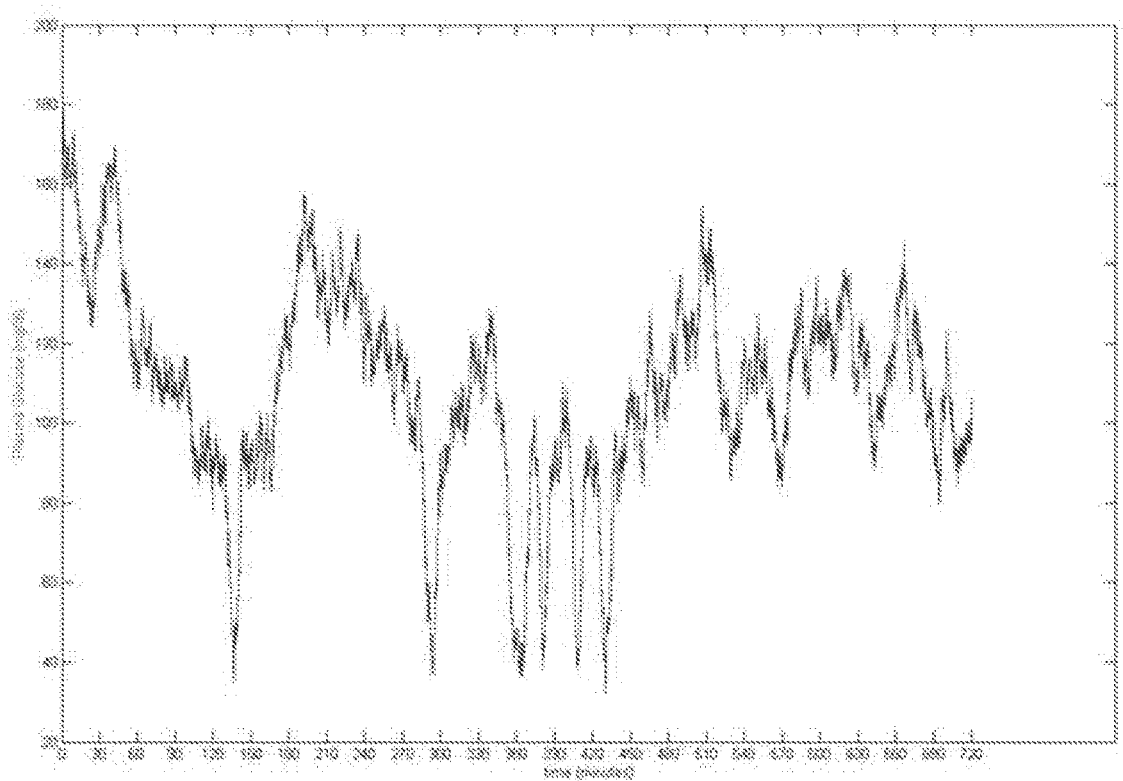
FIG. 12C is a graph illustrating an example of noise-polluted blood glucose time-series measurements from a subject's medical history.

The measurements $y_1(t) = \{x_1(t_i)\}_{i=0}^{8640}$ were taken from an example medical history. The noise-polluted blood glucose time-series is shown in FIG. 12C, in response to a noise-polluted insulin input time-series $u_1(t)$ shown in FIG. 12B, generated from the commanded (known) insulin input time-series $\{u_{Ins}(t_i)\}_{i=0}^{8640}$.

Fitness and texturing worked as follows: there were 200 generations ($g^+ = 200$). At first the Trinities had to be generated such that enough solution trajectories were descending the Lyapunov contours to make Textured constraints viable, i.e. enough chromosomes had to be "fit" under Textured Fitness to maintain a viable population. Consequently for the early generations the Weak TEA operated analogously to a conventional GA, using Fitness only, until at some generation $g = g^\dagger$ enough chromosomes had trajectories descending the Lyapunov function to make texturing viable (assumed to be 80).

Then for the generation $g = g^\dagger + 1$ the Block switched to imposing the Textured Fitness and the Weak TEA constraint for all subsequent evolution:

$$g \in [1, g^\dagger]: F^\triangleleft(\xi, \lambda_i) = F(\lambda_i) = \frac{1}{V_\eta(\xi, \{y_1(t_i)\}_{i=0}^{8640}, \lambda_i) + \varepsilon_{Pole}}$$

$$g \in [g^\dagger, g^+]: F^\triangleleft(\xi, \lambda_i) =$$

$$G(V_\eta, \dot{V}_\eta) \cdot F(\lambda_i) = \begin{cases} F(\lambda_i), & \dot{V}_\eta(\xi, \{y_1(t_i)\}_{i=0}^{8640}, \lambda_i) \leq 0 \\ \varepsilon_{Pole}, & \dot{V}_\eta(\xi, \{y_1(t_i)\}_{i=0}^{8640}, \lambda_i) > 0 \end{cases}.$$

This evolutionary process was repeated by the Weak TEA Block eight times ("runs"). For one run the evolutionary process failed to produce Trinities that produced trajectories that tracked the observed $y_1(t) = \{x_1(t_i)\}_{i=0}^{8640}$ in response to the input $\{u_{Ins}(t_i)\}_{i=0}^{8640}$; the results from that run were discarded. The 700 chromosomes from the remaining runs were aggregated into a final set of chromosomes.

Figure 12D:
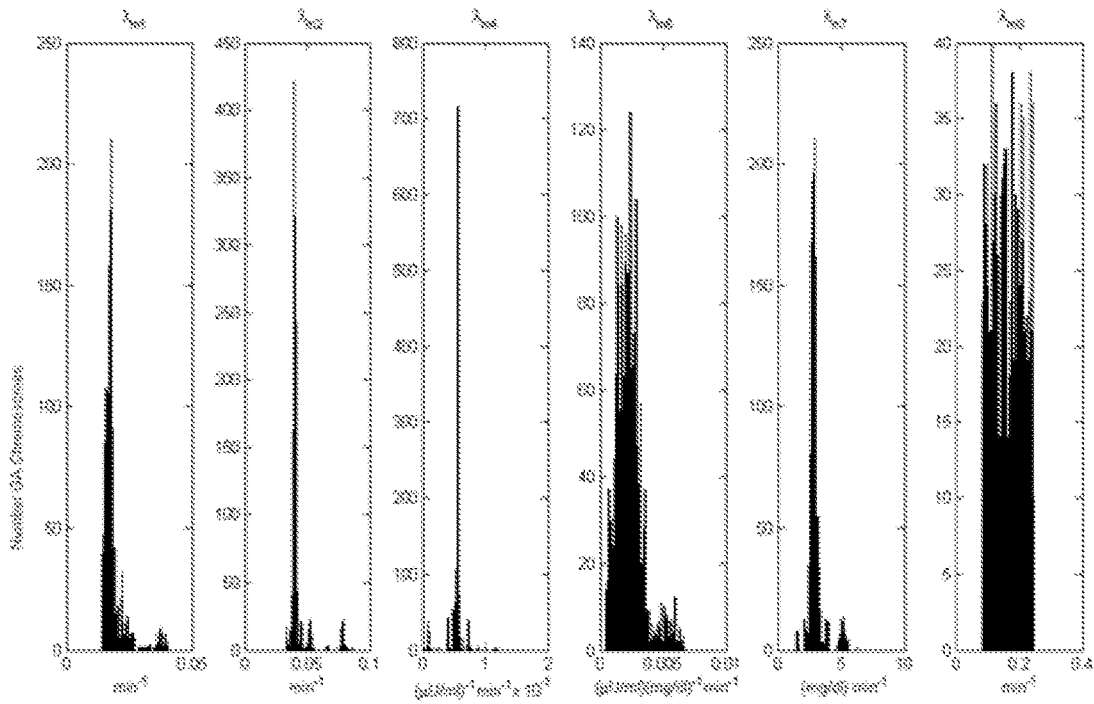
FIG. 12D illustrates histogram plots for genes in a final generation.

Once this final set of chromosomes is generated, the histograms for the genes across the entire set can be plotted, as shown in FIG. 12D. It should be noted that these histograms reveal that, based on the narrowness and number of peaks in the histograms, the algorithm "knew" it had apparently good estimates for $\lambda_1, \lambda_2, \lambda_4, \lambda_7$, while it "knew" significant uncertainty remained in its estimate for $\lambda_6$, while $\lambda_8$ was a "known unknown".

This set of chromosomes was then passed to the Selection/Construction Block, where statistical analysis took place. The results are shown in Table 7 below.

TABLE 7

| Parameter | Actual | $\langle\lambda_{mi}^{dom}\rangle$, set 1 | $\langle\lambda_{mi}^{dom}\rangle$, all sets | $\lambda_{mi}^{dom}$ [$\cup$] | Units |
| --- | --- | --- | --- | --- | --- |
| $b_1$ | 0.018063 | 0.017 | 0.0181 | 0.016693 | min$^{-1}$ |
| $b_2$ | 0.041351 | 0.0413 | 0.0416 | 0.042059 | min$^{-1}$ |
| $b_4$ | 0.000646 | 0.0006 | 0.0008 | 0.0008453 | ($\mu$U/ml)$^{-1}$min$^{-1}$ |
| $b_6$ | 0.000689 | 0.0008 | 0.0011 | 0.0007835 | ($\mu$U/ml)(mg/dl)$^{-1}$min$^{-1}$ |
| $b_7$ | 3.6 | 3.3010 | 3.9467 | 3.8873 | (mg/dl)min$^{-1}$ |
| $\gamma$ | 0.1022 | 0.1551 | 0.1501 | 0.18249 | min$^{-1}$ |

In Table 7, where the statistical operations are defined as follows: denoting the number of runs as $r = 1, \ldots, R$ where here $R = 7$ (ignoring the rejected run), then a minor change in notation has the $i^{th}$ component of the $j^{th}$ element in the set of vectors $\{\lambda_1, \ldots, \lambda_{100}\}$ in the $r^{th}$ run written $\lambda_i^{(j)}[r]$. Then defining the "dominant" value of each histogram done over a single run by its mode gives:

$$\lambda_{mi}^{dom}[r] \triangleq \text{mode}\{\lambda_i^{(1)}[r], \ldots, \lambda_i^{(100)}[r]\}$$

with the dominant vector arising from each run being $$\lambda_m^{dom}[r] \triangleq [\lambda_{m1}^{dom}[r], \ldots, \lambda_{m8}^{dom}[r]]^T.$$

For contrast, the mean value for dominant values across runs was given by:

$$\langle \lambda_{mi}^{dom} \rangle \triangleq \frac{1}{R} \sum_{r=1}^{R} \lambda_{mi}^{dom}[r]$$

and the vector of these mean dominant values was given by:

$$\langle \lambda_m^{dom} \rangle \triangleq [\langle \lambda_{m1}^{dom} \rangle, \ldots, \langle \Lambda_{m8}^{dom} \rangle]^T.$$

This was again contrasted with the global "dominant" value (mode) across the union of all runs, viz.

$$\lambda_{mi}^{dom}[\bigcup] \triangleq \text{mode}\left\{\bigcup_{r=1}^{R}\bigcup_{j=1}^{100} \lambda_i^{(j)}[r]\right\}$$

and hence:

$$\lambda_m^{dom}[\cup] \triangleq [\lambda_{m1}^{dom}[\cup], \ldots, \lambda_{m8}^{dom}[\cup]]^T.$$

Figure 12E:
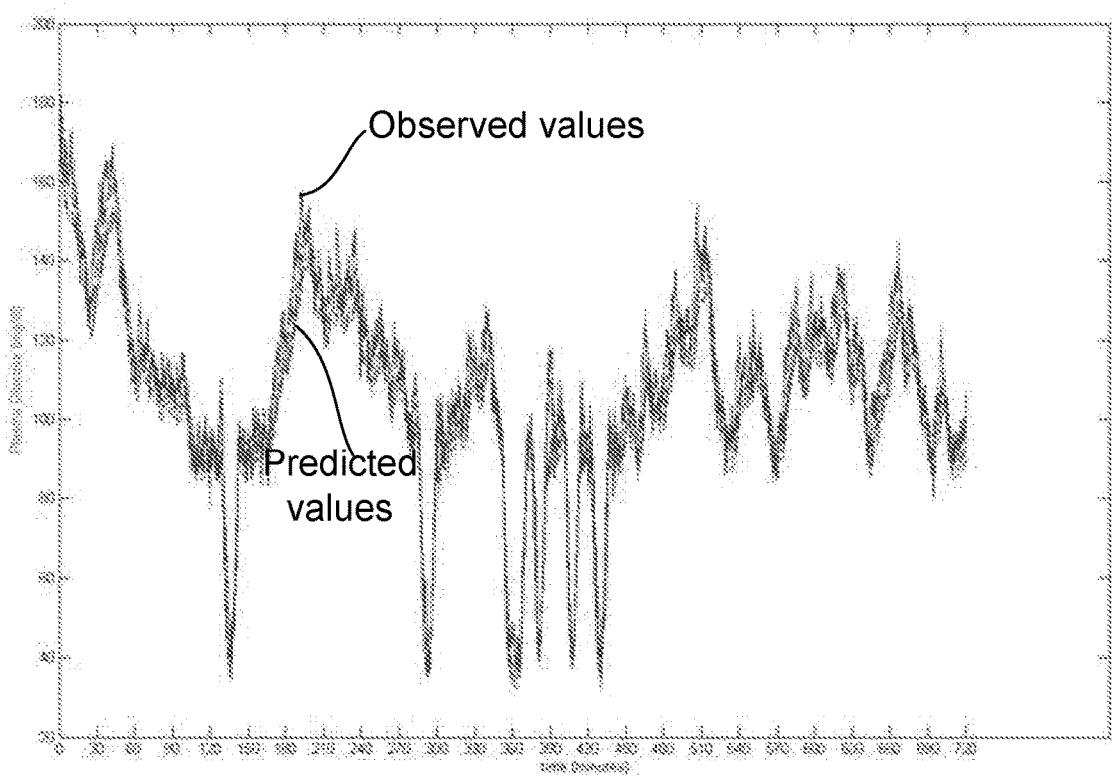
FIG. 12E is a graph illustrating an example of trajectories from "dominant" chromosomes constructed using the modelling system compared with actual blood glucose data measured for the subject.

Predictions plotted from each run's dominant vector $\lambda_n^{dom}[r]$ (chromosomes constructed by the Block) as compared with the observed noise-polluted data are shown in FIG. 12E. As clearly shown, the predicted values track observed values very closely, highlighting the accuracy and ability to predict actual behaviour closely.

Figure 12F:
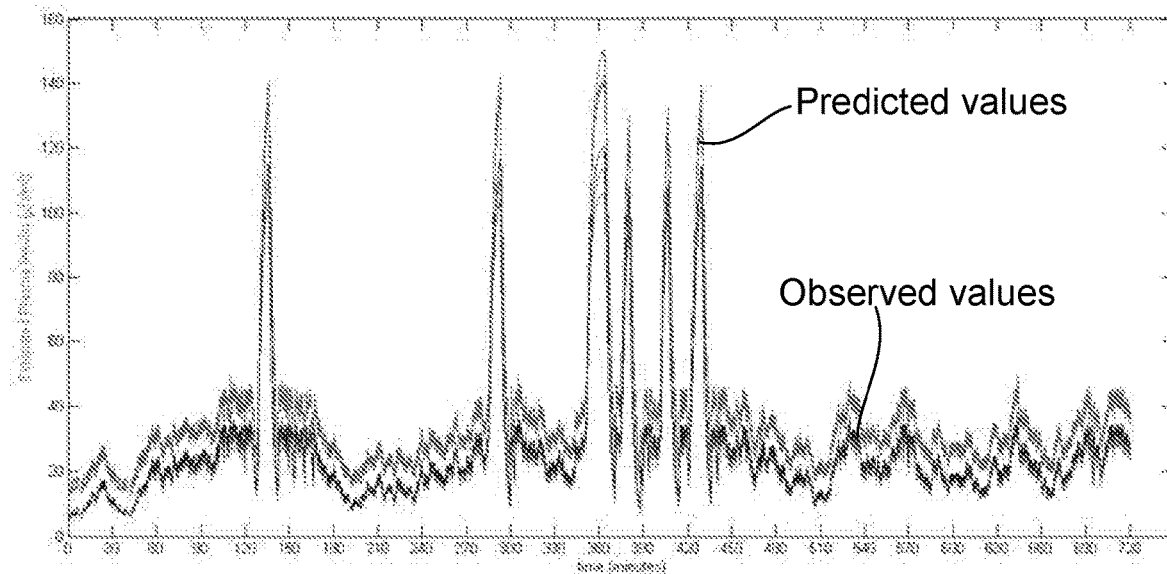
FIG. 12F is a graph illustrating an example of predicted plasma insulin from chromosomes constructed using the modelling system compared with actual values measured for the subject.

FIG. 12F also shows the multiple time-series values for the "hidden" (i.e. not directly observed) time-series for plasma insulin predicted by the $\lambda_m^{dom}[r]$ (magenta), compared with the actual time-series values (blue).

Figure 12G:
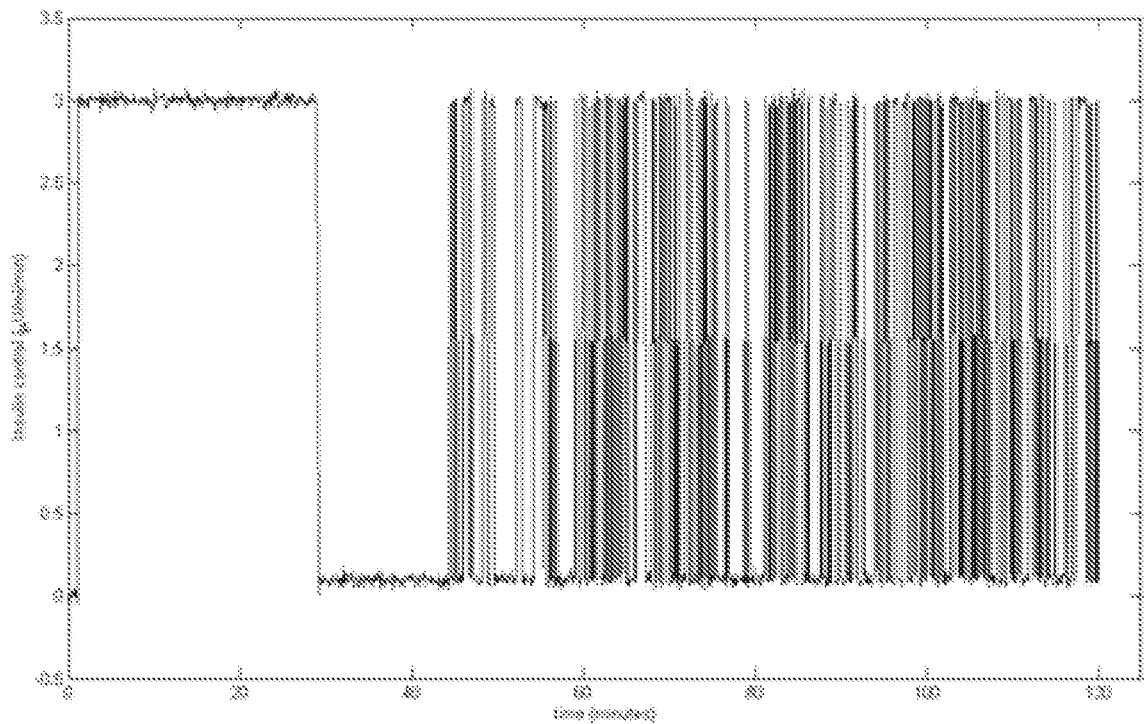
FIG. 12G is a graph illustrating an example of insulin IV time-series controls generated by the modelling system controller to steer blood glucose to 80 mg/dl; and, FIG. 12H is a graph illustrating an example of results showing blood glucose successfully steered to target interval (80+/−20 mg/dl).
Figure 12H:
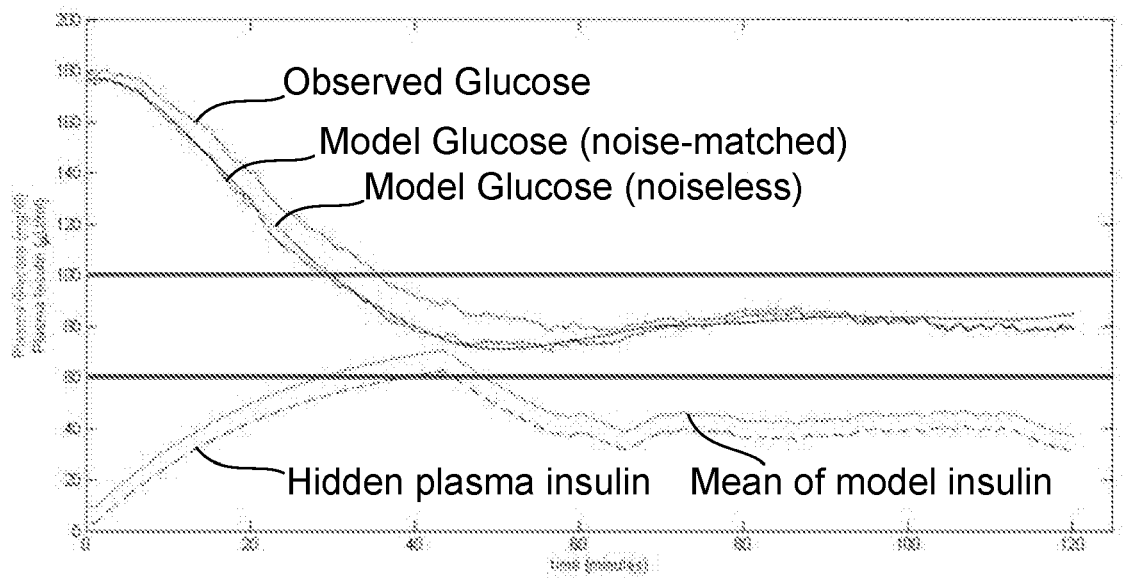

Finally these constructed Trinities (associated with $\lambda_m^{dom}[r]$ and $\langle \lambda_m^{dom} \rangle$) are passed to the Controller module. In this instance it used $\langle \lambda_m^{dom} \rangle$ and a single Lyapunov function $V_s(\xi,\lambda)$, combined with the ongoing $y_1(t)$ data as the basis for its insulin-control decisions, steering trajectories to the target set T such that the model achieves $\xi_1(t) \in [60,100]$ mg/dl. The results are shown in FIGS. 12G and 12H.

Accordingly, it will be appreciated that the above described approach not only accurately predicts system behaviour, but more importantly can also determine effective control strategies allowing system behaviour to be controlled.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A method of modelling system behaviour of a physical system, the method including, in one or more electronic processing devices:
    a) obtaining quantified system data measured for the physical system, the quantified system data being at least partially indicative of the system behaviour for at least a time period, the quantified system data including measured attributes of a physical system obtained from sensor data received from sensors;
    b) forming at least one population of model units, each model unit including model parameters and at least part of a model, the model parameters being at least partially based on the quantified system data, each model including one or more mathematical equations for modelling system behaviour;
    c) for each model unit:
        i) calculating at least one solution trajectory to the one or more mathematical equations for at least part of the at least one time period;
        ii) determining a fitness value based at least in part on the at least one solution trajectory; and,
        iii) iteratively modifying the model unit over a number of generations in accordance with the fitness value of each model unit by modifying at least one of:
            (1) at least part of the model; and,
            (2) the model parameters; and,
    d) selecting a combination of model units using the fitness values of each model unit, the combination of model units representing a collective model that models the system behaviour.

2. A method according to claim 1, wherein the method includes:
    a) forming a plurality of populations; and,
    b) at least one of:
        i) selecting a combination of model units including model units from at least two populations
        ii) exchanging, between the populations, at least one of:
            (1) model parameters;
            (2) at least part of a model; and,
            (3) model units;
        iii) selectively isolating a number of model units in an isolated population; and,
        iv) selectively reintroducing model units from the isolated population.

3. A method according to claim 1, wherein the method includes, modifying:
    the model units at least one of:
    i) by at least one of inheritance, mutation, selection, and crossover;
    ii) in accordance with speciation constraint;
    iii) by exchanging or modifying at least part of a chromosome.

4. A method according to claim 1, wherein each model unit includes:
    a) at least part of the model;
    b) a chromosome indicative of the model parameters and fitness value; and,
    c) details indicative of behaviour of at least some solution trajectories calculated for the model unit.

5. A method according to claim 1, wherein the method includes, at least one of:
    a) determining the fitness value at least in part using a behaviour of the at least one solution trajectory;
    b) determining the fitness of a model unit by comparing the at least one solution trajectory to quantified system data indicative of system behaviour;
    c) determining the fitness value at least in part using a texture set representing a geometrical set in state space;
    d) determining the fitness value at least in part using a texture set representing a geometrical set in state space, wherein at least one of:
        i) the properties of the texture sets are initially defined independently of the chromosomes, the chromosomes including model parameters at least partially based on the quantified system data; and, ii) the texture sets are built from mathematical formulations of the interaction between trajectory elements and observed data;
e) in accordance with the behaviour of at least one solution trajectory, at least one of:
  i) introducing the texture set into state space;
  ii) deleting the texture set from state space;
  iii) moving the texture set through state space;
  iv) modifying the texture set by at least one of:
    (1) enlarging;
    (2) compressing;
    (3) deforming; and,
    (4) subdividing;
f) determining the fitness value at least in part using fitness criteria based on:
  i) qualitative behaviour of solution trajectories in state space;
  ii) quantitative behaviour of solution trajectories in state space;
  iii) collision of solution trajectories with sets in state space;
  iv) capture of solution trajectories by sets in state space;
  v) avoidance of sets in state space by solution trajectories;
  vi) divergence of solution trajectories in state space; and,
  vii) intersection with a geometrical surface in state space;
g) modifying fitness criteria for successive generations of model units;
h) at least one of selectively activating and deactivating fitness criteria for at least one generation of model units; and,
i) determining the fitness value at least in part using texturing achieved by at least one of:
  i) using one or more solution trajectories achieving one or more discretely-distributed qualitative objectives in state space, defined in discrete terms of the trajectories' collision, capture or avoidance with, by, or of one or more specified sets in state space;
  ii) using one or more solution trajectories exhibiting specified behaviour in respect of qualitative objectives in state space described by a continuously distributed or stepwise-continuous function;
  iii) using contours permeating state space and parameter space that are associated with one or more Lyapunov functions and/or the derivatives of Lyapunov functions;
  iv) mapping the fitness to a mathematical structure that captures geometrical information with respect of at least one of:
    (1) trajectories corresponding with distinct chromosomes, which remain geometrically close or diverge in state space; and,
    (2) the value of a pattern over a geometrical surface or hypersurface, generated by a patterning algorithm and mapped to the complex plane and inserted or mapped into the state space, at the point where it is intersected by the trajectory.

6. A method according to claim 5, wherein at least one of:
a) the sets in state space are texture sets;
b) the texture sets undergo changes within generations of a population of model units; and,
c) the properties of texture sets are initially defined independently of chromosomes including model parameters being at least partially based on the quantified system data.

7. A method according to claim 1, wherein the method includes:
a) determining control variable values representing control inputs; and,
b) determining the solution trajectory in accordance with the control variable values.

8. A method according to claim 1, wherein the method includes at least one of:
segmenting quantified system data into respective time period segments and
a) at least one of:
  i) determining respective model units for each time period segment; and,
  ii) selecting a combination of model units so as to include model units for each of the time period segments using an optimisation technique; and,
b) subdividing quantified system data into smaller subsets of types of quantified system data across the same time period segment; and determining respective model units for each subset, and then combining these models into a collective model to more accurately model system behaviour across this same time period segment, and wherein the method optionally includes establishing an optimal model for each subset.

9. A method according to claim 1, wherein the method includes:
a) selecting a number of model units in accordance with the fitness values;
b) determining a plurality of candidate combinations of model units;
c) determining a combination fitness value for each candidate combination; and,
d) selecting the combination in accordance with the combination fitness value.

10. A method according to claim 1, wherein the method includes:
a) defining one or more circuits, each of the one or more circuits including a sequence of Blocks, each Block representing a respective population of model units;
b) transferring at least one of model units and model parameters between the Blocks in accordance with circuit connections; and,
c) using the one or more circuits to select at least one of the combination of model units and model parameters.

11. A method according to claim 10, wherein the method includes modifying the one or more circuits by modifying model units of the Blocks.

12. A method according to claim 1, wherein the method includes:
a) generating a network including a number of nodes;
b) associating parts of a model with a node;
c) for each node on a path through the network:
  i) determining at least one model unit using parts of a model associated with the node; and,
  ii) optimising model parameters of the at least one model unit; and,
d) generating a candidate model based on the model units and model parameters.

13. A method according to claim 12, wherein the method includes at least one of:
a) optimising the path to determine the combination;
b) optimising the path by:
  i) traversing at least one path;
  ii) assessing the resulting candidate combination; and,
  iii) traversing modified paths based on the assessment of the candidate combination;

c) optimising the path using a swarm optimisation technique.

14. A method according to any one of the claim 10, wherein the method includes:
   a) defining a network including a plurality of circuits, each circuit including a sequence of Blocks;
   b) for each node in the network populating each Block with parts of models associated with the node;
   c) transferring at least one of model units and model parameters between the Blocks in accordance with circuit connections to thereby optimise model parameters of the model units.

15. A method according to claim 10, wherein the method includes:
   a) transferring a plurality of circuits along respective paths in the network;
   b) at each node, calculating a respective circuit fitness; and,
   c) selecting an optimum path using the circuit fitness, the selected path representing the combination.

16. A method according to claim 1, wherein the method includes using the model to at least one of:
   a) develop a control program including one or more control variable values indicative of control input to the system to modify system behaviour in a desirable manner;
   b) derive system data that cannot be physically measured; and,
   c) determine a scenario or likelihood of system behaviour resulting in a failure by comparing at least one of system data and system behaviour to defined limits; and,
   d) manipulating or altering the behaviour of the physical system at least partially by applying the control program.

17. A method according to claim 1, wherein the method includes:
   a) determining a selected model parameter corresponding to system data that cannot be at least one of directly manipulated and directly measured;
   b) comparing the selected model parameter to a respective operating range; and
   c) in response to the selected model parameter falling outside the respective range, determining a control input to at least one of:
      i) prevent the selected model parameter falling outside the respective range; and,
      ii) restore the selected model parameter to within the range once the excursion has occurred.

18. A method according to claim 1, wherein the method includes, using a modular system including at least one of:
   a) a Model Selector module for selecting the at least part of a model;
   b) an Identifier module for identifying the combination of model units by requesting parts of a model from the Model Selector; and,
   c) a Controller module that uses the combination of model units to determine a control program.

19. A method according to claim 1, wherein the method includes:
   a) defining meta-model units representing at least one of:
      i) different combinations of model units; and,
      ii) different Blocks, each representing a respective population of model units; and,
   b) optimising the meta-model units to determine at least one of:
      i) a combination of model units; and,
      ii) an optimal Block.

* * * * *